United States Patent
Desai et al.

(10) Patent No.: US 11,427,814 B2
(45) Date of Patent: Aug. 30, 2022

(54) MODIFIED CLEAVASES, USES THEREOF AND RELATED KITS

(71) Applicant: Encodia, Inc., San Diego, CA (US)

(72) Inventors: Kevin Desai, San Diego, CA (US); Kevin L. Gunderson, San Diego, CA (US); Robert C. James, San Diego, CA (US); Lei Shi, San Diego, CA (US); Stephen Verespy, III, San Diego, CA (US)

(73) Assignee: ENCODIA, INC., San Diego, CA (US)

( * ) Notice: Subject to any disclaimer, the term of this patent is extended or adjusted under 35 U.S.C. 154(b) by 0 days.

(21) Appl. No.: 17/213,169

(22) Filed: Mar. 25, 2021

(65) Prior Publication Data

US 2021/0214701 A1 Jul. 15, 2021

Related U.S. Application Data

(63) Continuation-in-part of application No. PCT/US2020/024521, filed on Mar. 24, 2020.

(60) Provisional application No. 63/085,977, filed on Sep. 30, 2020, provisional application No. 62/931,737, filed on Nov. 6, 2019, provisional application No. 62/823,927, filed on Mar. 26, 2019, provisional application No. 62/824,157, filed on Mar. 26, 2019.

(51) Int. Cl.
*C12N 9/48* (2006.01)
*C12P 21/06* (2006.01)

(52) U.S. Cl.
CPC .............. *C12N 9/485* (2013.01); *C12P 21/06* (2013.01)

(58) Field of Classification Search
CPC ..................................................... C12N 9/485
See application file for complete search history.

(56) References Cited

U.S. PATENT DOCUMENTS

| | | |
|---|---|---|
| 6,864,363 B2 | 3/2005 | Travis et al. |
| 6,875,851 B1 | 4/2005 | Travis et al. |
| 7,642,079 B2 | 1/2010 | Cayouette et al. |
| 2006/0259995 A1 | 11/2006 | Cayouette et al. |
| 2009/0264300 A1 | 10/2009 | Franch et al. |
| 2017/0052194 A1 | 2/2017 | Havranek et al. |
| 2019/0145982 A1 | 5/2019 | Chee et al. |
| 2020/0231956 A1 | 7/2020 | Callewaert et al. |
| 2020/0348307 A1 | 11/2020 | Beierle et al. |
| 2020/0348308 A1 | 11/2020 | Chee et al. |

FOREIGN PATENT DOCUMENTS

| | | |
|---|---|---|
| WO | 2005/015239 A1 | 2/2005 |
| WO | 2010/065322 A1 | 6/2010 |
| WO | 2017/192633 A9 | 12/2017 |
| WO | 2019/063827 A1 | 4/2019 |
| WO | 2019/089836 A1 | 5/2019 |

OTHER PUBLICATIONS

Sakamoto et al., "S46 Peptidases are the First Exopeptidases to be Members of Clan PA", Scientific Reports, 2014, 4:4977; pp. 1-11. DOI: 10.1038/srep04977.*
Sakamoto et al., "Structural and mutational analyses of dipeptidyl peptidase 11 from Porphyromonas gingivalis reveal the molecular basis for strict", Scientific Reports, 2015, 5:11151, pp. 1-16. DOI:10:1038/srep11151.*
Han R, et al., "Inhibition of dipeptidyl peptidase 8/9 impairs preadipocyte differentiation," Sci Rep. Aug. 5, 2015;5:12348.
Matovina M et al., "New findings about human dipeptidyl peptidase III based on mutations found in cancer," RSC Adv., 2017, 7, 36326-36334.
Wilson CH, et al., "Identifying natural substrates for dipeptidyl peptidases 8 and 9 using terminal amine isotopic labeling," J Biol Chem. May 17, 2013;288(20):13936-13949.
Zhang H, et al., "Identification of novel dipeptidyl peptidase 9 substrates by two-dimensional differential in-gel electrophoresis," FEBS J. Oct. 2015;282(19):3737-57.
International Search Report for International application PCT/US2020/024521, dated Jul. 2, 2020, 5 pages.
Written Opinion of the International Searching Authority for International application PCT/US2020/024521, dated Jul. 2, 2020, 8 pages.

* cited by examiner

*Primary Examiner* — Suzanne M Noakes
(74) *Attorney, Agent, or Firm* — Rimon, P.C.

(57) ABSTRACT

Provided herein are modified cleavases for removing amino acids from peptides, polypeptides, and proteins. Also provided are methods of using the modified cleavases for treating polypeptides, and kits comprising the modified cleavase. In some embodiments, the methods and the kits also include other components for macromolecule sequencing and/or analysis.

27 Claims, 24 Drawing Sheets

Specification includes a Sequence Listing.

DAP BII Sequence

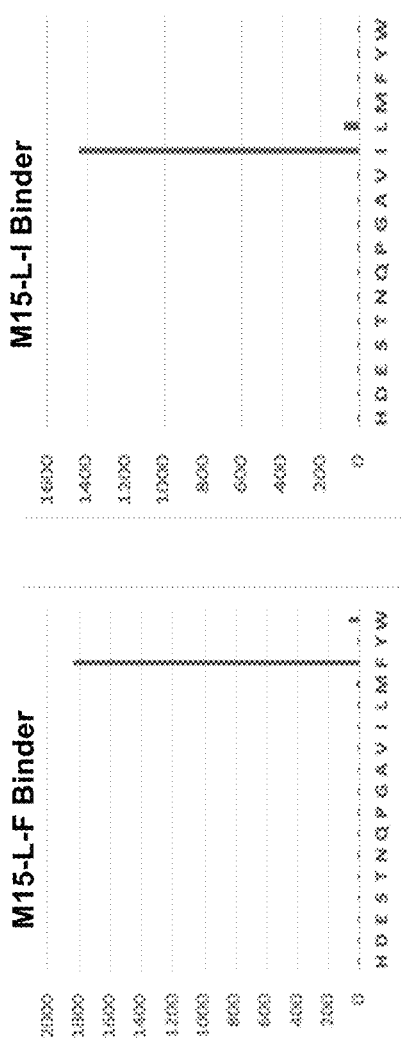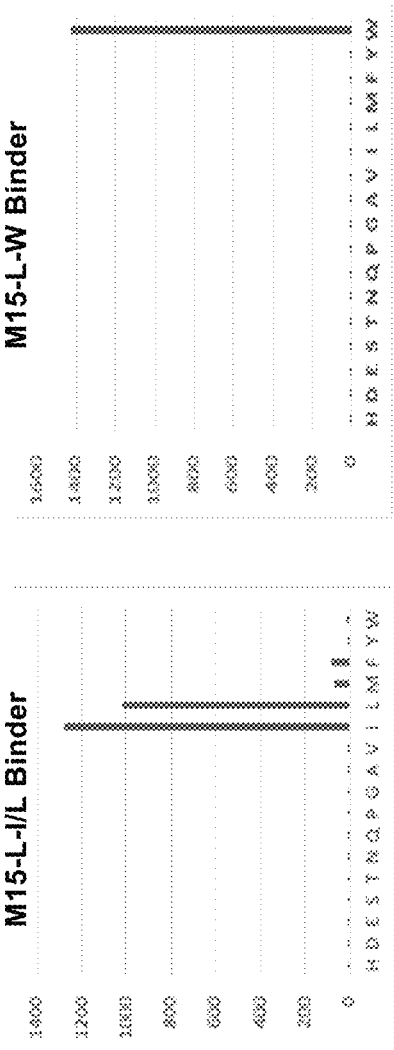
FIG. 6A  FIG. 6B  FIG. 6C  FIG. 6D

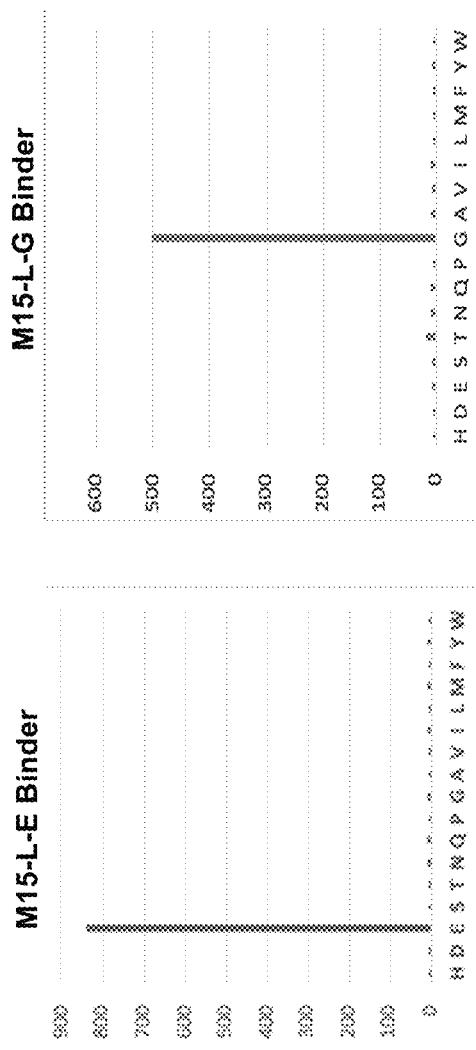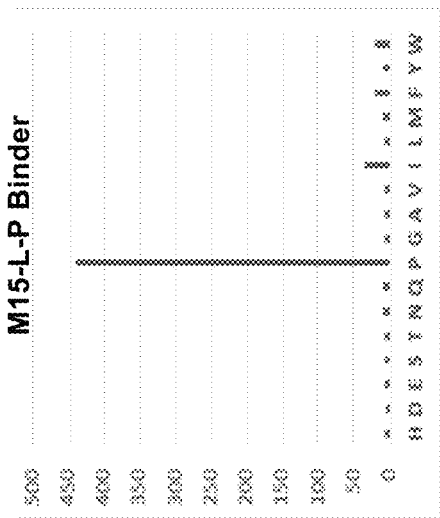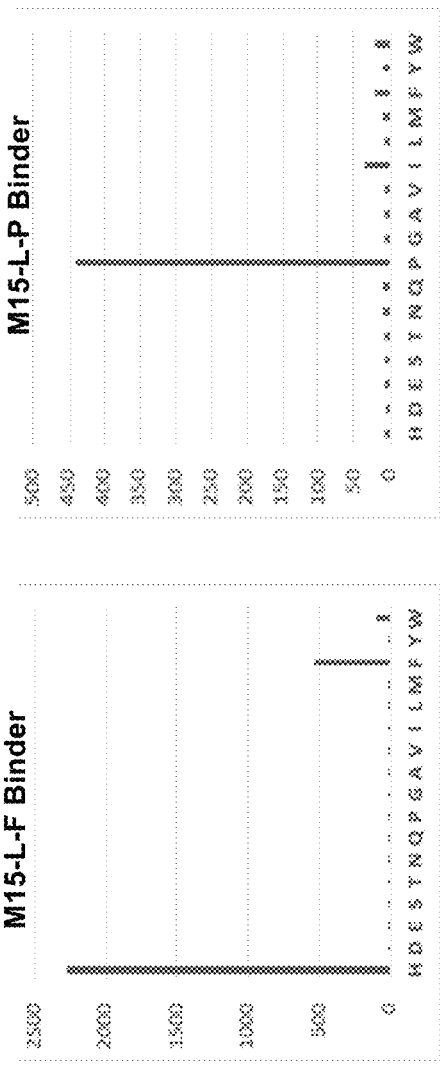
FIG. 6E
FIG. 6F
FIG. 6G
FIG. 6H

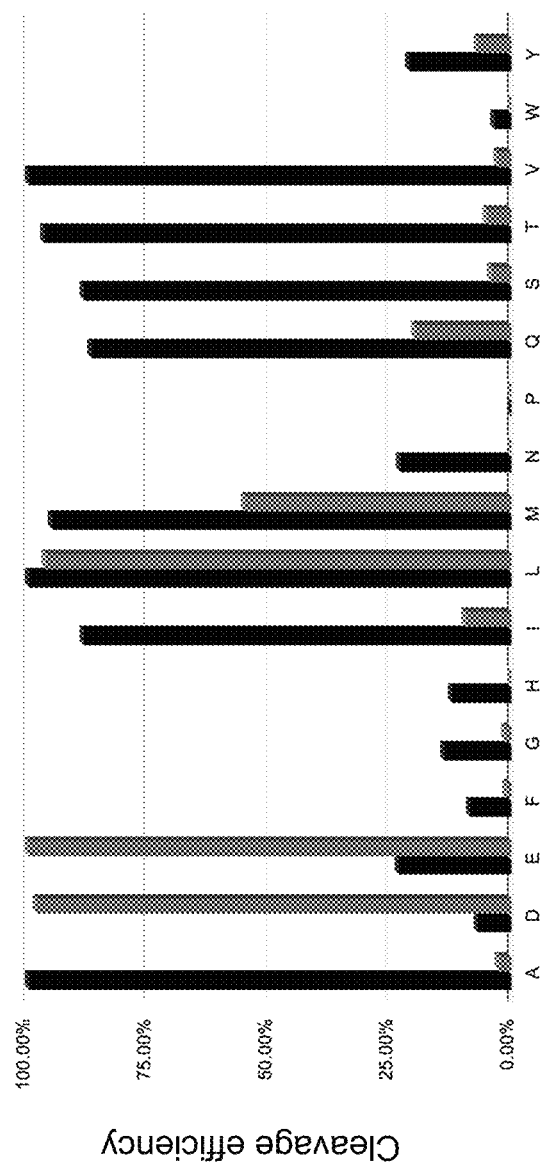

MODIFIED CLEAVASES, USES THEREOF AND RELATED KITS

CROSS-REFERENCE TO RELATED APPLICATIONS

This application is a continuation-in-part of International Patent Application Serial No. PCT/US2020/024521, entitled "MODIFIED CLEAVASES, USES THEREOF AND RELATED KITS", having an international filing date of Mar. 24, 2020, which claims priority to U.S. provisional patent application Nos. 62/823,927, filed on Mar. 26, 2019; 62/824,157, filed on Mar. 26, 2019 and 62/931,737, filed on Nov. 6, 2019. The present application also claims priority to U.S. Provisional Patent Application No. 63/085,977, filed on Sep. 30, 2020. The disclosures and contents of the above-referenced applications are incorporated herein by reference in their entireties for all purposes.

STATEMENT REGARDING FEDERALLY SPONSORED RESEARCH

This invention was made with Government support awarded by National Institute of General Medical Sciences of the National Institutes of Health under Grant No. 1R43GM130185-01 and Grant No. 5R44GM123836-03. The United States Government has certain rights in this invention.

SEQUENCE LISTING ON ASCII TEXT

This patent or application file contains a Sequence Listing submitted in computer readable ASCII text format (file name: 4614-2001300_20210927_SeqList_ST25.txt, recorded: Sep. 27, 2021, size: 256,367 bytes). The content of the Sequence Listing file is incorporated herein by reference in its entirety.

TECHNICAL FIELD

The present disclosure relates to modified cleavases for cleaving amino acids from peptides, polypeptides, and proteins, including modified peptides, polypeptides, and proteins. Also provided are methods of using the modified cleavases for treating polypeptides, and kits comprising the modified cleavase. In some embodiments, the methods and the kits also include other components for macromolecule sequencing and/or analysis.

BACKGROUND

Enzymes that are involved in degradation of peptides and proteins, e.g., aminopeptidases, dipeptidyl peptidases, carboxypeptidases, endopeptidases, and others, hydrolyze peptide bonds (Sanderink et al., J. Clin. Chem. Clin. Biochem. (1988) 26:795-807). Various peptidases have been isolated and discovered in a number of organisms and from various tissues. Aminopeptidases naturally occur as monomeric and multimeric enzymes, and may be metal or ATP-dependent. Some substrate-specific peptidases specifically remove one or two amino acid residues at a time from the amino-terminus of the peptide while others remove from the carboxy-terminus of the protein or peptide. Natural aminopeptidases generally have limited specificity and eliminate amino acids in a processive manner, eliminating one amino acid one after another.

In some embodiments, methods for peptide degradation are useful for applications in protein analysis and/or sequencing. For example, peptide sequencing may involve Edman degradation to achieve stepwise degradation of the N-terminal amino acid (NTAA) on a peptide through a series of chemical modifications and downstream HPLC analysis or mass spectrometry analysis. However, in general, Edman degradation peptide sequencing may be limited, for example, typical Edman degradation requires deployment of high temperature and harsh chemical conditions (e.g., strong acids; anhydrous TFA) for long incubation times. In some cases, Edman degradation may not be compatible with processes for protein analysis methods which may be sensitive to harsh chemical conditions, such as analysis methods which employ nucleic acids (e.g., DNA).

Accordingly, there remains a need for improved reagents for degradation of amino acids. For example, enzymatic methods for removing, eliminating, or cleaving amino acids from polypeptides may be desired. Furthermore, the availability of additional substrate-specific enzymes which can bind and remove desired amino acids from a polypeptide is also desired. In some cases, such improved reagents for removing amino acids are useful for protein sequencing and/or analysis. The present disclosure fulfills these and other related needs.

These and other aspects of the invention will be apparent upon reference to the following detailed description. To this end, various references are set forth herein which describe in more detail certain background information, procedures, compounds and/or compositions, and are each hereby incorporated by reference in their entireties.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Provided herein is a modified cleavase comprising a mutation, e.g., one or more amino acid modification(s) in an unmodified cleavase, wherein the modified cleavase is derived from a dipeptide cleavase and removes or is configured to remove a single labeled terminal amino acid from a polypeptide. Provided herein is a modified cleavase comprising a mutation, e.g., one or more amino acid modification(s) in an unmodified cleavase, wherein the modified cleavase is derived from a tripeptide cleavase and removes or is configured to remove a single labeled terminal amino acid from a polypeptide or a single labeled terminal dipeptide from a polypeptide. In some embodiments, a modified cleavase is provided comprising an unmodified cleavase comprising at least one mutation in a substrate binding site, wherein: the unmodified cleavase is a dipeptide cleavase and the modified cleavase removes or is configured to remove a single labeled terminal amino acid from a polypeptide; or the unmodified cleavase is a tripeptide cleavase and the modified cleavase removes or is configured to remove a single labeled terminal amino acid from a polypeptide or a single labeled terminal dipeptide from a polypeptide. In some embodiments, the modified cleavase is configured to remove a single labeled terminal amino acid from the C-terminus or N-terminus of a polypeptide. In some embodiments, the modified cleavase is configured to remove a single labeled dipeptide (the terminal and penultimate terminal amino acids) from the C-terminus or N-terminus of a polypeptide. In some embodiments, the modified cleavase is derived from a wild-type or unmodified cleavase (e.g., a dipeptide cleavase or tripeptide cleavase). For example, the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof.

In some embodiments, a set of dipeptide cleavase enzymes is provided, comprising at least two different modified dipeptide cleavases, wherein: (i) each of the modified dipeptide cleavases from the set of dipeptide cleavase enzymes is configured to remove a single labeled terminal amino acid from a polypeptide, and comprises an unmodified dipeptide cleavase comprising at least one mutation in a substrate binding site; (ii) the unmodified dipeptide cleavase is configured to remove two terminal amino acids from the polypeptide; and (iii) the modified dipeptide cleavases from the set of dipeptide cleavase enzymes have different specificities for the labeled terminal amino acids, which the modified dipeptide cleavases are configured to remove. Working together, the modified dipeptide cleavases from the set will or can complement each other and provide broad specificity towards the labeled terminal amino acids, e.g., will cleave off many, if not all, labeled terminal amino acids from the polypeptide.

Also provided herein is a method of treating a polypeptide, comprising contacting the polypeptide with a modified cleavase comprising a mutation, e.g., one or more amino acid modification(s) in an unmodified cleavase, wherein the modified cleavase is derived from a dipeptide cleavase and removes a single labeled terminal amino acid from a polypeptide. Provided herein is a method of treating a polypeptide, comprising contacting the polypeptide with a modified cleavase comprising a mutation, e.g., one or more amino acid modifications in an unmodified cleavase, wherein the modified cleavase is derived from a tripeptide cleavase and removes a single labeled terminal amino acid from a polypeptide or a single labeled terminal dipeptide from a polypeptide. In some embodiments, a method of treating a polypeptide is provided, comprising the steps of: (a) contacting the polypeptide with a reagent for labeling a terminal amino acid of the polypeptide to produce a labeled polypeptide; (b) contacting the labeled polypeptide with a modified cleavase, the modified cleavase comprising an unmodified cleavase comprising at least one mutation in a substrate binding site, wherein: the unmodified cleavase is a dipeptide cleavase and the modified cleavase removes or is configured to remove a single labeled terminal amino acid from the polypeptide; or the unmodified cleavase is a tripeptide cleavase and the modified cleavase removes or is configured to remove a single labeled terminal amino acid from the polypeptide or a single labeled terminal dipeptide from the polypeptide. In some embodiments, the modified cleavase removes a single labeled terminal amino acid from the C-terminus or N-terminus of the polypeptide treated with the modified cleavase. In some embodiments, the modified cleavase removes a single labeled dipeptide (the terminal and penultimate terminal amino acids) from the C-terminus or N-terminus of the polypeptide treated with the modified cleavase. In some embodiments, the modified cleavase is derived from a wild-type or unmodified cleavase (e.g., a dipeptide cleavase or tripeptide cleavase). For example, the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof. In some embodiments, the method further comprises contacting the polypeptide with a reagent for labeling the terminal amino acid of the polypeptide. In some embodiments, the method further comprises contacting the polypeptide with a binding agent capable of binding to the terminal amino acid of the polypeptide, wherein the binding agent comprises a coding tag with identifying information regarding the binding agent. In some embodiments, the method also further comprises transferring the identifying information of the coding tag to a recording tag attached to the polypeptide, thereby generating an extended recording tag(s) on the polypeptide. In some cases, the method further comprises removing the binding agent. In some further embodiments, the method further comprises analyzing the one or more extended recording tag(s). In some further embodiments, the method further comprises repeating some or all of the above steps one or more times.

Also provided herein is a method for analyzing a polypeptide, comprising the steps of: (a) contacting a polypeptide with a binding agent capable of binding to the terminal amino acid of the polypeptide, wherein the binding agent comprises a coding tag with identifying information regarding the binding agent; (b) transferring the identifying information of the coding tag to a recording tag associated with each of the polypeptide to generate an extended recording tag; (c) contacting the polypeptide with a reagent to label the terminal amino acid of the polypeptide; and (d) contacting the polypeptide with a modified cleavase comprising a mutation, e.g., one or more amino acid modification(s), in an unmodified cleavase, wherein the modified cleavase is derived from a dipeptide cleavase and removes a single terminal amino acid labeled by the reagent in step (c) from the polypeptide; or the modified cleavase is derived from a tripeptide cleavase and removes a single terminal amino acid or a single terminal dipeptide labeled by the reagent in step (c) from the polypeptide.

Provided herein is a kit for treating a polypeptide, the kit comprising a modified cleavase comprising a mutation, e.g., one or more amino acid modifications, in an unmodified cleavase and a reagent for labeling the terminal amino acid of the polypeptide. In some aspects, the modified cleavase is derived from a dipeptide cleavase and removes or is configured to remove a single labeled terminal amino acid from a polypeptide or the modified cleavase is derived from a tripeptide cleavase and removes or is configured to remove a single labeled terminal amino acid from a polypeptide or a single labeled terminal dipeptide from a polypeptide. In some embodiments, a kit for treating a polypeptide is provided, comprising: a reagent for labeling a terminal amino acid of the polypeptide configured to produce a labeled terminal amino acid of the polypeptide; and a modified cleavase comprising an unmodified cleavase comprising at least one mutation in a substrate binding site, wherein: the unmodified cleavase is derived from a dipeptide cleavase and the modified cleavase removes or is configured to remove a single labeled terminal amino acid from a polypeptide; or the unmodified cleavase is derived from a tripeptide cleavase and the modified cleavase removes or is configured to remove a single labeled terminal amino acid from a polypeptide or a single labeled terminal dipeptide from a polypeptide. In some embodiments, the kit further comprises one or more binding agents, wherein each binding agent is configured to bind to the single labeled terminal amino acid of a polypeptide. In some embodiments, the one or more binding agents comprises a coding tag with identifying information regarding the binding agent. In some embodiments, the kit further comprises a reagent for transferring the identifying information of the coding tag to a recording tag attached to the polypeptide, wherein the transferring of the identifying information to the recording tag generates an extended recording tag on the polypeptide. In some embodiments, the kit further comprises one or more amplification reagent(s) for amplifying the extended recording tags. In some embodiments, the kit further comprises one or more substrates or supports. In some embodiments, the kit also comprises a reagent for nucleic acid sequencing analysis.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

In FIG. 1A on the left, an exemplary unmodified cleavase derived from a dipeptide cleavase removes two amino acids from the N-terminus of the polypeptide, cleaving the bond between the penultimate (P2) and antepenultimate amino acid (P3) residues. On the right, an exemplary modified cleavase derived from a dipeptide cleavase removes a single labeled amino acid from the N-terminus of the polypeptide, cleaving the bond between the labeled terminal amino acid (P1; diamond indicates label) and the penultimate amino acid residue (P2). In FIG. 1B on the left, an exemplary unmodified cleavase derived from a tripeptide cleavase removes three amino acids from the N-terminus of the polypeptide, cleaving the bond C-terminal to the antepenultimate amino acid on the N-terminus (between P3 and P4). On the right of FIG. 1B, two exemplary modified cleavases are derived from a tripeptide cleavase. On the top, the modified tripeptide cleavase removes a single labeled amino acid from the N-terminus of the polypeptide, cleaving the bond between the labeled terminal amino acid (P1; diamonds indicates label) and the penultimate amino acid residue (P2). On the bottom, the modified tripeptide cleavase removes a labeled dipeptide (P1-P2) from the N-terminus of the polypeptide, cleaving the bond between the penultimate terminal amino acid residue (P2) and the antepenultimate amino acid residue (P3).

In FIG. 2A-2B, a polypeptide with a labeled N-terminal amino acid residue is cleaved at the bond between the terminal amino acid and penultimate amino acid by the modified cleavase and the labeled terminal amino acid is released. In FIG. 2C, the new terminal amino acid is labeled and the modified cleavase is able to recognize the new labeled terminal amino acid for further cleavage and release.

FIG. 6A-6H illustrates exemplary Luminex-based binding affinity profile of anticalin clones chosen from a phage display screen against M15-L-P1 peptides. Eight exemplary engineered anticalin binders are shown to have mostly mono-specificity for P1 residues except for the I/L binder. The anticalin clones are isolated from phage library panning. Clones with specificity to different P1 residues, such as E, F, G, H, I, L, P, W, as well as clones with specificity to two different P1 residues, such as T/S, A/T/S, T/V/I/A, F/L, were successfully isolated.

FIG. 7A shows Encoding versus Luminex binding signal for M15-L-G clone shown in FIG. 4. FIG. 7B shows P2 dependence determined by ProteoCode™ encoding assay using the M15-L-G binder clone on various M15-L-G-P2 peptides.

FIG. 9C shows a cleavage profile for an exemplary set of two selected modified Cleavase clones, M15-L_Z001, having specificity towards A, I, L, M, Q, V in the P1 position (cleavage efficiency of M15-L_Z001 is shown by the left columns for each amino acid), and M15-L_Z002, having specificity towards D and E in the P1 position (cleavage efficiency of M15-L_Z002 is shown by the right columns for each amino acid).

FIG. 11A. Structures of a bipartite NTM comprised of an amino acid-like portion (NTMaa) and a N-terminal blocking group (NTM$_{blk}$) connected by an amide bond (upper) and other possible NTMs that would accommodate modified substrate binding pockets of cleavases. NTM can also be a small chemical entity (NTM$_B$) with a similar bipartite shape configuration as NTM$_A$, or a differently shaped NTM$_C$. FIG. 11B. NTMs are activated using standard methods (activated ester) and are coupled to the N-terminal amine on the P1 residue of a polypeptide. The arrow indicates a cleavage site of the modified dipeptide cleavase enzyme.

DETAILED DESCRIPTION

Figure 1A:
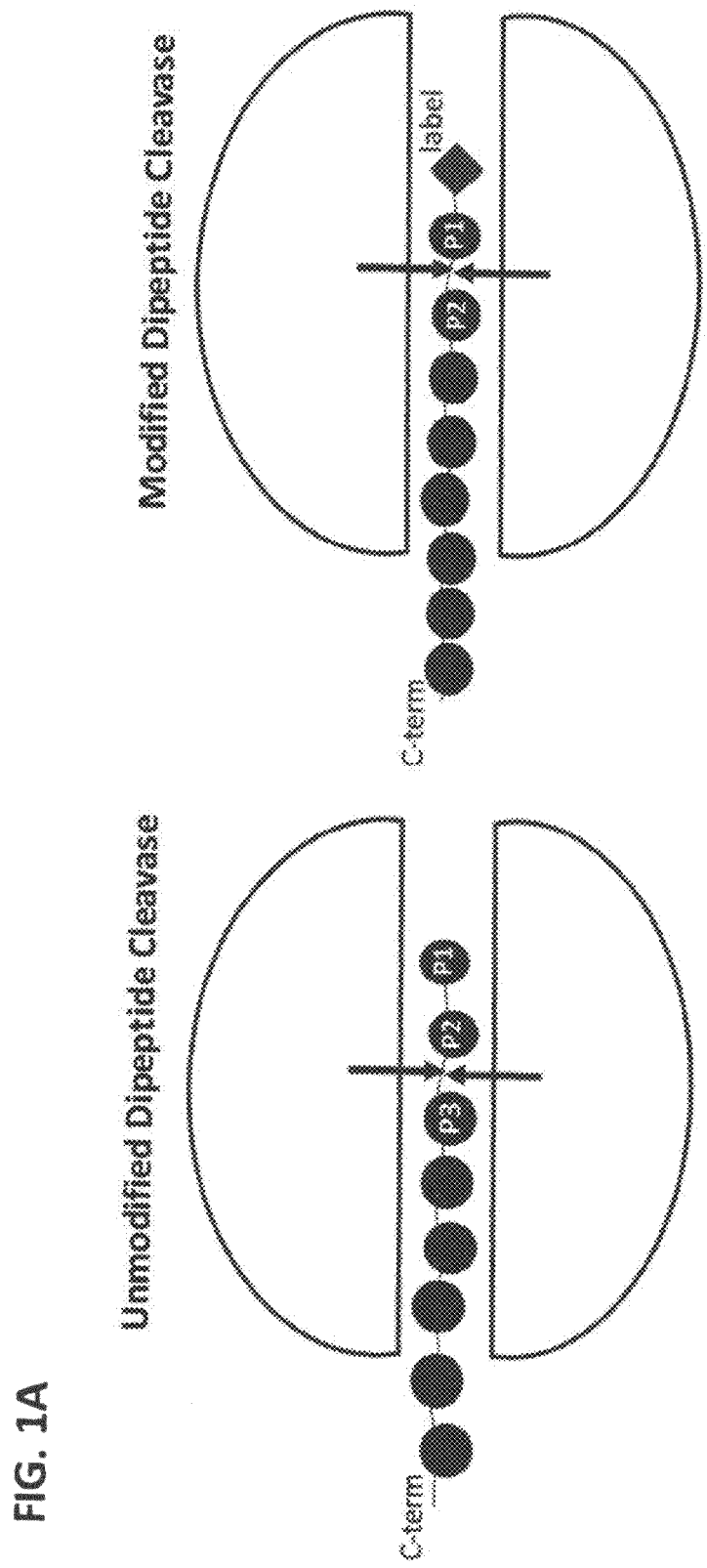
FIG. 1A-1B is a schematic depicting the removal of a single modified amino acid by exemplary modified cleavases as provided herein.

Provided herein are modified cleavases comprising a mutation (e.g., one or more modifications in an unmodified cleavase) and related methods of selecting, engineering, and using the modified cleavases. Provided herein are methods for labeling a polypeptide (e.g. with a chemical reagent) and treating the labeled polypeptide with a modified cleavase to remove the labeled terminal amino acid from the polypeptide. Also provided are kits comprising the modified cleavases. In some embodiments, the kits comprising the modified cleavase is used for treating peptides, polypeptides, and proteins, such as for sequencing and/or analysis. In some embodiments, protein analysis using the modified cleavase employs barcoding and nucleic acid encoding of molecular recognition events, and/or detectable labels. In some embodiments, the kits also include other components for treating the polypeptides, including tags (e.g., DNA tag or DNA recording tag), solid supports, and other reagents for preparing the polypeptides and other reagents for polypeptide analysis.

Various enzymes that degrade peptides and proteins by hydrolyzing peptide bonds, (e.g., aminopeptidases, dipeptidyl peptidases, carboxypeptidases, endopeptidases) have been isolated and discovered in a number of organisms and from various tissues. However, natural aminopeptidases may have limited specificity, and generically eliminate N-terminal amino acids in a processive manner, eliminating one amino acid off after another. Some substrate-specific peptidases specifically remove one or two amino acid residues at a time from the amino-terminus or carboxy-terminus of peptides.

In some embodiments, methods for peptide degradation are useful for applications in protein analysis and/or sequencing. For example, peptide sequencing may involve Edman degradation to achieve stepwise degradation of the N-terminal amino acid on a peptide through a series of chemical modifications and downstream HPLC analysis or mass spectrometry analysis. However, in general, Edman degradation peptide sequencing may be limited, for example, typical Edman degradation requires deployment of high temperature and harsh chemical conditions (e.g., strong acids; anhydrous TFA) for long incubation times. In some cases, Edman degradation may not be compatible with processes for protein analysis methods which may be sensitive to harsh chemical conditions, such as analysis methods which employ nucleic acids (e.g., DNA).

Accordingly, there remains a need for improved reagents and techniques for degradation of amino acids from a polypeptide. For example, enzymatic methods for removing, eliminating, or cleaving amino acids from polypeptides may be desired. Provided herein are modified peptidases that meet such needs. In some embodiments, provided herein are enzymatic methods and reagents for removing amino acids from polypeptides. In some cases, the removal of amino acids by the provided modified enzymes (e.g., cleavases) are used for stepwise degradation of amino acids from polypeptides. In some embodiments, the removal of amino acids by the provided modified cleavase are suitable for cyclic removal of amino acids from the polypeptide. In some embodiments, the modified cleavase removes or is configured to remove a single labeled terminal amino acid from a polypeptide. In some embodiments, the modified cleavase removes a single labeled terminal amino acid from the C-terminus or N-terminus of a polypeptide. For example, the modified cleavase is configured to cleave the peptide bond between a terminal labeled amino acid residue and a penultimate terminal amino acid residue of the polypeptide. In some embodiments, the modified cleavase is configured to remove a single labeled dipeptide (the terminal and penultimate terminal amino acids) from the C-terminus or N-terminus of a polypeptide. In some embodiments, the modified cleavase is derived from a wild-type or unmodified cleavase (e.g., a dipeptide cleavase or tripeptide cleavase). For example, the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof. For example, the modified cleavase is derived from a wild-type or unmodified cleavase (e.g., a dipeptidyl peptidase, a dipeptidyl aminopeptidase, a peptidyl-dipeptidase, or a dipeptidyl carboxypeptidase).

In some embodiments, peptidases may be engineered to possess specific binding or catalytic activity to specific terminal amino acids only when modified with a label. For example, a cleavase may be engineered or modified, compared to a wild-type or unmodified cleavase, such than it only eliminates a terminal amino acid if it is labeled by a chemical label. Using this exemplary approach, the modified cleavase eliminates only labeled amino acid(s) from the terminus of the polypeptide, and allows control of degradation in a desired manner. In some embodiments, the modified cleavase is configured to remove a single labeled terminal amino acid from the C-terminus or N-terminus of a polypeptide. In some embodiments, the modified cleavase is configured to remove a single labeled terminal dipeptide (the terminal and penultimate terminal amino acids) from the C-terminus or N-terminus of a polypeptide. In some embodiments, the modified cleavase is non-selective as to amino acid residue identity while being selective for the label (e.g., will remove any labeled terminal amino acid). In some other embodiments, the modified cleavase exhibits some preference for certain amino acid residues or classes of amino acids (e.g. at the P1 and/or P2 terminal positions of the polypeptide). In some cases, two or more modified cleavases with different preferences for certain amino acids (or classes of amino acids) may be used in combination. In some embodiments, the modified cleavase binds and removes amino acids from the N-terminus of the polypeptide. In some embodiments, the modified cleavase binds and removes amino acids from the C-terminus of the polypeptide.

In some embodiments, known peptidases may be modified to achieve specific characteristics for binding and/or cleaving. An example of a model of modifying the specificity of enzymatic N-terminal amino acid (NTAA) degradation involves a methionine aminopeptidase converted into a leucine aminopeptidase (Borgo et al., Protein Sci. (2014) 23(3):312-320). In another example, aminopeptidase mutants were engineered to bind to and eliminate individual or small groups of labelled (biotinylated) NTAAs (see, PCT Publication No. WO2010/065322). Provided herein are modified cleavases which are selected or modified to remove terminal amino acids that are labeled, such as a chemically-modified (e.g., PTC/DNP/acetyl/Cbz-modified) terminal amino acid on a polypeptide. In some embodiments, a wild-type cleavase is engineered (e.g., using structural-function based-design and/or directed evolution) to cleave or remove only an N-terminal amino acid having a PTC/DNP/acetyl/Cbz group present as the label. In some examples, the terminal amino acid to be removed is a Cbz labeled terminal amino acid. In some examples, the removed labeled terminal amino acid is removed as a single amino acid or as part of a dipeptide.

In certain embodiments, a compact monomeric metalloenzymatic aminopeptidase is engineered to recognize and eliminate isothiourea or Cbz labeled NTAAs. In some cases, the modified peptidase is a metallo-peptidase and requires a metal ion for activation. In some embodiments, the use of a monomeric metallo-aminopeptidase has two key advantages: 1) compact monomeric proteins are easier to display and screen using phage display; 2) a metallo-aminopeptidase has the unique advantage in that its activity can be turned on/off at will by adding or removing the appropriate metal cation. The unmodified cleavase may be from any suitable organism. In some examples, the wild-type or unmodified cleavase is from a mammal, e.g., *Homo sapiens*, a fungus or yeast, e.g., *Saccharomyces cerevisiae*, or a bacterium, e.g., *Bacteroides thetaiotaomicron, Porphyromonas gingivalis, Pseudomonas sp., Pseudoxanthomonas mexicana* or *Caldithrix abyssi*. In some cases, these enzymes are stable, robust, and active at room temperature and at or around pH 8.0, and thus compatible with mild conditions preferred for peptide analysis. In some embodiments, it is preferred to have a thermophilic cleavase capable of removing labeled modified or terminal amino acid(s) at elevated temperatures to minimize peptide secondary structure.

In another embodiment, provided herein is a modified or an engineered cleavase comprising a mutation, e.g., one or more amino acid modification(s), in an unmodified cleavase, wherein: said modified or engineered cleavase is derived from a dipeptidyl peptidase of *Thermomonas hydrothermalis* or *Caldithrix abyssii* and removes or is configured to remove a single N-terminally modified amino acid from a target polypeptide.

In some embodiments, the present modified or engineered cleavase is derived from a dipeptidyl peptidase of *Thermomonas hydrothermalis* comprising an amino acid sequence set forth in SEQ ID NO: 43 (WT sequence with the signal peptide) or SEQ ID NO: 42 (WT sequence without the signal peptide). In some embodiments, the present modified or engineered cleavase is derived from a dipeptidyl peptidase of *Caldithrix abyssii* comprising an amino acid sequence set forth in SEQ ID NO:45 (WT sequence with the signal peptide) or SEQ ID NO:44 (WT sequence without the signal peptide).

In another embodiment, cyclic elimination or removal of amino acids is attained by engineering the peptidase (e.g., cleavase) to be active only in the presence of a terminal amino acid label. In some embodiments, the label is a chemical label. In some cases, the label is or comprises a blocked or labeled amino acid. In some embodiments, the label comprises an exogenous labeled or modified amino acid. Moreover, the peptidase may be engineered to be non-specific, such that it does not selectively recognize one particular amino acid over another, but recognizes any amino acid at the terminus that has a label. In some embodiments, the modified cleavase is selective for one or more, two or more, three or more, four or more, five or more, ten or more, fifteen or more, twenty or more etc. amino acids.

The present modified or engineered cleavase can be derived from any suitable type of dipeptidyl peptidase. For example, the present modified or engineered cleavase can be derived from a protein or enzyme classified as a S46 dipeptidyl peptidase (see e.g., Shakh M. A. Rouf, Yuko Ohara-Nemoto, Tomonori Hoshino, Taku Fujiwara, Toshio Ono, Takayuki K. Nemoto, Discrimination based on Gly and Arg/Ser at position 673 between dipeptidyl-peptidase (DPP) 7 and DPP11, widely distributed DPPs in pathogenic and environmental gram-negative bacteria, Biochimie, Volume 95, Issue 4, 2013, Pages 824-832, ISSN 0300-9084), or a functional homolog or fragment thereof.

The present modified or engineered cleavase can remove or can be configured to remove any suitable single N-terminally modified amino acid from a target polypeptide. For example, the present modified or engineered cleavase can remove or can be configured to remove a N-terminal amino acid that is labeled with a chemical or an enzymatic reagent or moiety.

The present modified or engineered cleavase can remove or can be configured to remove any suitable single N-terminally modified amino acid from a target polypeptide containing any suitable N-terminal modification (NTM), such as synthetic NTM. In another example, NTM can comprise an amino acid moiety and/or has a size, e.g., length axis or volume, shape, and/or configuration similar to or exceeding a natural amino acid. In some embodiments, NTM can be a bipartite N-terminal modification that comprises a natural or unnatural amino acid portion (NTMaa) and a N-terminal blocking group ($NTM_{blk}$). The amino acid-like portion (NTMaa) and the N-terminal blocking group ($NTM_{blk}$) can be connected or linked by any suitable bond or linkage. For example, the amino acid portion (NTMaa) and the N-terminal blocking group ($NTM_{blk}$) can be connected with an amide bond.

In some embodiments, NTM does not comprise an amino acid moiety. In some embodiments, NTM comprises a N-terminal blocking group ($NTM_{blk}$) and does not comprise a NTMaa group. In some embodiments, NTM can be a bipartite N-terminal modification that comprises a small (or small molecule) chemical entity having a size, e.g., length axis or volume, shape, and/or configuration similar to or exceeding a natural amino acid, and a N-terminal blocking group ($NTM_{blk}$). The small (or small molecule) chemical entity and the N-terminal blocking group ($NTM_{blk}$) can be connected or linked by any suitable bond or linkage. For example, the small (or small molecule) chemical entity and the N-terminal blocking group can be connected with an amide bond. The small (or small molecule) chemical entity can have any suitable size, e.g., length axis or volume. For example, the small (or small molecule) chemical entity can have a size, e.g., length axis of about 5-10 Å and volume of about 100-1000 Å$^3$. In some embodiments, the small (or small molecule) chemical entity has a length axis of about 5, 6, 7, 8, 9 or 10 Å, or any range thereof. In some embodiments, the small (or small molecule) chemical entity has a volume of about 100, 200, 300, 400, 500, 600, 700, 800, 900, 1000 Å$^3$ or any range thereof.

In another example, the N-terminal modification can comprise a chemical label.

In some embodiments, a chemical reagent for the N-terminal modification is selected from the group consisting of: 2-aminobenzamide, 2-(N-methylamino)-benzamide, 2-(N-acetylamine)-benzamide, 2-(N-benzylamine)-benzamide, 4-methylbenzamide, 4-(dimethylamino)benzamide, nicotinamide, 3-aminonicotinamide, 2-pyrazinecarbonyl, 5-amino-2-fluoro-isonicotinamide, 2-carboxylic acid pyrazinecarbonyl, 3,6-difluoro-2-carboxybenzamide, 4-chloro-2-aminobenzamide, 4-nitro-2-aminobenzamide, 4-methoxy-2-aminobenzamide, 4-carboxylic acid-2-aminobenzamide, 5-(trifluoromethyl-2-aminobenzamide, 4-(trifluoromethyl-2-aminobenzamide, 6-fluoro-2-aminobenzamide, 4-fluoro-2-aminobenzamide, 5-methoxy-2-aminobenzamide, 4-fluorobenzamide, 4-(trifluoromethyl)benzamide, 8-fluoroisoquinolinium, 1-hydroxy-2,3,1-benzodiazaborinine-2(1H)-carbonyl, Succinamide, 3,6-Difluoropyridine-2-carbamide, 2-Fluoronicotinamide, 5-Bromo-2-hydroxynicotinamide, 4-(Trifluoromethyl)pyrimidine-5-carbamide, 2-Oxo-1,2-dihydropyridine-3-carbamide, 5-Methyl-2-aminobenzamide, 6-Fluoropicolinamide, 3-Methyl-2-aminobenzamide, 4-Methyl-2-aminobenzamide, 2-Amino-6-methylbenzamide, 2-Amino-6-fluorobenzamide, 2-Amino-5-fluorobenzoamide, 2-Amino-3-fluorobenzoamide, 2-Amino-4-fluorobenzoamide, 2-Aminonicotinamide, 4-Aminonicotinamide, 3-Aminopicolinamide, or a derivative thereof. In some embodiments, the chemical reagent for the N-terminal modification is an isatoic anhydride, an isonicotinic anhydride, an azaisatoic anhydride, a succinic anhydride, an aryl activated ester, a heteroaryl activated ester, a non-aromatic ring activated ester, or a derivative thereof. In some embodiments, the chemical reagent for the N-terminal modification is selected from the group consisting of wherein the chemical reagent is selected from the group consisting of 4-Nitrophenyl Anthranilate, N-Methyl-isatoic anhydride, N-acetyl-isatoic anhydride, N-benzyl-isatoic anhydride, 4-methylbenzoic acid, 4-(dimethylamino) benzoyl chloride, nicotinic acid-NHS, 3-aminonicotinic acid, 2-pyrazinecarbonyl chloride, 5-amino-2-fluoro-isonicotinic acid, 2,3-pyrazinedicarboxylic anhydride, 3,6-difluorophthalic anhydride, 4-chloroisatoic anhydride, 4-nitroisatoic anhydride, 7-methoxy-1h-benzo[d][1,3]oxazine-2,4-dione, 4-carboxylic acid isatoic anhydride, 6-(Trifluoromethyl)-2,4-dihydro-1h-3,1-benzoxazine-2,4-dione, 7-(Trifluoromethyl)-1h-benzo[d][1,3]oxazine-2,4-dione, 6-fluoroisatoic anhydride, 4-fluoroisatoic anhydride, 5-methoxyisatoic anhydride, 4-fluorobenzoic acid anhydride, 4-(trifluoromethyl)benzoic acid anhydride, 2-ethynyl-6-fluorobenzaldehyde, 1-hydroxy-2,3,1-benzodiazaborinine-2(1H)-carboxylic acid, Isatoic anhydride, Succinic anhydride 3,6-Difluoropyridine-2-carboxylic acid, 2-Fluoronicotinic acid, 5-Bromo-2-hydroxynicotinic acid, 4-(Trifluoromethyl)pyrimidine-5-carboxylic acid, 2-Oxo-1,2-dihydropyridine-3-carboxylic acid, 5-Methylisatoic anhydride, 6-Fluoropicolinic acid, 3-Methylisatoic anhydride, 4-Methyl-isatoic anhydride, 2-Amino-6-methylbenzoic acid, 2-Amino-6-fluorobenzoic acid, 2-Amino-5-fluorobenzoic acid, 2-Amino-3-fluorobenzoic acid, 2-Amino-4-fluorobenzoic acid, 2-Aminonicotinic acid, 4-Aminonicotinic acid, 3-Aminopicolinic acid, or a derivative thereof.

In some embodiments, the provided modified cleavases are used for treating polypeptides obtained from a sample. In some cases, the sample and/or the polypeptide obtained from the sample is treated with other reagents for processing the polypeptides, such as digesting the polypeptides. In some embodiments, the polypeptides comprise a plurality of polypeptides obtained from a sample. In some embodiments, the sample is obtained from a subject.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, the term "sample" refers to anything which may contain an analyte for which an analyte assay is desired. As used herein, a "sample" can be a solution, a suspension, liquid, powder, a paste, aqueous, non-aqueous or any combination thereof. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

The terms "level" or "levels" are used to refer to the presence and/or amount of a target, e.g., a substance or an organism that is part of the etiology of a disease or disorder, and can be determined qualitatively or quantitatively. A "qualitative" change in the target level refers to the appearance or disappearance of a target that is not detectable or is present in samples obtained from normal controls. A "quantitative" change in the levels of one or more targets refers to a measurable increase or decrease in the target levels when compared to a healthy control.

As used herein, the term "polypeptide" encompasses peptides and proteins, and refers to a molecule comprising a chain of two or more amino acids joined by peptide bonds. In some embodiments, a polypeptide comprises 2 to 50 amino acids, e.g., having more than 20-30 amino acids. In some embodiments, a peptide does not comprise a secondary, tertiary, or higher structure. In some embodiments, the polypeptide is a protein. In some embodiments, a protein comprises 30 or more amino acids, e.g. having more than 50 amino acids. In some embodiments, in addition to a primary structure, a protein comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides may be naturally occurring, synthetically produced, or recombinantly expressed. Polypeptides may be synthetically produced, isolated, recombinantly expressed, or be produced by a combination of methodologies as described above. Polypeptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, β-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "post-translational modification" refers to modifications that occur on a peptide after its translation, e.g., translation by ribosomes, is complete. A post-translational modification may be a covalent chemical modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristoylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

As used herein, the term "binding agent" refers to a nucleic acid molecule, a peptide, a polypeptide, a protein, carbohydrate, or a small molecule that binds to, associates, unites with, recognizes, or combines with a binding target, e.g., a polypeptide or a component or feature of a polypeptide. A binding agent may form a covalent association or non-covalent association with the polypeptide or component or feature of a polypeptide. A binding agent may also be a chimeric binding agent, composed of two or more types of molecules, such as a nucleic acid molecule-peptide chimeric binding agent or a carbohydrate-peptide chimeric binding agent. A binding agent may be a naturally occurring, synthetically produced, or recombinantly expressed molecule. A binding agent may bind to a single monomer or subunit of a polypeptide (e.g., a single amino acid of a polypeptide) or bind to a plurality of linked subunits of a polypeptide (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may preferably bind to a chemically modified or labeled amino acid (e.g., an amino acid that has been labeled by a reagent comprising a compound of any one of Formula (I)-(IV) as described herein) over a non-modified or unlabeled amino acid. For example, a binding agent may preferably bind to an amino acid that has been labeled or modified over an amino acid that is unlabeled or unmodified. A binding agent may bind to a post-translational modification of a peptide molecule. A binding agent may exhibit selective binding to a component or feature of a polypeptide (e.g., a binding agent may selectively bind to one of the 20 possible natural amino acid residues and with bind with very low affinity or not at all to the other 19 natural amino acid residues). A binding agent may exhibit less selective binding, where the binding agent is capable of binding or configured to bind to a plurality of components or features of a polypeptide (e.g., a binding agent may bind with similar affinity to two or more different amino acid residues). A binding agent may comprise a coding tag, which may be joined to the binding agent by a linker.

As used herein, the term "linker" refers to one or more of a nucleotide, a nucleotide analog, an amino acid, a peptide, a polypeptide, a polymer, or a non-nucleotide chemical moiety that is used to join two molecules. A linker may be used to join a binding agent with a coding tag, a recording tag with a polypeptide, a polypeptide with a solid support, a recording tag with a solid support, etc. In certain embodiments, a linker joins two molecules via enzymatic reaction or chemistry reaction (e.g., click chemistry).

The term "ligand" as used herein refers to any molecule or moiety connected to the compounds described herein. "Ligand" may refer to one or more ligands attached to a compound. In some embodiments, the ligand is a pendant group or binding site (e.g., the site to which the binding agent binds).

As used herein, the term "proteome" can include the entire set of proteins, polypeptides, or peptides (including conjugates or complexes thereof) expressed by a genome, cell, tissue, or organism at a certain time, of any organism. In one aspect, it is the set of expressed proteins in a given type of cell or organism, at a given time, under defined conditions. Proteomics is the study of the proteome. For example, a "cellular proteome" may include the collection of proteins found in a particular cell type under a particular set of environmental conditions, such as exposure to hormone stimulation. An organism's complete proteome may include the complete set of proteins from all of the various cellular proteomes. A proteome may also include the collection of proteins in certain sub-cellular biological systems. For example, all of the proteins in a virus can be called a viral proteome. As used herein, the term "proteome" include subsets of a proteome, including but not limited to a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof. As used herein, the term "proteomics" refers to quantitative analysis of the proteome within cells, tissues, and bodily fluids, and the corresponding spatial distribution of the proteome within the cell and within tissues. Additionally, proteomics studies include the dynamic state of the proteome, continually changing in time as a function of biology and defined biological or chemical stimuli.

The terminal amino acid at one end of a peptide or polypeptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being amino acids in length. As used herein, NTAA is considered the $n^{th}$ amino acid (also referred to herein as the "n NTAA"). Using this nomenclature, the next amino acid is the n−1 amino acid, then the n−2 amino acid, and so on down the length of the peptide from the N-terminal end to C-terminal end. In certain embodiments, an NTAA, CTAA, or both may be modified or labeled with a moiety or a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a polypeptide, a binding agent, a set of binding agents from a binding cycle, a sample polypeptides, a set of samples, polypeptides within a compartment (e.g., droplet, bead, or separated location), polypeptides within a set of compartments, a fraction of polypeptides, a set of polypeptide fractions, a spatial region or set of spatial regions, a library of polypeptides, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error correcting barcodes. Barcodes can be used to computationally deconvolute the multiplexed sequencing data and identify sequence reads derived from an individual polypeptide, sample, library, etc. A barcode can also be used for deconvolution of a collection of polypeptides that have been distributed into small compartments for enhanced mapping. For example, rather than mapping a peptide back to the proteome, the peptide is mapped back to its originating protein molecule or protein complex.

As used herein, the term "coding tag" refers to a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag or coding tag. In certain embodiments, a spacer sequence flanks an encoder sequence of a coding tag on one end or both ends. Following binding of a binding agent to a polypeptide, annealing between complementary spacer sequences on their associated coding tag and recording tag, respectively, allows transfer of binding information through a primer extension reaction or ligation to the recording tag, coding tag, or a di-tag construct. Sp' refers to spacer sequence complementary to Sp. Preferably, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of polypeptides, or be binding cycle number specific. Polypeptide class-specific spacers permit annealing of a cognate binding agent's coding tag information present in an extended recording tag from a completed binding/extension cycle to the coding tag of another binding agent recognizing the same class of polypeptides in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "recording tag" refers to a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred, or from which identifying information about the macromolecule (e.g., UMI information) associated with the recording tag can be transferred to the coding tag. Identifying information can comprise any information characterizing a molecule such as information pertaining to sample, fraction, partition, spatial location, interacting neighboring molecule(s), cycle number, etc. Additionally, the presence of UMI information can also be classified as identifying information. In certain embodiments, after a binding agent binds to a polypeptide, information from a coding tag linked to a binding agent can be transferred to the recording tag associated with the polypeptide while the binding agent is bound to the polypeptide. In other embodiments, after a binding agent binds to a polypeptide, information from a recording tag associated with the polypeptide can be transferred to the coding tag linked to the binding agent while the binding agent is bound to the polypeptide. A recoding tag may be directly linked to a polypeptide, linked to a polypeptide via a multifunctional linker, or associated with a polypeptide by virtue of its proximity (or co-localization) on a solid support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) in length providing a unique identifier tag for each macromolecule, polypeptide or binding agent to which the UMI is linked. A polypeptide UMI can be used to computationally deconvolute sequencing data from a plurality of extended recording tags to identify extended recording tags that originated from an individual polypeptide. A polypeptide UMI can be used to accurately count originating polypeptide molecules by collapsing NGS reads to unique UMIs. A binding agent UMI can be used to identify each individual molecular binding agent that binds to a particular polypeptide. For example, a UMI can be used to identify the number of individual binding events for a binding agent specific for a single amino acid that occurs for a particular peptide molecule. It is understood that when UMI and barcode are both referenced in the context of a binding agent or polypeptide, that the barcode refers to identifying information other that the UMI for the individual binding agent or polypeptide (e.g., sample barcode, compartment barcode, binding cycle barcode).

As used herein, the term "universal priming site" or "universal primer" or "universal priming sequence" refers to a nucleic acid molecule, which may be used for library amplification and/or sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. Universal priming sites can be used for other types of amplification, including those commonly used in conjunction with next generation digital sequencing. For example, extended recording tag molecules may be circularized and a universal priming site used for rolling circle amplification to form DNA nanoballs that can be used as sequencing templates (Drmanac et al., 2009, Science 327:78-81). Alternatively, recording tag molecules may be circularized and sequenced directly by polymerase extension from universal priming sites (Korlach et al., 2008, Proc. Natl. Acad. Sci. 105:1176-1181). The term "forward" when used in context with a "universal priming site" or "universal primer" may also be referred to as "5'" or "sense". The term "reverse" when used in context with a "universal priming site" or "universal primer" may also be referred to as "3'" or "antisense".

As used herein, the term "extended recording tag" refers to a recording tag to which information of at least one binding agent's coding tag (or its complementary sequence) has been transferred following binding of the binding agent to a polypeptide. Information of the coding tag may be transferred to the recording tag directly (e.g., ligation) or indirectly (e.g., primer extension). Information of a coding tag may be transferred to the recording tag enzymatically or chemically. An extended recording tag may comprise binding agent information of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 125, 150, 175, 200 or more coding tags. The base sequence of an extended recording tag may reflect the temporal and sequential order of binding of the binding agents identified by their coding tags, may reflect a partial sequential order of binding of the binding agents identified by the coding tags, or may not reflect any order of binding of the binding agents identified by the coding tags. In certain embodiments, the coding tag information present in the extended recording tag represents with at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity the polypeptide sequence being analyzed. In certain embodiments where the extended recording tag does not represent the polypeptide sequence being analyzed with 100% identity, errors may be due to off-target binding by a binding agent, or to a "missed" binding cycle (e.g., because a binding agent fails to bind to a polypeptide during a binding cycle, because of a failed primer extension reaction), or both.

As used herein, the term "extended coding tag" refers to a coding tag to which information of at least one recording tag (or its complementary sequence) has been transferred following binding of a binding agent, to which the coding tag is joined, to a polypeptide, to which the recording tag is associated. Information of a recording tag may be transferred to the coding tag directly (e.g., ligation), or indirectly (e.g., primer extension). Information of a recording tag may be transferred enzymatically or chemically. In certain embodiments, an extended coding tag comprises information of one recording tag, reflecting one binding event. As used herein, the term "di-tag" or "di-tag construct" or "di-tag molecule" refers to a nucleic acid molecule to which information of at least one recording tag (or its complementary sequence) and at least one coding tag (or its complementary sequence) has been transferred following binding of a binding agent, to which the coding tag is joined, to a polypeptide, to which the recording tag is associated. Information of a recording tag and coding tag may be transferred to the di-tag indirectly (e.g., primer extension). Information of a recording tag may be transferred enzymatically or chemically. In certain embodiments, a di-tag comprises a UMI of a recording tag, a compartment tag of a recording tag, a universal priming site of a recording tag, a UMI of a coding tag, an encoder sequence of a coding tag, a binding cycle specific barcode, a universal priming site of a coding tag, or any combination thereof.

As used herein, the term "solid support", "solid surface", or "solid substrate", or "sequencing substrate", or "substrate" refers to any solid material, including porous and non-porous materials, to which a polypeptide can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter. In certain embodiments, "a bead" solid support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays (See e.g., Service, *Science* (2006) 311:1544-1546).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Single molecule sequencing includes methods that need to pause the sequencing reaction after each base incorporation ('wash-and-scan' cycle) and methods which do not need to halt between read steps. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" the polypeptide means to identify, detect, quantify, characterize, distinguish, or a combination thereof, all or a portion of the components of the polypeptide. For example, analyzing a peptide, polypeptide, or protein includes determining all or a portion of the amino acid sequence (contiguous or non-continuous) of the peptide. Analyzing a polypeptide also includes partial identification of a component of the polypeptide. For example, partial identification of amino acids in the polypeptide protein sequence can identify an amino acid in the protein as belonging to a subset of possible amino acids. Analysis typically begins with analysis of the n NTAA, and then proceeds to the next amino acid of the peptide (i.e., n−1, n−2, n−3, and so forth). This is accomplished by elimination of the n NTAA, thereby converting the n−1 amino acid of the peptide to an N-terminal amino acid (referred to herein as the "n−1 NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

The term "unmodified" (also "wild-type" or "native") as used herein is used in connection with biological materials such as nucleic acid molecules and proteins (e.g., cleavase), refers to those which are found in nature and not modified by human intervention.

The term "modified" (or "variant" or mutant") as used in reference to nucleic acid molecules and proteins, e.g., a modified cleavase created by human intervention. The variant, mutant or modified cleavase is a polypeptide having an altered amino acid sequence, relative to an unmodified or wild-type cleavase. The variant or modified cleavase is a polypeptide which differs from a wild-type cleavase sequence by one or more amino acid substitutions, deletions, additions, or combinations thereof. A variant, mutant or modified cleavase can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences (e.g., mutations) compared to the wild-type cleavase. A variant or modified cleavase polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified cleavase. Non-naturally occurring amino acids as well as naturally occurring amino acids are included within the scope of permissible substitutions or additions. A variant, mutant or modified cleavase is not limited to any variant, mutant or modified cleavase made or generated by a particular method of making and includes, for example, a variant, mutant or modified cleavase made or generated by genetic selection, protein engineering, directed evolution, de novo recombinant DNA techniques, or combinations thereof. A mutant, variant or modified cleavase polypeptide is altered in primary amino acid sequence by substitution, addition, or deletion of amino acid residues. The term "variant" in the context of variant or modified cleavase is not be construed as imposing any condition for any particular starting composition or method by which the variant or modified cleavase is created. Thus, variant or modified cleavase denotes a composition and not necessarily a product produced by any given process. A variety of techniques including genetic selection, protein engineering, recombinant methods, chemical synthesis, or combinations thereof, may be employed.

In some embodiments, variants of a modified dipeptide cleavase displaying only non-substantial or negligible differences in structure can be generated by making conservative amino acid substitutions in the modified dipeptide cleavase. By doing this, modified dipeptide cleavase variants that comprise a sequence having at least 90% (90%, 91%, 92%, 93%, 94%, 95%, 96%, 97%, 98%, and 99%) sequence identity with the modified or unmodified dipeptide cleavase sequences provided in the attached Sequence Listing can be generated, retaining at least one functional activity, e g., cleavase activity for a given substrate. Examples of conservative amino acid changes are known in the art. Examples of non-conservative amino acid changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamic acid or aspartic acid; or (d) a residue having a bulky side chain, e.g., phenylalanine, for (or by) one not having a side chain, e g., glycine. Methods of making targeted amino acid substitutions, deletions, truncations, and insertions are generally known in the art. For example, amino acid sequence variants can be prepared by mutations in the DNA. Methods for polynucleotide alterations are well known in the art, for example, Kunkel et al. (1987) Methods in Enzymol. 154: 367-382; U.S. Pat. No. 4,873,192 and the references cited therein.

The term "corresponding to" with reference to positions of or within a protein, a polypeptide or a polynucleotide, such as recitation that nucleotides or amino acid positions "correspond to" nucleotides or amino acid positions in a disclosed sequence, such as set forth in the Sequence Listing, refers to nucleotides or amino acid positions identified upon alignment with the disclosed sequence based on structural sequence alignment or using a standard alignment algorithm, such as the GAP algorithm. For example, corresponding residues can be determined by alignment with a reference sequence, such as set forth in SEQ ID NOs: 5-8, 10-16, 20, by structural alignment methods as described herein. By aligning the sequences, one skilled in the art can identify corresponding residues, for example, using conserved and identical amino acid residues as guides. For example, one skilled in the art can identify a residue in a given polypeptide at a position corresponding to position 191 of SEQ ID NO: 13 by making a BLASTP alignment of the polypeptide sequence together with SEQ ID NO: 13, and find the residue in the polypeptide that is aligned with the residue 191 of SEQ ID NO: 13. Similarly, one skilled in the art can identify any given amino acid residue in a given polypeptide at a position corresponding to a particular position of a reference sequence, such as set forth in the Sequence Listing, by performing alignment of the polypeptide sequence with the reference sequence (for example, by BLASTP publicly available through the NCBI website), matching the corresponding position of the reference sequence with the position in polypeptide sequence and thus identifying the amino acid residue within the polypeptide.

As used herein, domain (such as a sequence of amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distinguished by homology of the primary sequence or structure to related family members, such as homology to motifs. In another example, a domain can be distinguished by its function, such as an ability to interact with a molecule, such as a cognate binding partner. A domain independently can exhibit a biological function or activity such that the domain independently or fused to another molecule can perform an activity, such as, for example, binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed, appropriate software can be employed to identify domains.

The term "sequence identity" as used herein refers to the sequence identity between genes or proteins at the nucleotide or amino acid level, respectively. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. In exemplary embodiment, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence of 10 nucleotides in length are identical to the corresponding positions in a second 10-nucleotide sequence, then the two sequences have 70% sequence identity. Methods for the alignment of sequences for comparison are well known in the art, such methods include GAP, BESTFIT, BLAST, FASTA and TFASTA. The BLAST algorithm calculates percent sequence identity and performs a statistical analysis of the similarity between the two sequences. The software for performing BLAST analysis is publicly available through the National Center for Biotechnology Information (NCBI) website.

As used herein, the term "alkyl" refers to and includes saturated linear and branched univalent hydrocarbon structures and combination thereof, having the number of carbon atoms designated (i.e., $C_1$-$C_{10}$ or $C_{1-10}$ means one to ten carbons). Particular alkyl groups are those having 1 to 20 carbon atoms (a "$C_1$-$C_{10}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"), unless otherwise specified Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, "alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

The term "aminoalkyl" refers to an alkyl group that is substituted with one or more —$NH_2$ groups. In certain embodiments, an aminoalkyl group is substituted with one, two, three, four, five or more —$NH_2$ groups. An aminoalkyl group may optionally be substituted with one or more additional substituents as described herein.

As used herein, "aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. In some embodiments, phenyl is a preferred aryl group.

As used herein, the term "arylalkyl" refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-yl-ethyl, and the like.

As used herein, the term "cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. In some embodiments, the cycloalkyl is a cyclic hydrocarbon having from 3 to 13 annular carbon atoms. In some embodiments, the cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

As used herein, the "halogen" represents chlorine, fluorine, bromine, or iodine. The term "halo" represents chloro, fluoro, bromo, or iodo.

The term "haloalkyl" refers to an alkyl group as described above, wherein one or more hydrogen atoms on the alkyl group have been replaced by a halo group. Examples of such groups include, without limitation, fluoroalkyl groups, such as fluoroethyl, trifluoromethyl, difluoromethyl, trifluoroethyl and the like.

As used herein, the term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. It is understood that the selection and order of heteroatoms in a heteroaryl ring must conform to standard valence requirements and provide an aromatic ring character, and also must provide a ring that is sufficiently stable for use in the reactions described herein. Typically, a heteroaryl ring has 5-6 ring atoms and 1-4 heteroatoms, which are selected from N, O and S unless otherwise specified; and a bicyclic heteroaryl group contains two 5-6 membered rings that share one bond and contain at least one heteroatom and up to 5 heteroatoms selected from N, O and S as ring members. A heteroaryl group can be attached to the remainder of the molecule at an annular carbon or at an annular heteroatom, in which case the heteroatom is typically nitrogen. Heteroaryl groups may contain additional fused rings (e.g., from 1 to 3 rings), including additionally fused aryl, heteroaryl, cycloalkyl, and/or heterocyclyl rings. Examples of heteroaryl groups include, but are not limited to, pyrazolyl, imidazolyl, triazolyl, pyrrolyl, pyridyl, pyrimidyl, pyrazinyl, pyridazinyl, triazinyl, thiophenyl, furanyl, thiazolyl, and the like.

As used herein, the term "heterocycle", "heterocyclic", or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

The term "substituted" means that the specified group or moiety bears one or more substituents in place of a hydrogen atom of the unsubstituted group, including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents and thus includes both substituted and unsubstituted versions of the group. Where the term "substituted" is used to describe a structural system, the substitution is meant to occur at any valency-allowed position on the system.

Structures described or depicted herein may be capable of forming multiple tautomers, as is well understood in the art. The particular tautomer or tautomers present often depend on solvent, pH, and other environmental factors as well as the structure itself. An example of tautomerism is shown here, where at least three different tautomers could be drawn to represent one compound:

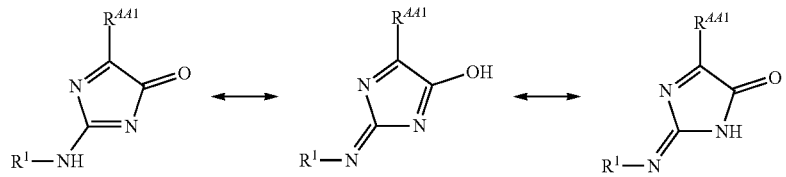

Where a compound can exist in more than one tautomeric form, typically one tautomer is depicted or described, and the structure is understood to represent each stable tautomer as well as mixtures of the tautomers. In particular, guanidine groups and heteroaryl groups substituted by hydroxyl or amine groups are often able to exist in multiple tautomers, and the description or depiction of one tautomer is understood to include the other tautomers of the same compound.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

I. Modified Cleavase

Provided herein is a modified cleavase comprising a mutation, e.g., one or more amino acid modification(s) in an unmodified cleavase, wherein the modified cleavase is derived from a dipeptide cleavase and removes or is configured to remove a single labeled terminal amino acid from a polypeptide. Provided herein is a modified cleavase comprising a mutation, e.g., one or more amino acid modification(s) in an unmodified cleavase, wherein the modified cleavase is derived from a tripeptide cleavase and removes or is configured to remove a single labeled terminal amino acid from a polypeptide or a single labeled terminal dipeptide from a polypeptide. In some embodiments, the modified cleavase is configured to remove a single labeled terminal amino acid from the C-terminus or N-terminus of a polypeptide. In some embodiments, the modified cleavase is configured to remove a single labeled dipeptide (the terminal and penultimate terminal amino acids) from the C-terminus or N-terminus of a polypeptide. In some embodiments, the modified cleavase is derived from a wild-type or unmodified cleavase (e.g., a dipeptide cleavase or tripeptide cleavase). In some cases, the terminal labeled amino acid residue is an N-terminal amino acid. In some embodiments, the terminal labeled amino acid residue is a C-terminal amino acid. In some embodiments, the removed labeled terminal amino acid is removed as a single amino acid or as part of a dipeptide.

In some aspects, a labeled amino acid is a terminal amino acid that is modified by treating with a chemical reagent. In some specific examples, the removed single labeled terminal amino acid or single labeled terminal dipeptide comprises an amide bond. In some aspects, the modified cleavase comprises an active site that interacts with the amide bond (e.g., amide bond between the terminal labeled amino acid residue and a penultimate terminal amino acid residue of the polypeptide). In some embodiments, the mutation is or comprises an amino acid substitution, deletion, addition, or any combinations thereof.

In some embodiments, the modified cleavase exhibits activity that is different from the activity of the unmodified or wild-type cleavase. "Unmodified cleavase" or "wild-type cleavase" as used herein refers to any natural or wild-type exopeptidase that possesses catalytic activity to remove a dipeptide or tripeptide from the terminus of a polypeptide (e.g., from the C-terminus or N-terminus of a polypeptide). The unmodified or wild-type cleavase may be an exopeptidase that catalyzes the cleavage of a penultimate peptide bond to release a dipeptide from the peptide chain or that catalyzes the cleavage of an antepenultimate peptide bond to release a tripeptide from the peptide chain. The unmodified or wild-type cleavase may be a proteolytic enzyme such as an aminopeptidase or a carboxypeptidase. The unmodified cleavase described herein may be used to refer to a protein classified by the Enzyme Commission (EC) as EC 3.4.14, EC 3.4.15, MEROPS S8, MEROPS S9, MEROPS S33, MEROPS S46, MEROPS M49, or MEROPS S53, or a functional homolog or fragment thereof. The unmodified cleavase described herein may be used to refer to a dipeptidyl peptidase, a dipeptidyl aminopeptidase, a peptidyl-dipeptidase, a dipeptidyl carboxypeptidase, a sedolisin, or a tripeptidyl peptidase.

A "modified cleavase" or "variant cleavase" refers to any exopeptidase that has been modified from a unmodified or wild-type cleavase as described. The modified or variant cleavase may be derived from an unmodified or wild-type dipeptide cleavase (e.g. a dipeptidyl peptidase, a dipeptidyl aminopeptidase, a peptidyl-dipeptidase, a dipeptidyl carboxypeptidase) or from a unmodified or wild-type tripeptide cleavase (e.g. a sedolisin, or a tripeptidyl peptidase). As compared to an unmodified or wild-type dipeptide cleavase which removes the P1-P2 terminal amino acids from a peptide as a dipeptide at a time, a modified cleavase derived from a dipeptide cleavase removes only a labeled P1 terminal amino acid from the peptide at a time. As compared to an unmodified or wild-type tripeptide cleavase which removes the P1-P2-P3 terminal amino acids from a peptide as a tripeptide at a time, a modified cleavase derived from a tripeptide cleavase removes a labeled P1 terminal amino acid from the peptide at a time or a labeled P1-P2 dipeptide from the peptide at a time, (see e.g., FIG. 1A-1B)

In some embodiments, the modified cleavase removes a labeled terminal amino acid, e.g., a labeled N-terminal amino acid (NTAA). In some cases, the modified cleavase removes a labeled C-terminal amino acid (CTAA). In some embodiments, the removed labeled terminal amino acid is removed as a single amino acid or as part of a dipeptide. In some embodiments, the modified cleavase derived from the dipeptide cleavase or tripeptide cleavase is configured to cleave the peptide bond between a terminal labeled amino acid residue and a penultimate terminal amino acid residue of the polypeptide. In some embodiments, the modified cleavase derived from the tripeptide cleavase is configured to cleave the peptide bond between a penultimate terminal labeled amino acid residue and a antepenultimate terminal amino acid residue of the polypeptide.

Information regarding various known unmodified or wild-type exopeptidases is available from databases such as MEROPS and/or the BRENDA enzyme information system (See e.g., Schomburg et al., J Biotechnol. (2017) 261:194-206). A protein may be classified using more than one classification system. The Enzyme Commission (EC) sets forth a numbering system for the classification of enzyme based upon specificity using recommendations from Nomenclature Committee of the International Union of Biochemistry and Molecular Biology (IUBMB) for describing each type of characterized enzyme for which an EC (Enzyme Commission) number has been provided (See e.g., Bairoch A., (2000) Nucleic Acids Res. 28:304-305). In some aspects, the unmodified or wild-type cleavase is a protein classified in EC 3.4.14, EC 3.4.15, MEROPS S8, MEROPS S9, MEROPS S33, MEROPS S46, MEROPS M49, or MEROPS S53, or a homolog thereof. In some aspects, the unmodified or wild-type cleavase is a protein provided in Tables 1, 2, 3, 4, 5, 6, 7, and 8A-8B. In some embodiments, the modified cleavase is derived from a protein classified EC 3.4.14, EC 3.4.15, MEROPS S8, MEROPS S9, MEROPS S33, MEROPS S46, MEROPS M49, or MEROPS S53, or a functional homolog or fragment thereof, (as provided in Tables 1, 2, 3, 4, 5, 6, 7, and 8A-8B)

TABLE 1

Exemplary Cleavases from EC 3.4.14

| Enzyme Commission Number | Name |
|---|---|
| 3.4.14.1 | dipeptidyl-peptidase I |
| 3.4.14.2 | dipeptidyl-peptidase II |
| 3.4.14.3 | acylamino-acid-releasing enzyme |
| 3.4.14.4 | dipeptidyl-peptidase III |
| 3.4.14.5 | dipeptidyl-peptidase IV |
| 3.4.14.6 | dipeptidyl-dipeptidase |
| 3.4.14.7 | tetralysine endopeptidase |
| 3.4.14.8 | tripeptidyl peptidase |
| 3.4.14.9 | tripeptidyl-peptidase I |
| 3.4.14.10 | tripeptidyl-peptidase II |
| 3.4.14.11 | Xaa-Pro dipeptidyl-peptidase |
| 3.4.14.12 | Xaa-Xaa-Pro tripeptidyl-peptidase |
| 3.4.14.13 | gamma-D-glutamyl-L-lysine dipeptidyl-peptidase |

TABLE 2

Exemplary Cleavases from EC 3.4.15

| Enzyme Commission Number | Name |
|---|---|
| 3.4.15.1 | peptidyl-dipeptidase A |
| 3.4.15.2 | pepdidyl carboxyamidase |
| 3.4.15.3 | dipeptidyl carboxypeptidase |
| 3.4.15.4 | peptidyl-dipeptidase B |
| 3.4.15.5 | peptidyl-dipeptidase Dcp |
| 3.4.15.6 | cyanophycinase |

TABLE 3

Exemplary Cleavases from MEROPS S8

| MEROPS ID | Name |
|---|---|
| S08.090 | tripeptidyl-peptidase/tripeptidyl-peptidase II |
| S08.091 | tripeptidyl-peptidase S |

TABLE 4

Exemplary Cleavases from MEROPS S9

| MEROPS ID | Name |
|---|---|
| S09.003 | dipeptidyl-peptidase IV (eukaryote) |
| S09.009 | dipeptidyl-peptidase 4 (bacteria-type 1) |
| S09.012 | dipeptidyl-peptidase V/dipeptidyl-peptidase 5 |
| S09.013 | dipeptidyl-peptidase 4 (bacteria-type 2) |
| S09.017 | prolyl tripeptidyl peptidase |
| S09.018 | dipeptidyl-peptidase 8 |
| S09.019 | dipeptidyl-peptidase 9 |
| S09.056 | dipeptidyl-peptidase IV, membrane-type (protistan) |
| S09.075 | dipeptidyl-peptidase 5 (*Porphyromonas* sp.) |
| Unassigned | subfamily S9B unassigned peptidases |

TABLE 5

Exemplary Cleavases from MEROPS S33

| MEROPS ID | Name |
|---|---|
| S33.002 | tripeptidyl-peptidase A |
| S33.006 | tripeptidyl-peptidase B |
| S33.007 | tripeptidyl-peptidase C |

TABLE 6

Exemplary Cleavases from MEROPS S46

| MEROPS ID | Name |
|---|---|
| S46.001 | dipeptidyl-peptidase 7 |
| S46.002 | dipeptidyl-peptidase 11 |
| S46.003 | dipeptidyl-peptidase BII |
| S46.004 | BF9343_2924 g.p. |

TABLE 7

Exemplary Cleavases from MEROPS M49

| MEROPS ID | Name |
|---|---|
| M49.001 | dipeptidyl-peptidase III |
| M49.003 | dipeptidyl-peptidase IIIB (*Bacteroides thetaiotaomicron*-type) |
| M49.004 | dipeptidyl-peptidase III (*Saccharomyces*-type) |

TABLE 8A

Exemplary Cleavases from MEROPS S53

| MEROPS ID | Name |
|---|---|
| S53.001 | sedolisin |
| S53.002 | sedolisin-B |
| S53.003 | tripeptidyl-peptidase/tripeptidyl-peptidase 1/tripeptidyl-peptidase I |
| S53.004 | kumamolisin |
| S53.005 | kumamolisin-B |
| S53.006 | physarolisin |
| S53.007 | aorsin |
| S53.008 | physarolisin II |
| S53.009 | kumamolisin-As |
| S53.010 | grifolisin |
| S53.011 | scytalidolisin |
| S53.A01 | DDB_G0287357 g.p. |
| S53.A02 | V4-7 g.p. |

TABLE 8B

Other Exemplary Cleavases

| MEROPS ID | Name |
|---|---|
| C01.070 | dipeptidyl-peptidase I |
| S28.002 | dipeptidyl-peptidase II |
| S15.001 | Xaa-Pro dipeptidyl-peptidase |
| S9G.084 | dipeptidyl-peptidase IV beta |

Various peptidases (e.g., cleavases) that sequentially cleave off dipeptides or tripeptides from unsubstituted N-terminals of oligopeptides have been identified. Some peptidases cleave dipeptides from a range of tripeptides to decapeptides. Cleavases as described herein refer to enzymes that are classified under the Enzyme Commission (EC) Class 3 of hydrolases. Dipeptidyl peptidases and tripeptidyl peptidases (DPPs and TPPs, respectively, from Enzyme Commission number 3.4.14; Table 1) are a class of exopeptidases which digest dipeptides (two amino acid residues, P1-P2) or tripeptides (three amino acid residues, P1-P2-P3) from the N-terminal end of a peptide, typically in a processive manner. Peptidyl dipeptidases also known as dipeptidyl carboxypeptidases (EC 3.4.15; Table 2) act from the C-terminal end in removing dipeptides in a processive manner. In some embodiments, the unmodified or wild-type cleavase is an exoaminopeptidase or an exopeptidase. In some aspects, the unmodified or wild-type cleavase is a metallopeptidase, e.g., a zinc-dependent metallopeptidase or a zinc-dependent hydrolase. In some aspects, the unmodified or wild-type cleavase is a serine exopeptidase or a serine protease. DPPs typically recognize the N-terminal alpha amine, and cleave the peptide bond between the penultimate and antepenultimate amino acid residues of a polypeptide (P2-P3). See e.g., Sanderink et al., J. Clin. Chem. Clin. Biochem. (1988) 26:795-807) and Baral et al., J Biol Chem (2008) 283(32): 22316-22324. Various peptidases that remove tripeptides from the terminus of a polypeptide (e.g., TPPs) have also been identified. For example, Tripeptidyl Peptidases A, B, and C are classified in the MEROPS family S33 (MEROPS S33.002, S33.006, S33.007). Sedolisins, also known as serine-carboxyl peptidases, are proteolytic enzymes MEROPS family of peptidases, S53 (See e.g., Wlodawer et al., Acta Biochim Pol. 2003; 50(1):81-102).

In some embodiments, the modified cleavase exhibits activity including the removal of a terminal amino acid from polypeptides or proteins (e.g., from the N-terminus or C-terminus). The terminal amino acid may be removed from the polypeptide as a single amino acid or as part of a dipeptide. In a general manner, the peptidase activity is capable of removing the amino acid $Xaa_1$ and/or $Xaa_2$ from the terminus of a peptide, polypeptide, or protein, wherein Xaa may represent any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val. It will be understood that the modified cleavase of the present disclosure may be unspecific as to the amino acid sequence of the peptide, polypeptide, or protein to be cleaved. In some embodiments, the modified cleavase is partially specific or selective. In some aspects, the modified cleavase preferentially cleaves or removes some amino acids at the P1 or P2 position of the peptide over others. In some cases, the modified cleavase preferentially cleaves or removes a class of amino acids over others, e.g., preferentially removing hydrophobic amino acids over other classes of amino acids. In some aspects, the modified cleavase may also have a preference for one or more amino acids at the second, third, fourth, fifth, etc. positions from the terminal amino acid. In some cases, the modified cleavase exhibits specificity to subsets of amino acids and preferentially removes 1, 2, 3, 4, 5, 6, 7, 8, 9, 10, 15 or more specific terminal amino acid over others.

In some embodiments, the modified cleavase is a polypeptide having an altered amino acid sequence, relative to an unmodified or wild-type cleavase. In some cases, the modified cleavase is a polypeptide which differs from a wild-type cleavase sequence by one or more amino acid substitutions, deletions, additions, or combinations thereof. A variant or modified cleavase can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more modifications or mutations, e.g., amino acid differences, compared to the wild-type cleavase.

In some embodiments, the variant or modified cleavase polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified cleavase. In some embodiments, the wild-type or unmodified cleavase comprises the amino acid sequence of any one of SEQ ID NO: 5-8, 10-16, 20, a mature sequence thereof, or a portion thereof containing the active site. In some embodiments, the variant or modified cleavase polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a wild-type or unmodified cleavase set forth in SEQ ID NOs: 5-8, 10-16, 20, or a homolog thereof.

It is within the level of a skilled artisan to identify the corresponding position of a mutation or modification, e.g., amino acid substitution, in a cleavase polypeptide, including a portion thereof, such as by alignment with a reference sequence. In some embodiments, the unmodified or reference cleavase polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to any of the sequences set forth in SEQ ID NOs: 5-8 and 10-16, 20. For example, corresponding residues can be determined by alignment of a reference sequence with a sequence provided herein (for example, sequences set forth in SEQ ID NOs: 5-8, 10-16, 20, or a functional homolog or fragment thereof) using known alignment methods. By aligning the sequences, one skilled in the art can identify corresponding residues, for example, using conserved and identical amino acid residues as guides. In some cases, while the numbering of the residues provided herein may differ from a reference sequence, using the alignment method will allow determination of corresponding residues.

In some embodiments, the modified cleavase comprises a mutation, e.g., one or more amino acid modification(s), in an unmodified cleavase, wherein the unmodified cleavase is a dipeptidyl peptidase 3. Dipeptidyl peptidase 3 (also known as dipeptidyl peptidase III, dipeptidyl aminopeptidase III, dipeptidyl arylamidase III, enkephalinase B, red cell angiotensinase, DPP3, or DPP III) is a metalloproteinase (zinc-dependent) that sequentially removes dipeptides (two amino acid residues) from the N-terminus of short peptides. Wild-type or unmodified DPP3 is classified in the M49 family (MEROPS database identifier M49.001). In some cases, the unmodified dipeptidyl peptidase 3 exhibits at least 50%, 60%, 70%, 80%, 85%, 86%, 87%, 88%, 89%, 90%, 91%, 92%, 93%, 94%, 95%, 96%, 97%, 98%, 99% or more sequence identity to UniProt Accession No. Q9NY33 as set forth in SEQ ID NO: 5, UniProt Accession No. Q08225 as set forth in SEQ ID NO: 6, UniProt Accession No. Q8A6N1 as set forth in SEQ ID NO: 7, UniProt Accession No. H1XW48 as set forth in SEQ ID NO: 8, or UniProt Accession No. O55096 as set forth in SEQ ID NO: 15. See e.g., Prajapati et al., FEBS J. 2011; 278(18):3256-276; Fukasawa et al., Biochem J. 1998 Jan. 15; 329(Pt2): 275-282; Fukasawa et al., J Amino Acids. 2011; 2011: 574816). DPP3 preferentially digests peptides that are 3 to 10 amino acids in length. DPP3 harbors a unique HEXXGH catalytic motif (SEQ ID NO: 1). Both histidines in this motif along with the glutamate residue of a second conserved EEXRAE/D motif are involved in zinc coordination (SEQ ID NO: 2). In some cases, C-terminal peptide modifications do not affect the activity of DPP3 enzymes. See Kumar et al., Sci Rep. (2016) 6:23787. Several substrate-bound structures of DPP3 have been solved, including in complex with peptides that have an N-terminal tyrosine. An N-terminal tyrosine is structurally similar to a phenylisothiocyanate (PITC), nitro-PITC, sulfo-PITC, or a phenylisocyanate version of these modifiers, and these substrate-bound structures may be useful for a targeted active-site design approach. In some embodiments, provided is a modified cleavase derived from a dipeptidyl peptidase 3 that cleaves labeled terminal amino acid residues, e.g., labeled N-terminal amino acid residues.

In some embodiments, the modified cleavase comprises a mutation, e.g., one or more amino acid modification(s), in an unmodified cleavase, wherein the unmodified cleavase is a dipeptidyl peptidase 5. Dipeptidyl peptidase 5 is also known as allergen Tri m 4 (*Trichophyton mentagrophytes*), allergen Tri r 4 (*Trichophyton rubrum*), allergen Tri 14 (*Trichophyton tonsurans*), dipeptidyl-peptidase V, DPP V, and secreted alanyl dipeptidyl peptidase (*Aspergillus oryzae*). Wild-type or unmodified dipeptidyl peptidase 5 is classified in the peptidase family S9 (MEROPS database identifier S09.012). Wild-type or unmodified dipeptidyl peptidase 5 has been observed to catalyze the hydrolysis of X-Ala, His-Ser, and Ser-Tyr dipeptides at a neutral pH optimum (See e.g., Beauvais et al., J Biol Chem. 1997; 272(10):6238-44). Wild-type or unmodified dipeptidyl peptidase 5 is described as a secreted dipeptidyl peptidase which contains the consensus sequences of the catalytic site of the nonclassical serine proteases. In some cases, the unmodified cleavase exhibits at least 50%, 60%, 70%, 80%, 85%, 86%, 87%, 88%, 89%, 90%, 91%, 92%, 93%, 94%, 95%, 96%, 97%, 98%, 99% or more sequence identity to UniProt Accession No. P0C959 as set forth in SEQ ID NO: 10 or UniProt Accession No. B2RIT0 as set forth in SEQ ID NO: 16. In some embodiments, the mutations, e.g., one or more amino acid modifications (e.g., substitutions, deletions, additions) in the modified cleavase is in reference to the amino acid sequence set forth in reference to numbering of SEQ ID NO: 10 or 16.

In some embodiments, the modified cleavase comprises a mutation, e.g., one or more amino acid modification(s), in an unmodified cleavase, wherein the unmodified cleavase is a dipeptidyl peptidase 7 (DPP7). Wild-type or unmodified DPP7 is classified in S46 protease family (MEROPS database identifier S46.001). Wild-type or unmodified DPP7 has been observed to catalyze the removal of dipeptides from the N-terminus of oligopeptides, including a broad specificity for both aliphatic and aromatic residues in the P1 position, with glycine or proline being not acceptable in this position (See e.g., Banbula et al., J. Biol. Chem. 2001, 276:6299-6305). DPP7 has been shown to exhibit activity for cleaving the synthetic substrates Met-Leu-methylcoumaryl-7-amide (Met-Leu-MCA), Leu-Arg-MCA, and Lys-Ala-MCA (Rouf et al., FEBS Open Bio. 2013; 3:177-83). In some cases, the unmodified cleavase exhibits at least 50%, 60%, 70%, 80%, 85%, 86%, 87%, 88%, 89%, 90%, 91%, 92%, 93%, 94%, 95%, 96%, 97%, 98%, 99% or more sequence identity to UniProt Accession No. B2RKV3 as set forth in SEQ ID NO: 11. In some embodiments, the mutations, e.g., one or more amino acid modification(s) (e.g., substitutions, deletions, additions) in the modified cleavase is in reference to the amino acid sequence set forth in reference to numbering of SEQ ID NO: 11.

In some embodiments, the modified cleavase comprises a mutation, e.g., one or more amino acid modification(s), in an unmodified cleavase, wherein the unmodified cleavase is a dipeptidyl peptidase 11. Dipeptidyl peptidase 11 is also known as Asp/Glu-specific dipeptidyl-peptidase or DPP11. Wild-type or unmodified dipeptidyl peptidase 11 is classified in S46 protease family (MEROPS database identifier S46.002), and shares 38.7% sequence identity with dipeptidyl peptidase 7. Wild-type or unmodified dipeptidyl peptidase 11 has been observed to catalyze the removal of dipeptides from the N-terminus of oligopeptides, including removing dipeptides from oligopeptides with the penultimate N-terminal Asp and Glu and has a P2-position preference to hydrophobic residues (See e.g., Ohara-Nemoto et al., J Biol Chem. 2011; 286(44):38115-27). In some cases, the unmodified cleavase exhibits at least 50%, 60%, 70%, 80%, 85%, 86%, 87%, 88%, 89%, 90%, 91%, 92%, 93%, 94%, 95%, 96%, 97%, 98%, 99% or more sequence identity to UniProt Accession No. B2RID1 or F8WQK8 as set forth in SEQ ID NO: 12 and 14, respectively. In some embodiments, the mutations, e.g., one or more amino acid modifications (e.g., substitutions, deletions, additions) in the modified cleavase is in reference to the amino acid sequence set forth in reference to numbering of SEQ ID NO: 12. In some embodiments, the mutations, e.g., one or more amino acid modifications (e.g., substitutions, deletions, additions) in the modified cleavase is in reference to the amino acid sequence set forth in reference to numbering of SEQ ID NO: 14.

In some embodiments, the modified cleavase comprises a mutation, e.g., one or more amino acid modification(s), in an unmodified cleavase, wherein the unmodified cleavase is a dipeptidyl aminopeptidase BII (DAP BII or dipeptidyl peptidase BII). Wild-type or unmodified DAP BII catalyzes the removal of dipeptides from the amino terminus of peptides (See e.g., Ogasawara et al., J. Bacteriol. 1996, 178:6288-6295); Sakamoto et al., Scientific Reports 2014, 4:4977). DAP BII is a serine protease that belongs to the serine peptidase family S46 (MEROPS database identifier S46.003). The amino acid sequence of the catalytic unit of DAP BII exhibits significant similarity to those classified in the clan PA endopeptidases. In some cases, the unmodified cleavase exhibits at least 50%, 60%, 70%, 80%, 85%, 86%, 87%, 88%, 89%, 90%, 91%, 92%, 93%, 94%, 95%, 96%, 97%, 98%, 99% or more sequence identity to UniProt Accession No. V5YM14 as set forth in SEQ ID NO: 13. In some embodiments, the modified cleavase contains one or more amino acids modifications in the catalytic domain of an unmodified DAP BII (e.g., residues 1-252 and residues 550 to 698 of SEQ ID NO: 13). In some embodiments, the mutations, e.g., one or more amino acid modifications (e.g., substitutions, deletions, additions) in the modified cleavase is in reference to the amino acid sequence set forth in reference to numbering of SEQ ID NO: 13. It has been shown that the unmodified or wild-type DAP BII hydrolyses peptides from the N-terminus of oligopeptides and small proteins, cleaving dipeptide units (NH2-P2-P1-) when the second (P1) residue is Ala, Leu, lie, Phe, Tyr, Arg, or His (but not Pro) (See e.g., Sakamoto et al., Scientific Reports 2014, 4:4977).

In some embodiments, the modified cleavase is derived from DAP BII and removes or is configured to remove a labeled terminal single amino acid from a polypeptide. In some embodiments, the modified cleavase has one or more amino acid modifications (e.g. substitutions, deletions, additions, or combinations thereof) in an unmodified DAP BII cleavase or fragment thereof corresponding to any one or more of position(s) 126, 188, 189, 190, 191, 192, 196, 238, 302, 306, 307, 310, 525, 528, 546, 604, 650, 651, 665, and/or 692, with reference to numbering of SEQ ID NO: 13. In some embodiments, the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 665, and/or 692, with reference to numbering of SEQ ID NO: 13, and comprises an amino acid sequence that exhibits at least 30% identity, at least 40% identity, at least 50% identity, at least 60% identity, at least 70% identity, at least 80% identity, or at least 90% or more identity to any of SEQ ID NOs: 17-19, 23-28, or 31-39.

In some embodiments, the modified cleavase has one or more amino acid modifications (e.g. substitutions, deletions, additions, or combinations thereof) in an unmodified DAP BII cleavase or fragment thereof corresponding to any one or more of position(s) 183, 184, 185, 186, 187, 188, 189, 190, 191, 192, 193, 194, 195, 196, 197, 198, 199, 200, 201, and/or 202, with reference to numbering of SEQ ID NO: 13. In some embodiments, the modified cleavase has one or more amino acid modifications (e.g. substitutions, deletions, additions, or combinations thereof) in an unmodified DAP BII cleavase or fragment thereof corresponding to any one or more of position(s) 188, 189, 190, 191, 192, 302, and/or 310, with reference to numbering of SEQ ID NO: 13. In some embodiments, the modified cleavase has one or more amino acid modifications (e.g. substitutions, deletions, additions, or combinations thereof) in an unmodified DAP BII cleavase or fragment thereof corresponding to any one or more of position(s) 191, 192, 196, 306, and/or 650, with reference to numbering of SEQ ID NO: 13. In some embodiments, the modified cleavase has one or more amino acid modifications (e.g. substitutions, deletions, additions, or combinations thereof) in an unmodified DAP BII cleavase or fragment thereof corresponding to any one or more of position(s) 323-544 with reference to numbering of SEQ ID NO: 13. In some embodiments, the modified cleavase has one or more amino acid modifications (e.g. substitutions, deletions, additions, or combinations thereof) in an unmodified DAP BII cleavase or fragment thereof corresponding to any one or more of position(s) 310, 651, 655, and/or 656 with reference to numbering of SEQ ID NO: 13. In some embodiments, the modified cleavase has one or more amino acid modifications (e.g. substitutions, deletions, additions, or combinations thereof) in an unmodified DAP BII cleavase or fragment thereof corresponding to any one or more of position(s) 627, 628, 630, 648, 651, 655, and/or 669, with reference to numbering of SEQ ID NO: 13.

In some embodiments, the modified dipeptide cleavase comprises an amino acid sequence having at least 30% sequence identity to the amino acid sequence of SEQ ID NO: 13 and also comprising an asparagine residue at a position corresponding to position 191 of SEQ ID NO: 13, a tryptophan residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, an aspartate residue at a position corresponding to position 650 of SEQ ID NO: 13; and wherein the modified dipeptide cleavase comprises one or more amino acid modifications in residues corresponding to positions 191, 192, 196, 306, 650 of SEQ ID NO: 13.

In some embodiments, the modified dipeptide cleavase comprises one or more amino acid modifications in residues corresponding to positions 191, 192, 196, 306, 650 of SEQ ID NO: 13 and the modifications being selected from the group consisting of: N191C, N191F, N191L, N191M, N191R, N191S, N191T, N191V, W192F, W192G, W192L, R196H, R196K, R196S, R196T, R196V, N306A, N306G, N306R, N306S, D650A, D650G and D650S.

In some embodiments, the unmodified dipeptide cleavase comprises an amino acid sequence having at least 30% sequence identity to the amino acid sequence of SEQ ID NO: 43 and also comprising an asparagine residue at a position corresponding to position 214 of SEQ ID NO: 43, a tryptophan residue at a position corresponding to position 215 of SEQ ID NO: 43, an arginine residue at a position corresponding to position 219 of SEQ ID NO: 43, an asparagine residue at a position corresponding to position 329 of SEQ ID NO: 43, an aspartate residue at a position corresponding to position 673 of SEQ ID NO: 43; and wherein the modified dipeptide cleavase comprises one or more amino acid modifications in residues corresponding to positions 214, 215, 219, 329, 673 of SEQ ID NO: 43.

In some embodiments, the modified cleavase is derived from DAP BII and removes or is configured to remove a labeled terminal single amino acid from a polypeptide. In some embodiments, the modified cleavase has one or more amino acid modifications (e.g. substitutions, deletions, additions, or combinations thereof) in an unmodified DAP BII cleavase or fragment thereof corresponding to any one or more of position(s) 126, 183, 184, 185, 186, 187, 188, 189, 190, 191, 192, 193, 194, 195, 196, 197, 198, 199, 200, 201, 202, 238, 302, 306, 307, 310, 525, 528, 546, 604, 627, 628, 630, 648, 650, 651, 655, 656, 665, 669, and/or 692, with reference to numbering of SEQ ID NO: 13.

In some embodiments, the modified cleavase has one or more amino acid substitutions selected from the group consisting of A126T, D188V, I189A, D190S, N191C, N191F, N191L, N191M, N191R, N191S, N191T, N191V, W192F, W192G, W192L, R196H, R196K, R196S, R196T, R196V, G238V, A302W, N306A, N306G, N306R, N306S, T307K, N310D, N310G, N310K, N310L, N525K, A528V, F546L, A604V, D650A, D650G, D650S, G651H, G651T, G651V, G651Y, S655G, S655T, V656E, V656G, V656S, K665I, and K692N, with reference to numbering of SEQ ID NO: 13, or a conservative amino acid substitution thereof. In some embodiments, the one or more amino acid modification is N191M/W192G/R196V/N306R/D650A, D188V/I189A/D190S/N191L/W192G/R196S/A302W/N310K/D650A, N191M/W192G/R196T/N306R/T307K/D650A, N191M/W192G/R196T/N306R/N525K/A528V/A604V/D650A/K692N, A126T/N191M/W192G/R196T/G238V/N306R/D650A, N191M/W192G/R196T/N306R/F546L/D650A, N191M/W192G/R196T/N306R/D650A/G651V/K665I, N191M/W192G/R196T/N306R/D650A/G651V, N191C/W192L/R196K/N306R/N310D/G651Y/S655G/V656G, N191C/W192L/N306R/N310D/G651Y/S655G/V656G, N191F/W192F/N306R/N310G/G651H/V656E, N191R/W192L/N306S/N310L/G651T/S655T/V656S, N191S/R196H/N306A/D650G, N191T/R196H/N306A/D650G, N191M/R196H/N306A/D650G, N191V/N306A/D650S, or N191S/N306G/D650S.

In some embodiments, the modified cleavase has an amino acid sequence that has at least 20% identity, at least 30% identity, at least 40% identity, at least 50% identity, at least 60% identity, at least 70% identity, at least 80% identity, or at least 90% or more identity to any of SEQ ID NOs: 17-19, 23-28, 31-39 or a specific binding fragment thereof. In some embodiments, the specific binding fragment has a length ranging from about 10 amino acids to about 400 amino acids, from about 10 amino acids to about 300 amino acids, from about 10 amino acids to about 200 amino acids, from about 10 amino acids to about 100 amino acids, or from about 10 amino acids to about 50 amino acids. In some examples, the modified cleavase contains one or more of the amino acid substitutions provided in SEQ ID NO: 17-19, 23-28, or 31-39. In some specific examples, the modified cleavase comprises the sequence of amino acids set forth in any of SEQ ID NO: 17-19, 23-28, 31-39, or a sequence of amino acids that exhibits at least 95% sequence identity to any of SEQ ID NOs: 17-19, 23-28, 31-39, or a specific binding fragment thereof. In some aspects, the modified cleavase comprises one or more amino acid modifications in an unmodified cleavase, corresponding to position(s) 188, 189, 190, 191, 192, 196, 302, 306, 310, and/or 650, with reference to numbering of SEQ ID NO: 13, and has an amino acid sequence that has at least 30% identity, at least 40% identity, at least 50% identity, at least 60% identity, at least 70% identity, at least 80% identity, or at least 90% or more identity to any of SEQ ID NOs: 17-19, 23-28, 31-39. In some aspects, the modified cleavase comprises one or more amino acid modifications in an unmodified cleavase, corresponding to position(s) 191, 192, 196, 306, and/or 650, with reference to numbering of SEQ ID NO: 13, and has an amino acid sequence that has at least 30% identity, at least 40% identity, at least 50% identity, at least 60% identity, at least 70% identity, at least 80% identity, or at least 90% or more identity to any of SEQ ID NOs: 17-19, 23-28, or 31-39. In some embodiments, the modified cleavase has the substrate specificity of any one of the sequences in SEQ ID NOs: 17-19, 23-28, or 31-39. In some embodiments, the modified cleavase has the cleaving activity of any one of the sequences in SEQ ID NOs: 17-19, 23-28, or 31-39.

In some embodiments, the modified cleavase has an amino acid sequence that comprises a catalytic domain with at least 20% identity, at least 30% identity, at least 40% identity, at least 50% identity, at least 60% identity, at least 70% identity, at least 80% identity, or at least 90% or more identity with the catalytic domain of any of SEQ ID NOs: 17-19, 23-28, or 31-39. In some embodiments, the modified cleavase has an amino acid sequence that comprises an amine binding site with at least 20% identity, at least 30% identity, at least 40% identity, at least 50% identity, at least 60% identity, at least 70% identity, at least 80% identity, or at least 90% or more identity with the amine binding site of any of SEQ ID NOs: 17-19, 23-28, or 31-39. In some embodiments, the modified cleavase has an amino acid sequence that comprises a loop domain with at least 20% identity, at least 30% identity, at least 40% identity, at least 50% identity, at least 60% identity, at least 70% identity, at least 80% identity, or at least 90% or more identity with the loop domain of any of SEQ ID NOs: 17-19, 23-28, or 31-39.

In some specific examples, a desired modified cleavase may exhibit reduced bias towards specific amino acids in the P1 or P2 position of the polypeptide. In some embodiments, such modified cleavases may be obtained by targeting the P1 or P1 pocket of the wildtype or unmodified enzyme in genetic selection. In some cases, the residues N310, G651, S655, and/or V656 with reference to numbering of SEQ ID NO: 13 may be targeted to reduce bias. In some cases, the residues N215, W216, R220, N330, and/or D674 with reference to numbering of SEQ ID NO: 13 may be targeted to reduce bias.

Table 9 also provides exemplary sequences by reference to SEQ ID NO for exemplary modified cleavases. In some examples, the modified cleavase contains one or more of the amino acid substitutions provided in Table 9.

TABLE 9

Exemplary Modified Cleavases

| Mutation(s) | SEQ ID NO |
|---|---|
| D188V/I189A/D190S/N191L/W192G/R196S/A302W/N310K/D650A | 17 |
| N191M/W192G/R196T/N306R/D650A | 18 |
| N191M/W192G/R196V/N306R/D650A | 19 |

TABLE 9-continued

Exemplary Modified Cleavases

| Mutation(s) | SEQ ID NO |
|---|---|
| N191M/W192G/R196T/N306R/T307K/D650A | 23 |
| N191M/W192G/R196T/N306R/N525K/A528V/A604V/D650A/K692N | 24 |
| A126T/N191M/W192G/R196T/G238V/N306R/D650A | 25 |
| N191M/W192G/R196T/N306R/F546L/D650A | 26 |
| N191M/W192G/R196T/N306R/D650A/G651V/K665I | 27 |
| N191M/W192G/R196T/N306R/D650A/G651V | 28 |
| N191C/W192L/R196K/N306R/N310D/G651Y/S655G/V656G | 31 |
| N191C/W192L/N306R/N310D/G651Y/S655G/V656G | 32 |
| N191F/W192F/N306R/N310G/G651H/V656E | 33 |
| N191R/W192L/N306S/N310L/G651T/S655T/V656S | 34 |
| N191S/R196H/N306A/D650G | 35 |
| N191T/R196H/N306A/D650G | 36 |
| N191M/R196H/N306A/D650G | 37 |
| N191V/N306A/D650S | 38 |
| N191S/N306G/D650S | 39 |

In some embodiments, the removed amino acid is labeled or modified by a chemical reagent or enzymatic reagent. For example, the labeled amino acid is removed as a single terminal amino acid or as part of a dipeptide. In some embodiments, the label is or includes a modifier or label that "mimics" the size/shape of a terminal amino acid (e.g., an N-terminal amino acid). In some embodiments, the removed amino acid is labeled with an amino acid (e.g., an exogenous amino acid), a modified amino acid, a portion of an amino acid, a blocked or protected amino acid, or any combinations thereof. In some embodiments, the label attached to the terminal amino acid is an N-terminal blocked (devoid of alpha amine) amino acid. In some embodiments, selection of the appropriate label with an appropriately engineered or modified cleavase derived from a dipeptide cleavase enables removal of a single labeled terminal amino acid residue. In some embodiments, selection of the appropriate label with an appropriately engineered or modified cleavase derived from a tripeptide cleavase enables cleavage of a labeled terminal dipeptide. In some embodiments, the active site and/or amino acid binding site(s) of the unmodified cleavase is modified. In some embodiments, the modified cleavase comprises a modification or mutation within its substrate binding site, at the boundary of the substrate binding site, in the catalytic domain, in the P1 or P2 pocket, in a chymotrypsin fold, at an amine binding site, in the loop domain, or a combination thereof. For example, the present modified or engineered cleavase can comprise a modification within its substrate binding site. Substrate binding site of a cleavase is comprised of amino acid residues that are involved in interaction with the substrate during substrate recognition and cleavage. The specificity for the substrate is due to the favorable binding interaction of the substrate amino acid side chains with residues that form the substrate binding site of the cleavase (also called specificity pocket). For example, the binding site of dipeptidyl aminopeptidases comprises residues that are involved in interaction with the N-terminal amino group of a polypeptide (these residues form an amine binding site that is a part of the substrate binding site), and residues that are involved in interaction with P1 and P2 residues of the polypeptide. For modified dipeptidyl aminopeptidases, amino acid residues in the substrate binding site are modified to interact with the NTM of a labeled polypeptide, and also with P1 or P2 residues of the polypeptide. In some cases, amino acid residues in the substrate binding site of a modified dipeptidyl aminopeptidase are modified such that the modified dipeptidyl aminopeptidase would not recognize the N-terminal amino group of a polypeptide, and thus the modified dipeptidyl aminopeptidase would not cleave unlabeled (or non-labeled) polypeptide. The substrate binding site of a dipeptidyl cleavase can be determined for example using crystal structure of the dipeptidyl cleavase with its substrate or with an inhibitor, mimicking the substrate.

Figure 1B:
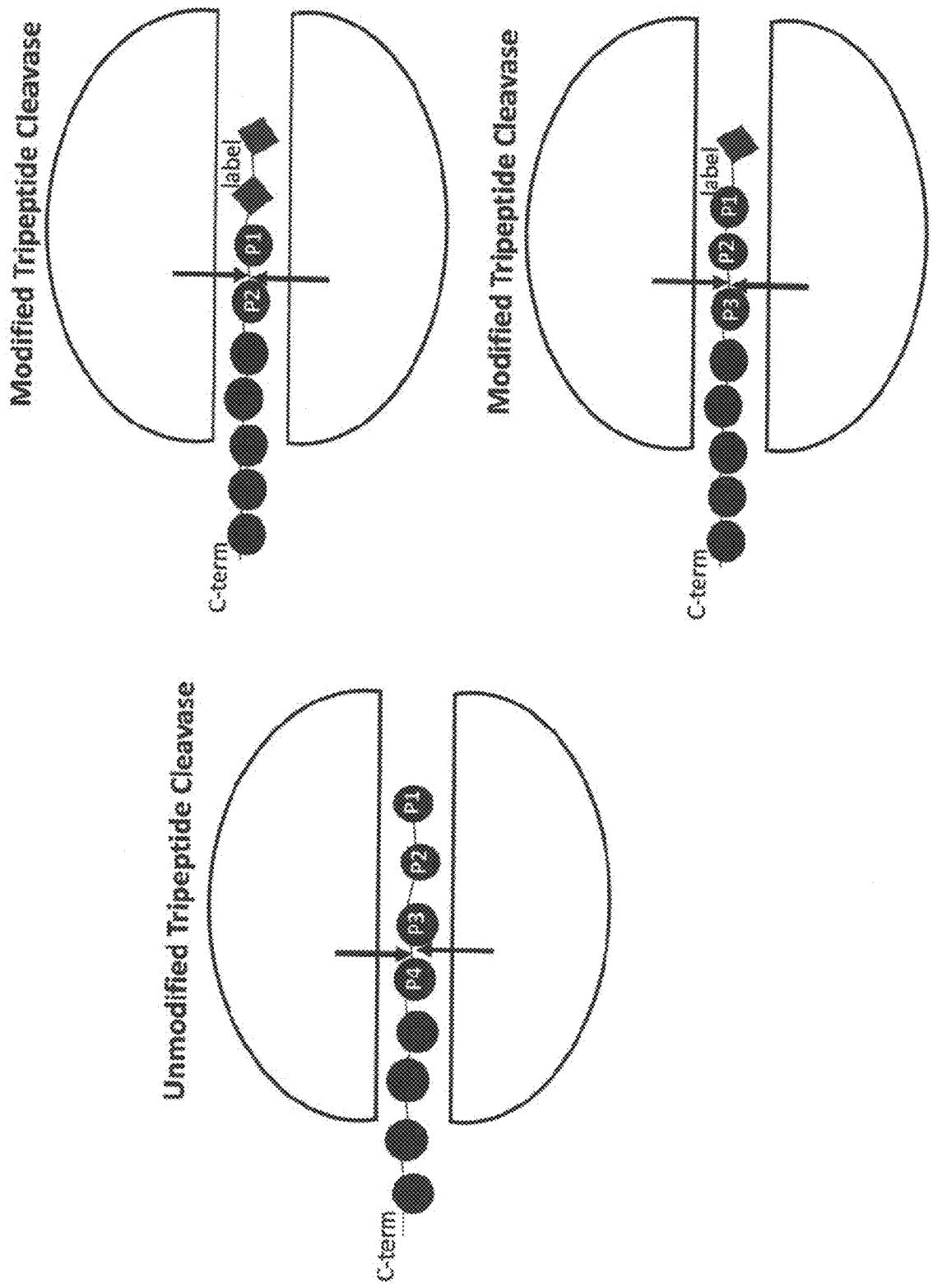

In some embodiments, within the active site, the label-P1 replaces the native P1-P2 residue of the peptide, such that cleavage in the modified cleavase then occurs between P1 and P2 (modified cleavase derived from a dipeptide cleavase) rather than between P2 and P3 (native dipeptide cleavase) (See e.g., FIG. 1A). In some embodiments, within the active site, the label-P1 replaces the native P1-P2-P3 residue of the peptide or portion thereof, such that cleavage in the modified cleavase then occurs between P1 and P2 (modified cleavase derived from a tripeptide cleavase) rather than between P3 and P4 (native tripeptide cleavase) (See e.g., FIG. 1B top right). In some embodiments, within the active site, the label-P1-P2 replaces the native P1-P2-P3 residue of the peptide or portion thereof, such that cleavage in the modified cleavase then occurs between P2 and P3 (modified cleavase derived from a tripeptide cleavase) rather than between P3 and P4 (native tripeptide cleavase) (See e.g., FIG. 1B bottom right). In some embodiments, the modified cleavase is derived from a dipeptide cleavase (e.g., a dipeptidyl peptidase, a dipeptidyl aminopeptidase, a peptidyl-dipeptidase, or a dipeptidyl carboxypeptidase) and one of the spaces of the unmodified cleavase that fits one residue of the dipeptide for removal is configured in the modified cleavase to fit a label instead (e.g. a chemical label or a chemical modification). In some embodiments, the modified cleavase is derived from a tripeptide cleavase (e.g., a sedolisin or a tripeptidyl peptidase) and one or two of the spaces of the unmodified cleavase that fits one or two residue(s) of the tripeptide for removal is configured in the modified cleavase to fit a label instead (e.g. a chemical label or a chemical modification).

In some embodiments, the modified cleavase comprises an amino acid mutation (e.g., modifications, substitutions, deletions, additions, or combinations thereof) compared to the wild-type cleavase polypeptide in the chymotrypsin fold of the cleavase. In some embodiments, the modified cleavase comprises an amino acid mutation (e.g, modifications, substitutions, deletions, additions, or combinations thereof) compared to the wild-type cleavase polypeptide in at an amine binding site. In some embodiments, the modified cleavase comprises an amino acid mutation (e.g., modifications, substitutions, deletions, additions, or combinations thereof) compared to the wild-type cleavase polypeptide in the loop domain. In some aspects, the modified cleavase comprises an amino acid mutation (e.g., modifications, substitutions, deletions, additions, or combinations thereof) compared to the wild-type cleavase polypeptide for improving accessibility to the active site of the modified cleavase. In some cases, the modified cleavase exhibits greater accessibility of the substrate (e.g., polypeptide) to the active site compared to the unmodified cleavase. For example, the modified cleavase may allow larger substrates to access the active site.

In some embodiments, the modified cleavase comprises an amino acid mutation (e.g., modifications, substitutions, deletions, additions, or combinations thereof) compared to the wild-type cleavase polypeptide in the active site or catalytic domain of the cleavase or the binding pockets of the cleavase. In some embodiments, the modified cleavase comprises an amino acid mutation (e.g., substitutions, deletions, additions, or combinations thereof) compared to the wild-type cleavase polypeptide in the hinge region of the cleavase. In some embodiments, the modified cleavase comprises an amino acid mutation compared to the wild-type cleavase polypeptide in the binding cleft of the cleavase. In some cases, the modified cleavase comprises an amino acid mutation compared to the wild-type cleavase polypeptide in the inter-lobe cleft of the cleavase. In some embodiments, the modified cleavase comprises an amino acid mutation compared to the wild-type cleavase polypeptide in the alpha amine binding region of the cleavase. For example, the modified cleavase exhibits reduced alpha amine binding compared to the wild-type cleavase polypeptide. See e.g., Kumar et al., Sci Rep. (2016) 6:23787.

In some embodiments, the modified cleavase exhibits altered activity, substrate binding capability, or cleavage characteristics compared to the unmodified cleavase. In some embodiments, the modified cleavase is modified in the catalytic motif or catalytic domain of the unmodified cleavase (e.g., the HEXXGH catalytic motif as set forth in SEQ ID NO: 1). In some embodiments, the mutations, e.g., one or more amino acid modifications (e.g., substitutions, deletions, additions) corresponds to position(s) 316, 391, or 394 with reference to numbering of SEQ ID NO: 5. In some embodiments, the mutations, e.g., one or more amino acid modifications (e.g., substitutions, deletions, additions) corresponds to position(s) amino acid residues 419, 420, 421, 422, 423, 424, 425, 426, or a combination thereof, with reference to numbering of SEQ ID NO: 5.

In some embodiments, the unmodified cleavase is a metallopeptidase. In some embodiments, the modified cleavase is a metallopeptidase. In some embodiments, the modified cleavase is a zinc-dependent metallopeptidase or a zinc-dependent hydrolase or derived from such. Some known metallopeptidase are characterized by the presence of a conventional catalytic signature motif HEXXH. In some aspects, the two His residues of the HEXXH motif contribute to coordinate the divalent metal ion (e.g., $Zn^{2+}$, $Mn^{2+}$, $Co^{2+}$, $Ni^{2+}$, $Cu^{2+}$). For example, the modified cleavase requires the presence of or contact with specific metal ions (e.g., zinc ions, chloride ions) for activation. In some embodiments, function of the modified cleavase can be modulated or controlled by the presence or absence of metal ions, or by contacting with metal chelating agents.

In some embodiments, the modified cleavase exhibits altered binding affinity and/or specificity to specific substrates compared to the unmodified cleavase. For example, the modified cleavase exhibits increased binding affinity and/or specificity for labeled terminal amino acids compared to the unmodified cleavase. In some embodiments, the modified cleavase exhibits decreased binding affinity and/or specificity for a substrate compared to the unmodified cleavase. In some embodiments, the modified cleavase exhibits one or more desired characteristics, such as binding rate, rate of hydrolysis, rate of release. In some embodiments, the modified cleavase can be removed or released from the polypeptide at a desired rate.

In some of any such embodiments, a reaction with a modified cleavase can be enhanced by recruiting the modified cleavase to the labeled terminal amino acid. For example, one or more modified cleavases can be recruited to the labeled terminal amino acid of the polypeptide via hybridization of complementary universal priming sequences a DNA tag or sequence associated with the modified cleavase and a DNA tag or sequence associated with the polypeptide to be treated with the modified cleavase (s). This hybridization step may improve the effective affinity of the modified cleavase for the labeled terminal amino acid (e.g., NTAA). In some cases, after the labeled terminal amino acid is removed, it may diffuse away, and the associated modified cleavase can be removed by stripping the hybridized DNA tag.

In some embodiments, the modified cleavase is attached to an anchoring sequence. In some cases, the modified cleavase is attached to the anchoring sequence directly or indirectly. In some cases, the anchoring sequence is complementary to a sequence attached to the polypeptides. In some embodiments, the anchoring sequence is a universal sequence or a universal DNA tag. In some embodiments, the polypeptide is also attached to a universal sequence. In some examples, the anchoring sequence on the modified cleavase brings the enzyme in proximity to the polypeptide. In some embodiments, the anchoring sequence brings the enzyme in proximity or co-localizes the modified cleavase to the polypeptide. In some embodiments, this co-localization of the modified cleavase and the polypeptide aids in binding and/or removal of the single labeled amino acid or dipeptide from said polypeptide.

In any of the embodiments provided herein, recruitment of one or more modified dipeptide cleavases to the terminal amino acid of the polypeptide may be enhanced by utilizing a chimeric modified dipeptide cleavase containing a first tethering moiety and a second tethering moiety associated with the polypeptide, or is colocalized with the polypeptide, wherein the first tethering moiety is configured to form a stable complex with the second tethering moiety upon contact (moieties are capable of a binding reaction with each other). For example, the polypeptide may be immobilized on a solid support, and the second tethering moiety is attached to the solid support in proximity to the polypeptide, or attached directly to the polypeptide. Examples of first and second tethering moieties include biotin-streptavidin pair, two complementary polynucleotide molecules that form a stable double strand complex upon contact, or other known molecules or binding pair in the art that can strongly interact upon contact under physiological conditions (or under conditions used in a cleavase assay). In one example, a modified cleavase may be a low affinity enzyme (>µM Kd) and it is recruited to labeled NTAA associated with a biotin using a streptavidin-chimeric modified cleavase. In some cases, the efficiency of modified cleavase to remove labeled terminal amino acid(s) can be improved due to the increase in effective local concentration as a result of the biotin-strepavidin interaction. In some cases, this approach effectively increases the affinity $K_D$ from µM to subpicomolar. A number of other bioconjugation recruitment strategies can also be employed. An azide modified PITC is commercially available (4-Azidophenyl isothiocyanate, Sigma), allowing a number of simple transformations of azide-PITC into other bioconjugates of PITC, such as biotin-PITC via a click chemistry reaction with alkyne-biotin. In some aspects, after the labeled terminal amino acid is removed, it may diffuse away with the associated modified cleavase from the polypeptide.

In some embodiments, the modified cleavase can be a single polypeptide chain or a multimer (dimers or higher order multimers) of at least two polypeptide chains. Thus, monomeric, dimeric, and higher order multimeric modified cleavase polypeptides are within the scope of the defined term. Multimeric polypeptides can be homomultimeric (of identical polypeptide chains) or heteromultimeric (of non-identical polypeptide chains). In some embodiments, the modified cleavase is a monomeric enzyme. In some embodiments, the modified cleavase is a fusion molecule or a chimeric molecule. For example, the modified cleavase may be attached or associated, directly or indirectly via a linker, to a oligonucleotide. In some specific cases, the modified cleavase may be joined to a moiety such as a SpyTag/SpyCatcher or SnoopTag/SnoopCatcher.

A. Labeled Terminal Amino Acid

In some embodiments, the terminal amino acid of a peptide removed by the modified cleavase is labeled or modified. A label can comprise any suitable material or moiety. Any suitable molecule or materials may be employed for this purpose, including proteins, amino acids, nucleic acids, carbohydrates, chemical moieties, and small molecules. In some embodiments, a suitable label is capable of fitting in the binding pocket of the modified cleavase. In some aspects, the labeling of a terminal amino acid is performed in a manner that is nucleic acid-compatible (e.g., the labeling is performed in a manner that is not damaging to nucleic acids). In some embodiments, a suitable label enables the modified cleavase to remove a single labeled terminal amino acid residue or dipeptide from the polypeptide. The terminal amino acid of the polypeptides may be labeled by any suitable methods. In some examples, the terminal amino acid is labeled chemically or enzymatically. In some embodiments, the terminal amino acid is labeled by a reagent that is or comprises a chemical agent, an enzyme, and/or a biological agent. In some cases, the terminal amino acid is labeled with a chemical label or moiety. In some examples, the terminal amino acid is labeled with a blocked or modified amino acid.

In some embodiments, a precursor polypeptide (e.g., an unlabeled polypeptide) is contacted with a reagent for labeling the terminal amino acid of the precursor polypeptide to provide a polypeptide prepared for treatment with the modified cleavase. In some cases, the contacting of the precursor polypeptide with the reagent for labeling the terminal amino acid is performed prior to contacting the polypeptide with a modified cleavase. In some aspects, the modified cleavase is contacted with a polypeptide that has been labeled or modified. In some cases, the contacting of the precursor polypeptide with the reagent for labeling the terminal amino acid and contacting the polypeptide with a modified cleavase are performed simultaneously or substantially simultaneously.

1. Chemical Labels

In some embodiments, the amino acid for removal by the modified cleavase is labeled with a chemical label. In some examples, the amino acid for removal by the modified cleavase is labeled with a chemical reagent. In some aspects, the labeling of a terminal amino acid by treating with a chemical reagent is performed in a manner that is nucleic acid-compatible (e.g., the labeling is performed under conditions that is not damaging to nucleic acids).

In some embodiments, the modified cleavase removes amino acid(s) that are labeled, such as a chemically-modified or labeled (e.g., PTC/DNP/acetyl/Cbz-modified or labeled) amino acids on a polypeptide. In some cases, the removed amino acid is a single labeled terminal amino acid. In some cases, the removed amino acid is part of a terminal dipeptide. In some embodiments, the modified cleavase (e.g. dipeptide cleavase) removes an N-terminal amino acid having a PTC/DNP/acetyl/Cbz group present as the label.

In some embodiments, the amino acid for removal by the modified cleavase, which may be the single terminal amino acid or the terminal amino acid of a dipeptide to be removed by the cleavase, is labeled with a reagent selected from the group consisting of a phenyl isothiocyanate (PITC), a nitro- PITC, a sulfo-PITC, a phenyl isocyanate (PIC), a nitro-PIC, a sulfo-PIC, benzyloxycarbonyl chloride or carbobenzoxy chloride (Cbz-Cl), N-(Benzyloxycarbonyloxy)succinimide (Cbz-OSu or Cbz-O-NHS), a carboxyl-activated amino-blocked amino acid (e.g. Cbz-amino acid-OSu), a 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), an anhydride, 2-Pyridinecarboxaldehyde, 2-Formylphenylboronic acid, 2-Acetylphenylboronic acid, 1-Fluoro-2,4-dinitrobenzene, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N'-Bis(pivaloyl)-1H-pyrazole-1-carboxamidine, N,N'-Bis(benzyloxycarbonyl)-1H-pyrazole-1-carboxamidine, an acetylating reagent, a guanidinylation reagent, a thioacylation reagent, a thioacetylation reagent, a thiobenzylation reagent, a diheterocyclic methanimine reagent, or a derivative thereof.

In some embodiments, the terminal amino acid for removal by the modified cleavase, which may be the terminal amine of a dipeptide to be removed by the cleavase, is labeled with an anhydride or derivative thereof. In some embodiments, the reagent for labeling the amino acid for removal by the modified cleavase is selected from the group consisting of: S-Acetylmercaptosuccinic anhydride, cis-Aconitic anhydride, 4-Amino-1,8-naphthalic anhydride, endo-Bicyclo[2.2.2]oct-5-ene-2,3-dicarboxylic anhydride, 5-Bromoisatoic anhydride, Bromomaleic anhydride, 4-Bromo-1,8-naphthalic anhydride, Citraconic anhydride, Crotonic anhydride, trans-1,2-Cyclohexanedicarboxylic anhydride, 1-Cyclopentene-1,2-dicarboxylic anhydride, 2,3-Dichloromaleic anhydride, 3,6-Dichlorophthalic anhydride, 3,6-Difluorophthalic anhydride, Diglycolic anhydride, 2,2-Dimethylglutaric anhydride, 3,3-Dimethylglutaric anhydride, 2,3-Dimethylmaleic anhydride, 2,2-Dimethylsuccinic anhydride, (2-Dodecen-1-yl)succinic anhydride, Dodecenylsuccinic anhydride, Glutaric anhydride, Hexafluoroglutaric anhydride, Hexahydro-4-methylphthalic anhydride, Homophthalic anhydride, 3-Hydroxyphthalic anhydride, Itaconic anhydride, Maleic anhydride, 3-Methylglutaric anhydride, N-Methylisatoic anhydride, Methylsuccinic anhydride, 1,8-Naphthalic anhydride, 3-Nitro-1,8-naphthalic anhydride, 4-Nitro-1,8-naphthalic anhydride, 3-Nitrophthalic anhydride, 4-Nitrophthalic anhydride, 2-Octen-1-ylsuccinic anhydride, 2,5-Oxazolidinedione, 2-Phenylglutaric anhydride, Phenylmaleic anhydride, Phenylsuccinic anhydride, N-Phthaloyl-DL-glutamic anhydride, 2,3-Pyrazinedicarboxylic anhydride, 3,4-Pyridinedicarboxylic anhydride, Succinic anhydride, 4-Sulfo-1,8-naphthalic anhydride, Tetrabromophthalic anhydride, Tetrachlorophthalic anhydride, Tetrafluorophthalic anhydride, 3,4,5,6-Tetrahydrophthalic anhydride, 3,3-Tetramethyleneglutaric anhydride, Trimellitic anhydride chloride, and 2-(Triphenylphosphoranylidene)succinic anhydride. See e.g. Staiger et al., J. Org. Chem. 1959, 24, 9, 1214-1219; Jiang et al. J. Org. Chem. 2019, 84, 4, 2022-2031; U.S. Pat. No. 9,867,883.

In some examples, in preparation for treatment with a modified cleavase of the invention, a polypeptide is treated with a chemical reagent that comprises an isatoic anhydride, an isonicotinic anhydride, an azaisatoic anhydride, a succinic anhydride, or a derivative of one of these, and the terminal amino acid of the polypeptide is modified, or labeled, by the chemical reagent. Specific examples of labeling of a terminal amino acid of a polypeptide to be treated with a modified cleavase of the invention include:

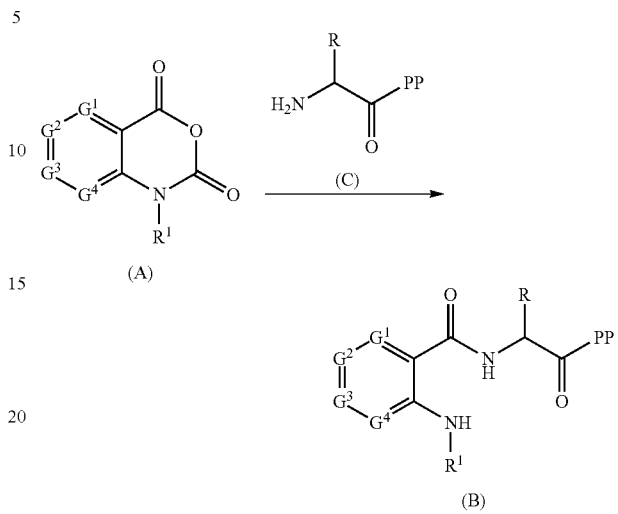

wherein:

$G^1$-$G^4$ are each independently selected from CH, CX, and N;

X at each occurrence is independently selected from $C_1$-$C_2$ alkyl, $NO_2$, $C_1$-$C_2$ haloalkyl, $C_1$-$C_2$ haloalkoxy, halo, —$OR^2$, —$N(R^2)_2$, —$SR^2$, $SO_2R^3$, $SO_3R^2$, —$B(OR^2)_2$, $C(=O)R^2$, CN, $CON(R^2)_2$, —$COOR^2$, —C(=O)Ar, and tetrazole;

R represents the side chain of an amino acid, e.g. one of the side chains of the 20 common amino acids;

$R^1$ is selected from H, $R^3$, C(=O)$R^2$, —C(=O)N$(R^2)_2$, —C(=O)Ar, and —$SO_2N(R^2)_2$;

$R^2$ is independently at each occurrence selected from H and $C_1$-$C_2$ alkyl;

$R^3$ is independently at each occurrence selected from $C_1$-$C_2$ alkyl;

Ar is independently selected at each occurrence from phenyl, pyridinyl, pyrimidinyl, pyridazinyl, and pyrazinyl, each of which is optionally substituted by one or two groups selected from halo, CN, $NO_2$, $C_1$-$C_2$ alkyl, $C_1$-$C_2$ haloalkyl, $C_1$-$C_2$ haloalkoxy, and —$OR^2$; and PP represents a portion of a polypeptide, particularly the portion of a polypeptide being prepared for treatment with a modified cleavase of the invention excluding the N-terminal amino acid. Thus the compound of Formula (C) is typically a polypeptide for use in the methods of the invention, and R represents the side chain of the terminal amino acid of the polypeptide.

In preferred embodiments, the terminal amino acid shown in Formula (C) is in the L-configuration when R is not H.

The compounds of Formula (B) are polypeptides, sometimes referred to as labeled polypeptides, that have been prepared for use in the modified cleavase reactions described herein.

In some aspects, the amino acid for removal by the modified cleavase is labeled with an exemplary reagent derived from an isatoic anhydride, an isonicotinic anhydride or an azaisatoic anhydride, especially compounds of Formula (A) as described herein. In some embodiments, the amino acid for removal by the modified cleavase is labeled with an exemplary reagent selected from the list consisting of N-Methyl-isatoic anhydride, N-acetyl-isatoic anhydride, 4-carboxylic acid isatoic anhydride, 5-methoxy-isatoic anhydride, 5-nitro-isatoic anhydride, 4-chloro-isatoic anhydride, 4-fluoro-isatoic anhydride, 6-fluoro-isatoic anhydride, N-benzyl-isatoic anhydride, 4-trifluoromethyl-isatoic anhydride, 5-trifluoromethyl-isatoic anhydride, 4-nitro-isatoic anhydride, 4-methoxy-isatoic anhydride, and 5-Amino-2-fluoro-isonicotinic anhydride (6-fluoro-1H-pyrido[3,4-d][1,3]oxazine-2,4-dione), or a derivative thereof. In some examples, the labeled amino acid or dipeptide removed by the action of a modified cleavase of the invention comprises an optionally substituted benzamide, typically one derived from any of the optionally substituted isatoic anhydrides disclosed herein, including a compound of Formula (B) as described herein.

In other favored embodiments of the invention, in preparation for treatment with a modified cleavase of the invention, the polypeptide is treated with a chemical reagent that comprises a succinic anhydride, a phthalic anhydride, a pyrazinedicarboxylic anhydride, or a derivative of one of these, and the terminal amino acid is modified, or labeled, by the chemical reagent.

Additional specific examples of reactions for labeling of a terminal amino acid of a polypeptide to be treated with a modified cleavase of the invention include:

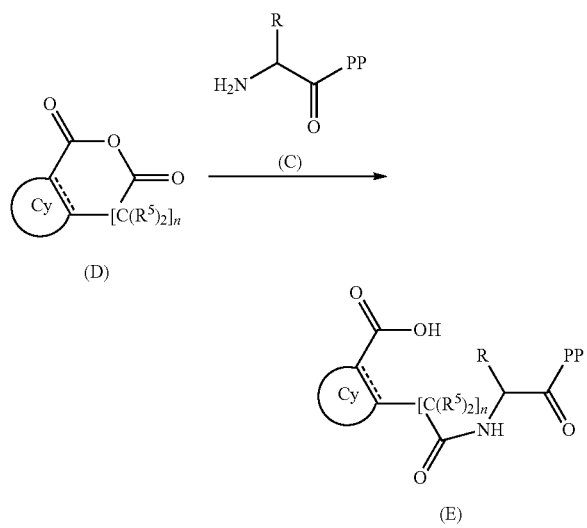

wherein:
n is 0 or 1;
Ring Cy represents a 5- or 6-membered ring or an 8-10 membered bicyclic ring that may be absent or present; when present, ring Cy may be saturated, unsaturated, or aromatic, and the dashed bond may be a single bond, double bond, or aromatic bond;
when Cy is present, it may be a carbocyclic ring, or it may contain one or two heteroatoms selected from N, O and S as ring members;
when Ring Cy is present, it is optionally substituted with one to six groups (or with one to four groups when Cy is aromatic) selected from halo, CN, $NO_2$, $C_1$-$C_2$ alkyl, $C_1$-$C_2$ haloalkyl, $C_1$-$C_2$ haloalkoxy, and —$OR^4$;
when ring Cy is absent, the dashed bond may be a single bond or a double bond, and the dashed bond is optionally substituted by one or two groups selected from halo, CN, $C_1$-$C_2$ alkyl, $C_1$-$C_2$ haloalkyl, $C_1$-$C_2$ haloalkoxy, $CO_2R^4$, and —$OR^4$;

R represents the side chain of an amino acid, e.g. one of the side chains of the 20 common amino acids;
$R^4$ is independently selected at each occurrence from H, $C_1$-$C_2$ alkyl, and $C_1$-$C_2$ haloalkyl;
$R^5$ is independently selected at each occurrence from H, halo, $C_1$-$C_2$ alkyl, $C_1$-$C_2$ haloalkyl, $C_1$-$C_2$ alkoxy, and $C_1$-$C_2$ haloalkoxy;
PP represents a portion of a polypeptide, particularly the portion of a polypeptide being prepared for treatment with a modified cleavase of the invention excluding the N-terminal amino acid. Thus the compound of Formula (C) is typically a polypeptide for use in the methods of the invention, and R represents the side chain of the terminal amino acid of the polypeptide.

In preferred embodiments of these reagents of Formula (D), ring Cy is absent when n is 1. In additional preferred embodiments of the chemical reagents of Formula (D), ring Cy is present and is a phenyl ring or a 2,3-pyrazine ring, each of which is optionally substituted as described above, and n is 0.

In preferred embodiments, the terminal amino acid shown in Formula (C) is in the L-configuration when R is not H.

The compounds of Formula (E) are polypeptides, sometimes referred to as labeled polypeptides, that have been prepared for use in the modified cleavase reactions described herein.

In some embodiments, the amino acid for removal by the modified cleavase is labeled with an exemplary reagent derived from succinic anhydride, or a compound of Formula (D) wherein ring Cy is absent and the dashed bond represents a single bond. In some embodiments, the reagent is 3,6, difluorophthalic anhydride, 2,3 pyrazinedicarboxylic anhydride, or succinic anhydride. In some examples, the removed labeled amino acid or dipeptide comprises 4-carboxybutyl-amide.

In some embodiments, in preparation for treatment with a modified cleavase of the invention, a polypeptide is treated with any suitable chemical reagent that is capable of forming an amide bond with the α-amine of the polypeptide N-terminus. A number of chemical reagents react with terminal amines of the polypeptide to form a modified polypeptide with an amide bond linking the polypeptide to the modification; this N-terminal modified polypeptide can be a substrate for a modified cleavase. Chemical reagents that react with amines to form an amide bond are known from the field of peptide coupling, including but not limited to: acyl halides (chlorides, fluorides, bromides), acyl imidazoles, O-acyl isoureas, activated esters [N-hydroxysuccinimide (NHS or HOSu), N-hydroxysulfosuccinimide (sulfo-NHS) p-nitrophenyl (PNP), Pentafluorophenyl (Pfp), 4-sulfo-2,3,5,6,-tetrafluorophenyl, 2,4,5-trichlorophenol, N-hydroxy-5-norbomene-2,3-dicarboximide (HONB), 3-hydroxy-4-oxo-3,4-dihydro-1,2,3-benzotriazine (HODhbt), hydroxybenzotriazole (HOBt), 1-hydroxy-7-azabenzotriazole (HOAt), 1-Hydroxy-1H-1,2,3-triazole-4-carboxylate (HOCt)], Ethyl (2Z)-2-cyano-2-hydroxyiminoacetate (Oxyma)], alkyl esters, carbodiimides, etc. (Hermanson (2013) Bioconjugation Techniques, Academic Press; Montalbetti et al., (2005) Tetrahedron 61: 10827-10852; Montalbetti et al., Wiley Encyclopedia of Chemical Biology: 1-17. de Figueiredo et al., (2016) Chem Rev 116(19): 12029-12122; each of which are incorporated herein by reference in their entirety). N-terminal modifications can be installed with an amide bond linking to the polypeptide via enzymatic methods as well (Philpott et al., (2018) Green Chemistry 20(15): 3426-3431, incorporated herein by reference in its entirety). An example of labeling a polypeptide with a PNP ester is provided with 4-Nitrophenyl Anthranilate which can be used to label a polypeptide under the following conditions: 4-Nitrophenol anthranilate (PNPA) is dissolved in DMSO at 100 mM; and PNPA used at 10 mM with 1 mM peptide in 1XPBS (pH 8.5) or 100 mM NaHCO3 carbonate buffer (pH 8.5) in 10% DMSO for 37° C. for 1 hr. The resulting peptide product generated is equivalent to labeling a peptide with isatoic anhydride, and generates a 2-aminobenzamide-modified peptide suitable as a substrate for a modified cleavase (e.g., derived from DAP BII) as illustrated in Table 11.

In some examples, in preparation for treatment with a modified cleavase of the invention, a polypeptide is treated with a chemical reagent that comprises an amine-protected activated ester to form an amide bond and the terminal amino acid of the polypeptide is modified, or labeled, by the chemical reagent. This modified polypeptide can then be further appropriately treated to remove the designated protecting group, yielding a modified polypeptide for treatment with a modified cleavase.

Specific examples of labeling of a terminal amino acid of a polypeptide to be treated with a modified cleavase of the invention include:

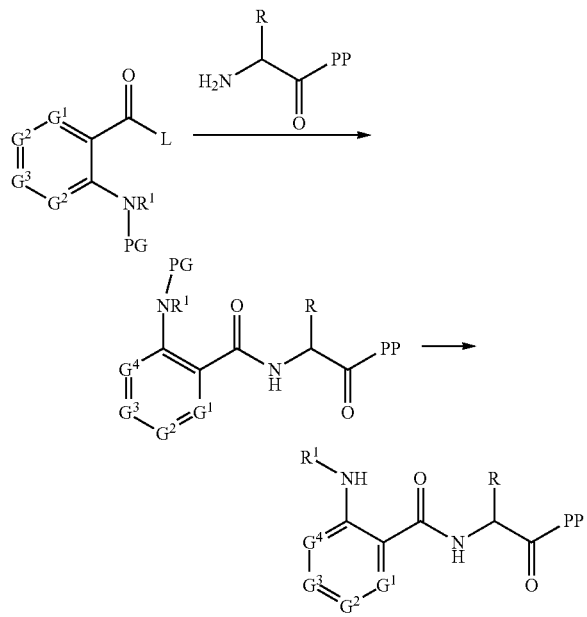

wherein:

$G^1$-$G^4$ are each independently selected from CH, CX, and N;

X at each occurrence is independently selected from H, $C_1$-$C_2$ alkyl, $NO_2$, $C_1$-$C_2$ haloalkyl, $C_1$-$C_2$ haloalkoxy, halo, —$OR^2$, —$N(R^2)_2$, —$SR^2$, $SO_2R^3$, $SO_3R^2$, —$B(OR^2)_2$, $C(=O)R^2$, CN, $CON(R^2)_2$, —$COOR^2$, —C(=O)Ar, and tetrazole;

R represents the side chain of an amino acid, e.g. one of the side chains of the 20 common amino acids;

$R^1$ is selected from H, $R^3$, C(=O)$R^2$, —C(=O)$N(R^2)_2$, —C(=O)Ar, and —$SO_2N(R^3)_2$;

$R^2$ is independently at each occurrence selected from H and $C_1$-$C_2$ alkyl;

$R^3$ is independently at each occurrence selected from $C_1$-$C_2$ alkyl;

Ar is independently selected at each occurrence from phenyl, pyridinyl, pyrimidinyl, pyridazinyl, and pyrazinyl, each of which is optionally substituted by one or two groups selected from halo, CN, $NO_2$, $C_1$-$C_2$ alkyl, $C_1$-$C_2$ haloalkyl, $C_1$-$C_2$ haloalkoxy, and —$OR^2$;

L is a leaving group selected from halo, N-hydroxysuccinimide (NHS), N-hydroxybenzotriazole, sulfo N-hydroxysuccinimide (sulfoNHS), 2,3,4,5,6-pentafluorophenol (pFP), 4-sulfo-2,3,5,6-tetrafluoro phenol, chloro, 4-nitrophenol, and —O(C=)—O—($C_{1-6}$ alkyl);

optionally, —$NR^1$-PG can be replaced by —$N_3$; and

PG is H or a nitrogen protecting groups which may be selected from tert-butyloxycarbonyl (Boc), 2,2,2-trichloroethoxycarbonyl (Troc), 2-(trimethylsilyl)ethoxycarbonyl (Teoc), carboxylbenzyl (Cbz), para-nitrocarboxylbenzyl (p-$NO_2$Cbz), allyloxycarbonyl (Alloc), 9-fluorenylmethoxycarbonyl (Fmoc), para-azidocarboxylbenzyl (p-$N_3$Cbz), 2,2,6,6-tetramethylpiperidin-1-yloxycarbonyl (Tempoc), and other N-protecting groups.

In some examples, in preparation for treatment with a modified cleavase of the invention, a polypeptide is treated with 4-Nitrophenyl Anthranilate.

In some embodiments, the chemical reagent for modifying or labeling the amino acid for removal by the modified cleavase is one or more of any of the compounds of Formula (A) or (D), described herein, or a salt or conjugate thereof.

In some embodiments, the chemical reagent for modifying or labeling the amino acid for removal by the modified cleavase is one or more of any of the compounds of Formula (I), (II), (III), (IV), or (AB), described herein, or a salt or conjugate thereof.

In some embodiments, the reagent for modifying or labeling the amino acid for removal by the modified cleavase comprises a compound selected from the group consisting of a compound of Formula (I):

(I)

or a salt or conjugate thereof, wherein $R^1$ and $R^2$ are each independently H, $C_{1-6}$alkyl, cycloalkyl, —C(O)$R^a$, —C(O)$OR^b$, or —S(O)$_2R^c$;

$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

$R^3$ is heteroaryl, —$NR^dC(O)OR^e$, or —$SR^f$, wherein the heteroaryl is unsubstituted or substituted;

$R^d$, $R^e$, and $R^f$ are each independently H or $C_{1-6}$alkyl.

In some embodiments, when $R^3$ is

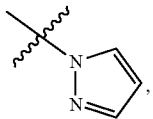 [SMILES: *n1cccn1]

$R^1$ and $R^2$ are not both H. In some embodiments of Formula (I), both $R^1$ and $R^2$ are H. In some embodiments, neither $R^1$ nor $R^2$ are H. In some embodiments, one of $R^1$ and $R^2$ is $C_{1-6}$alkyl. In some embodiments, one of $R^1$ and $R^2$ is H, and the other is $C_{1-6}$alkyl, cycloalkyl, —C(O)$R^a$, —C(O)O$R^b$, or —S(O)$_2R^c$. In some embodiments, one or both of $R^1$ and $R^2$ is $C_{1-6}$alkyl. In some embodiments, one or both of $R^1$ and $R^2$ is cycloalkyl. In some embodiments, one or both of $R^1$ and $R^2$ is —C(O)$R^a$. In some embodiments, one or both of $R^1$ and $R^2$ is —C(O)O$R^b$. In some embodiments, one or both of $R^1$ and $R^2$ is —S(O)$_2R^c$. In some embodiments, one or both of $R^1$ and $R^2$ is —S(O)$_2R^c$, wherein $R^c$ is $C_{1-6}$alkyl, $C_{1-6}$haloalkyl, arylalkyl, aryl, or heteroaryl. In some embodiments, $R^1$ is

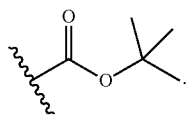 [SMILES: *C(=O)OC(C)(C)C]

In some embodiments, $R^2$ is

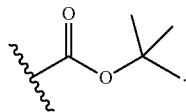

In some embodiments, both $R^1$ and $R^2$ are

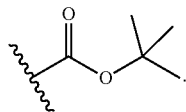 [SMILES: *C(=O)OC(C)(C)C]

In some embodiments, $R^1$ or $R^2$ is

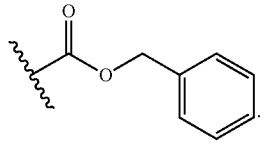 [SMILES: *C(=O)OCc1ccccc1]

In some embodiments of the compound of Formula (I), $R^3$ is a monocyclic heteroaryl group. In some embodiments of Formula (I), $R^3$ is a 5- or 6-membered monocyclic heteroaryl group. In some embodiments of Formula (I), $R^3$ is a 5- or 6-membered monocyclic heteroaryl group containing one or more N. Preferably, $R^3$ is selected from pyrazole, imidazole, triazole and tetrazole, and is linked to the amidine of Formula (I) via a nitrogen atom of the pyrazole, imidazole, triazole or tetrazole ring, and $R^3$ is optionally substituted by a group selected from halo, $C_{1-3}$ alkyl, $C_{1-3}$ haloalkyl, and nitro. In some embodiments, $R^3$ is

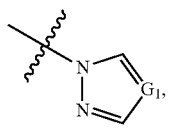

wherein $G_1$ is N, CH, or CX where X is halo, $C_{1-3}$ alkyl, $C_{1-3}$ haloalkyl, or nitro. In some embodiments, $R^3$ is

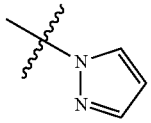 [SMILES: *n1cccn1]

or, where X is Me, F, Cl, CF$_3$, or NO$_2$. In some embodiments, $R^3$ is

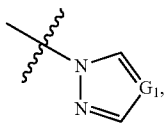

wherein $G_1$ is N or CH. In some embodiments, $R^3$ is

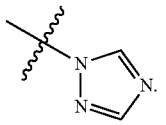 [SMILES: *n1cncn1]

In some embodiments, $R^3$ is a bicyclic heteroaryl group. In some embodiments, $R^3$ is a 9- or 10-membered bicyclic heteroaryl group. In some embodiments, $R^3$ is

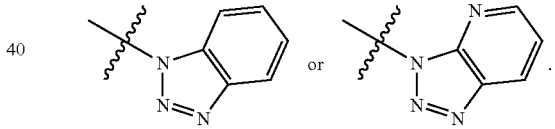

In some embodiments, the compound of Formula (I) is

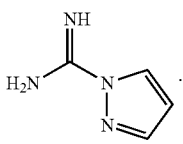

In some embodiments, the compound of Formula (I) is not

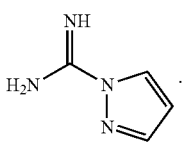

In some embodiments, the compound of Formula (I) is selected from the group consisting of

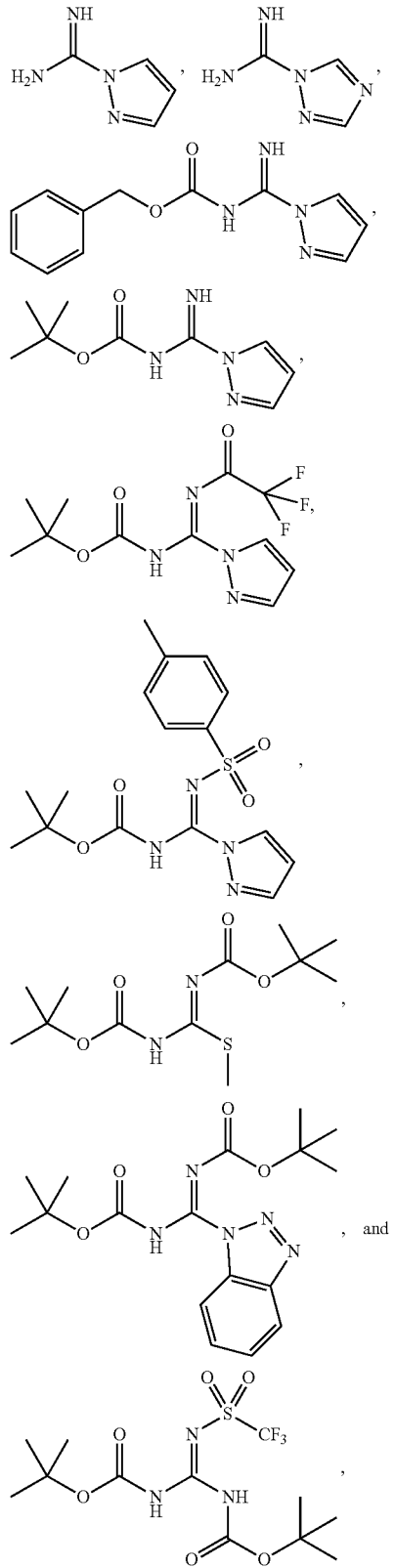

and

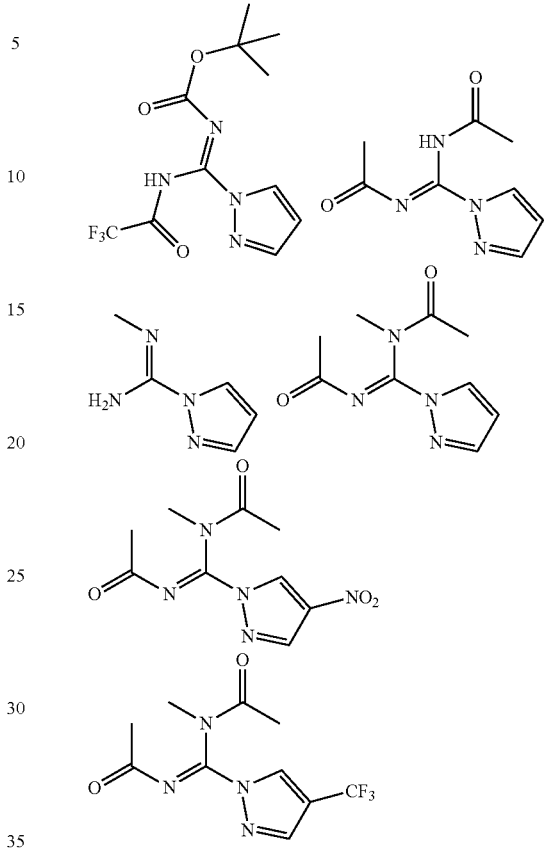

and optionally also including (N-Boc,N'-trifluoroacetyl-pyrazolecarboxamidine, N,N'-bisacetyl-pyrazolecarboxamidine, N-methyl-pyrazolecarboxamidine, N,N'-bisacetyl-N-methyl-pyrazolecarboxamidine, N,N'-bisacetyl-N-methyl-4-nitro-pyrazolecarboxamidine, and N,N'-bisacetyl-N-methyl-4-trifluoromethyl-pyrazolecarboxamidine), or a salt or conjugate of any of these.

In some embodiments, the chemical reagent additionally comprises Mukaiyama's reagent (2-chloro-1-methylpyridinium iodide). In some embodiments, the reagent comprises at least one compound of Formula (I) and Mukaiyama's reagent.

In some embodiments, the chemical reagent comprising a cyanamide derivative is used to label one or more amino acids of the polypeptide. (See, e.g., Kwon et al., *Org. Lett.* 2014, 16, 6048-6051, incorporated by reference in its entirety).

In some embodiments, the chemical reagent comprises a compound selected from the group consisting of a compound of Formula (II):

(II)

or a salt or conjugate thereof,
wherein
$R^4$ is H, $C_{1-6}$alkyl, cycloalkyl, —C(O)R$^g$, or —C(O)OR$^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted.

In some embodiments, a reagent comprising an isothiocyanate derivative is used to label the terminal amino acid (e.g., NTAA) of a polypeptide. (See, e.g., Martin et al., Organometallics. 2006, 34, 1787-1801, incorporated by reference in its entirety).

In some embodiments, the chemical reagent comprises a compound selected from the group consisting of a compound of Formula (III):

$$R^5\text{—N}=\text{C}=\text{S} \quad (III)$$

or a salt or conjugate thereof,
wherein
$R^5$ is $C_{1-6}$alkyl, $C_{2-6}$alkenyl, cycloalkyl, heterocyclyl, aryl or heteroaryl;
wherein the $C_{1-6}$alkyl, $C_{2-6}$alkenyl, cycloalkyl, heterocyclyl, aryl or heteroaryl are each unsubstituted or substituted with one or more groups selected from the group consisting of halo, —NR$^h$R$^i$, —S(O)$_2$R$^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted.

In some embodiments of Formula (III), $R^5$ is substituted phenyl. In some embodiments, $R^5$ is substituted phenyl substituted with one or more groups selected from halo, —NR$^h$R$^i$, —S(O)$_2$R$^j$, or heterocyclyl. In some embodiments, $R^5$ is unsubstituted $C_{1-6}$alkyl. In some embodiments, $R^5$ is substituted $C_{1-6}$alkyl. In some embodiments, $R^5$ is substituted $C_{1-6}$alkyl, substituted with one or more groups selected from halo, —NR$^h$R$^i$, —S(O)$_2$R$^j$, or heterocyclyl. In some embodiments, $R^5$ is unsubstituted $C_{2-6}$alkenyl. In some embodiments, $R^5$ is $C_{2-6}$alkenyl. In some embodiments, $R^5$ is substituted $C_{2-6}$alkenyl, substituted with one or more groups selected from halo, —NR$^h$R$^i$, —S(O)$_2$R$^j$, or heterocyclyl. In some embodiments, $R^5$ is unsubstituted aryl. In some embodiments, $R^5$ is substituted aryl. In some embodiments, $R^5$ is aryl, substituted with one or more groups selected from halo, —NR$^h$R$^i$, —S(O)$_2$R$^j$, or heterocyclyl. In some embodiments, $R^5$ is unsubstituted cycloalkyl. In some embodiments, $R^5$ is substituted cycloalkyl. In some embodiments, $R^5$ is cycloalkyl, substituted with one or more groups selected from halo, —NR$^h$R$^i$, —S(O)$_2$R$^j$, or heterocyclyl. In some embodiments, $R^5$ is unsubstituted heterocyclyl. In some embodiments, $R^5$ is substituted heterocyclyl. In some embodiments, $R^5$ is heterocyclyl, substituted with one or more groups selected from halo, —NR$^h$R$^i$, —S(O)$_2$R$^j$, or heterocyclyl. In some embodiments, $R^5$ is unsubstituted heteroaryl. In some embodiments, $R^5$ is substituted heteroaryl. In some embodiments, $R^5$ is heteroaryl, substituted with one or more groups selected from halo, —NR$^h$R$^i$, —S(O)$_2$R$^j$, or heterocyclyl.

In some embodiments, the compound of Formula (III) is trimethylsilyl isothiocyanate (TMSITC) or pentafluorophenyl isothiocyanate (PFPITC).

In some embodiments, the compound is not trifluoromethyl isothiocyanate, allyl isothiocyanate, dimethylaminoazobenzene isothiocyanate, 4-sulfophenyl isothiocyanate, 3-pyridyl isothiocyanate, 2-piperidinoethyl isothiocyanate, 3-(4-morpholino) propyl isothiocyanate, or 3-(diethylamino)propyl isothiocyanate.

In some embodiments, the reagent is or comprises an alkyl amine. In some embodiments, the reagent additionally comprises DIPEA, trimethylamine, pyridine, and/or N-methylpiperidine. In some embodiments, the reagent additionally comprises pyridine and triethylamine in acetonitrile. In some embodiments, the reagent additionally comprises N-methylpiperidine in water and/or methanol.

In some embodiments, the polypeptide is also contacted with a carbodiimide compound.

In some embodiments, the chemical reagent comprises a carbodiimide derivative (See, e.g., Chi et al., 2015, *Chem. Eur. J.* 2015, 21, 10369-10378, incorporated by reference in their entireties).

In some embodiments, the NTAA of a polypeptide is labeled via acylation. (See, e.g., *Protein Science* (1992), I, 582-589, incorporated by reference in their entireties).

In some embodiments, the chemical reagent comprises a compound selected from the group consisting of a compound of Formula (IV):

(IV)

or a salt or conjugate thereof,
wherein
$R^8$ is halo or —OR$^m$;
$R^m$ is H, $C_{1-6}$alkyl, or heterocyclyl; and
$R^9$ is hydrogen, halo, or $C_{1-6}$haloalkyl.

In some embodiments of Formula (IV), $R^8$ is halo. In some embodiments, $R^8$ is chloro. In some embodiments, $R^8$

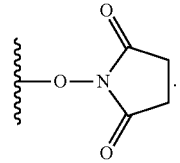 [SMILES: *ON1C(=O)CCC1=O]

In some embodiments, $R^9$ is hydrogen. In some embodiments, $R^9$ is halo, such as bromo. In some embodiments, the compound of Formula (IV) is selected from acetyl chloride, acetyl anhydride, and acetyl-NHS. In some embodiments, the compound is not acetyl anhydride or acetyl-NHS.

In some embodiments, the polypeptide is also contacting with a peptide coupling reagent. In some embodiments, the peptide coupling reagent is a carbodiimide compound. In some embodiments, the carbodiimide compound is diisopropylcarbodiimide (DIC) or 1-ethyl-3-(3-dimethylaminopropyl)carbodiimide (EDC). In some embodiments, the method includes contacting with at least one compound of Formula (I) and a carbodiimide compounds, such as DIC or EDC.

In some embodiments, the chemical reagent comprises a metal complex. (See, e.g., Bentley et al., *Biochem. J.* 7973 (135), 507-511; Bentley et al., *Biochem. J.* 1976(153), 137-138; Huo et al., *J. Am. Chem. Soc.* 2007, 139, 9819-9822; Wu et al., *J. Am. Chem. Soc.* 2016, 138(44), 14554-14557 incorporated by reference in their entireties). In some embodiments, the metal complex is a metal directing/chelating group. In some embodiments, the metal complex comprises one or more ligands chelated to a metal center. In some embodiments, the ligand is a monodentate ligand. In some embodiments, the ligand is a bidentate or polydentate ligand. In some embodiments, the metal complex comprises a metal selected from the group consisting of Co, Cu, Pd, Pt, Zn, and Ni.

In some embodiments, the chemical reagent comprises a conjugate of Formula (I), Formula (II), Formula (III), or Formula (IV). In some embodiments, the reagent used to modify the terminal amino acid of a polypeptide comprises a compound of Formula (I), Formula (II), Formula (III), or Formula (IV), conjugated to a ligand.

In some embodiments, the chemical reagent comprises a conjugate of Formula (I)-Q, Formula (II)-Q, Formula (III)-Q, or Formula (IV)-Q, wherein Formula (I)-(IV) are as defined above, and Q is a ligand.

In some embodiments, the ligand Q is a pendant group or binding site (e.g., the site to which the binding agent binds). In some embodiments, the polypeptide binds covalently to a binding agent. In some embodiments, the polypeptide comprises a terminal amino acid which includes a ligand group that is capable of covalent binding to a binding agent. In certain embodiments, the polypeptide comprises a labeled NTAA with a compound of Formula (I)-Q, Formula (II)-Q, Formula (III)-Q, or Formula (IV)-Q, wherein the Q binds covalently to a binding agent. In some embodiments, a coupling reaction is carried out to create a covalent linkage between the polypeptide and the binding agent (e.g., a covalent linkage between the ligand Q and a functional group on the binding agent).

In some embodiments, the chemical reagent comprises a conjugate of Formula (I)-Q

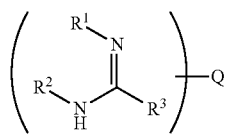

(I)-Q wherein $R^1$, $R^2$, and $R^3$ are as defined above and Q is a ligand.

In some embodiments, the chemical reagent comprises a conjugate of Formula (II)-Q

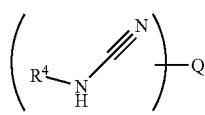

(II)-Q wherein $R^4$ is as defined above, and Q is a ligand.

In some embodiments, the chemical reagent comprises a conjugate of Formula (III)-Q

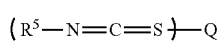

(III)-Q wherein $R^5$ is as defined above and Q is a ligand.

In some embodiments, the chemical reagent comprises a conjugate of Formula (IV)-Q

(IV)-Q wherein $R^8$ and $R^9$ are as defined above and Q is a ligand.

In some embodiments, Q is selected from the group consisting of —$C_{1-6}$alkyl, —$C_{2-6}$alkenyl, —$C_{2-6}$alkynyl, aryl, heteroaryl, heterocyclyl, —N=C=S, —CN, —C(O)R″, —C(O)OR°, —SR$^p$ or —S(O)$_2$R$^q$; wherein the —$C_{1-6}$alkyl, —$C_{2-6}$alkenyl, —$C_{2-6}$alkynyl, aryl, heteroaryl, and heterocyclyl are each unsubstituted or substituted, and R″, R°, R$^p$, and R$^q$ are each independently selected from the group consisting of —$C_{1-6}$alkyl, —$C_{1-6}$haloalkyl, —$C_{2-6}$alkenyl, —$C_{2-6}$alkynyl, aryl, heteroaryl, and heterocyclyl. In some embodiments, Q is selected from the group consisting of

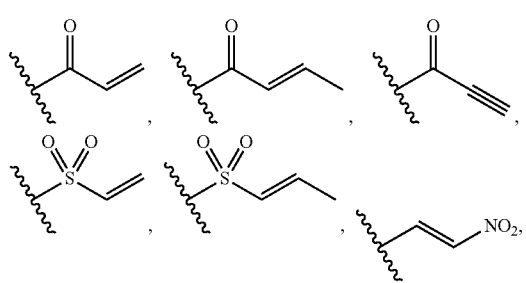

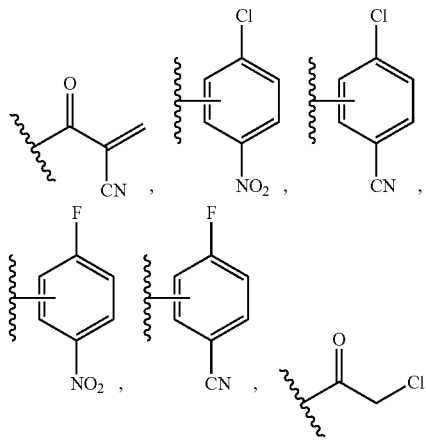

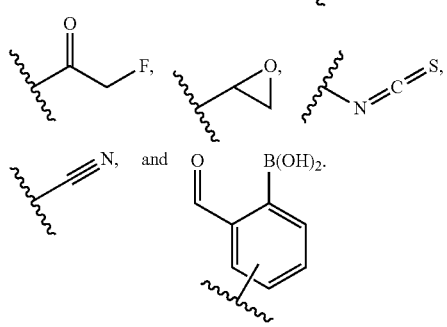

In some embodiments, Q is a fluorophore. In some embodiments, Q is selected from a lanthanide, europium, terbium, XL665, d2, quantum dots, green fluorescent protein, red fluorescent protein, yellow fluorescent protein, fluorescein, rhodamine, eosin, Texas red, cyanine, indocarbocyanine, ocacarbocyanine, thiacarbocyanine, merocyanine, pyridyloxadole, benzoxadiazole, cascade blue, nile red, oxazine 170, acridine orange, proflavin, auramine, malachite green crystal violet, porphine phtalocyanine, and bilirubin.

Provided in other aspects are reagents used in labeling the terminal amino acid or amino acid for removal by the modified cleavase with more than one label.

In some embodiments, labeling the terminal amino acid (e.g., NTAA) or amino acid for removal by the modified cleavase includes using a first reagent and a second reagent. In some embodiments, the terminal amino acid is concurrently or sequentially labeled with the first reagent and the second reagent. In some embodiments, the first reagent comprises a compound selected from the group consisting of a compound of Formula (I), (II), (III), and (IV), or a salt or conjugate thereof, as described herein.

In some embodiments, the second reagent comprises a compound of Formula (Va) or (Vb):

(Va)

or a salt or conjugate thereof,
wherein
$R^{13}$ is H, $C_{1-6}$alkyl, aryl, heteroaryl, cycloalkyl, or heterocyclyl, wherein the $C_{1-6}$alkyl, aryl, heteroaryl, cycloalkyl, and heterocyclyl are each unsubstituted or substituted; or $$R^{13}-X \qquad (Vb)$$

wherein
$R^{13}$ is $C_{1-6}$alkyl, aryl, heteroaryl, cycloalkyl, or heterocyclyl, each of which is unsubstituted or substituted; and
X is a halogen.

In some embodiments of Formula (Va), $R^{13}$ is H. In some embodiments, $R^{13}$ is methyl. In some embodiments, $R^{13}$ is ethyl, propyl, isopropyl, butyl, isobutyl, secbutyl, pentyl, or hexyl. In some embodiments, $R^{13}$ is $C_{1-6}$alkyl, which is substituted. In some embodiments, $R^{13}$ is $C_{1-6}$alkyl, which is substituted with aryl, heteroaryl, cycloalkyl, or heterocyclyl. In some embodiments, $R^{13}$ is $C_{1-6}$alkyl, which is substituted with aryl. In some embodiments, $R^{13}$ is —CH$_2$CH$_2$Ph, —CH$_2$Ph, —CH(CH$_3$)Ph, or —CH(CH$_3$)Ph.

In some embodiments of Formula (Vb), $R^{13}$ is methyl. In some embodiments, $R^{13}$ is ethyl, propyl, isopropyl, butyl, isobutyl, secbutyl, pentyl, or hexyl. In some embodiments, $R^{13}$ is $C_{1-6}$alkyl, which is substituted. In some embodiments, $R^{13}$ is $C_{1-6}$alkyl, which is substituted with aryl, heteroaryl, cycloalkyl, or heterocyclyl. In some embodiments, $R^{13}$ is $C_{1-6}$alkyl, which is substituted with aryl. In some embodiments, $R^{13}$ is —CH$_2$CH$_2$Ph, —CH$_2$Ph, —CH(CH$_3$)Ph, or —CH(CH$_3$)Ph.

In some embodiments, the reagent for modifying or labeling the terminal amino acid or amino acid for removal by the modified cleavase comprises formaldehyde. In some embodiments, the reagent for modifying or labeling the terminal amino acid comprises methyl iodide.

In some embodiments, the polypeptide is also contacted with a reducing agent. In some embodiments, the reducing agent comprises a borohydride, such as NaBH$_4$, KBH$_4$, ZnBH$_4$, NaBH$_3$CN or LiBu$_3$BH. In some embodiments, the reducing agent comprises an aluminum or tin compound, such as LiAlH$_4$ or SnCl. In some embodiments, the reducing agent comprises a borane complex, such as B$_2$H$_6$ and dimethyamine borane. In some embodiments, the reagent additionally comprises NaBH$_3$CN.

In some embodiments, the reagents that may be used to label the terminal amino acid (e.g., NTAA) include: 4-sulfophenyl isothiocyanate (sulfo-PITC), 4-nitrophenyl isothiocyanate (nitro-PITC), 3-pyridyl isothiocyanate (PYITC), a phenyl isocyanate (PIC), a nitro-PIC, a sulfo-PIC, a carboxyl-activated amino-blocked amino acid, an anhydride (e.g., an isatoic anhydride, an isonicotinic anhydride, an azaisatoic anhydride, a succinic anhydride), 2-piperidinoethyl isothiocyanate (PEITC), 3-(4-morpholino) propyl isothiocyanate (MPITC), 3-(diethylamino)propyl isothiocyanate (DEPTIC) (Wang et al., 2009, Anal Chem 81: 1893-1900), (1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), acetylation reagents, amidination (guanidinylation) reagents (including PCA and PCA derivatives), 2-carboxy-4,6-dinitrochlorobenzene, 7-methoxycoumarin acetic acid, a thioacylation reagent, a thioacetylation reagent, and/or a thiobenzylation reagent. Many of these reagents are unreactive or minimally reactive with DNA including PITC, nitro-PITC, sulfo-PITC, PYITC, and guanidinylation reagents (e.g., PCA compounds). If the amino acid is blocked to labeling, there are a number of approaches to unblock the terminus, such as removing N-acetyl blocks with acyl peptide hydrolase (APH) (Farries, Harris et al., 1991, Eur. J. Biochem. 196:679-685). Methods of unblocking the N-terminus of a peptide are known in the art (see, e.g., Krishna et al., 1991, Anal. Biochem. 199:45-50; Leone et al., 2011, Curr. Protoc. Protein Sci., Chapter 11:Unit11.7; Fowler et al., 2001, Curr. Protoc. Protein Sci., Chapter 11: Unit 11.7, each of which is hereby incorporated by reference in its entirety).

Dansyl chloride reacts with the free amine group of a peptide to yield a dansyl derivative of the NTAA. DNFB and SNFB react the α-amine groups of a peptide to produce DNP-NTAA, and SNP-NTAA, respectively. Additionally, both DNFB and SNFB also react with the with ε-amine of lysine residues. DNFB also reacts with tyrosine and histidine amino acid residues. In some embodiments, SNFB has better selectivity for amine groups than DNFB (Carty et al., J Biol Chem (1968) 243(20): 5244-5253). In certain embodiments, lysine ε-amines are pre-blocked with an organic anhydride prior to polypeptide protease digestion into peptides.

Isothiocyanates, in the presence of ionic liquids, have been shown to have enhanced reactivity to primary amines. Ionic liquids are excellent solvents (and serve as a catalyst) in organic chemical reactions and can enhance the reaction of isothiocyanates with amines to form thioureas. Moreover, ionic liquids may act as absorbers of microwave radiation to further enhance reactivity (Martinez-Palou, J. Mex. Chem. Soc (2007) 51(4): 252-264). An example is the use of the ionic liquid 1-butyl-3-methyl-imidazolium tetraflouoraborate [Bmim][BF4] for rapid and efficient functionalization of aromatic and aliphatic amines by phenyl isothiocyanate (PITC) (Le, Chen et al. 2005).

In some embodiments, the peptide may be labeled by treating with a chemical reagent comprising a compound of Formula (AB) as shown in the scheme below:

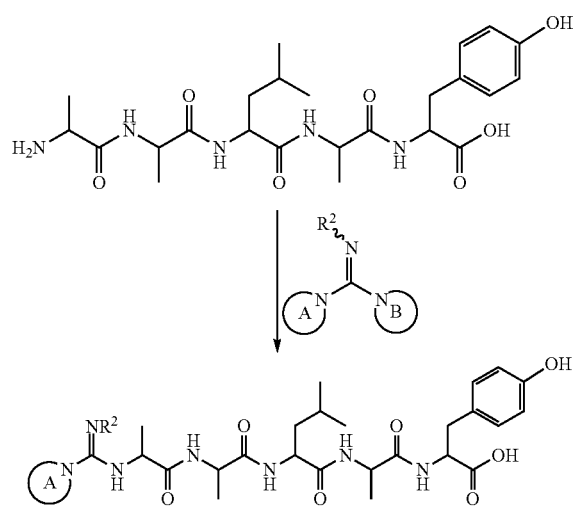

In some embodiments, the peptide treated with a chemical reagent to modify the N-terminal amino acid (NTAA) of peptides is treated with a diheterocyclic methanimine reagent. In some embodiments, the reagent for modifying or labeling the terminal amino acid or amino acid for removal by the modified cleavase comprises a compound of Formula (AB):

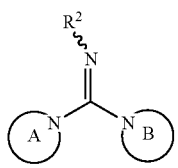

(AB)

wherein:

$R^2$ is H, $R^4$, OH, $OR^4$, $NH_2$, or —$NHR^4$;

$R^4$ is $C_{1-6}$ alkyl, which is optionally substituted with one or two members selected from halo, $C_{1-3}$ alkyl, $C_{1-3}$ alkoxy, $C_{1-3}$ haloalkyl, phenyl, 5-membered heteroaryl, and 6-membered heteroaryl, wherein each phenyl, 5-membered heteroaryl, and 6-membered heteroaryl is optionally substituted with one or two members selected from halo, —OH, $C_{1-3}$ alkyl, $C_{1-3}$ alkoxy, $C_{1-3}$ haloalkyl, $NO_2$, CN, COOR", and $CON(R")_2$, where each R" is independently H or $C_{1-3}$ alkyl;

ring A and ring B are each independently a 5-membered heteroaryl ring containing up to three N atoms as ring members and each is optionally fused to an additional phenyl or a 5-6 membered heteroaryl ring, and wherein the 5-membered heteroaryl ring and optional fused phenyl or 5-6 membered heteroaryl ring are each optionally substituted with one or two groups selected from $C_{1-4}$ alkyl, $C_{1-4}$alkoxy, —OH, halo, $C_{1-4}$haloalkyl, $NO_2$, COOR, COMO, —$SO_2R^*$, —$NR_2$, phenyl, and 5-6 membered heteroaryl;

wherein each R is independently selected from H and $C_{1-3}$ alkyl optionally substituted with OH, $OR^*$, —$NH_2$, —$NHR^*$, or —$NR^*_2$; and each $R^*$ is $C_{1-3}$ alkyl, optionally substituted with OH, oxo, $C_{1-2}$ alkoxy, or CN;

wherein two R, or two R", or two $R^*$ on the same N can optionally be taken together to form a 4-7 membered heterocyclic ring, optionally containing an additional heteroatom selected from N, O and S as a ring member, and optionally substituted with one or two groups selected from halo, $C_{1-2}$ alkyl, OH, oxo, $C_{1-2}$ alkoxy, or CN.

or a salt thereof. In some embodiments, Ring A and Ring B are not both unsubstituted imidazole, and that Ring A and Ring B are not both unsubstituted benzotriazole;

In an example of this embodiment, $R^2$ is H or $R^4$. In these embodiments, In these embodiments, the 5-membered heteroaryl group, when present, can be a 5-membered ring comprising one to three heteroatoms selected from N, O and S as ring members, and the 6-membered heteroaryl group when present can be a 6-membered ring comprising one to three nitrogen atoms as ring members. In some of these embodiments, neither ring A nor ring B is unsubstituted imidazole or unsubstituted benzotriazole. In some embodiments, $R^2$ is H. In some of these embodiments, neither ring A nor ring B is unsubstituted imidazole or unsubstituted benzotriazole.

In some embodiments, Ring A and Ring B are different. In some embodiments, Ring A and Ring B are the same. Specific compounds of this embodiment include:

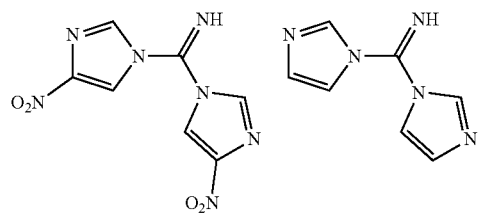

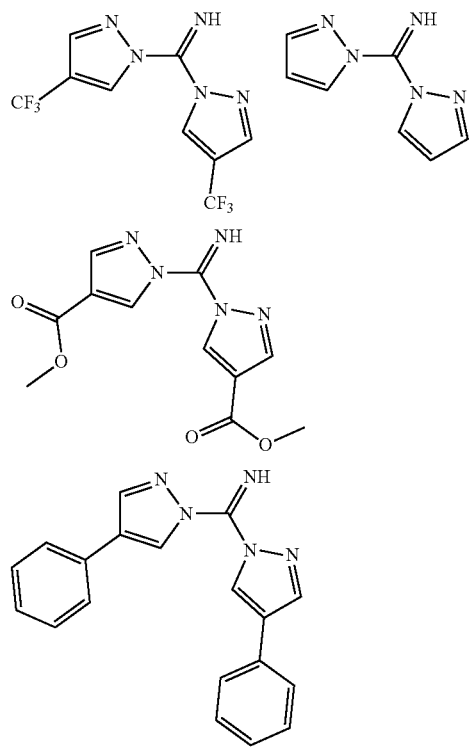

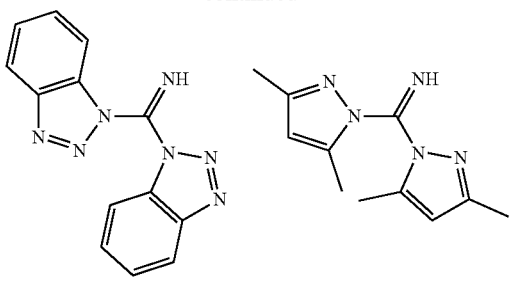

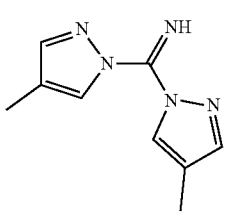

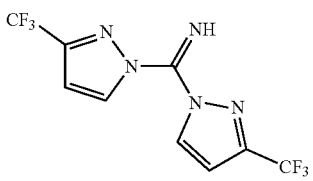

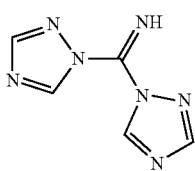

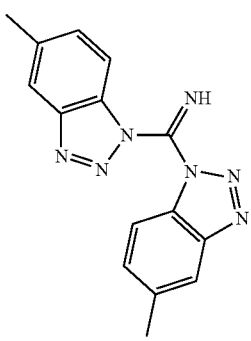

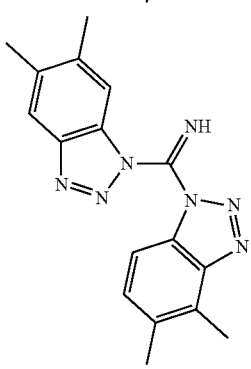

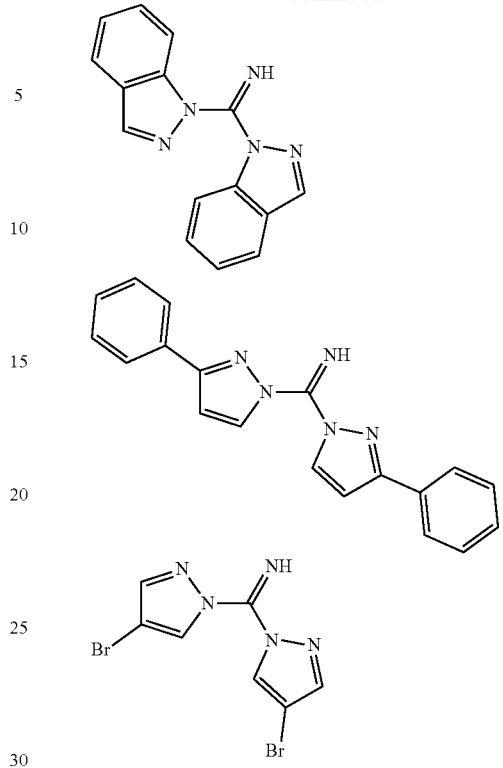

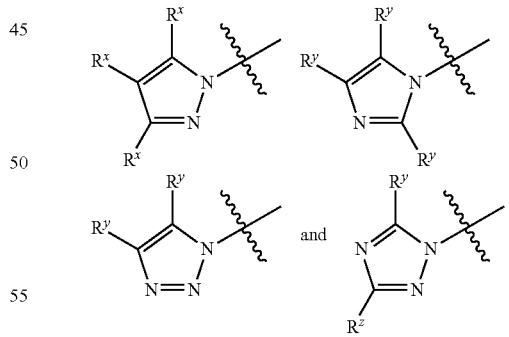

In some aspects, each 5-6 membered heteroaryl ring is independently selected and contains 1 or 2 heteroatoms selected from N, O and S as ring members. In these embodiments, each 5-membered heteroaryl group present can be a 5-membered ring comprising one or two heteroatoms selected from N, O and S as ring members, and the 6-membered heteroaryl group can be a 6-membered ring comprising one to two nitrogen atoms as ring members.

In some specific embodiments. Ring A and Ring B are selected from:

wherein:
each $R^x$, $R^y$ and $R^z$ is independently selected from H, halo, $C_{1-2}$ alkyl, $C_{1-2}$ haloalkyl, $NO_2$, $SO_2(C_{1-2}$ alkyl), $COOR^\#$, $C(O)N(R^\#)_2$, and phenyl optionally substituted with one or two groups selected from halo, $C_{1-2}$ alkyl, $C_{1-2}$haloalkyl, $NO_2$, $SO_2(C_{1-2}$ alkyl), $COOR^\#$, and $C(O)N(R^\#)_2$, and two $R^x$, $R^y$ or $R^z$ on adjacent atoms of a ring can optionally be taken together to form a phenyl group, 5-membered heteroaryl group, or 6-membered heteroaryl group fused to the ring, and the fused phenyl, 5-membered heteroaryl, or 6-membered heteroaryl group can optionally be substituted with one or two groups selected from halo, $C_{1-2}$ alkyl, $C_{1-2}$ haloalkyl, $NO_2$, $SO_2(C_{1-2}$ alkyl), $COOR^{\#}$, and $C(O)N(R^{\#})_2$;

wherein each $R^{\#}$ is independently H or $C_{1-2}$ alkyl; and wherein two R# on the same nitrogen can optionally be taken together to form a 4-7 membered heterocycle optionally containing an additional heteroatom selected from N, O and S as a ring member, wherein the 4-7 membered heterocycle is optionally substituted with one or two groups selected from halo, OH, OMe, Me, oxo, $NH_2$, NHMe and $NMe_2$;

or a salt thereof.

In these embodiments, each 5-membered heteroaryl group present can be a 5-membered ring comprising one to three heteroatoms selected from N, O and S as ring members, and the 6-membered heteroaryl group can be a 6-membered ring comprising one to three nitrogen atoms as ring members.

In some embodiments, Ring A and Ring B are the same and are selected from:

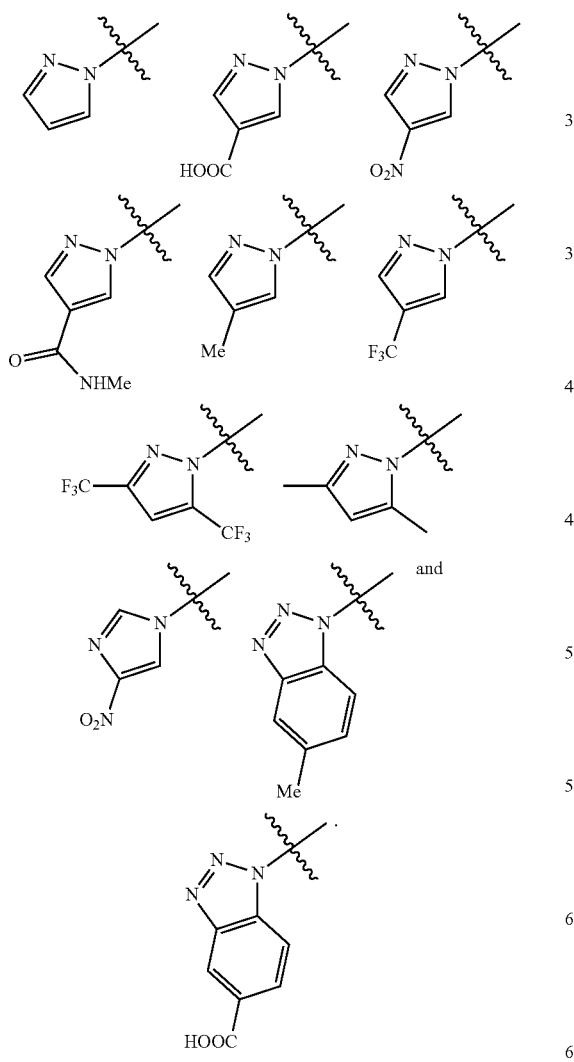

The compound of embodiment 30, which is selected from the following:

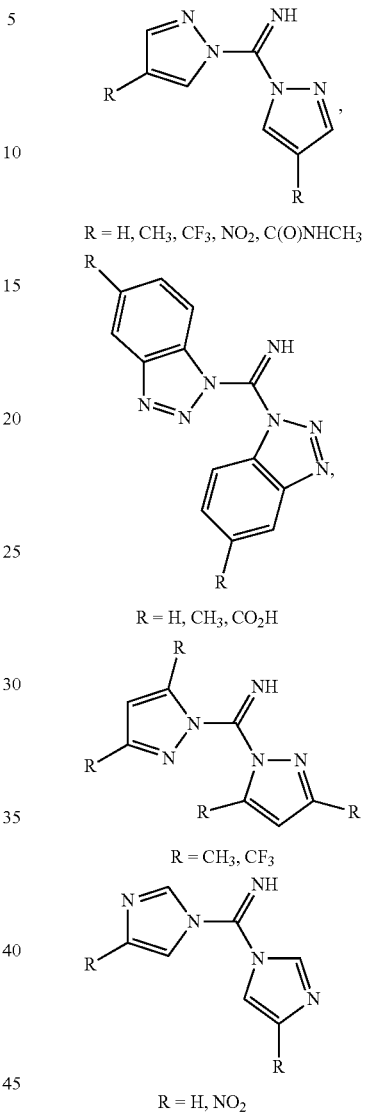

2. Other Labels

In some embodiments, the label is any label that is capable of being recognized or bound by the modified cleavase. In some embodiments, the terminal amino acid label is or includes a label that "mimics" the size/shape of a terminal amino acid (e.g., an N-terminal amino acid). In some embodiments, the label is a modified amino acid, a portion of an amino acid, a protected amino acid, a blocked amino acid, or any combination thereof. In some embodiments, the label attached to the terminal amino acid is an N-terminal blocked (devoid of alpha amine) amino acid.

In some embodiments, the label comprises an amino acid that is any amino acid, naturally occurring or synthetic. In some embodiments, the label is a synthesized blocked amino acid. In general, any suitable methods of introducing amino acid blocking groups may be used. In some embodiments, blocking groups are introduced by reacting an amino acid with a reagent to introduce the blocking group. Any suitable activated and blocked amino acid may be used to label the terminal amino acid. See e.g., Kruse et al., J. Org. Chem. (1985) 50(15):2792-2794. For example, a synthesized label that comprises one or more exogenous amino acids (e.g., -Xaa-label or -Xaa-Xaa-label) may be used as a label and attached to the polypeptide for treatment with the modified cleavase.

In some embodiments, amino acid blocking groups may be mono- or di-valent, suitable groups including acyl groups, for example lower alkanoyl such as acetyl, substituted lower alkanoyl, e.g., lower haloalkanoyl such as chloroacetyl, aryl-lower alkanoyl such as phenylacetyl, and aroyl such as benzoyl or phthaloyl; lower alkoxycarbonyl groups such as ethoxycarbonyl, isobutyloxycarbonyl or t-butyloxycarbonyl and substituted lower alkoxycarbonyl groups, e.g., lower haloalkoxycarbonyl such as 2,2,2-trichioroethoxycarbonyl; aryl-lower alkoxycarbonyl groups such as benzyloxycarbonyl; sulphonyl groups, for example lower alkyl sulphonyl such as methanesulphonyl and arylsulphonyl such as benzenesulphonyl or p-toluenesulphonyl; ylidene groups formed by reaction with aldehydes and ketones which form Schiffs bases, for example benzaldehyde, salicaldehyde or acetcacetic ester; and divalent groups such that the nitrogen atom forms part of a dihydropyridine ring, such protecting groups being obtained by, for example, reaction with formaldehyde and a β-ketoester, e.g., acetoacetic ester.

In some of any such embodiments, the labeling of a peptide (e.g. labeling of the NTAA) for removal includes attaching a label that comprises an amino acid with a label. For example, labeled amino acids are commercially available, such as Cbz-amino acids (e.g., N-CBZ-DL-serine, N-CBZ-L-aspartic acid) or N-protected amino acids. In some embodiments, the labeling of a terminal amino acid for removal includes attaching a Cbz-amino acid as a label to the terminal amino acid for removal. In some particular embodiments, the labeling includes attaching a label that comprises two amino acids with a label. For example, a synthesized label that includes -Xaa-Xaa-label (e.g., Z-gly-gly-osu) may be used as a label and attached to the peptide for treatment with the modified cleavase.

In some embodiments, the label comprises an amino acid with an Ac protected amine. In some examples, the label comprises an amino acid that is Fmoc, Boc, or Cbz protected. In other examples, the labeled amino acid comprises an amino acid with an amine that is dialkyl. In other examples, the carboxylic acid of the amino acid of the label is free and the amino acid is coupled using standard peptide coupling reagents such as HATU+DIEA or EDC+DIEA+HOBt. In other examples, the label comprises an amino acid that could be D or L chirality.

In some embodiments wherein a synthesized label that comprises one or more exogenous amino acids (e.g., -Xaa-label) is used as a label and attached to the polypeptide, the modified cleavase may remove a dipeptide from the polypeptide that includes one amino acid of the polypeptide and one exogenous amino acid that was added as part of the label. In some cases, the exogenous amino acid Xaa may represent any amino acid residue selected from the group consisting of Ala, Arg, Asn, Asp, Cys, Gin, Glu, Gly, His, lie, Leu, Lys, Met, Phe, Pro, Ser, Thr, Trp, Tyr, and Val. For example, if a polypeptide at the N-terminus has -P3-P2-P1, a label comprising Xaa-label is added to the polypeptide at the terminus to form -P3-P2-P1-Xaa-label. An exemplary modified cleavase is then contacted with the labeled polypeptide to cleave a dipeptide comprising -P1-Xaa-label from the polypeptide, thereby removing the P1 amino acid from the N-terminus of the polypeptide. In some particular embodiments, a modified cleavase derived from a unmodified or wild-type tripeptide cleavase may remove a tripeptide comprising P2-P1-Xaa-label from the polypeptide, thereby removing the P1 and P2 amino acids from the N-terminus of the polypeptide.

In some embodiments wherein a synthesized label that comprises two exogenous amino acids (e.g., -Xaa-Xaa-label) is used as a label and attached to the polypeptide, the modified cleavase may remove a tripeptide from the polypeptide that includes one amino acid of the polypeptide and two exogenous amino acid that was added as part of the label. For example, if a polypeptide at the N-terminus has -P3-P2-P1, a label comprising Xaa-Xaa-label is added to the polypeptide at the terminus to form -P3-P2-P1-Xaa-Xaa-label. An exemplary modified cleavase is then contacted with the labeled polypeptide to cleave a tripeptide comprising -P1-Xaa-Xaa-label from the polypeptide, thereby removing the P1 amino acid from the N-terminus of the polypeptide.

B. Engineering and Genetic Selection

In some embodiments, the modified cleavase provided herein can be made, isolated, engineered, or selected for using any suitable methods. In some cases, the variant or modified cleavase polypeptide is altered in primary amino acid sequence compared to the wild-type or unmodified cleavase by introducing one or more substitutions, additions, or deletions of amino acid residues. In some embodiments, the modified cleavase is derived from a wild-type or unmodified cleavase (e.g., a dipeptidyl peptidase, a dipeptidyl aminopeptidase, a peptidyl-dipeptidase, a dipeptidyl carboxypeptidase, a sedolisin, a tripeptidyl peptidase, or a protein classified in EC 3.4.14, EC 3.4.15, MEROPS S8, MEROPS S9, MEROPS S33, MEROPS S46, MEROPS M49, or MEROPS S53, or a functional homolog or fragment thereof) via engineering and genetic selection. A variety of techniques including genetic selection, protein engineering, recombinant methods, chemical synthesis, or combinations thereof, may be employed.

In some embodiments, the modified cleavase is engineered using a rational design approach for select activities, substrate binding capability, or other cleaving characteristics. In some embodiments, a rational design approach is based on crystal structure of the unmodified cleavase. In some examples, the rational design approach is based on crystal structure of the unmodified cleavase with substrates to identify target amino acid residues for modification. In some cases, the modifications may be targeted at residues of specific domains of the unmodified cleavase (See e.g., Sakamoto et al., Scientific Reports 2014, 4:4977). In some embodiments, a rational design is used to engineer a modified cleavase with modified amino acids in the substrate binding domain of the unmodified cleavase. In some embodiments, the mutations, e.g., one or more amino acid modifications (e.g., substitutions, additions, deletions) corresponds to position(s) 316, 391, 394, or a combination thereof, with reference to numbering of SEQ ID NO: 5 or the sequence of a human dipeptidyl peptidase 3 (DPP3) or a homolog thereof. In some embodiments, a rational design is used to engineer a modified cleavase that is able to bind or cleave polypeptides of increased length compared to an unmodified cleavase. In some embodiments, the mutations, e.g., one or more amino acid modifications (e.g., substitutions, additions, deletions) corresponds to position(s) amino acid residues 419, 420, 421, 422, 423, 424, 425, 426, or a combination thereof, with reference to numbering of SEQ ID NO: 5. In some embodiments, a rational design is used to engineer a modified cleavase with modified amino acids in the hinge region of the unmodified cleavase.

In some embodiments, the genetic selection or other engineering methods are designed to identify modified cleavases that are active on labeled polypeptides (e.g. chemically labeled polypeptides). In some embodiments, the genetic selection or other engineering methods are designed to identify modified cleavases that are active on modified or labeled polypeptides having a labeled N-terminal amino acid. In some cases, the size or other characteristics of the moiety or label on the labeled polypeptide is considered in the design of the genetic selection or other engineering methods to obtain a desired modified cleavase.

It is understood that reference to amino acids, including to a specific sequence set forth as a SEQ ID NO used to describe domain organization of a wild-type or modified cleavase are for illustrative purposes and are not meant to limit the scope of the embodiments provided. It is understood that polypeptides and the description of domains thereof are theoretically derived based on homology analysis and alignments with similar molecules. Thus, the exact locus can vary, and is not necessarily the same for each protein. Hence, the specific domain, such as specific binding domain, loop domain, or other functional domain), can be identified in a homolog or enzyme derived from another species using known analyses and alignment methods.

Figure 4A:
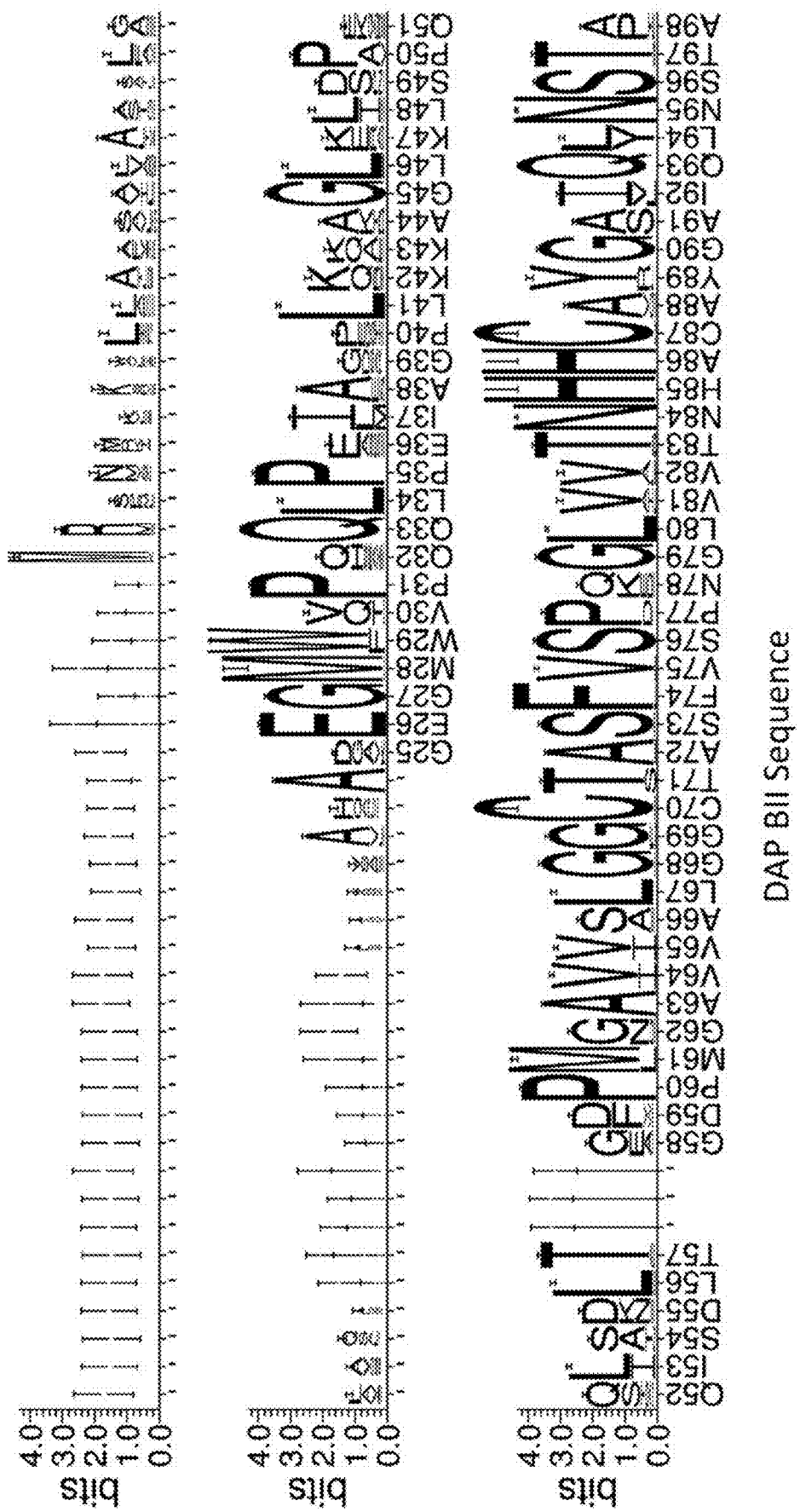
FIG. 4A-4C depict results from a WebLogo analysis of sequence conservation of DAP BII homologs with 60% sequence similarity or identity. The height of each stack indicates the sequence conservation at that position (measured in bits), and the height of symbols within the stack reflects the relative frequency of the corresponding amino acid at the indicated position (in reference to SEQ ID NO: 20).
Figure 4A:
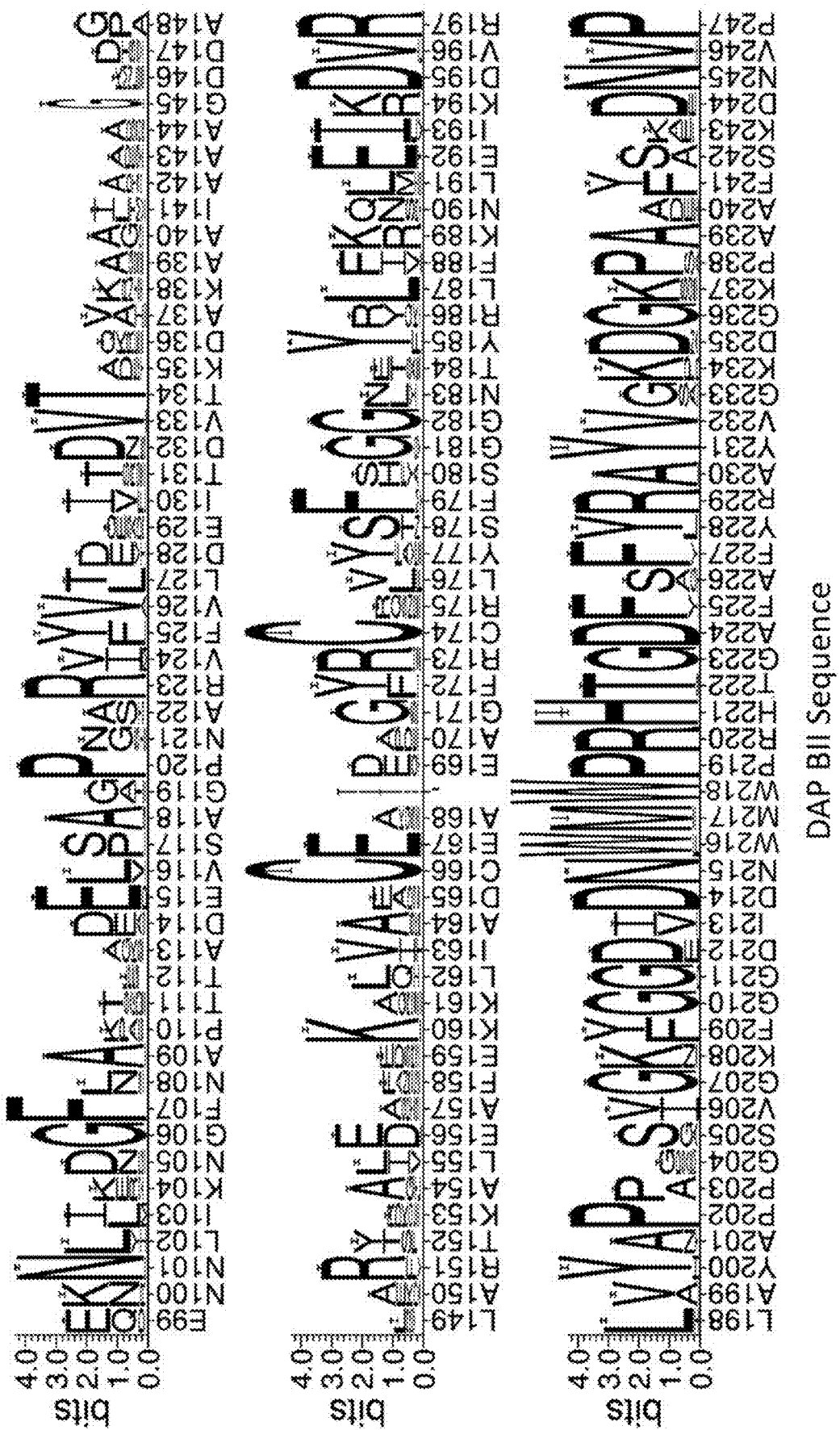
Figure 4B:
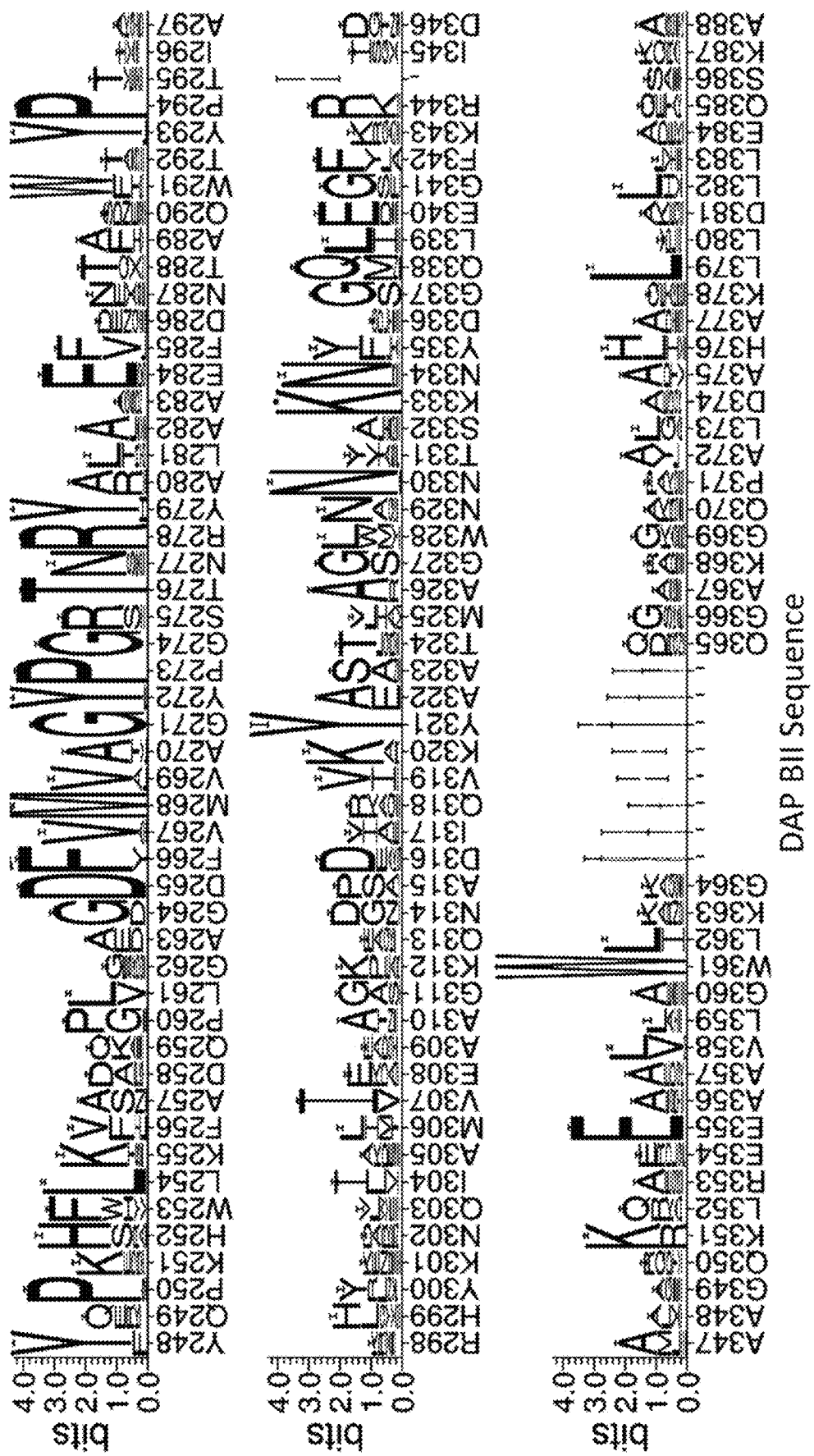
Figure 4B:
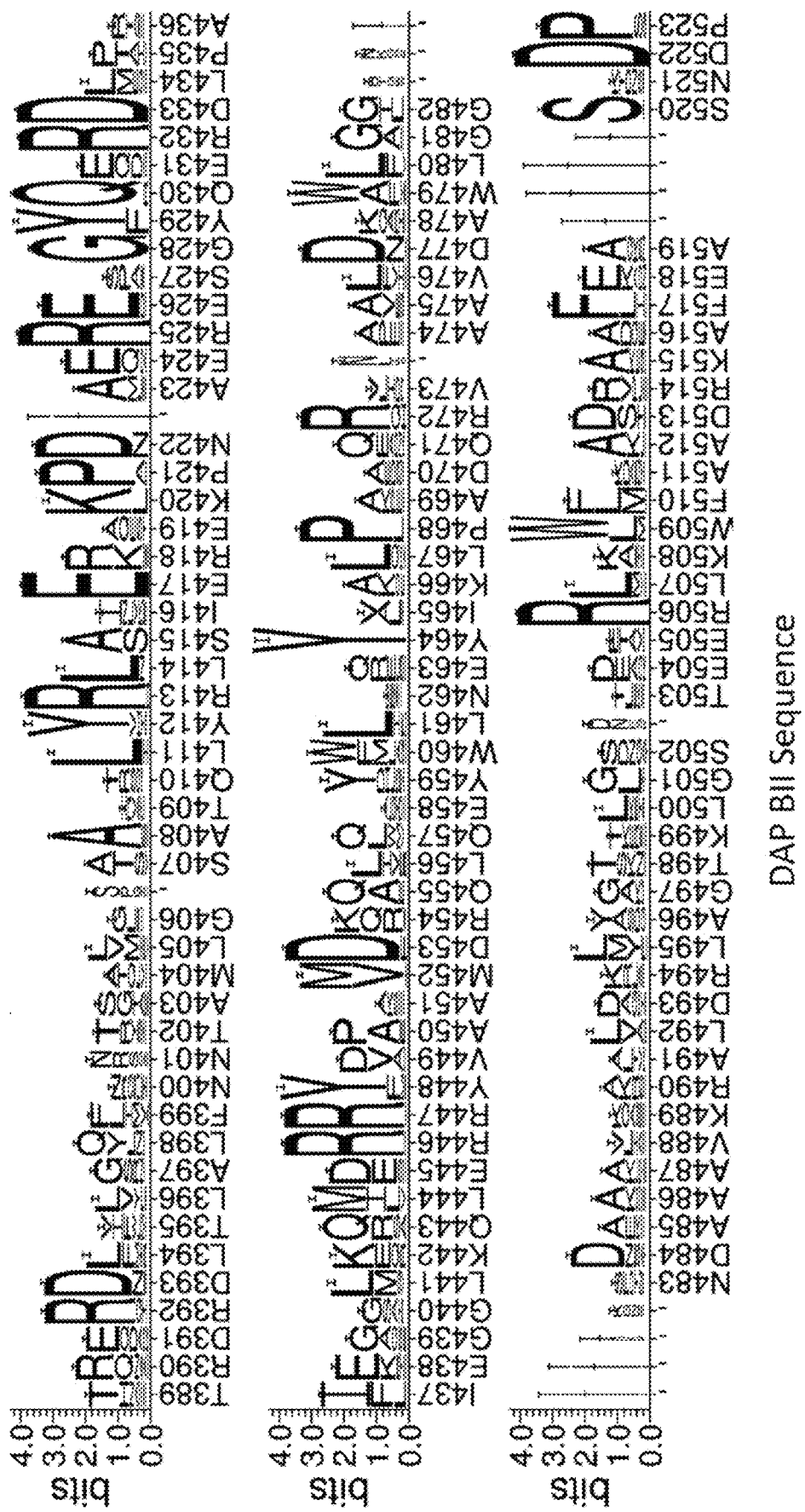
Figure 4C:
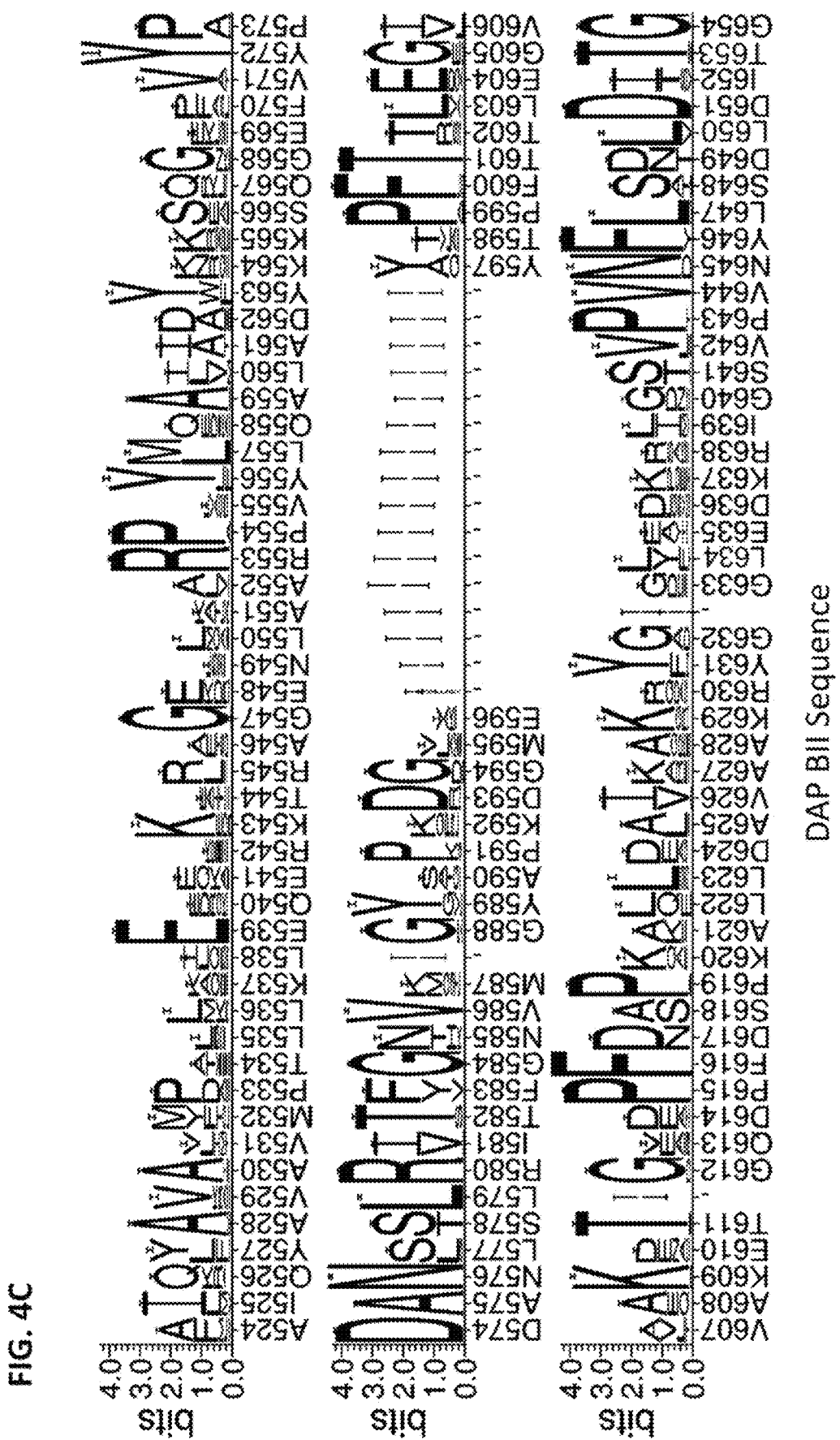
Figure 4C:
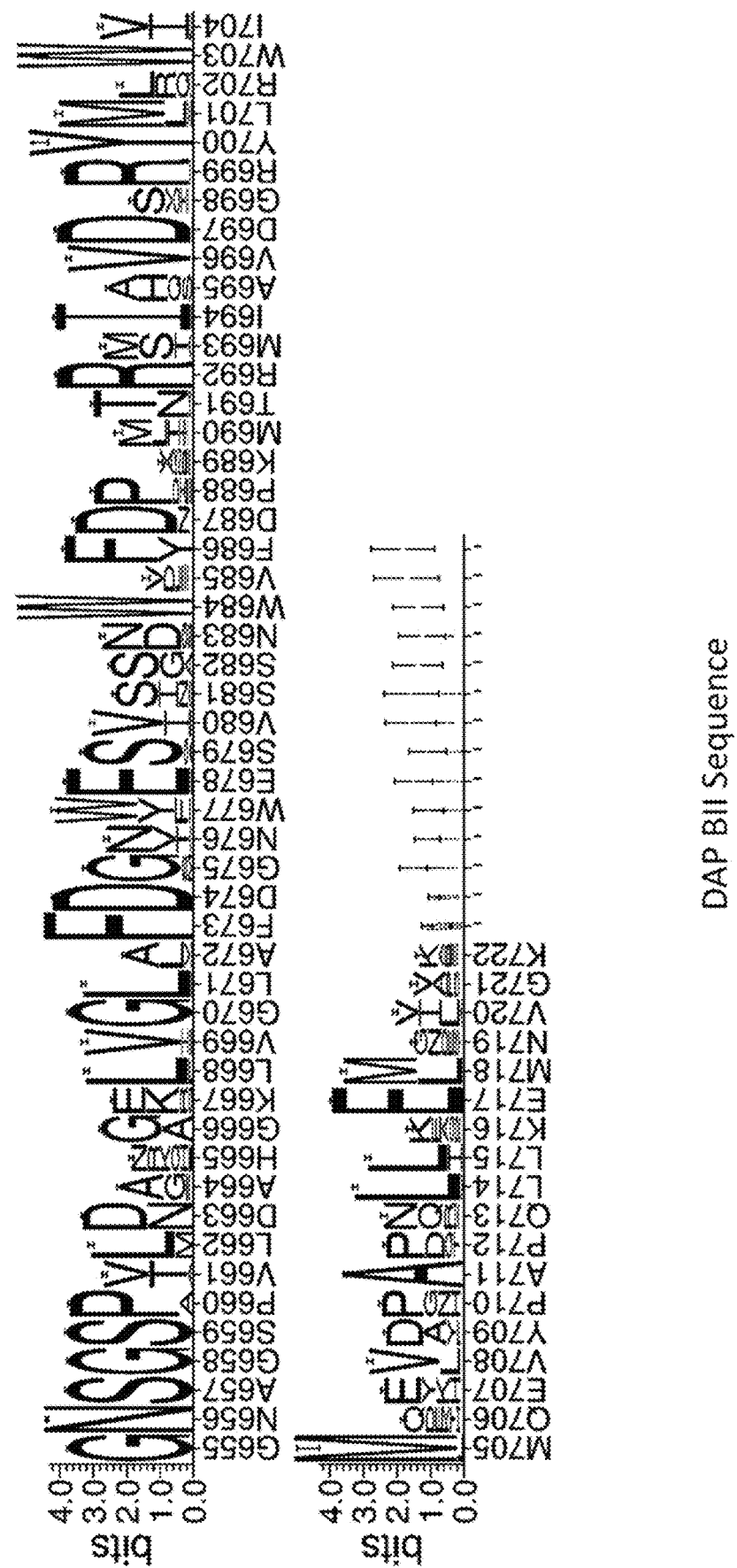
Figure 5:
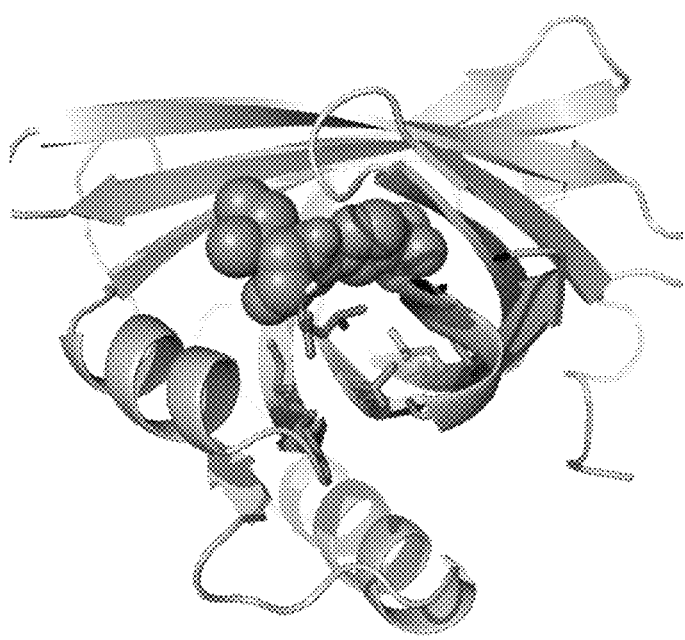
FIG. 5 depicts a model of an exemplary anticalin scaffold bound with N-terminal modified amino acid. The modification is shown in orange spheres and preferably occupies part of a surface accessible pocket. The P1 sidechain (i.e., Leucine in magenta) is surrounded by amino acids (shown in blue stick) that can be mutated to provide specificity.

In some examples, amino acids for modification in a wildtype dipeptide cleavase can be chosen using analysis of crystal structure of the wild-type cleavase (e.g. wildtype DAP BII) and its substrate to identify contact residues and other residues at the protein interaction interface. This analysis can be performed for example, using Rosetta software suite for macromolecular modeling (Das et al., Annu Rev Biochem (2008) 77:363-382). In some embodiments, using the selected target residues for modification, an alignment of wildtype cleavase sequences of other organisms can be used to identify conserved residues (Crooks et al., Genome Res (2004) 14(6): 1188-1190). Based on this analysis, conserved target residues or corresponding residues in homologs can be modified. In some embodiments, the identified contact residues or other residues of interest are modified to introduce new functions. As shown in FIG. 4A-4C, a WebLogo analysis of DAP BII homologs with 60% sequence similarity or identity showed sequence conservation across various residues. For example, sequence conservation was observed for residues at the amine binding sites of DAP BII including positions N215, W216, R220, N330, and D674 in reference to the wildtype DAP BII sequence set forth in SEQ ID NO: 20. In another example, sequence conservation was observed for residues at the amine binding sites of DAP BII including positions G207, K208, F209, G210, G211, D212, I213, D214, N215, W216, M217, W218, P219, R220, H221, T222, G223, A224, F225, A226, A326, and/or N334, in reference to the wildtype DAP BII sequence set forth in SEQ ID NO: 20.

In some aspects, a rational design approach for engineering DAP BII may be used to target domains or residues such that the resulting modified cleavase removes or is configured to remove a labeled N-terminal amino acid (NTAA) using crystal structures of DAP BII in complex with substrates (Sakamoto et al., Scientific Reports 2014, 4:4977). For example, the DAP BII structure in complex with a peptide substrate at the residues N191, W192, R196, N306, and D650 (based on the sequence of the protein set forth in SEQ ID NO: 13; UniProt Accession No. V5YM14) interacts with the peptide N-terminal amine group. Additionally, a loop of approximately 20 residues (residue 183-202 in reference to SEQ ID NO: 13) makes contact with the N-terminal residue and penultimate residue of a bound peptide substrate. These amine binding residues and NTAA and penultimate NTAA binding residues, individually or in combination, may be targeted for modification.

In some aspects, it may be desired to modify the specificity of the unmodified or wildtype cleavase (See e.g., Sakamoto et al., Scientific Reports 2014, 4:4977). In some examples, residues in the S1 subsite or pocket of DAP BII can be targeted to engineer a modified cleavase with preferred specificity (e.g., reduced specificity for a specific amino acid residue at the P1 position of the polypeptide treated with the modified cleavase). In some embodiments, the modified cleavase comprises mutations, e.g., one or more amino acid modifications (e.g., substitutions, additions, deletions) corresponding to position(s) D627, I628, G630, A648, G651, S655, M669, or a combination thereof, with reference to numbering of SEQ ID NO: 13.

In some embodiments, a modified cleavase variant can be identified using a genetic screen. In some cases, the genetic screen uses a cell-based system. In some embodiments, the genetic screen uses prokaryotic cells, such as *E. coli* strains including *E. coli* variants or mutants. In some embodiments, the genetic screen uses eukaryotic cells, such as yeast two-hybrid systems. In some embodiments, the genetic selection is designed to select for modified cleavases with desired characteristics for binding of substrates, cleaving, and/or removal of labeled terminal amino acids.

In some embodiments, carrying out a genetic selection screen involves preparing various cleavase genes (e.g., a dipeptidyl peptidase, a dipeptidyl aminopeptidase, a peptidyl-dipeptidase, a dipeptidyl carboxypeptidase, a sedolisin, or a tripeptidyl peptidase) for expression. A plasmid or cosmid containing nucleic acid sequences encoding mutated or modified cleavase polypeptides is readily constructed using standard techniques well known in the art. In some embodiments, the expression of any of the cleavases (e.g., any of SEQ ID NOs: 5-8, 10-16, 20) may further include a signal sequence. In some cases, the use of a signal sequence may be useful for purification purposes. For example, a periplasm targeting sequence such as PelB can be included in the expression construct. Recombinant vectors can be generated using any of the recombinant techniques known in the art.

In some embodiments, the vectors can include a prokaryotic origin of replication and/or a gene whose expression confers a detectable or selectable marker for propagation and/or selection in prokaryotic systems. Once the vector or DNA sequence containing the constructs has been prepared for expression, the DNA constructs may be introduced into an appropriate host. In some embodiments, prokaryotic hosts can be used including bacteria such as *E. coli., Bacillus, Streptomyces, Pseudomonas, Salmonella, Serratia*, etc. Various techniques may be employed, such as protoplast fusion, calcium phosphate precipitation, electroporation or other conventional techniques. After the fusion, the cells are grown in media and screened for appropriate activities.

In some examples, libraries of mutated cleavase genes can be generated by error prone PCR or rational mutagenesis using the crystal structure of the cleavase as a guide, or a combination thereof. Other suitable methods for generating mutations or generating a library may also be used. A library of mutated cleavase genes can be subsequently cloned into a vector and transformed into an *E. coli* auxotroph strain (available from CSSC *E. coli* Genetic Stock Center at Yale). In some embodiments, the screen involves isolating colonies growing on the selection media and extracting and analyzing plasmid DNA to identify modified cleavase polypeptides that remove a labeled terminal amino acid or labeled terminal dipeptide from a polypeptide. In some embodiments, a screen can be performed to identify and isolate a modified cleavase that cleaves or is configured to cleave a polypeptide with a labeled amino acid (e.g., a PITC-labeled NTAA or a Cbz-labeled NTAA). In some embodiments, the genetic screen is aimed at selecting for the binding of the label but not for a specific amino acid, therefore, the screen uses polypeptides with various labeled terminal amino acids. In some embodiments, selecting a modified cleavase further includes purifying, characterizing, assessing and/or optimizing of the activity of the modified cleavase. The modified cleavase may be isolated and purified in accordance with conventional methods, such as extraction, precipitation, chromatography, affinity chromatography, electrophoresis, or the like.

In some embodiments, a genetics screen or other selection methods can also be used to select for and obtain modified cleavases with an altered active site of the cleavase or with altered binding pockets of the cleavase. In some embodiments, genetics screen or selection methods can also be used to select for and obtain modified cleavases with an altered hinge region of the cleavase. In some embodiments, genetic screen or selection methods can also be used to select for and obtain modified cleavases with an altered binding cleft of the cleavase. In some cases, genetic screen or selection methods can also be used to select for and obtain modified cleavases with an altered inter-lobe cleft of the cleavase. In some embodiments, genetic screen or selection methods can also be used to select for and obtain modified cleavases with an altered alpha amine binding region of the cleavase. For example, the modified cleavase exhibits reduced alpha amine binding compared to the wild-type cleavase polypeptide.

In some embodiments, a genetic screen or other selection methods can also be used to select for and obtain modified cleavases configured to remove a labeled terminal amino acid from polypeptides of various lengths. In some cases, porin size in the *E. coli* outer membrane limits the peptide length that can be uptaken. In some embodiments, this length limitation is overcome by briefly treating *E. coli* with Tris-EDTA or the small molecule MAC 13243 which permeabilizes the *E. coli* outer membrane (e.g., Leive, L. (1974). Ann N Y Acad Sci 235(0): 109-129; Muheim, C. (2017). Scientific Reports 7(1): 17629) and allows uptake of peptides into the periplasmic space. In some embodiments, the modified cleavase is capable of cleaving or is configured to remove amino acids from polypeptides that are greater than 5 amino acids in length, greater than 6 amino acids in length, greater than 7 amino acids in length, greater than 8 amino acids in length, greater than 9 amino acids in length, greater than 10 amino acids in length, greater than 15 amino acids in length, greater than 20 amino acids in length, greater than 25 amino acids in length, or greater than 30 amino acids in length. In some embodiments, the modified dipeptidyl peptidase is capable of cleaving or is configured to remove amino acids from polypeptides that are less than 30 amino acids in length, less than 40 amino acids in length, less than 50 amino acids in length, less than 75 amino acids in length, less than 100 amino acids in length, less than 200 amino acids in length, less than 300 amino acids in length, less than 400 amino acids in length, less than 500 amino acids in length, less than 600 amino acids in length, less than 700 amino acids in length, less than 800 amino acids in length, less than 900 amino acids in length, or less than 1000 amino acids in length. In some embodiments, the modified cleavase is capable of cleaving or is configured to remove amino acids from polypeptides that are between 5 to 100 amino acids in length, between 10 to 100 amino acids in length, between 20 to 100 amino acids in length, between 30 to 100 amino acids in length, between 5 to 50 amino acids in length, between 10 to 50 amino acids in length, between 20 to 50 amino acids in length, between 30 to 50 amino acids in length, between 5 to 30 amino acids in length, between 10 to 30 amino acids in length, between 20 to 30 amino acids in length, between 10 to 20 amino acids in length. In some embodiments, the modified cleavase is capable of cleaving or is configured to remove amino acids from polypeptides that are between 50 to 1000 amino acids in length, between 100 to 1000 amino acids in length, between 300 to 1000 amino acids in length, between 500 to 1000 amino acids in length, between 10 to 500 amino acids in length, between 50 to 500 amino acids in length, between 100 to 500 amino acids in length, or between 200 to 500 amino acids in length.

In some embodiments, the modified cleavase is capable or configured to remove amino acids from partial or digested proteins and polypeptides (e.g., protein or polypeptide fragments). In some embodiments, the modified cleavase is capable or configured to remove amino acids from whole or undigested proteins and polypeptides.

In some embodiments, the modified cleavase removes the single terminal amino acid or terminal dipeptide by contacting the polypeptide with a modified cleavase for less than 5 minutes, less than 10 minutes, less than 20 minutes, less than 30 minutes, less than 40 minutes, less than 50 minutes, less than 60 minutes, less than 2 hours, less than 5 hours, less than 8 hours, or less than 10 hours.

In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 15 minutes. In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 30 minutes. In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 45 minutes. In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 1 hour. In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 2 hours. In some embodiments, the modified cleavase achieves a yield of polypeptides with the terminal amino acid removed of >30%, >40%, >50%, >60%, >70%, >80%, >90%, >95%, >99% or more by treating the polypeptide with the modified cleavase for about less than 5 hours.

In some embodiments, the modified dipeptide or tripeptide cleavase is capable of cleaving terminal amino acids or functions at a temperature of higher than about 10° C., higher than about 20° C. higher than about 30° C., or higher than about 40° C. In some embodiments, the modified dipeptide or tripeptide cleavase is capable of cleaving terminal amino acids or functions at a temperature of about 10° C. to 20° C., about 10° C. to 30° C., about 10° C. to 40° C., about 10° C. to 50° C., about 10° C. to 60° C., about 10° C.

to 70° C., about 10° C. to 80° C., about 10° C. to 90° C. or about 10° C. to 100° C.; about 20° C. to 30° C., about 20° C. to 40° C., about 20° C. to 50° C., about 20° C. to 60° C., about 20° C. to 70° C., about 20° C. to 80° C., about 20° C. to 90° C., or about 20° C. to 100° C.; about 30° C. to 40° C., about 30° C. to 50° C., about 30° C. to 60° C.; about 50° C. to 70° C., about 50° C. to 80° C., about 50° C. to 90° C., or about 50° C. to 100° C. In some embodiments, the modified cleavase is capable of cleaving terminal amino acids at a temperature at which the secondary structure of the polypeptide is disrupted. In some embodiments, the modified cleavase functions at about 20 to 25° C. In some embodiments, the method includes contacting the modified cleavase with the polypeptide while applying heating. In some embodiments, the heating is achieved by applying microwave energy. In some embodiments of any of the methods provided herein, the contacting of the modified cleavase with the polypeptide to remove a terminal amino acid is performed in the presence of microwave energy.

Provided herein are isolated DNA molecules encoding any of the modified cleavases as described in Section I. Also provided are recombinant expression vectors comprising a DNA molecule encoding any of the modified cleavases as described in Section I. In some cases, the DNA molecules and recombinant expression vectors are isolated from the genetic engineering and selection methods described. In some cases, a host cell comprising the DNA molecule is also provided.

In some embodiments, provided herein is a method of producing a modified or variant cleavase, comprising introducing the nucleic acid molecule according to any one of the embodiments described herein or vector according to any one of the embodiments described herein into a host cell under conditions to express the protein in the cell. Also provided herein are methods for producing any of the modified cleavases provided herein including: cultivating a transformed host cell under conditions suitable for expression of the modified cleavase, and separating, purifying and/or recovering the mutant organism expressing the modified cleavase. In some embodiments, provided herein is a host cell comprising a DNA molecule encoding a modified cleavase. In some embodiments, the host cell comprises a recombinant expression vector for expressing a modified cleavase. In some embodiments, the method further includes isolating or purifying the variant or modified cleavase from the cell.

In some embodiments, provided herein is an engineered cell, expressing the variant or modified cleavase polypeptide according to any one of the embodiments described herein or the nucleic acid molecule encoding a variant or modified cleavase described herein, or the vector according to any one of the embodiments described herein. In some embodiments, the variant or modified cleavase polypeptide contains a signal peptide.

II. Polypeptides

In some embodiments, the present disclosure relates to the treatment of polypeptides with any of the modified cleavases provided herein. In some embodiments, the labeled terminal amino acid is removed from a polypeptide (including a partial or fragmented polypeptide).

In some embodiments, the terminal amino acid is removed from a polypeptide that has a length of greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids. In some cases, the length of the polypeptide is greater than 10 amino acids. In some embodiments, the terminal amino acid is removed from a polypeptide that has a length of less than 30 amino acids, less than 40 amino acids, less than 50 amino acids, less than 75 amino acids, less than 100 amino acids, less than 200 amino acids, less than 300 amino acids, less than 400 amino acids, less than 500 amino acids, less than 600 amino acids, less than 700 amino acids, less than 800 amino acids, less than 900 amino acids, or less than 1000 amino acids. In some embodiments, the terminal amino acid is removed from a polypeptide that has a length of between 5 to 100 amino acids, between 10 to 100 amino acids, between 20 to 100 amino acids, between 30 to 100 amino acids, between 5 to 50 amino acids, between 10 to 50 amino acids, between 20 to 50 amino acids, between 30 to 50 amino acids, between 5 to 30 amino acids, between 10 to 30 amino acids, between 20 to 30 amino acids, between 10 to 20 amino acids. In some embodiments, the terminal amino acid is removed from a polypeptide that has a length of between 50 to 1000 amino acids, between 100 to 1000 amino acids, between 300 to 1000 amino acids, between 500 to 1000 amino acids, between 10 to 500 amino acids, between 50 to 500 amino acids, between 100 to 500 amino acids, or between 200 to 500 amino acids.

In some embodiments, the terminal amino acid is removed from a partial or digested protein and polypeptide (e.g., a polypeptide fragment). In some embodiments, the terminal amino acid is removed from a whole or undigested protein and polypeptide.

A polypeptide treated with the modified cleavases provided herein and according the methods disclosed herein may be obtained from a suitable source or sample, including but not limited to: biological samples, such as cells (both primary cells and cultured cell lines), cell lysates or extracts, cell organelles or vesicles, including exosomes, tissues and tissue extracts; biopsy; fecal matter; bodily fluids (such as blood, whole blood, serum, plasma, urine, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (normal joint or a joint affected by disease such as rheumatoid arthritis, osteoarthritis, gout or septic arthritis) of virtually any organism, with mammalian-derived samples, including microbiome-containing samples, being preferred and human-derived samples, including microbiome-containing samples, being particularly preferred; environmental samples (such as air, agricultural, water and soil samples); microbial samples including samples derived from microbial biofilms and/or communities, as well as microbial spores; research samples including extracellular fluids, extracellular supernatants from cell cultures, inclusion bodies in bacteria, cellular compartments including mitochondrial compartments, and cellular periplasm.

In certain embodiments, the polypeptide is a protein or a protein complex. Amino acid sequence information and post-translational modifications of the polypeptide are transduced into a nucleic acid encoded library that can be analyzed via next generation sequencing methods. A polypeptide may comprise L-amino acids, D-amino acids, or both. A polypeptide may comprise a standard, naturally occurring amino acid, a modified amino acid (e.g., post-translational modification), an amino acid analog, an amino acid mimetic, or any combination thereof. In some embodiments, the polypeptide is naturally occurring, synthetically produced, or recombinantly expressed. In any of the aforementioned embodiments, the polypeptide may further comprise a post-translational modification.

Standard, naturally occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). Non-standard amino acids include selenocysteine, pyrrolysine, and N-formylmethionine, β-amino acids, Homo-amino acids, Proline and Pyruvic acid derivatives, 3-substituted Alanine derivatives, Glycine derivatives, Ring-substituted Phenylalanine and Tyrosine Derivatives, Linear core amino acids, and N-methyl amino acids.

A post-translational modification (PTM) of a polypeptide may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide, polypeptide, or protein. Modifications of the terminal amino group include, but are not limited to, desamino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. Phosphorylation is the most common post-translational modification and plays an important role in regulation of protein, particularly in cell signaling (Prabakaran et al., (2012) Wiley Interdiscip Rev Syst Biol Med 4: 565-583). The addition of sugars to proteins, such as glycosylation, has been shown to promote protein folding, improve stability, and modify regulatory function. The attachment of lipids to proteins enables targeting to the cell membrane. A post-translational modification can also include modifications to include one or more detectable labels.

In certain embodiments, the polypeptide can be fragmented. For example, the fragmented polypeptide can be obtained by fragmenting a polypeptide, protein or protein complex from a sample, such as a biological sample. The polypeptide, protein or protein complex can be fragmented by any means known in the art, including fragmentation by a protease or endopeptidase. In some embodiments, fragmentation of a polypeptide, protein or protein complex is targeted by use of a specific protease or endopeptidase. A specific protease or endopeptidase binds and cleaves at a specific consensus sequence (e.g., TEV protease which is specific for ENLYFQ\S consensus sequence). In other embodiments, fragmentation of a peptide, polypeptide, or protein is non-targeted or random by use of a non-specific protease or endopeptidase. A non-specific protease may bind and cleave at a specific amino acid residue rather than a consensus sequence (e.g., proteinase K is a non-specific serine protease). Proteinases and endopeptidases are well known in the art, and examples of such that can be used to cleave a protein or polypeptide into smaller peptide fragments include proteinase K, trypsin, chymotrypsin, pepsin, thermolysin, thrombin, Factor Xa, furin, endopeptidase, papain, pepsin, subtilisin, elastase, enterokinase, Genenase™ I, Endoproteinase LysC, Endoproteinase AspN, Endoproteinase GluC, etc. (Granvogl et al., (2007) Anal Bioanal Chem 389: 991-1002). In certain embodiments, a peptide, polypeptide, or protein is fragmented by proteinase K, or optionally, a thermolabile version of proteinase K to enable rapid inactivation. Proteinase K is quite stable in denaturing reagents, such as urea and SDS, enabling digestion of completely denatured proteins.

In some embodiments, the polypeptide is contacted with one or more enzymes in addition to a modified cleavase to eliminate the NTAA (e.g., a proline aminopeptidase to remove an N-terminal proline, if present). In some embodiments, the additional enzyme eliminates an NTAA from the polypeptide that is a proline. In some specific examples, the enzyme is a proline aminopeptidase, a proline iminopeptidase (PIP), or a pyroglutamate aminopeptidase (pGAP). In some embodiments, one or more modified cleavases are used in combination with other enzymes to treat the polypeptides. In some embodiments, the polypeptide is first contacted with a proline aminopeptidase under conditions suitable to remove an N-terminal proline, if present.

Chemical reagents can also be used to digest proteins into peptide fragments. A chemical reagent may cleave at a specific amino acid residue (e.g., cyanogen bromide hydrolyzes peptide bonds at the C-terminus of methionine residues). Chemical reagents for fragmenting polypeptides or proteins into smaller peptides include cyanogen bromide (CNBr), hydroxylamine, hydrazine, formic acid, BNPS-skatole [2-(2-nitrophenylsulfenyl)-3-methylindole], iodosobenzoic acid, .NTCB+Ni (2-nitro-5-thiocyanobenzoic acid), etc.

In certain embodiments, some polypeptides can be treated with a reagent for enzymatic or chemical elimination. In certain embodiments, following enzymatic or chemical elimination, the resulting polypeptide fragments are approximately the same desired length, e.g., from about 10 amino acids to about 70 amino acids, from about 10 amino acids to about 60 amino acids, from about 10 amino acids to about 50 amino acids, about 10 to about 40 amino acids, from about 10 to about 30 amino acids, from about 20 amino acids to about 70 amino acids, from about 20 amino acids to about 60 amino acids, from about 20 amino acids to about 50 amino acids, about 20 to about 40 amino acids, from about 20 to about 30 amino acids, from about 30 amino acids to about 70 amino acids, from about 30 amino acids to about 60 amino acids, from about 30 amino acids to about 50 amino acids, or from about 30 amino acids to about 40 amino acids. A elimination reaction may be monitored, preferably in real time, by spiking the protein or polypeptide sample with a short test FRET (fluorescence resonance energy transfer) polypeptide comprising a peptide sequence containing a proteinase or endopeptidase elimination site. In the intact FRET peptide, a fluorescent group and a quencher group are attached to either end of the peptide sequence containing the elimination site, and fluorescence resonance energy transfer between the quencher and the fluorophore leads to low fluorescence. Upon elimination of the test peptide by a protease or endopeptidase, the quencher and fluorophore are separated giving a large increase in fluorescence. An elimination reaction can be stopped when a certain fluorescence intensity is achieved, allowing a reproducible elimination end point to be achieved.

A. Providing the Polypeptide Joined to a Support or in Solution

In some embodiments, polypeptides of the present disclosure are joined to a surface of a solid support (also referred to as "substrate surface"). In some cases, the polypeptides are joined to a solid support prior to contacting with the modified cleavase. In some cases, the modified cleavase removes a labeled terminal amino acid from a polypeptide that is join (directly or indirectly) to a solid support. In some embodiments, the labeled terminal amino acid is removed as a single amino acid or as part of a dipeptide.

The solid support can be any porous or non-porous support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow cell, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, or any combination thereof. Solid supports further include thin film, membrane, bottles, dishes, fibers, woven fibers, shaped polymers such as tubes, particles, beads, microparticles, or any combination thereof. For example, when solid surface is a bead, the bead can include, but is not limited to, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, glass bead, a controlled pore bead, a silica-based bead, or any combinations thereof.

In certain embodiments, a solid support is a bead, which may refer to an individual bead or a plurality of beads. In some embodiments, the bead is compatible with a selected next generation sequencing platform that will be used for downstream analysis (e.g., SOLiD or 454). In some embodiments, a solid support is an agarose bead, a paramagnetic bead, a polystyrene bead, a polymer bead, an acrylamide bead, a solid core bead, a porous bead, a glass bead, or a controlled pore bead. In further embodiments, a bead may be coated with a binding functionality (e.g., amine group, affinity ligand such as streptavidin for binding to biotin labeled polypeptide, antibody) to facilitate binding to a polypeptide.

Proteins, polypeptides, or peptides can be joined to the solid support, directly or indirectly, by any means known in the art, including covalent and non-covalent interactions, or any combination thereof (see, e.g., Chan et al., 2007, PLoS One 2:e1164; Cazalis et al., Bioconj. Chem. 15:1005-1009; Soellner et al., 2003, J. Am. Chem. Soc. 125:11790-11791; Sun et al., 2006, Bioconjug. Chem. 17-52-57; Decreau et al., 2007, J. Org. Chem. 72:2794-2802; Camarero et al., 2004, J. Am. Chem. Soc. 126:14730-14731; Girish et al., 2005, Bioorg. Med. Chem. Lett. 15:2447-2451; Kalia et al., 2007, Bioconjug. Chem. 18:1064-1069; Watzke et al., 2006, Angew Chem. Int. Ed. Engl. 45:1408-1412; Parthasarathy et al., 2007, Bioconjugate Chem. 18:469-476; and Bioconjugate Techniques, G. T. Hermanson, Academic Press (2013), and are each hereby incorporated by reference in their entirety). For example, the peptide may be joined to the solid support by a ligation reaction. Alternatively, the solid support can include an agent or coating to facilitate joining, either direct or indirectly, the peptide to the solid support. Any suitable molecule or materials may be employed for this purpose, including proteins, nucleic acids, carbohydrates and small molecules. For example, in one embodiment the agent is an affinity molecule. In another example, the agent is an azide group, which group can react with an alkynyl group in another molecule to facilitate association or binding between the solid support and the other molecule.

Proteins, polypeptides, or peptides can be joined to the solid support using methods referred to as "click chemistry." For this purpose, any reaction which is rapid and substantially irreversible can be used to attach proteins, polypeptides, or peptides to the solid support. Exemplary reactions include the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO); or pTet and an alkene), alkene and tetrazole photoreaction, Staudinger ligation of azides and phosphines, and various displacement reactions, such as displacement of a leaving group by nucleophilic attack on an electrophilic atom (Horisawa, Front Physiol (2014). 5: 457; Knall, Hollauf et al., Tetrahedron Lett (2014) 55(34): 4763-4766). Exemplary displacement reactions include reaction of an amine with: an activated ester; an N-hydroxysuccinimide ester; an isocyanate; an isothioscyanate, an aldehyde, an epoxide, or the like.

In some embodiments, the polypeptide and solid support are joined by a functional group capable of formation by reaction of two complementary reactive groups, for example a functional group which is the product of one of the foregoing "click" reactions. In various embodiments, functional group can be formed by reaction of an aldehyde, oxime, 98erivatiz, hydrazide, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester, pentynoic acid STP ester), ketone, α,β-unsaturated carbonyl, alkene, maleimide, α-haloimide, epoxide, aziridine, tetrazine, tetrazole, phosphine, biotin or thiirane functional group with a complementary reactive group. An exemplary reaction is a reaction of an amine (e.g., primary amine) with an N-hydroxysuccinimide ester or isothiocyanate.

In some embodiments, the functional group comprises an alkene, ester, amide, thioester, disulfide, carbocyclic, heterocyclic or heteroaryl group. In further embodiments, the functional group comprises an alkene, ester, amide, thioester, thiourea, disulfide, carbocyclic, heterocyclic or heteroaryl group. In other embodiments, the functional group comprises an amide or thiourea. In some more specific embodiments, functional group is a triazolyl functional group, an amide, or thiourea functional group.

In some embodiments, iEDDA click chemistry is used for immobilizing polypeptides to a solid support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction.

In some embodiments, the substrate surface is functionalized with TCO, and the recording tag-labeled protein, polypeptide, peptide is immobilized to the TCO coated substrate surface via an attached m-tetrazine moiety.

In some embodiments, polypeptides are immobilized to a surface of a solid support by its C-terminus, N-terminus, or an internal amino acid, for example, via an amine, carboxyl, or sulfydryl group. Standard activated supports used in coupling to amine groups include CNBr-activated, NHS-activated, aldehyde-activated, azlactone-activated, and CDI-activated supports. Standard activated supports used in carboxyl coupling include carbodiimide-activated carboxyl moieties coupling to amine supports. Cysteine coupling can employ maleimide, idoacetyl, and pyridyl disulfide activated supports. An alternative mode of peptide carboxy terminal immobilization uses anhydrotrypsin, a catalytically inert derivative of trypsin that binds peptides containing lysine or arginine residues at their C-termini without cleaving them.

In certain embodiments, a polypeptide is immobilized to a solid support via covalent attachment of a solid surface bound linker to a lysine group of the protein, polypeptide, or peptide.

In certain embodiments, a polypeptide is first labeled with a DNA tag, and the chimeric DNA-polypeptide molecule is immobilized to a solid support via nucleic acid hybridization and ligation to a DNA sequence attached to the solid support. In some embodiments, protein and polypeptide fragmentation into peptides can be performed before or after attachment of a DNA tag or DNA recording tag.

B. Optional Processing of Polypeptides

A sample of polypeptides can undergo protein fractionation methods prior to attachment to a solid support, where proteins or peptides are separated by one or more properties such as cellular location, molecular weight, hydrophobicity, or isoelectric point, or protein enrichment methods. Alternatively, or additionally, protein enrichment methods may be used to select for a specific protein or peptide (see, e.g., Whiteaker et al., (2007) Anal. Biochem. 362:44-54) or to select for a particular post translational modification (see, e.g., Huang et al., (2014) J. Chromatogr. A 1372:1-17). Alternatively, a particular class or classes of proteins such as immunoglobulins, or immunoglobulin (Ig) isotypes such as IgG, can be affinity enriched or selected for analysis. In the case of immunoglobulin molecules, analysis of the sequence and abundance or frequency of hypervariable sequences involved in affinity binding are of particular interest, particularly as they vary in response to disease progression or correlate with healthy, immune, and/or disease phenotypes. Overly abundant proteins can also be subtracted from the sample using standard immunoaffinity methods. Depletion of abundant proteins can be useful for plasma samples where over 80% of the protein constituent is albumin and immunoglobulins. Several commercial products are available for depletion of plasma samples of overly abundant proteins, such as PROTIA and PROT20 (Sigma-Aldrich).

In some embodiments, the methods provided herein may be performed on polypeptides that have been normalized. In some embodiments, subtraction of certain protein species (e.g., highly abundant proteins) from the sample is performed. This can be accomplished, for example, using commercially available protein depletion reagents such as Sigma's PROT20 immuno-depletion kit, which deplete the top 20 plasma proteins. Additionally, it would be useful to have an approach that greatly reduced the dynamic range even further to a manageable 3-4 orders. In certain embodiments, a protein sample dynamic range can be modulated by fractionating the protein sample using standard fractionation methods, including electrophoresis and liquid chromatography (Zhou et al., Anal Chem (2012) 84(2): 720-734), or partitioning the fractions into compartments (e.g., droplets) loaded with limited capacity protein binding beads/resin (e.g. hydroxylated silica particles) (McCormick, Anal Biochem (1989) 181(1): 66-74) and eluting bound protein. Excess protein in each compartmentalized fraction is washed away.

Examples of electrophoretic methods include capillary electrophoresis (CE), capillary isoelectric focusing (CIEF), capillary isotachophoresis (CITP), free flow electrophoresis, gel-eluted liquid fraction entrapment electrophoresis (GEL-FrEE). Examples of liquid chromatography protein separation methods include reverse phase (RP), ion exchange (IE), size exclusion (SE), hydrophilic interaction, etc. Examples of compartment partitions include emulsions, droplets, microwells, physically separated regions on a flat substrate, etc. Exemplary protein binding beads/resins include silica nanoparticles 101erivatized with phenol groups or hydroxyl groups (e.g., StrataClean Resin from Agilent Technologies, RapidClean from LabTech, etc.). By limiting the binding capacity of the beads/resin, highly-abundant proteins eluting in a given fraction will only be partially bound to the beads, and excess proteins removed.

III. Exemplary Use of Modified Cleavase and Related Methods

Figure 2A:
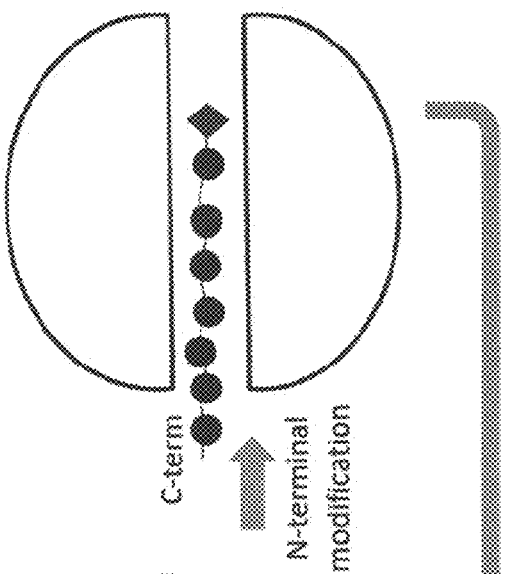
FIG. 2A-2C is a schematic depicting a cycle of terminal amino acid removal using the modified cleavase and terminal amino acid labeling.
Figure 2B:
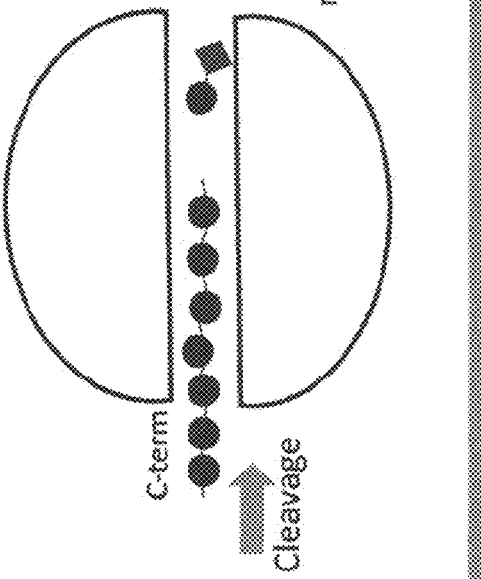
Figure 2C:
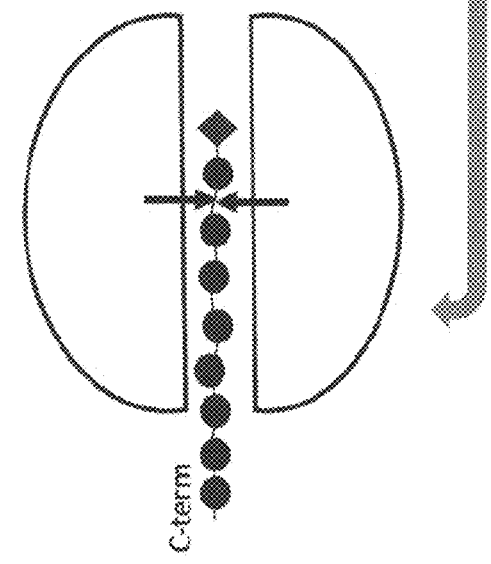

Provided herein is a method of treating one or more polypeptides comprising contacting the polypeptide with a modified cleavase. In some embodiments, the modified cleavase comprises a mutation, e.g., one or more amino acid modifications in an unmodified cleavase, wherein the modified cleavase is derived from a dipeptide cleavase and removes a single labeled terminal amino acid from a polypeptide. In some embodiments, the modified cleavase is derived from a tripeptide cleavase and removes a single labeled terminal amino acid from a polypeptide or a single labeled terminal dipeptide from a polypeptide. In some embodiments, polypeptides are contacted with any one or more of the modified cleavases as described in Section I. In some embodiments, the method further comprises contacting the polypeptide with a reagent for labeling the terminal amino acid. In some embodiments, the contacting with the reagent for labeling the terminal amino acid is with any one or more of the reagents described in Section I. A. In some embodiments, one or more cycles of contacting the polypeptide with the modified cleavase and contacting with a reagent to label the terminal amino acid is performed, such as in a cyclic manner as depicted in FIG. 2A-2C. In some embodiments, the polypeptide is bound to a support. In some embodiments, the method includes joining the polypeptides to a solid support (e.g., directly or indirectly). In some embodiments, the removal of NTAA from a peptide using the provided modified cleavases can be combined with a chemical method for removing the NTAA from a peptide, such as described in PCT publication number WO 2019/089846. In some embodiments, the removed labeled terminal amino acid is removed as a single amino acid or as part of a dipeptide.

In some embodiments, the modified cleavases provided herein can be used for treating polypeptides to be analyzed and/or sequenced. In some embodiments, the methods are for determining the sequence of at least a portion of the polypeptide. In some embodiments, the provided methods can be used in the context of a degradation-based polypeptide sequencing assay. In some cases, the method may include performing any of the methods as described in International Patent Publication No. WO 2017/192633. In some cases, the sequence of the polypeptide is analyzed by construction of an extended recording tag (e.g., DNA sequence) representing the polypeptide sequence, such as an extended recording tag. In some cases, the methods provided herein apply to or can be used in combination with a ProteoCode assay. In some embodiments employing a cyclic degradation-based polypeptide analysis method, the provided modified cleavase provides certain advantages. For example, the recognition and removal of labeled amino acids may provide a pause to amino acid removal as compared to an enzyme which removes unlabeled amino acids, which may continuously remove amino acids from the polypeptide before other steps of the assay can be performed (e.g, binding of the NTAA by a binding agent and recording information of the NTAA to a recording tag). Thus, in some cases, by recognizing and removing labeled amino acids, the modified cleavase removes the NTAA only after a labeling step has occurred. Thereby, the modified cleavase provides control over the removal of amino acids compared to the unmodified cleavase which removes unlabeled amino acids.

In some embodiments, a method comprising the modified cleavase is conducted in the absence of a condition that degrades nucleic acids (e.g., DNA, such as a recording tag). In some embodiments, the method comprising the modified cleavase is conducted in the absence of a chemical condition that degrades nucleic acids. In some embodiments, the method comprising the modified cleavase is conducted in conditions compatible with a degradation-based polypeptide sequencing assay (e.g., the methods as described in International Patent Publication No. WO 2017/192633). In some cases, the method comprising the modified cleavase is conducted in the presence of conditions compatible with nucleic acids. In some embodiments, the method comprising the modified cleavase is conducted in the absence of a strong acid or a strong base. In some aspects, the strong acid is a strong anhydrous acid. In some examples, the method comprising the modified cleavase is conducted in the absence of anhydrous TFA.

In some embodiments, the method includes contacting the polypeptide with more than one modified cleavase. In some cases, various modified cleavases may exhibit different characteristics, for example, binding preferences for polypeptides and/or differences in cleaving amino acids. In some embodiments, different modified cleavases may be used in any of the described methods, as a mixture of enzymes or each separately. In some embodiments, the different modified cleavases are contacted with polypeptides simultaneously or sequentially.

In some embodiments, the polypeptide is contacted with one or more additional enzymes to eliminate the NTAA (e.g., a proline aminopeptidase to remove an N-terminal proline, if present). The methods of the invention may include optionally treating the polypeptides with an enzyme to remove one or more NTAAs (e.g., proline aminopeptidase) before, during, or after treatment with any of the provided chemical reagents for labeling the NTAA. The methods of the invention may include optionally treating the polypeptides with an enzyme to remove one or more NTAAs (e.g., proline aminopeptidase) before, during, or after treatment with any of the provided modified cleavases. In some embodiments, the enzyme eliminates an NTAA from the polypeptide that is a proline. In some specific examples, the enzyme is a proline aminopeptidase, a proline iminopeptidase (PIP), or a pyroglutamate aminopeptidase (pGAP). In some embodiments, one or more modified cleavases are used in combination with other enzymes to treat the polypeptides. In some specific cases, the modified cleavase and/or other enzymes are provided as a cocktail.

In some embodiments, the method further comprises contacting the polypeptide with a one or more binding agents capable of binding to the terminal amino acid of the polypeptide, wherein each binding agent comprises a coding tag with identifying information regarding the binding agent. In some cases, the binding agent may bind to a labeled terminal amino acid of the polypeptide. In some further embodiments, the method further comprises transferring the identifying information of the coding tag to a recording tag attached to the polypeptide, thereby generating an extended recording tag on the polypeptide. In some particular embodiments, the method further comprises removing or releasing the one or more binding agents from the polypeptide.

In some embodiments, one or more steps of contacting the polypeptide with various reagents, including for example, contacting with the modified cleavase, with the reagent to label the terminal amino acid, and/or with binding reagent(s), is repeated in a cyclic manner. In some embodiments, provided is a method for analyzing a polypeptide, comprising the steps of: (a) contacting a polypeptide with a binding agent capable of binding to the terminal amino acid of the polypeptide, wherein each binding agent comprises a coding tag with identifying information regarding the binding agent; (b) transferring the identifying information of the coding tag to a recording tag associated with each of the polypeptides to generate an extended recording tag; (c) contacting the polypeptide with a reagent to label the terminal amino acid of the polypeptide; and (d) contacting the polypeptide with a modified cleavase comprising a mutation, e.g., one or more amino acid modifications in an unmodified cleavase, wherein the modified cleavase removes a single terminal amino acid labeled by the reagent in step (c) from the polypeptide. The removed terminal amino acid may be removed as a single amino acid residue or as part of a dipeptide. In some embodiments, steps (a)-(d) are repeated for "n" binding cycles, wherein the information of each coding tag of each binding agent that binds to the polypeptide is transferred to the extended recording tag generated from the previous binding cycle to generate an nth order extended recording tag. In some embodiments, the method further comprises (b1) removing or releasing the one or more binding agents from the plurality of polypeptides. In some embodiments, the polypeptides includes a plurality of polypeptides. In some embodiments, the polypeptide is contacted with a plurality of binding agents. In some embodiments, the polypeptide is contacted with two or more binding agents.

In some examples, step (a) is performed before step (b); step (a) is performed before step (c); step (a) is performed before step (d); step (b) is performed before step (c); step (b) is performed before step (d); step (c) is performed before step (a); step (c) is performed before step (b); and/or step (c) is performed before step (d). In some particular embodiments, the steps are performed in the order: (a), (b), (c), and (d). In some particular embodiments, the steps are performed in the order: (c), (a), (b), and (d). In some embodiments, the method further comprises (e) analyzing the nth order extended recording tag. In some embodiments, the method further comprises removing the one or more binding agents. In some embodiments, step (b1) is performed after step (a); step (b1) is performed after step (b); step (b1) is performed before step (c); and/or step (b1) is performed before step (d).

In an exemplary workflow, the treatment and analysis of the polypeptides is as follows: a large collection of polypeptides (e.g., 50 million-1 billion or more) from a proteolytic digest are immobilized randomly on a single molecule sequencing substrate (e.g., beads) at an appropriate intramolecular spacing. In some cases, the polypeptides are attached to recording tags. In a cyclic manner, the terminal amino acid (e.g., N-terminal amino acid) of each peptide is labeled (e.g., PTC, modified-PTC, Cbz, DNP, SNP, acetyl, guanidinyl, amino guanidinyl, heterocyclic methanimine). In some cases, the labeling of the terminal amino acid can be performed as a later step. The labeled N-terminal amino acid (e.g., PITC-NTAA, Cbz-NTAA, DNP-NTAA, SNP-NTAA, acetyl-NTAA, guanidinylated-NTAA, heterocyclic methanimine-NTAA) of each immobilized peptide is bound by the cognate NTAA binding agent which is attached to a coding tag, and information from the coding tag associated with the bound NTAA binding agent is transferred to the recording tag associated with the immobilized peptide, thereby generating an extended recording tag. In some embodiments, the one or more bindings agents is removed or released from the polypeptides. The labeled NTAA is removed by contacting with a modified cleavase which is capable of removing a single amino acid that is labeled from the polypeptide. One or more cycles of the labeling, contacting with the binding agent, transferring identifying information, and removal of the single amino acid can be performed.

In some examples, the final extended recording tag is optionally flanked by universal priming sites to facilitate downstream amplification and/or DNA sequencing. The forward universal priming site (e.g., Illumina's P5-S1 sequence) can be part of the original recording tag design and the reverse universal priming site (e.g., Illumina's P7-S2' sequence) can be added as a final step in the extension of the recording tag. In some embodiments, the addition of forward and reverse priming sites can be done independently of a binding agent.

In some embodiments, the order of the steps in the process for a degradation-based peptide or polypeptide sequencing assay can be reversed or be performed in various orders. For example, in some embodiments, the terminal amino acid labeling can be conducted before and/or after the polypeptide is bound to the binding agent. In some embodiments, contacting with the one or more binding agents is before contacting the polypeptide with the reagent for labeling the terminal amino acid. In some cases, contacting with the one or more binding agents is before contacting the polypeptide with the modified cleavase to remove the labeled terminal amino acid.

In some embodiments, the terminal amino acid labeling can be conducted before or after the polypeptide is bound to a support. In some embodiments, the terminal amino acid removal can be conducted before and/or after the polypeptide is bound to the binding agent. In some embodiments, the contacting of the polypeptides with the reagent for labeling the terminal amino acid is before the contacting with the binding agent and the contacting with the one or more binding agents is before the contacting of the polypeptides with the modified cleavase. In some embodiments, transferring of the identifying information is performed after the contacting of the polypeptide with the one or more binding agents and before the contacting of the polypeptide with the modified cleavase.

In some of any such embodiments, removing the one or more binding agents is after the transferring of identifying information from the coding tag to a recording tag associated with each of the polypeptides to generate an extended recording tag. In some of any such embodiments, removing the one or more binding agents is before contacting the polypeptides with a reagent to label the terminal amino acid of the polypeptide. In some embodiments, removing the one or more binding agents is before contacting the polypeptide with a modified cleavase.

In some embodiments, the order of any of the steps of the provided methods for treating the proteins or polypeptides can be reversed or be performed in various orders.

A. Attaching Recording Tags to Polypeptides

In some embodiments, the methods provided comprise contacting polypeptides with the modified cleavase and optionally other reagents for polypeptide analysis. In one embodiment, the protein or polypeptide is labeled with DNA recording tags through standard amine coupling chemistries. The ε-amino group (e.g., of lysine residues) and the N-terminal amino group are particularly susceptible to labeling with amine-reactive coupling agents, depending on the pH of the reaction (Mendoza et al., Mass Spectrom Rev (2009) 28(5): 785-815). In a particular embodiment, the recording tag is comprised of a reactive moiety (e.g., for conjugation to a solid surface, a multifunctional linker, or a polypeptide), a linker, a universal priming sequence, a barcode (e.g., compartment tag, partition barcode, sample barcode, fraction barcode, or any combination thereof), an optional UMI, and a spacer (Sp) sequence for facilitating information transfer to/from a coding tag. In some cases, wherein ligation is used, the Sp sequence can serve as an overhang of 1-8 bases. In some cases, the recording tag does not include a spacer. In another embodiment, the protein can be first labeled with a universal DNA tag, and the barcode-Sp sequence (representing a sample, a compartment, a physical location on a slide, etc.) are attached to the protein later through and enzymatic or chemical coupling step. A universal DNA tag comprises a short sequence of nucleotides that are used to label a polypeptide and can be used as point of attachment for a barcode (e.g., compartment tag, recording tag, etc.). For example, a recording tag may comprise at its terminus a sequence complementary to the universal DNA tag. In certain embodiments, a universal DNA tag is a universal priming sequence. Upon hybridization of the universal DNA tags on the labeled protein to complementary sequence in recording tags (e.g., bound to beads), the annealed universal DNA tag may be extended via primer extension, transferring the recording tag information to the DNA tagged protein. In a particular embodiment, the protein is labeled with a universal DNA tag prior to proteinase digestion into peptides. The universal DNA tags on the labeled peptides from the digest can then be converted into an informative and effective recording tag. In some embodiments, protein and polypeptide fragmentation into peptides can be performed before or after attachment of a DNA tag or DNA recording tag.

At least one recording tag is associated or co-localized directly or indirectly with the polypeptide and joined to the solid support. A recording tag may comprise DNA, RNA, or polynucleotide analogs including PNA, gPNA, GNA, HNA, BNA, XNA, TNA, or a combination thereof. A recording tag may be single stranded, or partially or completely double stranded. A recording tag may have a blunt end or overhanging end. In certain embodiments, upon binding of a binding agent to a polypeptide, identifying information of the binding agent's coding tag is transferred to the recording tag to generate an extended recording tag. Further extensions to the extended recording tag can be made in subsequent binding cycles.

A recording tag can be joined to the solid support, directly or indirectly (e.g., via a linker), by any means known in the art, including covalent and non-covalent interactions, or any combination thereof. For example, the recording tag may be joined to the solid support by a ligation reaction. Alternatively, the solid support can include an agent or coating to facilitate joining, either direct or indirectly, of the recording tag, to the solid support. Strategies for immobilizing nucleic acid molecules to solid supports (e.g., beads) have been described in U.S. Pat. No. 5,900,481; Steinberg et al. (2004) Biopolymers 73:597-605; Lund et al., (1988) Nucleic Acids Res. 16: 10861-10880).

In certain embodiments, the co-localization of a polypeptide and associated recording tag is achieved by conjugating polypeptide and recording tag to a bifunctional linker attached directly to the solid support surface (Steinberg et al. (2004) Biopolymers 73:597-605). In further embodiments, a trifunctional moiety is used to derivatize the solid support (e.g., beads), and the resulting bifunctional moiety is coupled to both the polypeptide and recording tag. In other embodiments, the co-localization of a polypeptide and associated recording tag is achieved by coupling the polypeptide to the associated DNA recording tag and ligating the chimera to a DNA decorated solid support surface.

Methods and reagents (e.g., click chemistry reagents and photoaffinity labelling reagents) such as those described for attachment of polypeptides and solid supports, may also be used for attachment of recording tags.

In a particular embodiment, a single recording tag is attached to a polypeptide, preferably via the attachment to a de-blocked N- or C-terminal amino acid. In another embodiment, multiple recording tags are attached to the polypeptide, preferably to the lysine residues or peptide backbone. In some embodiments, a polypeptide labeled with multiple recording tags is fragmented or digested into smaller peptides, with each peptide labeled on average with one recording tag.

In certain embodiments, a polypeptide is first labeled with a DNA recording tag, and the chimeric DNA-polypeptide molecule is immobilized to a solid support via nucleic acid hybridization and ligation to a DNA sequence attached to the solid support.

In certain embodiments, a recording tag comprises an optional, unique molecular identifier (UMI), which provides a unique identifier tag for each polypeptide to which the UMI is associated with. A UMI can be about 3 to about 40 bases, or a subrange thereof, e.g., about 3 to about 30 bases, about 3 to about 20 bases, or about 3 to about 10 bases, or about 3 to about 8 bases. In some embodiments, a UMI is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, or 40 bases in length. A UMI can be used to de-convolute sequencing data from a plurality of extended recording tags to identify sequence reads from individual polypeptides. In some embodiments, within a library of polypeptides, each polypeptide is associated with a single recording tag, with each recording tag comprising a unique UMI. In other embodiments, multiple copies of a recording tag are associated with a single polypeptide, with each copy of the recording tag comprising the same UMI. In some embodiments, a UMI has a different base sequence than the spacer or encoder sequences within the binding agents' coding tags to facilitate distinguishing these components during sequence analysis.

In certain embodiments, a recording tag comprises a barcode, e.g., other than the UMI if present. A barcode is a nucleic acid molecule of about 3 to about 30 bases, or a subrange thereof, e.g., about 3 to about 25 bases, about 3 to about 20 bases, about 3 to about 10 bases, about 3 to about 10 bases, about 3 to about 8 bases in length. In some embodiments, a barcode is about 3 bases, 4 bases, 5 bases, 6 bases, 7 bases, 8 bases, 9 bases, 10 bases, 11 bases, 12 bases, 13 bases, 14 bases, 15 bases, 20 bases, 25 bases, or 30 bases in length. In one embodiment, a barcode allows for multiplex sequencing of a plurality of samples or libraries. A barcode may be used to identify a partition, a fraction, a compartment, a sample, a spatial location, or library from which the polypeptide derived. Barcodes can be used to de-convolute multiplexed sequence data and identify sequence reads from an individual sample or library. For example, a barcoded bead is useful for methods involving emulsions and partitioning of samples, e.g., for purposes of partitioning the proteome.

A barcode can represent a compartment tag in which a compartment, such as a droplet, microwell, physical region on a solid support, etc. is assigned a unique barcode. The association of a compartment with a specific barcode can be achieved in any number of ways such as by encapsulating a single barcoded bead in a compartment, e.g., by direct merging or adding a barcoded droplet to a compartment, by directly printing or injecting a barcode reagent to a compartment, etc. The barcode reagents within a compartment are used to add compartment-specific barcodes to the polypeptide or fragments thereof within the compartment. Applied to protein partitioning into compartments, the barcodes can be used to map analysed peptides back to their originating protein molecules in the compartment. This can greatly facilitate protein identification. Compartment barcodes can also be used to identify protein complexes.

In other embodiments, multiple compartments that represent a subset of a population of compartments may be assigned a unique barcode representing the subset.

Alternatively, a barcode may be a sample identifying barcode. A sample barcode is useful in the multiplexed analysis of a set of samples in a single reaction vessel or immobilized to a single solid substrate or collection of solid substrates (e.g., a planar slide, population of beads contained in a single tube or vessel, etc.). Polypeptides from many different samples can be labeled with recording tags with sample-specific barcodes, and then all the samples pooled together prior to immobilization to a solid support, cyclic binding, and recording tag analysis. Alternatively, the samples can be kept separate until after creation of a DNA-encoded library, and sample barcodes attached during PCR amplification of the DNA-encoded library, and then mixed together prior to sequencing. This approach could be useful when assaying analytes (e.g., proteins) of different abundance classes. For example, the sample can be split and barcoded, and one portion processed using binding agents to low abundance analytes, and the other portion processed using binding agents to higher abundance analytes. In a particular embodiment, this approach helps to adjust the dynamic range of a particular protein analyte assay to lie within the "sweet spot" of standard expression levels of the protein analyte.

In certain embodiments, polypeptides from multiple different samples are labeled with recording tags containing sample-specific barcodes. The multi-sample barcoded polypeptides can be mixed together prior to a cyclic binding reaction. In this way, a highly-multiplexed alternative to a digital reverse phase protein array (RPPA) is effectively created (Guo et al., Proteome Sci (2012) 10(1): 56; Assadi, Lamerz et al., Mol Cell Proteomics (2013) 12(9): 2615-2622; Akbani et al. 2014; Mol Cell Proteomics (2014) 13(7): 1625-1643; Creighton et al., Drug Des Devel Ther (2015) 9: 3519-3527). The creation of a digital RPPA-like assay has numerous applications in translational research, biomarker validation, drug discovery, clinical, and precision medicine.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (5'-AATGATACGGCGACCACCGA-3'—SEQ ID NO:3) or an Illumina P7 primer (5'-CAAGCAGAAGACGGCATACGAGAT-3'—SEQ ID NO:4).

In certain embodiments, a recording tag comprises a spacer at its terminus, e.g., 3' end. As used herein reference to a spacer sequence in the context of a recording tag includes a spacer sequence that is identical to the spacer sequence associated with its cognate binding agent, or a spacer sequence that is complementary to the spacer sequence associated with its cognate binding agent. The terminal, e.g., 3', spacer on the recording tag permits transfer of identifying information of a cognate binding agent from its coding tag to the recording tag during the first binding cycle (e.g., via annealing of complementary spacer sequences for primer extension or sticky end ligation).

In one embodiment, the spacer sequence is about 1-20 bases in length or a subrange thereof, e.g., about 2-12 bases in length, or 5-10 bases in length. The length of the spacer may depend on factors such as the temperature and reaction conditions of the primer extension reaction for transferring coding tag information to the recording tag. In some embodiments, the recording tag does not comprise a spacer.

In a preferred embodiment, the spacer sequence in the recording is designed to have minimal complementarity to other regions in the recording tag; likewise, the spacer sequence in the coding tag should have minimal complementarity to other regions in the coding tag. In other words, the spacer sequence of the recording tags and coding tags should have minimal sequence complementarity to components such unique molecular identifiers, barcodes (e.g., compartment, partition, sample, spatial location), universal primer sequences, encoder sequences, cycle specific sequences, etc. present in the recording tags or coding tags.

In some embodiments, the recording tags associated with a library of polypeptides share a common spacer sequence. In other embodiments, the recording tags associated with a library of polypeptides have binding cycle specific spacer sequences that are complementary to the binding cycle specific spacer sequences of their cognate binding agents, which can be useful when using non-concatenated extended recording tags.

In some cases, the collection of extended recording tags can be concatenated. For example, after the binding cycles are complete, the bead solid supports, each bead comprising on average one or fewer than one polypeptide per bead, each polypeptide having a collection of extended recording tags that are co-localized at the site of the polypeptide, are placed in an emulsion. The emulsion is formed such that each droplet, on average, is occupied by at most 1 bead. An optional assembly PCR reaction is performed in-emulsion to amplify the extended recording tags co-localized with the polypeptide on the bead and assemble them in co-linear order by priming between the different cycle specific sequences on the separate extended recording tags (Xiong et al., FEMS Microbiol Rev (2008) 32(3): 522-540). Afterwards the emulsion is broken and the assembled extended recording tags are sequenced.

In another embodiment, the DNA recording tag is comprised of a universal priming sequence (U1), one or more barcode sequences (BCs), and a spacer sequence (Sp1) specific to the first binding cycle. In the first binding cycle, binding agents employ DNA coding tags comprised of an Sp1 complementary spacer, an encoder barcode, and optional cycle barcode, and a second spacer element (Sp2). The utility of using at least two different spacer elements is that the first binding cycle selects one of potentially several DNA recording tags and a single DNA recording tag is extended resulting in a new Sp2 spacer element at the end of the extended DNA recording tag. In the second and subsequent binding cycles, binding agents contain just the Sp2' spacer rather than Sp1'. In this way, only the single extended recording tag from the first cycle is extended in subsequent cycles. In another embodiment, the second and subsequent cycles can employ binding agent specific spacers.

In some embodiments, a recording tag comprises from 5' to 3' direction: a universal forward (or 5') priming sequence, a UMI, and a spacer sequence. In some embodiments, a recording tag comprises from 5' to 3' direction: a universal forward (or 5') priming sequence, an optional UMI, a barcode (e.g., sample barcode, partition barcode, compartment barcode, spatial barcode, or any combination thereof), and a spacer sequence. In some other embodiments, a recording tag comprises from 5' to 3' direction: a universal forward (or 5') priming sequence, a barcode (e.g., sample barcode, partition barcode, compartment barcode, spatial barcode, or any combination thereof), an optional UMI, and a spacer sequence.

Combinatorial approaches may be used to generate UMIs from modified DNA and PNAs. In one example, a UMI may be constructed by "chemical ligating" together sets of short word sequences (4-15mers), which have been designed to be orthogonal to each other (Spiropulos and Heemstra 2012). A DNA template is used to direct the chemical ligation of the "word" polymers. The DNA template is constructed with hybridizing arms that enable assembly of a combinatorial template structure simply by mixing the sub-components together in solution. In certain embodiments, there are no "spacer" sequences in this design. The size of the word space can vary from 10's of words to 10,000's or more words or a subrange thereof. In certain embodiments, the words are chosen such that they differ from one another to not cross hybridize, yet possess relatively uniform hybridization conditions. In one embodiment, the length of the word will be on the order of 10 bases, with about 1000's words in the subset (this is only 0.1% of the total 10-mer word space $\sim 4^{10}=1$ million words). Sets of these words (1000 in subset) can be concatenated together to generate a final combinatorial UMI with complexity=$1000^n$ power. For 4 words concatenated together, this creates a UMI diversity of $10^{12}$ different elements. These UMI sequences will be appended to the polypeptide at the single molecule level. In one embodiment, the diversity of UMIs exceeds the number of molecules of polypeptides to which the UMIs are attached. In this way, the UMI uniquely identifies the polypeptide of interest. The use of combinatorial word UMI's facilitates readout on high error rate sequencers, (e.g., nanopore sequencers, nanogap tunneling sequencing, etc.) since single base resolution is not required to read words of multiple bases in length. Combinatorial word approaches can also be used to generate other identity-informative components of recording tags or coding tags, such as compartment tags, partition barcodes, spatial barcodes, sample barcodes, encoder sequences, cycle specific sequences, and barcodes. Methods relating to nanopore sequencing and DNA encoding information with error-tolerant words (codes) are known in the art (see, e.g., Kiah et al., 2015, *Codes for DNA sequence profiles*. IEEE International Symposium on Information Theory (ISIT); Gabrys et al., 2015, *Asymmetric Lee distance codes for DNA-based storage*. IEEE Symposium on Information Theory (ISIT); Laure et al., 2016, *Coding in 2D; Using Intentional Dispersity to Enhance the Information Capacity of Sequence-Coded Polymer Barcodes*. Angew. Chem. Int. Ed. doi: 10.1002/anie.201605279; Yazdi et al., 2015, IEEE Transactions on Molecular, Biological and Multi-Scale Communications 1:230-248; and Yazdi et al., 2015, Sci Rep 5:14138, each of which is incorporated by reference in its entirety). Thus, in certain embodiments, an extended recording tag, an extended coding tag, or a di-tag construct in any of the embodiments described herein is comprised of identifying components (e.g., UMI, encoder sequence, barcode, compartment tag, cycle specific sequence, etc.) that are error correcting codes. In some embodiments, the error correcting code is selected from: Hamming code, Lee distance code, asymmetric Lee distance code, Reed-Solomon code, and Levenshtein-Tenengolts code. For nanopore sequencing, the current or ionic flux profiles and asymmetric base calling errors are intrinsic to the type of nanopore and biochemistry employed, and this information can be used to design more robust DNA codes using the aforementioned error correcting approaches. An alternative to employing robust DNA nanopore sequencing barcodes, one can directly use the current or ionic flux signatures of barcode sequences (U.S. Pat. No. 7,060,507, incorporated by reference in its entirety), avoiding DNA base calling entirely, and immediately identify the barcode sequence by mapping back to the predicted current/flux signature as described by Laszlo et al. (2014, Nat. Biotechnol. 32:829-833, incorporated by reference in its entirety). For example, Laszlo et al. describe the current signatures generated by the biological nanopore, MspA, when passing different word strings through the nanopore, and the ability to map and identify DNA strands by mapping resultant current signatures back to an in silico prediction of possible current signatures from a universe of sequences (Laszlo et al., (2014) Nat. Biotechnol. 32:829-833). Similar concepts can be applied to DNA codes and the electrical signal generated by nanogap tunneling current-based DNA sequencing (Ohshiro et al., 2012, Sci Rep 2: 501).

Thus, in certain embodiments, the identifying components of a coding tag, recording tag, or both are capable of generating a unique current or ionic flux or optical signature, wherein the analysis step of any of the methods provided herein comprises detection of the unique current or ionic flux or optical signature in order to identify the identifying components. In some embodiments, the identifying components are selected from an encoder sequence, barcode, UMI, compartment tag, cycle specific sequence, or any combination thereof.

In certain embodiments, all or a substantial amount of the polypeptides (e.g., at least 50%, 55%, 60%, 65%, 70%, 75%, 80%, 85%, 90%, 95%, 96%, 97%, 98%, 99%, or 100%) within a sample are labeled with a recording tag. Attaching of the recording tag to the polypeptides may occur before or after immobilization of the polypeptides to a solid support.

In other embodiments, a subset of polypeptides within a sample are labeled with recording tags. In a particular embodiment, a subset of polypeptides from a sample undergo targeted (analyte specific) labeling with recording tags. Targeted recording tag labeling of proteins may be achieved using target protein-specific binding agents (e.g., antibodies, aptamers, etc.) that are linked a short target-specific DNA capture probe, e.g., analyte-specific barcode, which anneal to complementary target-specific bait sequence, e.g., analyte-specific barcode, in recording tags. The recording tags comprise a reactive moiety for a cognate reactive moiety present on the target protein (e.g., click chemistry labeling, photoaffinity labeling). For example, recording tags may comprise an azide moiety for interacting with alkyne-derivatized proteins, or recording tags may comprise a benzophenone for interacting with native proteins, etc. Upon binding of the target protein by the target protein specific binding agent, the recording tag and target protein are coupled via their corresponding reactive. After the target protein is labeled with the recording tag, the target-protein specific binding agent may be removed by digestion of the DNA capture probe linked to the target-protein specific binding agent. For example, the DNA capture probe may be designed to contain uracil bases, which are then targeted for digestion with a uracil-specific excision reagent (e.g., USER™), and the target-protein specific binding agent may be dissociated from the target protein.

In one example, antibodies specific for a set of target proteins can be labeled with a DNA capture probe that hybridizes with recording tags designed with complementary bait sequence. Sample-specific labeling of proteins can be achieved by employing DNA-capture probe labeled antibodies hybridizing with complementary bait sequence on recording tags comprising of sample-specific barcodes.

In another example, target protein-specific aptamers are used for targeted recording tag labeling of a subset of proteins within a sample. A target specific-aptamer is linked to a DNA capture probe that anneals with complementary bait sequence in a recording tag. The recording tag comprises a reactive chemical or photo-reactive chemical probes (e.g. benzophenone (BP)) for coupling to the target protein having a corresponding reactive moiety. The aptamer binds to its target protein molecule, bringing the recording tag into close proximity to the target protein, resulting in the coupling of the recording tag to the target protein.

Photoaffinity (PA) protein labeling using photo-reactive chemical probes attached to small molecule protein affinity ligands has been previously described (Park, Koh et al. 2016). Typical photo-reactive chemical probes include probes based on benzophenone (reactive diradical, 365 nm), phenyldiazirine (reactive carbon, 365 nm), and phenylazide (reactive nitrene free radical, 260 nm), activated under irradiation wavelengths as previously described (Smith et al., Future Med Chem. (2015) 7(2): 159-183). In a preferred embodiment, target proteins within a protein sample are labeled with recording tags comprising sample barcodes using the method disclosed by Li et al., in which a bait sequence in a benzophenone labeled recording tag is hybridized to a DNA capture probe attached to a cognate binding agent (e.g., nucleic acid aptamer (Li et al., Angew Chem Int Ed Engl (2013) 52(36): 9544-9549). For photoaffinity labeled protein targets, the use of DNA/RNA aptamers as target protein-specific binding agents are preferred over antibodies since the photoaffinity moiety can self-label the antibody rather than the target protein. In contrast, photoaffinity labeling is less efficient for nucleic acids than proteins, making aptamers a better vehicle for DNA-directed chemical or photo-labeling. Similar to photo-affinity labeling, one can also employ DNA-directed chemical labeling of reactive lysine's (or other moieties) in the proximity of the aptamer binding site in a manner similar to that described by Rosen et al. (Rosen et al, Nature Chemistry volume (2014) 6:804-809; Kodal et al., ChemBioChem (2016) 17:1338-1342).

In the aforementioned embodiments, other types of linkages besides hybridization can be used to link the target specific binding agent and the recording tag. For example, the two moieties can be covalently linked, using a linker that is designed to be cleaved and release the binding agent once the captured target protein (or other polypeptide) is covalently linked to the recording tag. A suitable linker can be attached to various positions of the recording tag, such as the 3' end, or within the linker attached to the 5' end of the recording tag.

Recording tags can be attached to the protein, polypeptide, or peptides pre- or post-immobilization to the solid support. For example, proteins, polypeptides, or peptides can be first labeled with recording tags and then immobilized to a solid surface via a recording tag comprising at two functional moieties for coupling. One functional moiety of the recording tag couples to the protein, and the other functional moiety immobilizes the recording tag-labeled protein to a solid support.

In other embodiments, polypeptides are immobilized to a solid support prior to labeling of the proteins, polypeptides or peptides with recording tags. For example, proteins can first be derivatized with reactive groups such as click chemistry moieties. The activated protein molecules can then be attached to a suitable solid support and then labeled with recording tags using the complementary click chemistry moiety. As an example, proteins derivatized with alkyne and mTet moieties may be immobilized to beads derivatized with azide and TCO and attached to recording tags labeled with azide and TCO.

In certain embodiments, the surface of a solid support is passivated (blocked) to minimize non-specific absorption to binding agents. A "passivated" surface refers to a surface that has been treated with outer layer of material to minimize non-specific binding of a binding agent. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moiety (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol, (PVA), and proteins like BSA and casein. Alternatively, density of proteins, polypeptide, or peptides can be titrated on the surface or within the volume of a solid substrate by spiking a competitor or "dummy" reactive molecule when immobilizing the proteins, polypeptides or peptides to the solid substrate.

In certain embodiments where multiple polypeptides are immobilized on the same solid support, the polypeptides can be spaced appropriately to reduce the occurrence of or prevent a cross-binding or inter-molecular event, e.g., where a binding agent binds to a first polypeptides and its coding tag information is transferred to a recording tag associated with a neighboring polypeptides rather than the recording tag associated with the first polypeptide. To control polypeptide spacing on the solid support, the density of functional coupling groups (e.g., TCO) may be titrated on the substrate surface. In some embodiments, multiple polypeptides are spaced apart on the surface or within the volume (e.g., porous supports) of a solid support at a distance of about 50 nm to about 500 nm, or a subrange thereof, e.g., or about 50 nm to about 400 nm, or about 50 nm to about 300 nm, or about 50 nm to about 200 nm, or about 50 nm to about 100 nm. In some embodiments, multiple polypeptides are spaced apart on the surface of a solid support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, multiple polypeptides are spaced apart on the surface of a solid support with an average distance of at least 50 nm. In some embodiments, polypeptides are spaced apart on the surface or within the volume of a solid support such that, empirically, the relative frequency of inter- to intra-molecular events is <1:10; <1:100; <1:1,000; or <1:10,000. A suitable spacing frequency can be determined empirically using a functional assay (see, Example 31 of International Patent Publication No. WO 2017/192633), and can be accomplished by dilution and/or by spiking a "dummy" spacer molecule that competes for attachments sites on the substrate surface.

For example, PEG-5000 (MW ~5000) is used to block the interstitial space between peptides on the substrate surface (e.g., bead surface). In addition, the peptide is coupled to a functional moiety that is also attached to a PEG-5000 molecule. In some embodiments, this is accomplished by coupling a mixture of NHS-PEG-5000-TCO+NHS-PEG-5000-Methyl to amine-derivatized beads. The stoichiometric ratio between the two PEGs (TCO vs. methyl) is titrated to generate an appropriate density of functional coupling moieties (TCO groups) on the substrate surface; the methyl-PEG is inert to coupling. The effective spacing between TCO groups can be calculated by measuring the density of TCO groups on the surface. In certain embodiments, the mean spacing between coupling moieties (e.g., TCO) on the solid surface is at least 50 nm, at least 100 nm, at least 250 nm, or at least 500 nm. After PEG5000-TCO/methyl derivatization of the beads, the excess $NH_2$ groups on the surface are quenched with a reactive anhydride (e.g. acetic or succinic anhydride). Other MW PEGs can also be used for passivation from MW ~300 Da to over 50 kDa.

In some embodiments, the spacing is accomplished by titrating the ratio of available attachment molecules on the substrate surface. In some examples, the substrate surface (e.g., bead surface) is functionalized with a carboxyl group (COOH) which is treated with an activating agent (e.g., activating agent is EDC and Sulfo-NHS). In some examples, the substrate surface (e.g., bead surface) comprises NHS moieties. In some embodiments, a mixture of mPEG$_n$-NH2 and NH2-PEG$_n$-mTet is added to the activated beads (wherein n is any number, such as 1-100). The ratio between the mPEG$_3$-NH$_2$ (not available for coupling) and NH2-PEG24-mTet (available for coupling) is titrated to generate an appropriate density of functional moieties available to attach the analyte on the substrate surface. In certain embodiments, the mean spacing between coupling moieties (e.g., NH$_2$-PEG$_4$-mTet) on the solid surface is at least 50 nm, at least 100 nm, at least 250 nm, or at least 500 nm. In some specific embodiments, the ratio of NH$_2$-PEG$_n$-mTet to mPEG$_3$-NH2 is about or greater than 1:1000, about or greater than 1:10,000, about or greater than 1:100,000, or about or greater than 1:1,000,000. In some further embodiments, the capture nucleic acid attaches to the NH2-PEG$_n$-mTet.

In particular embodiments, the polypeptide(s) and/or the recording tag(s) are immobilized on a substrate or support at a density such that the interaction between (i) a coding agent bound to a first polypeptide (particularly, the coding tag in that bound coding agent), and (ii) a second polypeptide and/or its recording tag, is reduced, minimized, or completely eliminated. Therefore, false positive assay signals resulting from "intermolecular" engagement can be reduced, minimized, or eliminated.

In certain embodiments, the density of the polypeptides and/or the recording tags on a substrate is determined for each type of polypeptide. For example, the longer a denatured polypeptide chain is, the lower the density should be in order to reduce, minimize, or prevent "intermolecular" interactions. In certain aspects, increasing the spacing between the polypeptide molecules and/or the recording tags (i.e., lowering the density) increases the signal to background ratio of the presently disclosed assays.

In some embodiments, the polypeptide molecules and/or the recording tags are deposited or immobilized on a substrate at any suitable average density, e.g., at an average density of about 0.0001 molecule/$\mu m^2$, 0.001 molecule/$\mu m^2$, 0.01 molecule/$\mu m^2$, 0.1 molecule/$\mu m^2$, 1 molecule/$\mu m^2$, about 2 molecules/$\mu m^2$, about 3 molecules/$\mu m^2$, about 4 molecules/$\mu m^2$, about 5 molecules/$\mu m^2$, about 6 molecules/$\mu m^2$, about 7 molecules/$\mu m^2$, about 8 molecules/$\mu m^2$, about 9 molecules/$\mu m^2$, or about 10 molecules/$\mu m^2$. In other embodiments, the polypeptide(s) and/or the recording tag(s) are deposited or immobilized at an average density of about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, or about 200 molecules/$\mu m^2$ on a substrate. In other embodiments, the polypeptide(s) and/or the recording tag(s) are deposited or immobilized at an average density of about 1 molecule/$mm^2$, about 10 molecules/$mm^2$, about 50 molecules/$mm^2$, about 100 molecules/$mm^2$, about 150 molecules/$mm^2$, about 200 molecules/$mm^2$, about 250 molecules/$mm^2$, about 300 molecules/$mm^2$, about 350 molecules/$mm^2$, 400 molecules/$mm^2$, about 450 molecules/$mm^2$, about 500 molecules/$mm^2$, about 550 molecules/$mm^2$, about 600 molecules/$mm^2$, about 650 molecules/$mm^2$, about 700 molecules/$mm^2$, about 750 molecules/$mm^2$, about 800 molecules/$mm^2$, about 850 molecules/$mm^2$, about 900 molecules/$mm^2$, about 950 molecules/$mm^2$, or about 1000 molecules/$mm^2$. In still other embodiments, the polypeptide(s) and/or the recording tag(s) are deposited or immobilized on a substrate at an average density between about $1\times10^3$ and about $0.5\times10^4$ molecules/$mm^2$, between about $0.5\times10^4$ and about $1\times10^4$ molecules/$mm^2$, between about $1\times10^4$ and about $0.5\times10^5$ molecules/$mm^2$, between about $0.5\times10^5$ and about $1\times10^5$ molecules/$mm^2$, between about $1\times10^5$ and about $0.5\times10^6$ molecules/$mm^2$, or between about $0.5\times10^6$ and about $1\times10^6$ molecules/$mm^2$. In other embodiments, the average density of the polypeptide(s) and/or the recording tag(s) deposited or immobilized on a substrate can be, for example, between about 1 molecule/$cm^2$ and about 5 molecules/$cm^2$, between about 5 and about 10 molecules/$cm^2$, between about 10 and about 50 molecules/$cm^2$, between about 50 and about 100 molecules/$cm^2$, between about 100 and about $0.5\times10^3$ molecules/$cm^2$, between about $0.5\times10^3$ and about $1\times10^3$ molecules/$cm^2$, $1\times10^3$ and about $0.5\times10^4$ molecules/$cm^2$, between about $0.5\times10^4$ and about $1\times10^4$ molecules/$cm^2$, between about $1\times10^4$ and about $0.5\times10^5$ molecules/$cm^2$, between about $0.5\times10^5$ and about $1\times10^5$ molecules/$cm^2$, between about $1\times10^5$ and about $0.5\times10^6$ molecules/$cm^2$, or between about $0.5\times10^6$ and about $1\times10^6$ molecules/$cm^2$.

B. Cyclic Transfer of Coding Tag Information to Recording Tags

In the methods described herein, upon binding of a binding agent to a polypeptide, identifying information of its linked coding tag is transferred to a recording tag associated with the polypeptide, thereby generating an "extended recording tag." An extended recording tag may comprise information from a binding agent's coding tag representing each binding cycle performed. However, an extended recording tag may also experience a "missed" binding cycle, e.g., because a binding agent fails to bind to the polypeptide, because the coding tag was missing, damaged, or defective, because the primer extension reaction failed. Even if a binding event occurs, transfer of information from the coding tag to the recording tag may be incomplete or less than 100% accurate, e.g., because a coding tag was damaged or defective, because errors were introduced in the primer extension reaction). Thus, an extended recording tag may represent 100%, or up to 95%, 90%, 85%, 80%, 75%, 70%, 65%, 60%, 65%, 55%, 50%, 45%, 40%, 35%, 30%, or any subrange thereof, of binding events that have occurred on its associated polypeptide. Moreover, the coding tag information present in the extended recording tag may have at least 30%, 35%, 40%, 45%, 50%, 55%, 60%, 65%, 70%, 75%, 80%, 85%, 90%, 95%, or 100% identity the corresponding coding tags.

In certain embodiments, a binding agent may bind to an NTAA, a CTAA, an intervening amino acid, dipeptide (sequence of two amino acids), tripeptide (sequence of three amino acids), or higher order peptide of a peptide molecule. In some embodiments, each binding agent in a library of binding agents selectively binds to a particular amino acid, for example one of the twenty standard naturally occurring amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or lie), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). In some embodiments, the binding agent binds to an unmodified or native amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a native or unmodified NTAA, high specificity for a native or unmodified NTAA, or both. In some embodiments, binding agents can be developed through directed evolution of promising affinity scaffolds using phage display.

A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may bind to an N-terminal or C-terminal diamino acid moiety. A binding agent may preferably bind to a chemically modified or labeled amino acid. For example, a binding agent may preferably bind to an amino acid that has been functionalized with an acetyl moiety, Cbz moiety, guanyl moiety, dansyl moiety, PTC moiety, DNP moiety, SNP moiety, heterocyclic methanimine moiety, etc., over an amino acid that does not possess said moiety.

In certain embodiments, an extended recording tag may comprise information from multiple coding tags representing multiple, successive binding events. In these embodiments, a single, concatenated extended recording tag can be representative of a single polypeptide. As referred to herein, transfer of coding tag information to a recording tag also includes transfer to an extended recording tag as would occur in methods involving multiple, successive binding events.

In certain embodiments, the binding event information is transferred from a coding tag to a recording tag in a cyclic fashion. Cross-reactive binding events can be informatically filtered out after sequencing by requiring that at least two different coding tags, identifying two or more independent binding events, map to the same class of binding agents (cognate to a particular protein). An optional sample or compartment barcode can be included in the recording tag, as well an optional UMI sequence. The coding tag can also contain an optional UMI sequence along with the encoder and spacer sequences. Universal priming sequences may also be included in extended recording tags for amplification and NGS sequencing.

Coding tag information associated with a specific binding agent may be transferred to a recording tag using a variety of methods. In certain embodiments, information of a coding tag is transferred to a recording tag via primer extension (Chan, McGregor et al. 2015). A spacer sequence on the 3'-terminus of a recording tag or an extended recording tag anneals with complementary spacer sequence on the 3' terminus of a coding tag and a polymerase (e.g., strand-displacing polymerase) extends the recording tag sequence, using the annealed coding tag as a template. In some embodiments, oligonucleotides complementary to coding tag encoder sequence and 5' spacer can be pre-annealed to the coding tags to prevent hybridization of the coding tag to internal encoder and spacer sequences present in an extended recording tag. The 3' terminal spacer, on the coding tag, remaining single stranded, preferably binds to the terminal 3' spacer on the recording tag. In other embodiments, a nascent recording tag can be coated with a single stranded binding protein to prevent annealing of the coding tag to internal sites. Alternatively, the nascent recording tag can also be coated with RecA (or related homologues such as uvsX) to facilitate invasion of the 3' terminus into a completely double stranded coding tag (Bell et al., 2012, Nature 491:274-278). This configuration prevents the double stranded coding tag from interacting with internal recording tag elements, yet is susceptible to strand invasion by the RecA coated 3' tail of the extended recording tag (Bell, et al., 2015, Elife 4: e08646). The presence of a single-stranded binding protein can facilitate the strand displacement reaction.

In some embodiments, a DNA polymerase that is used for primer extension possesses strand-displacement activity and has limited or is devoid of 3'-5 exonuclease activity. Several of many examples of such polymerases include Klenow exo-(Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9°N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

Additives useful in strand-displacement replication include any of a number of single-stranded DNA binding proteins (SSB proteins) of bacterial, viral, or eukaryotic origin, such as SSB protein of $E.$ $coli$, phage T4 gene 32 product, phage T7 gene 2.5 protein, phage Pf3 SSB, replication protein A RPA32 and RPA14 subunits (Wold, 1997); other DNA binding proteins, such as adenovirus DNA-binding protein, herpes simplex protein ICP8, BMRF1 polymerase accessory subunit, herpes virus UL29 SSB-like protein; any of a number of replication complex proteins known to participate in DNA replication, such as phage T7 helicase/primase, phage T4 gene 41 helicase, $E.$ $coli$ Rep helicase, $E.$ $coli$ recBCD helicase, recA, $E.$ $coli$ and eukaryotic topoisomerases (Annu Rev Biochem. (2001) 70:369-413).

Mis-priming or self-priming events, such as when the terminal spacer sequence of the recoding tag primes extension self-extension may be minimized by inclusion of single stranded binding proteins (T4 gene 32, $E.$ $coli$ SSB, etc.), DMSO (1-10%), formamide (1-10%), BSA (10-100 ug/ml), TMACl (1-5 mM), ammonium sulfate (10-50 mM), betaine (1-3 M), glycerol (5-40%), or ethylene glycol (5-40%), in the primer extension reaction.

Most type A polymerases are devoid of 3' exonuclease activity (endogenous or engineered removal), such as Klenow exo-, T7 DNA polymerase exo-(Sequenase 2.0), and Taq polymerase catalyzes non-templated addition of a nucleotide, preferably an adenosine base (to lesser degree a G base, dependent on sequence context) to the 3' blunt end of a duplex amplification product. For Taq polymerase, a 3' pyrimidine (C>T) minimizes non-templated adenosine addition, whereas a 3' purine nucleotide (G>A) favours non-templated adenosine addition. In some embodiments, using Taq polymerase for primer extension, placement of a thymidine base in the coding tag between the spacer sequence distal from the binding agent and the adjacent barcode sequence (e.g., encoder sequence or cycle specific sequence) accommodates the sporadic inclusion of a non-templated adenosine nucleotide on the 3' terminus of the spacer sequence of the recording tag. In this manner, the extended recording tag (with or without a non-templated adenosine base) can anneal to the coding tag and undergo primer extension.

Alternatively, addition of non-templated base can be reduced by employing a mutant polymerase (mesophilic or thermophilic) in which non-templated terminal transferase activity has been greatly reduced by one or more point mutations, especially in the O-helix region (see U.S. Pat. No. 7,501,237) (Yang et al., Nucleic Acids Res. (2002) 30(19): 4314-4320). Pfu exo-, which is 3' exonuclease deficient and has strand-displacing ability, also does not have non-templated terminal transferase activity.

In another embodiment, polymerase extension buffers are comprised of 40-120 mM buffering agent such as Tris-Acetate, Tris-HCl, HEPES, etc. at a pH of 6-9.

Self-priming/mis-priming events initiated by self-annealing of the terminal spacer sequence of the extended recording tag with internal regions of the extended recording tag may be minimized by including pseudo-complementary bases in the recording/extended recording tag (Lahoud et al., Nucleic Acids Res. (2008) 36:3409-3419), (Hoshika et al., Angew Chem Int Ed Engl (2010) 49(32): 5554-5557). Pseudo-complementary bases show significantly reduced hybridization affinities for the formation of duplexes with each other due the presence of chemical modification. However, many pseudo-complementary modified bases can form strong base pairs with natural DNA or RNA sequences. In certain embodiments, the coding tag spacer sequence is comprised of multiple A and T bases, and commercially available pseudo-complementary bases 2-aminoadenine and 2-thiothymine are incorporated in the recording tag using phosphoramidite oligonucleotide synthesis. Additional pseudocomplementary bases can be incorporated into the extended recording tag during primer extension by adding pseudo-complementary nucleotides to the reaction (Gamper et al., Biochemistry. (2006) 45(22):6978-86).

In some embodiments, to minimize non-specific interaction of the coding tag labeled binding agents in solution with the recording tags of immobilized proteins, competitor (also referred to as blocking) oligonucleotides complementary to recording tag spacer sequences can be added to binding reactions to minimize non-specific interactions. In some embodiments, blocking oligonucleotides are relatively short. Excess competitor oligonucleotides are washed from the binding reaction prior to primer extension, which effectively dissociates the annealed competitor oligonucleotides from the recording tags, especially when exposed to slightly elevated temperatures (e.g., 30-50° C.). Blocking oligonucleotides may comprise a terminator nucleotide at its 3' end to prevent primer extension.

In some embodiments, the coding tag may comprise a hairpin. In certain embodiments, the hairpin comprises mutually complementary nucleic acid regions are connected through a nucleic acid strand. In some embodiments, the nucleic acid hairpin can also further comprise 3' and/or 5' single-stranded region(s) extending from the double-stranded stem segment. In some examples, the hairpin comprises a single strand of nucleic acid.

In certain embodiments, the annealing of the spacer sequence on the recording tag to the complementary spacer sequence on the coding tag is metastable under the primer extension reaction conditions (i.e., the annealing Tm is similar to the reaction temperature). This allows the spacer sequence of the coding tag to displace any blocking oligonucleotide annealed to the spacer sequence of the recording tag.

Coding tag information associated with a specific binding agent may also be transferred to a recording tag via ligation. Ligation may be a blunt end ligation or sticky end ligation. Ligation may be an enzymatic ligation reaction. Examples of ligases include, but are not limited to CV DNA ligase (see U.S. Patent Publication No. US 2014/0378315), T4 DNA ligase, T7 DNA ligase, T3 DNA ligase, Taq DNA ligase, *E. coli* DNA ligase, 9°N DNA ligase, Electroligase®. Alternatively, a ligation may be a chemical ligation reaction. In the illustration, a spacer-less ligation is accomplished by using hybridization of a "recording helper" sequence with an arm on the coding tag. The annealed complement sequences are chemically ligated using standard chemical ligation or "click chemistry" (Gunderson et al., Genome Res (1998) 8(11): 1142-1153; Peng et al., European J Org Chem (2010) (22): 4194-4197; El-Sagheer et al., Proc Natl Acad Sci USA (2011) 108(28): 11338-11343; El-Sagheer et al., Org Biomol Chem (2011) 9(1): 232-235; Sharma et al., Anal Chem (2012) 84(14): 6104-6109; Roloff et al., Bioorg Med Chem (2013) 21(12): 3458-3464; Litovchick et al., Artif DNA PNA XNA (2014) 5(1): e27896; Roloff et al., Methods Mol Biol (2014) 1050:131-141).

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivatizing the 5' N-terminus with a cysteinyl moiety and the 3' C-terminus with a thioester moiety. Such modified PNAs easily couple using standard native chemical ligation conditions (Roloff et al., (2013) Bioorgan. Med. Chem. 21:3458-3464).

In some embodiments, coding tag information can be transferred using topoisomerase. Topoisomerase can be used be used to ligate a topo-charged 3' phosphate on the recording tag to the 5' end of the coding tag, or complement thereof (Shuman et al., 1994, J. Biol. Chem. 269:32678-32684).

As described herein, a binding agent may bind to a post-translationally modified amino acid. Thus, in certain embodiments, an extended recording tag comprises coding tag information relating to amino acid sequence and post-translational modifications of the polypeptide. In some embodiments, detection of internal post-translationally modified amino acids (e.g., phosphorylation, glycosylation, succinylation, ubiquitination, S-Nitrosylation, methylation, N-acetylation, lipidation, etc.) is be accomplished prior to detection and elimination of terminal amino acids (e.g., NTAA or CTAA). In one example, a peptide is contacted with binding agents for PTM modifications, and associated coding tag information are transferred to the recording tag. Once the detection and transfer of coding tag information relating to amino acid modifications is complete, the PTM modifying groups can be removed before detection and transfer of coding tag information for the primary amino acid sequence using N-terminal or C-terminal degradation methods. Thus, resulting extended recording tags indicate the presence of post-translational modifications in a peptide sequence, though not the sequential order, along with primary amino acid sequence information.

In some embodiments, detection of internal post-translationally modified amino acids may occur concurrently with detection of primary amino acid sequence. In one example, an NTAA (or CTAA) is contacted with a binding agent specific for a post-translationally modified amino acid, either alone or as part of a library of binding agents (e.g., library composed of binding agents for the 20 standard amino acids and selected post-translational modified amino acids). Successive cycles of terminal amino acid elimination and contact with a binding agent (or library of binding agents) follow. Thus, resulting extended recording tags indicate the presence and order of post-translational modifications in the context of a primary amino acid sequence.

In certain embodiments, an ensemble of recording tags may be employed per polypeptide to improve the overall robustness and efficiency of coding tag information transfer. The use of an ensemble of recording tags associated with a given polypeptide rather than a single recording tag improves the efficiency of library construction due to potentially higher coupling yields of coding tags to recording tags, and higher overall yield of libraries. The yield of a single concatenated extended recording tag is directly dependent on the stepwise yield of concatenation, whereas the use of multiple recording tags capable of accepting coding tag information does not suffer the exponential loss of concatenation.

For embodiments involving analysis of denatured proteins, polypeptides, and peptides, the bound binding agent and annealed coding tag can be removed following primer extension by using highly denaturing conditions (e.g., 0.1-0.2 NNaOH, 6M Urea, 2.4 M guanidinium isothiocyanate, 95% formamide, etc.).

C. Characterization of Polypeptides Via Cyclic Rounds of Amino Acid Recognition, Recording Tag Extension, and Amino Acid Removal In certain embodiments, the methods for analyzing a polypeptide provided in the present disclosure comprise multiple binding cycles, where the polypeptide is contacted with a plurality of binding agents, and successive binding of binding agents transfers historical binding information in the form of a nucleic acid based coding tag to at least one recording tag associated with the polypeptide. In this way, a historical record containing information about multiple binding events is generated in a nucleic acid format.

In certain embodiments, the concentration of the binding agents in a solution is controlled to reduce background and/or false positive results of the assay.

In some embodiments, the concentration of a binding agent can be at any suitable concentration, e.g., at about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1000 nM.

In some embodiments, the ratio between the soluble binding agent molecules and the immobilized polypeptides and/or the recording tags can be at any suitable range, e.g., at about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about $10^4$:1, about $10^5$:1, about $10^6$:1, or higher, or any ratio in between the above listed ratios. Higher ratios between the soluble binding agent molecules and the immobilized polypeptide(s) and/or the recording tag(s) can be used to drive the binding and/or the coding tag/recoding tag information transfer to completion. This may be particularly useful for detecting and/or analyzing low abundance polypeptides in a sample.

In embodiments relating to methods of analyzing peptide or polypeptides using an N-terminal degradation based approach, following contacting and binding of a first binding agent to an n NTAA of a peptide of n amino acids and transfer of the first binding agent's coding tag information to a recording tag associated with the peptide, thereby generating a first order extended recording tag, the n NTAA is eliminated as described herein. In some embodiments, the use of the modified cleavase in a polypeptide analysis assay is for removal of the labeled NTAA. In some aspects, two or more any of the modified cleavases described in Section I can be used in combination to remove the labeled NTAA. For example, a sample can be treated with a mixture of modified cleavase enzymes to achieve removal of various NTAAs in the peptides in the sample. Removal of the n labeled NTAA by contacting with the modified cleavase converts the n−1 amino acid of the peptide to an N-terminal amino acid, which is referred to herein as an n−1 NTAA. A second binding agent is contacted with the peptide and binds to the n−1 NTAA, and the second binding agent's coding tag information is transferred to the first order extended recording tag thereby generating a second order extended recording tag (e.g., for generating a concatenated $n^{th}$ order extended recording tag representing the peptide), or to a different recording tag (e.g., for generating multiple extended recording tags, which collectively represent the peptide). Elimination of the n−1 labeled NTAA by a modified cleavase converts the n−2 amino acid of the peptide to an N-terminal amino acid, which is referred to herein as n−2 NTAA. Additional binding, transfer, labeling, and removal, can occur as described above up to n amino acids to generate an $n^{th}$ order extended recording tag or n separate extended recording tags, which collectively represent the peptide. As used herein, an n "order" when used in reference to a binding agent, coding tag, or extended recording tag, refers to the n binding cycle, wherein the binding agent and its associated coding tag is used or the n binding cycle where the extended recording tag is created. In some embodiments, steps including the NTAA in the described exemplary approach can be performed instead with a CTAA.

In some embodiments, contacting of the first binding agent and second binding agent to the polypeptide, and optionally any further binding agents (e.g., third binding agent, fourth binding agent, fifth binding agent, and so on), are performed at the same time. For example, the first binding agent and second binding agent, and optionally any further order binding agents, can be pooled together, for example to form a library of binding agents. In another example, the first binding agent and second binding agent, and optionally any further order binding agents, rather than being pooled together, are added simultaneously to the polypeptide. In one embodiment, a library of binding agents comprises at least 20 binding agents that selectively bind to the 20 standard, naturally occurring amino acids.

In other embodiments, the first binding agent and second binding agent, and optionally any further order binding agents, are each contacted with the polypeptide in separate binding cycles, added in sequential order. In certain embodiments, multiple binding agents are used at the same time, in parallel. This parallel approach saves time and reduces non-specific binding by non-cognate binding agents to a site that is bound by a cognate binding agent (because the binding agents are in competition).

The length of the final extended recording tags generated by the methods described herein is dependent upon multiple factors, including the length of the coding tag (e.g., encoder sequence and spacer), the length of the recording tag (e.g., unique molecular identifier, spacer, universal priming site, bar code), the number of binding cycles performed, and whether coding tags from each binding cycle are transferred to the same extended recording tag or to multiple extended recording tags. In some examples, if the coding tag has an encoder sequence of 5 bases that is flanked on each side by a spacer of 5 bases, the coding tag information on the final extended recording tag, which represents the peptide's binding agent history, is 10 bases×number of degradation cycles.

After the final binding cycle and transfer of the final binding agent's coding tag information to the extended recording tag, the tag can be capped by addition of a universal reverse priming site via ligation, primer extension or other methods known in the art. In some embodiments, the universal forward priming site in the recording tag is compatible with the universal reverse priming site that is appended to the final extended recording tag. In some embodiments, a universal reverse priming site is an Illumina P7 primer (5'-CAAGCAGAAGACGGCATACGAGAT-3'—SEQ ID NO: 4) or an Illumina P5 primer (5'-AATGATACGGCGACCACCGA-3'—SEQ ID NO: 3). The sense or antisense P7 may be appended, depending on strand sense of the recording tag. An extended recording tag library can be cleaved or amplified directly from the solid support (e.g., beads) and used in traditional next generation sequencing assays and protocols.

In some embodiments, a primer extension reaction is performed on a library of single stranded extended recording tags to copy complementary strands thereof. In some embodiments, the peptide sequencing assay (e.g., ProteoCode assay), comprises several chemical and enzymatic steps in a cyclical progression. In some cases, one advantage of a single molecule assay is the robustness to inefficiencies in the various cyclical chemical/enzymatic steps. In some embodiments, the use of cycle-specific barcodes present in the coding tag sequence allows an advantage to the assay.

D. Processing and Analysis of Tags

Extended recording tag and any other tags representing the polypeptide(s) of interest can be processed and analysed using a variety of nucleic acid sequencing methods. Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy.

Suitable sequencing methods for use in the invention include, but are not limited to, sequencing by hybridization, sequencing by synthesis technology (e.g., HiSeq™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeq™, Illumina), massively parallel semiconductor sequencing (e.g., Ion Torrent), and pyrosequencing technology (e.g., GS FLX and GS Junior Systems, Roche/454), and nanopore sequence (e.g., Oxford Nanopore Technologies).

A library of extended recording tags, extended coding tags, or di-tags may be amplified in a variety of ways. A library of extended recording tags, extended coding tags, or di-tags may undergo exponential amplification, e.g., via PCR or emulsion PCR. Emulsion PCR is known to produce more uniform amplification (Hori, Fukano et al., Biochem Biophys Res Commun (2007) 352(2): 323-328). Alternatively, a library of extended recording tags, extended coding tags, or di-tags may undergo linear amplification, e.g., via in vitro transcription of template DNA using T7 RNA polymerase. The library of extended recording tags, extended coding tags, or di-tags can be amplified using primers compatible with the universal forward priming site and universal reverse priming site contained therein. A library of extended recording tags, extended coding tags, or di-tags can also be amplified using tailed primers to add sequence to either the 5'-end, 3'-end or both ends of the extended recording tags, extended coding tags, or di-tags. Sequences that can be added to the termini of the extended recording tags, extended coding tags, or di-tags include library specific index sequences to allow multiplexing of multiple libraries in a single sequencing run, adaptor sequences, read primer sequences, or any other sequences for making the library of extended recording tags, extended coding tags, or di-tags compatible for a sequencing platform. An example of a library amplification in preparation for next generation sequencing is as follows: a 20 µl PCR reaction volume is set up using an extended recording tag library eluted from ~1 mg of beads (~10 ng), 200 µM dNTP, 1 µM of each forward and reverse amplification primers, 0.5 µl (1U) of Phusion Hot Start enzyme (New England Biolabs) and subjected to the following cycling conditions: 98° C. for 30 sec followed by 20 cycles of 98° C. for 10 sec, 60° C. for 30 sec, 12° C. for 30 sec, followed by 12° C. for 7 min, then hold at 4° C.

In certain embodiments, either before, during or following amplification, the library of extended recording tags, extended coding tags, or di-tags can undergo target enrichment. In some embodiments, target enrichment can be used to selectively capture or amplify extended recording tags representing polypeptides of interest from a library of extended recording tags, extended coding tags, or di-tags before sequencing. In some aspects, target enrichment for protein sequencing is challenging because of the high cost and difficulty in producing highly-specific binding agents for target proteins. In some cases, antibodies are notoriously non-specific and difficult to scale production across thousands of proteins. In some embodiments, the methods of the present disclosure circumvent this problem by converting the protein code into a nucleic acid code which can then make use of a wide range of targeted DNA enrichment strategies available for DNA libraries. In some cases, peptides of interest can be enriched in a sample by enriching their corresponding extended recording tags. Methods of targeted enrichment are known in the art, and include hybrid capture assays, PCR-based assays such as TruSeq custom Amplicon (Illumina), padlock probes (also referred to as molecular inversion probes), and the like (see, Mamanova et al., (2010) Nature Methods 7: 111-118; Bodi et al., J. Biomol. Tech. (2013) 24:73-86; Ballester et al., (2016) Expert Review of Molecular Diagnostics 357-372; Mertes et al., (2011) Brief Funct. Genomics 10:374-386; Nilsson et al., (1994) Science 265:2085-8; each of which are incorporated herein by reference in their entirety).

In one embodiment, a library of extended recording tags, extended coding tags, or di-tags is enriched via a hybrid capture-based assay. In a hybrid-capture based assay, the library of extended recording tags, extended coding tags, or di-tags is hybridized to target-specific oligonucleotides or "bait oligonucleotide" that are labelled with an affinity tag (e.g., biotin). Extended recording tags, extended coding tags, or di-tags hybridized to the target-specific oligonucleotides are "pulled down" via their affinity tags using an affinity ligand (e.g., streptavidin coated beads), and background (non-specific) extended recording tags are washed away. The enriched extended recording tags, extended coding tags, or di-tags are then obtained for positive enrichment (e.g., eluted from the beads).

For bait oligonucleotides synthesized by array-based "in situ" oligonucleotide synthesis and subsequent amplification of oligonucleotide pools, competing baits can be engineered into the pool by employing several sets of universal primers within a given oligonucleotide array. For each type of universal primer, the ratio of biotinylated primer to non-biotinylated primer controls the enrichment ratio. The use of several primer types enables several enrichment ratios to be designed into the final oligonucleotide bait pool.

A bait oligonucleotide can be designed to be complementary to an extended recording tag, extended coding tag, or di-tag representing a polypeptide of interest. The degree of complementarity of a bait oligonucleotide to the spacer sequence in the extended recording tag, extended coding tag, or di-tag can be from 0% to 100%, and any integer in between. This parameter can be easily optimized by a few enrichment experiments. In some embodiments, the length of the spacer relative to the encoder sequence is minimized in the coding tag design or the spacers are designed such that they unavailable for hybridization to the bait sequences. One approach is to use spacers that form a secondary structure in the presence of a cofactor. An example of such a secondary structure is a G-quadruplex, which is a structure formed by two or more guanine quartets stacked on top of each other (Bochman et al., Nat Rev Genet (2012) 13(11):770-780). A guanine quartet is a square planar structure formed by four guanine bases that associate through Hoogsteen hydrogen bonding. The G-quadruplex structure is stabilized in the presence of a cation, e.g., K+ ions vs. Li+ ions.

To minimize the number of bait oligonucleotides employed, a set of relatively unique peptides from each protein can be bioinformatically identified, and only those bait oligonucleotides complementary to the corresponding extended recording tag library representations of the peptides of interest are used in the hybrid capture assay. In some embodiments, sequential rounds or enrichment can also be carried out, with the same or different bait sets.

To enrich the entire length of a polypeptide in a library of extended recording tags, extended coding tags, or di-tags representing fragments thereof (e.g., peptides), "tiled" bait oligonucleotides can be designed across the entire nucleic acid representation of the protein.

In another embodiment, primer extension and ligation-based mediated amplification enrichment (AmpliSeq, PCR, TruSeq TSCA, etc.) can be used to select and module fraction enriched of library elements representing a subset of polypeptides. Competing oligonucleotides can also be employed to tune the degree of primer extension, ligation, or amplification. In the simplest implementation, this can be accomplished by having a mix of target specific primers comprising a universal primer tail and competing primers lacking a 5' universal primer tail. After an initial primer extension, only primers with the 5' universal primer sequence can be amplified. The ratio of primer with and without the universal primer sequence controls the fraction of target amplified. In other embodiments, the inclusion of hybridizing but non-extending primers can be used to modulate the fraction of library elements undergoing primer extension, ligation, or amplification.

Targeted enrichment methods can also be used in a negative selection mode to selectively remove extended recording tags, extended coding tags, or di-tags from a library before sequencing. Thus, in the example described above using biotinylated bait oligonucleotides and streptavidin coated beads, the supernatant is retained for sequencing while the bait-oligonucleotide:extended recording tag, extended coding tag, or di-tag hybrids bound to the beads are not analysed. Examples of undesirable extended recording tags, extended coding tags, or di-tags that can be removed are those representing over abundant polypeptide species, e.g., for proteins, albumin, immunoglobulins, etc.

A competitor oligonucleotide bait, hybridizing to the target but lacking a biotin moiety, can also be used in the hybrid capture step to modulate the fraction of any particular locus enriched. The competitor oligonucleotide bait competes for hybridization to the target with the standard biotinylated bait effectively modulating the fraction of target pulled down during enrichment. The ten orders dynamic range of protein expression can be compressed by several orders using this competitive suppression approach, especially for the overly abundant species such as albumin. Thus, the fraction of library elements captured for a given locus relative to standard hybrid capture can be modulated from 100% down to 0% enrichment.

Additionally, library normalization techniques can be used to remove overly abundant species from the extended recording tag, extended coding tag, or di-tag library. This approach works best for defined length libraries originating from peptides generated by site-specific protease digestion such as trypsin, LysC, GluC, etc. In one example, normalization can be accomplished by denaturing a double-stranded library and allowing the library elements to re-anneal. The abundant library elements re-anneal more quickly than less abundant elements due to the second-order rate constant of bimolecular hybridization kinetics (Bochman, Paeschke et al. 2012). The ssDNA library elements can be separated from the abundant dsDNA library elements using methods known in the art, such as chromatography on hydroxyapatite columns (VanderNoot, et al., 2012, Biotechniques 53:373-380) or treatment of the library with a duplex-specific nuclease (DSN) from Kamchatka crab (Shagin et al., (2002) Genome Res. 12:1935-42) which destroys the dsDNA library elements.

Any combination of fractionation, enrichment, and subtraction methods, of the polypeptides before attachment to the solid support and/or of the resulting extended recording tag library can economize sequencing reads and improve measurement of low abundance species.

In some embodiments, a library of extended recording tags, extended coding tags, or di-tags is concatenated by ligation or end-complementary PCR to create a long DNA molecule comprising multiple different extended recorder tags, extended coding tags, or di-tags, respectively (Du et al., (2003) BioTechniques 35:66-72; Muecke et al., (2008) Structure 16:837-841; U.S. Pat. No. 5,834,252, each of which is incorporated by reference in its entirety). This embodiment is preferable for nanopore sequencing in which long strands of DNA are analyzed by the nanopore sequencing device.

In some embodiments, direct single molecule analysis is performed on an extended recording tag, extended coding tag, or di-tag (see, e.g., Harris et al., (2008) Science 320: 106-109). The extended recording tags, extended coding tags, or di-tags can be analysed directly on the solid support, such as a flow cell or beads that are compatible for loading onto a flow cell surface (optionally microcell patterned), wherein the flow cell or beads can integrate with a single molecule sequencer or a single molecule decoding instrument. For single molecule decoding, hybridization of several rounds of pooled fluorescently-labelled of decoding oligonucleotides (Gunderson et al., (2004) Genome Res. 14:970-7) can be used to ascertain both the identity and order of the coding tags within the extended recording tag. In some embodiments, the binding agents may be labelled with cycle-specific coding tags as described above (see also, Gunderson et al., (2004) Genome Res. 14:970-7). Cycle-specific coding tags will work for both a single, concatenated extended recording tag representing a single polypeptide, or for a collection of extended recording tags representing a single polypeptide.

Following sequencing of the extended reporter tag, extended coding tag, or di-tag libraries, the resulting sequences can be collapsed by their UMIs and then associated to their corresponding polypeptides and aligned to the totality of the proteome. Resulting sequences can also be collapsed by their compartment tags and associated to their corresponding compartmental proteome, which in a particular embodiment contains only a single or a very limited number of protein molecules. Both protein identification and quantification can easily be derived from this digital peptide information.

In some embodiments, the coding tag sequence can be optimized for the particular sequencing analysis platform. In a particular embodiment, the sequencing platform is nanopore sequencing. In some embodiments, the sequencing platform has a per base error rate of >1%, >5%, >10%, >15%, >20%, >25%, or >30%. For example, if the extended recording tag is to be analyzed using a nanopore sequencing instrument, the barcode sequences (e.g., encoder sequences) can be designed to be optimally electrically distinguishable in transit through a nanopore. Peptide sequencing according to the methods described herein may be well-suited for nanopore sequencing, given that the single base accuracy for nanopore sequencing is still rather low (75%-85%), but determination of the "encoder sequence" should be much more accurate (>99%). Moreover, a technique called duplex interrupted nanopore sequencing (DI) can be employed with nanopore strand sequencing without the need for a molecular motor, greatly simplifying the system design (Derrington et al., Proc Natl Acad Sci USA (2010) 107(37): 16060-16065). Readout of the extended recording tag via DI nanopore sequencing requires that the spacer elements in the concatenated extended recording tag library be annealed with complementary oligonucleotides. The oligonucleotides used herein may comprise LNAs, or other modified nucleic acids or analogs to increase the effective Tm of the resultant duplexes. As the single-stranded extended recording tag decorated with these duplex spacer regions is passed through the pore, the double strand region will become transiently stalled at the constriction zone enabling a current readout of about three bases adjacent to the duplex region. In a particular embodiment for DI nanopore sequencing, the encoder sequence is designed in such a way that the three bases adjacent to the spacer element create maximally electrically distinguishable nanopore signals (Derrington et al., Proc Natl Acad Sci USA (2010) 107(37): 16060-16065). As an alternative to motor-free DI sequencing, the spacer element can be designed to adopt a secondary structure such as a G-quartet, which will transiently stall the extended recording tag, extended coding tag, or di-tag as it passes through the nanopore enabling readout of the adjacent encoder sequence (Shim et al., Nucleic Acids Res (2009) 37(3): 972-982; Zhang et al., mAbs (2016) 8, 524-535). After proceeding past the stall, the next spacer will again create a transient stall, enabling readout of the next encoder sequence, and so forth.

The methods disclosed herein can be used for analysis, including detection, quantitation and/or sequencing, of a plurality of polypeptides simultaneously (multiplexing). Multiplexing as used herein refers to analysis of a plurality of polypeptides in the same assay. The plurality of polypeptides can be derived from the same sample or different samples. The plurality of polypeptides can be derived from the same subject or different subjects. The plurality of polypeptides that are analyzed can be different polypeptides, or the same polypeptide derived from different samples. A plurality of polypeptides includes 2 or more polypeptides, 5 or more polypeptides, 10 or more polypeptides, 50 or more polypeptides, 100 or more polypeptides, 500 or more polypeptides, 1000 or more polypeptides, 5,000 or more polypeptides, 10,000 or more polypeptides, 50,000 or more polypeptides, 100,000 or more polypeptides, 500,000 or more polypeptides, or 1,000,000 or more polypeptides.

Sample multiplexing can be achieved by upfront barcoding of recording tag labeled polypeptide samples. Each barcode represents a different sample, and samples can be pooled prior to cyclic binding assays or sequence analysis. In this way, many barcode-labeled samples can be simultaneously processed in a single tube. This approach is a significant improvement on immunoassays conducted on reverse phase protein arrays (RPPA) (Akbani et al., Mol Cell Proteomics (2014) 13(7): 1625-1643; Creighton et al., Drug Des Devel Ther (2015) 9: 3519-3527; Nishizuka et al., Drug Metab Pharmacokinet (2016) 31(1): 35-45). In this way, the present disclosure essentially provides a highly digital sample and analyte multiplexed alternative to the RPPA assay with a simple workflow.

IV. Kits and Related Articles of Manufacture

Provided herein are kits comprising one or more modified cleavases comprising a mutation, e.g., one or more amino acid modifications in an unmodified cleavase and a reagent for or labeling the terminal amino acid of the polypeptide. In some aspects, the modified cleavase is derived from a dipeptide cleavase and removes a single labeled terminal amino acid from a polypeptide or the modified cleavase is derived from a tripeptide cleavase and removes a single labeled terminal amino acid from a polypeptide or a single labeled terminal dipeptide from a polypeptide. In some embodiments, the kits also include instructions for using the reagents for treating polypeptides for analysis and/or sequencing. In some embodiments, the kits comprising one or more modified cleavases (e.g., as described in Section I) are for use in treating peptides, polypeptides, and proteins for sequencing and/or analysis. In some embodiments, the protein analysis employs barcoding and nucleic acid encoding of molecular recognition events, and/or detectable labels. In some embodiments, the kits also include other components for treating the polypeptides and analysis of the polypeptides, including tags (e.g., a DNA tag or a DNA recording tag), solid supports, and other reagents for preparing the polypeptides and reagents for polypeptide analysis.

In some embodiments, the kit comprises more than one modified cleavase. In some cases, a variety of modified cleavases may exhibit different characteristics, for example, preferences for binding polypeptides and/or cleaving amino acids. In some embodiments, two or more modified cleavases may be included in the kit as a mixture of enzymes or separately with each modified cleavase in a container. In some embodiments, the different modified cleavases are contacted with polypeptides simultaneously or sequentially.

In some embodiments, the kit also comprises one or more additional enzymes to eliminate the NTAA (e.g., a proline aminopeptidase). In some specific examples, the additional enzyme is a proline aminopeptidase, a proline iminopeptidase (PIP), or a pyroglutamate aminopeptidase (pGAP). In some embodiments, one or more modified cleavases are provided in combination with other enzymes in the kit. In some specific cases, the modified cleavase and other enzymes are provided as a cocktail in the kit.

In some embodiments, the kit also comprises one or more buffers or a reaction fluid that comprises the substrates, ions, and factors necessary for the desired reaction to occur. Buffers including wash buffers, reaction buffers, and binding buffers, elution buffers and the like are known to those or ordinary skill in the arts. In some embodiments, the modified cleavase is a metallopeptidase and the kit comprises a buffer comprising metal ions required for activation of the modified cleavase. In some examples, the kit comprises the require metal ions required for activation of the modified cleavase, e.g., zinc ions or chloride ions. In some embodiments, the kit further comprises metal-chelating agents or other reagents for inactivating the modified cleavase. In some embodiments, the kits further include buffers and other components to accompany other reagents described herein. The reagents, buffers, and other components may be provided in vials (such as sealed vials), vessels, ampules, bottles, jars, flexible packaging (e.g., sealed Mylar or plastic bags), and the like. Any of the components of the kits may be sterilized and/or sealed.

In some embodiments, the kits further comprise one or more binding agents, wherein each binding agent comprises a coding tag with identifying information regarding the binding agent. In some cases, the kit comprises two or more binding agents. In some examples, the kit comprises a library of binding agents. In some embodiments, the two or more binding agents may be provided in individual containers or as a mixture in a container. In some embodiments, the kit further includes a reagent for transferring the identifying information of the coding tag to a recording tag attached to the polypeptide, wherein the transferring of the identifying information to the recording tag generates an extended recording tag on the polypeptide. In some cases, the reagent for transferring identifying information is a chemical ligation reagent or a biological ligation reagent.

In some embodiments, the kit further includes an amplification reagent for amplifying the extended recording tags.

In some embodiments, the kit further comprises substrates selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof. In some embodiments, the kit comprises a plurality of substrates.

In some embodiments, the kit includes one or more reagents for nucleic acid sequence analysis. In some examples, the reagent for sequence analysis is for use in sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

In some embodiments, the kits or articles of manufacture may further comprise instruction(s) on the methods and uses described herein. In some embodiments, the instructions are directed to methods of preparing and treating polypeptides, including the modified cleavase provided herein. The kits described herein may also include other materials desirable from a commercial and user standpoint, including other buffers, diluents, filters, syringes, and package inserts with instructions for performing any methods described herein.

Any of the above-mentioned kit components, and any molecule, molecular complex or conjugate, reagent (e.g., chemical or biological reagents, including modified cleavases), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit. The kit may optionally comprise instructions for using the modified cleavase.

V. Exemplary Embodiments

Among the provided embodiments are:

1. A modified cleavase comprising a mutation, e.g., one or more amino acid modification(s), in an unmodified cleavase, wherein:

the modified cleavase is derived from a dipeptide cleavase and removes or is configured to remove a single labeled terminal amino acid from a polypeptide; or the modified cleavase is derived from a tripeptide cleavase and removes or is configured to remove a single labeled terminal amino acid from a polypeptide or a single labeled terminal dipeptide from a polypeptide.

2. The modified cleavase of embodiment 1, wherein the modified cleavase derived from the dipeptide cleavase or tripeptide cleavase is configured to cleave the peptide bond between a terminal labeled amino acid residue and a penultimate terminal amino acid residue of the polypeptide.

3. The modified cleavase of embodiment 1, wherein the modified cleavase derived from the tripeptide cleavase is configured to cleave the peptide bond between a penultimate terminal labeled amino acid residue and a antepenultimate terminal amino acid residue of the polypeptide.

4. The modified cleavase of any one of embodiments 1-3, wherein the modified cleavase comprises an active site that interacts with the amide bond between the terminal labeled amino acid residue and a penultimate terminal amino acid residue of the polypeptide.

5. The modified cleavase of any one of embodiments 1-4, wherein the unmodified cleavase is selected from the group consisting of a metallopeptidase, a zinc-dependent metallopeptidase, or a zinc-dependent hydrolase.

6. The modified cleavase of any one of embodiments 1-5, wherein the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof.

7. The modified cleavase of any one of embodiments 1-6, wherein the unmodified cleavase is a dipeptidyl peptidase, a dipeptidyl aminopeptidase, a peptidyl-dipeptidase, a dipeptidyl carboxypeptidase, a sedolisin, or a tripeptidyl peptidase.

8. The modified cleavase of any one of embodiments 1-7, wherein the unmodified cleavase is a dipeptidyl peptidase 3, dipeptidyl peptidase 5, dipeptidyl peptidase 7, dipeptidyl peptidase 11, dipeptidyl aminopeptidase BII, or dipeptidyl peptidase BIT 9. The modified cleavase of any one of embodiments 1-8, wherein the labeled terminal amino acid or dipeptide comprises an N-terminal amino acid (NTAA).

10. The modified cleavase of any one of embodiments 1-8, wherein the labeled terminal amino acid or dipeptide comprises a C-terminal amino acid (CTAA).

11. The modified cleavase of any of embodiments 1-10, wherein the terminal amino acid is labeled with a chemical or an enzymatic reagent or moiety.

12. The modified cleavase of any one of embodiments 1-11, wherein the label comprises a blocked amino acid.

13. The modified cleavase of any of embodiments 1-12, wherein the label comprises an exogenous amino acid.

14. The modified cleavase of any of embodiments 1-13, wherein the label comprises a chemical label.

15. The modified cleavase of embodiment 11, wherein the chemical reagent is selected from the group consisting of a phenyl isothiocyanate (PITC), a nitro-PITC, a sulfo-PITC, a phenyl isocyanate (PIC), a nitro-PIC, a sulfo-PIC, Cbz-Cl (benzyl chloroformate) or Cbz-OSu (benzyloxycarbonyl N-succinimide), a carboxyl-activated amino-blocked amino acid, an anhydride, a 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), 2-Pyridinecarboxaldehyde, 2-Formylphenylboronic acid, 2-Acetylphenylboronic acid, 1-Fluoro-2,4-dinitrobenzene, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N'-Bis(pivaloyl)-1H-pyrazole-1-carboxamidine, N,N'-Bis(benzyloxycarbonyl)-1H-pyrazole-1-carboxamidine, an acetylating reagent, a guanidinylation reagent, a thioacylation reagent, a thioacetylation reagent, a thiobenzylation reagent, and a diheterocyclic methanimine reagent, or a derivative thereof.

16. The modified cleavase of embodiment 11, wherein the chemical reagent is an isatoic anhydride, an isonicotinic anhydride, an azaisatoic anhydride, a succinic anhydride, or a derivative thereof.

17. The modified cleavase of embodiment 16, wherein the chemical reagent is selected from the group consisting of wherein the chemical reagent is selected from the group consisting of 4-Nitrophenyl Anthranilate, N-Methyl-isatoic anhydride, N-acetyl-isatoic anhydride, 4-carboxylic acid isatoic anhydride, 5-methoxy-isatoic anhydride, 5-nitro-isatoic anhydride, 4-chloro-isatoic anhydride, 4-fluoro-isatoic anhydride, 6-fluoro-isatoic anhydride, N-benzyl-isatoic anhydride, 4-trifluoromethyl-isatoic anhydride, 5-trifluoromethyl-isatoic anhydride, 4-nitro-isatoic anhydride, 4-methoxy-isatoic anhydride, 5-Amino-2-fluoro-isonicotinic anhydride (6-fluoro-1H-pyrido[3,4-d][1,3]oxazine-2,4-dione), 3,6, difluorophthalic anhydride, and 2,3 pyrazinedicarboxylic anhydride, or a derivative thereof.

18. The modified cleavase of any one of embodiments 1-17, wherein the modified cleavase comprises an amino acid sequence that exhibits at least 50% identity, at least 60% identity, at least 70% identity, at least 80% identity, or at least 90% or more identity with the unmodified cleavase.

19. The modified cleavase of any one of embodiments 1-18, wherein the mutation comprises an amino acid substitution, deletion, addition, or a combination thereof.

20. The modified cleavase of any one of embodiments 1-19, wherein the length of the polypeptide is greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids.

21. The modified cleavase of any one of embodiments 1-20, wherein the length of the polypeptide is greater than 10 amino acids.

22. The modified cleavase of any one of embodiments 1-21, wherein the modified cleavase comprises a modification within its substrate binding site.

23. The modified cleavase of any one of embodiments 1-22, wherein the modified cleavase comprises a modification within its catalytic domain.

24. The modified cleavase of any one of embodiments 1-23, wherein the modified cleavase comprises a modification within its chymotrypsin fold.

25. The modified cleavase of any one of embodiments 1-24, wherein the modified cleavase comprises a modification at an amine binding site.

26. The modified cleavase of any one of embodiments 1-25, wherein the modified cleavase comprises a modification in its loop domain.

27. The modified cleavase of any one of embodiments 1-26, wherein the modified cleavase comprises a modification for improving accessibility to the active site of the modified cleavase.

28. The modified cleavase of any one of embodiments 1-27, wherein the modified cleavase is derived from a dipeptidyl aminopeptidase BII or dipeptidyl peptidase BII as provided in SEQ ID NO: 13 or 20.

29. The modified cleavase of any one of embodiments 1-28, wherein the modified cleavase comprises an amino acid sequence that exhibits at least 20% identity, at least 30% identity, at least 40% identity, at least 50% identity, at least 60% identity, at least 70% identity, at least 80% identity, or at least 90% or more identity to any of SEQ ID NOs: 17-19, 23-28, 31-39, or a specific binding fragment thereof.

30. The modified cleavase of any one of embodiments 1-29, comprising the sequence of amino acids set forth in any of SEQ ID NOs: 17-19, 23-28, or a sequence of amino acids that exhibits at least 95% sequence identity to any of SEQ ID NOs: 17-19, 23-28, 31-39, or a specific binding fragment thereof.

31. The modified cleavase of any one of embodiments 1-30, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13.

32. The modified cleavase of any one of embodiments 1-31, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13, and comprises an amino acid sequence that exhibits at least 30% identity, at least 40% identity, at least 50% identity, at least 60% identity, at least 70% identity, at least 80% identity, or at least 90% or more identity to any of SEQ ID NOs: 17-19, 23-28, 31-39.

33. The modified cleavase of any one of embodiments 1-32, wherein the one or more amino acid substitution is A126T, D188V, I189A, D190S, N191C, N191F, N191L, N191M, N191R, N191S, N191T, N191V, W192F, W192G, W192L, R196H, R196K, R196S, R196T, R196V, G238V, A302W, N306A, N306G, N306R, N306S, T307K, N310D, N310G, N310K, N310L, N525K, A528V, F546L, A604V, D650A, D650G, D650S, G651H, G651T, G651V, G651Y, S655G, S655T, V656E, V656G, V656S, K665I, K692N, and/or a conservative amino acid substitution thereof.

34. The modified cleavase of any one of embodiments 1-33, wherein the one or more amino acid modification(s) is N191M/W192G/R196V/N306R/D650A, D188V/I189A/D190S/N191L/W192G/R196S/A302W/N310K/D650A, N191M/W192G/R196T/N306R/T307K/D650A, N191M/W192G/R196T/N306R/N525K/A528V/A604V/D650A/K692N, A126T/N191M/W192G/R196T/G238V/N306R/D650A, N191M/W192G/R196T/N306R/F546L/D650A, N191M/W192G/R196T/N306R/D650A/G651V/K665I, N191M/W192G/R196T/N306R/D650A/G651V, N191C/W192L/R196K/N306R/N310D/G651Y/S655G/V656G, N191C/W192L/N306R/N310D/G651Y/S655G/V656G, N191F/W192F/N306R/N310G/G651H/V656E, N191R/W192L/N306S/N310L/G651T/S655T/V656S, N191S/R196H/N306A/D650G, N191T/R196H/N306A/D650G, N191M/R196H/N306A/D650G, N191V/N306A/D650S, or N191S/N306G/D650S.

35. The modified cleavase of any one of embodiments 1-34, wherein the modified cleavase exhibits the substrate specificity of any of the sequences in SEQ ID NOs: 17-19, 23-28, or 31-39.

36. The modified cleavase of any one of embodiments 1-35, wherein the modified cleavase comprises an amino acid sequence that comprises a catalytic domain with at least 20% identity, at least 30% identity, at least 40% identity, at least 50% identity, at least 60% identity, at least 70% identity, at least 80% identity, or at least 90% or more identity with the catalytic domain of any of SEQ ID NOs: 17-19, 23-28, or 31-39.

37. The modified cleavase of any one of embodiments 1-36, wherein the modified cleavase comprises an amino acid sequence that comprises an amine binding site with at least 20% identity, at least 30% identity, at least 40% identity, at least 50% identity, at least 60% identity, at least 70% identity, at least 80% identity, or at least 90% or more identity with the amine binding site of any of SEQ ID NOs: 17-19, 23-28, or 31-39.

38. The modified cleavase of any one of embodiments 1-37, wherein the modified cleavase comprises an amino acid sequence that comprises a loop domain with at least 20% identity, at least 30% identity, at least 40% identity, at least 50% identity, at least 60% identity, at least 70% identity, at least 80% identity, or at least 90% or more identity with the loop domain of any of SEQ ID NOs: 17-19, 23-28, or 31-39.

39. The modified cleavase of any one of embodiments 1-38, wherein the modified cleavase comprises one or more amino acid modifications in an unmodified cleavase, corresponding to position(s) 183, 184, 185, 186, 187, 188, 189, 190, 191, 192, 193, 194, 195, 196, 197, 198, 199, 200, 201, and/or 202, with reference to numbering of SEQ ID NO: 13.

40. The modified cleavase of any one of embodiments 1-38, wherein the modified cleavase comprises one or more amino acid modifications in an unmodified cleavase, corresponding to position(s) 188, 189, 190, 191, 192, 302, and/or 310, with reference to numbering of SEQ ID NO: 13.

41. The modified cleavase of any one of embodiments 1-38, wherein the modified cleavase comprises one or more amino acid modifications in an unmodified cleavase, corresponding to position(s) 191, 192, 196, 306, 310, 627, 628, 630, 648, 650, 651, 655, 656, and/or 669 with reference to numbering of SEQ ID NO: 13.

42. The modified cleavase of any one of embodiments 1-38, wherein the modified cleavase comprises one or more amino acid modifications in an unmodified cleavase, corresponding to any of position(s) 323 to 544, with reference to numbering of SEQ ID NO: 13.

43. A method of treating a polypeptide, comprising contacting the polypeptide with a modified cleavase comprising a mutation, e.g., one or more amino acid modification(s), in an unmodified cleavase, wherein:
the modified cleavase is derived from a dipeptide cleavase and removes or is configured to remove a single labeled terminal amino acid from a polypeptide; or
the modified cleavase is derived from a tripeptide cleavase and removes or is configured to remove a single labeled terminal amino acid from a polypeptide or a single labeled terminal dipeptide from a polypeptide.

44. The method of embodiment 43, wherein the modified cleavase derived from the dipeptide cleavase or tripeptide cleavase is configured to cleave the peptide bond between a terminal labeled amino acid residue and a penultimate terminal amino acid residue of the polypeptide.

45. The method of embodiment 43 or embodiment 44, wherein the modified cleavase comprises an active site that interacts with the amide bond between the terminal labeled amino acid residue and a penultimate terminal amino acid residue of the polypeptide.

46. The method of any one of embodiments 43-45, wherein the removal of the single labeled terminal amino acid or single labeled terminal dipeptide exposes a new terminal amino acid of the polypeptide.

47. The method of any one of embodiments 43-46, wherein the unmodified cleavase is selected from the group consisting of a metallopeptidase, a zinc-dependent metallopeptidase, or a zinc-dependent hydrolase.

48. The method of any one of embodiments 43-47, wherein the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof.

49. The method of any one of embodiments 43-48, wherein the unmodified cleavase is a dipeptidyl peptidase, a dipeptidyl aminopeptidase, a peptidyl-dipeptidase, a dipeptidyl carboxypeptidase, a sedolisin, or a tripeptidyl peptidase.

50. The method of any one of embodiments 43-49, wherein the unmodified cleavase is a dipeptidyl peptidase 3, dipeptidyl peptidase 5, dipeptidyl peptidase 7, dipeptidyl peptidase 11, dipeptidyl aminopeptidase BII, or dipeptidyl peptidase BIT 51. The method of any one of embodiments 43-50, wherein the labeled terminal amino acid or dipeptide comprises an N-terminal amino acid (NTAA).

52. The method of any one of embodiments 43-50, wherein the labeled terminal amino acid or dipeptide comprises a C-terminal amino acid (CTAA).

53. The method of any one of embodiments 43-52, wherein the modified cleavase comprises an amino acid sequence that exhibits at least 50% identity, at least 60% identity, at least 70% identity, at least 80% identity, or at least 90% or more identity with the unmodified cleavase.

54. The method of any one of embodiments 43-53, wherein the mutation comprises an amino acid substitution, deletion, addition, or a combination thereof.

55. The method of any one of embodiments 43-54, wherein the length of the polypeptide is greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids.

56. The method of any one of embodiments 43-55, wherein the length of the polypeptide is greater than 10 amino acids.

57. The method of any one of embodiments 43-56, wherein the modified cleavase comprises a modification within its substrate binding site.

58. The method of any one of embodiments 43-57, wherein the modified cleavase comprises a modification within its catalytic domain.

59. The method of any one of embodiments 43-58, wherein the modified cleavase comprises a modification within its chymotrypsin fold.

60. The method of any one of embodiments 43-59, wherein the modified cleavase comprises a modification at an amine binding site.

61. The method of any one of embodiments 43-60, wherein the modified cleavase comprises a modification in its loop domain.

62. The method of any one of embodiments 43-61, wherein the modified cleavase comprises a modification for improving accessibility to the active site of the modified cleavase.

63. The method of any one of embodiments 43-62, wherein the modified cleavase is derived from a dipeptidyl aminopeptidase BII or dipeptidyl peptidase BII as provided in SEQ ID NO: 13 or 20.

64. The method of any one of embodiments 43-63, wherein the modified cleavase comprises an amino acid sequence that exhibits at least 20% identity, at least 30% identity, at least 40% identity, at least 50% identity, at least 60% identity, at least 70% identity, at least 80% identity, or at least 90% or more identity to any of SEQ ID NOs: 17-19, 23-28, 31-39, or a specific binding fragment thereof.

65. The method of any one of embodiments 43-64, wherein the modified cleavase comprises the sequence of amino acids set forth in any of SEQ ID NO: 17-19, 23-28, 31-39, or a sequence of amino acids that exhibits at least 95% sequence identity to any of SEQ ID NO: 17-19, 23-28, 31-39, or a specific binding fragment thereof.

66. The method of any one of embodiments 43-65, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13.

67. The method of any one of embodiments 43-66, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13, and comprises an amino acid sequence that exhibits at least 30% identity, at least 40% identity, at least 50% identity, at least 60% identity, at least 70% identity, at least 80% identity, or at least 90% or more identity to any of SEQ ID NOs: 17-19, 23-28, 31-39.

68. The method of any one of embodiments 43-67, wherein the one or more amino acid substitution is A126T, D188V, I189A, D190S, N191C, N191F, N191L, N191M, N191R, N191S, N191T, N191V, W192F, W192G, W192L, R196H, R196K, R196S, R196T, R196V, G238V, A302W, N306A, N306G, N306R, N306S, T307K, N310D, N310G, N310K, N310L, N525K, A528V, F546L, A604V, D650A, D650G, D650S, G651H, G651T, G651V, G651Y, S655G, S655T, V656E, V656G, V656S, K665I, K692N, and/or a conservative amino acid substitution thereof.

69. The method of any one of embodiments 43-68, wherein the one or more amino acid modification(s) is N191M/W192G/R196V/N306R/D650A, D188V/I189A/D190S/N191L/W192G/R196S/A302W/N310K/D650A, N191M/W192G/R196T/N306R/T307K/D650A, N191M/W192G/R196T/N306R/N525K/A528V/A604V/D650A/K692N, A126T/N191M/W192G/R196T/G238V/N306R/D650A, N191M/W192G/R196T/N306R/F546L/D650A, N191M/W192G/R196T/N306R/D650A/G651V/K665I, N191M/W192G/R196T/N306R/D650A/G651V, N191C/W192L/R196K/N306R/N310D/G651Y/S655G/V656G, N191C/W192L/N306R/N310D/G651Y/S655G/V656G, N191F/W192F/N306R/N310G/G651H/V656E, N191R/W192L/N306S/N310L/G651T/S655T/V656S, N191S/R196H/N306A/D650G, N191T/R196H/N306A/D650G, N191M/R196H/N306A/D650G, N191V/N306A/D650S, or N191S/N306G/D650S.

70. The method of any one of embodiments 43-69, wherein the modified cleavase exhibits the substrate specificity of the sequence of any of the sequences in SEQ ID NOs: 17-19, 23-28, or 31-39.

71. The method of any one of embodiments 43-70, wherein the modified cleavase comprises an amino acid sequence that comprises a catalytic domain with at least 20% identity, at least 30% identity, at least 40% identity, at least 50% identity, at least 60% identity, at least 70% identity, at least 80% identity, or at least 90% or more identity with the catalytic domain of any of SEQ ID NOs: 17-19, 23-28, or 31-39.

72. The method of any one of embodiments 43-71, wherein the modified cleavase comprises an amino acid sequence that comprises an amine binding site with at least 20% identity, at least 30% identity, at least 40% identity, at least 50% identity, at least 60% identity, at least 70% identity, at least 80% identity, or at least 90% or more identity with the amine binding site of any of SEQ ID NOs: 17-19, 23-28, or 31-39.

73. The method of any one of embodiments 43-72, wherein the modified cleavase comprises an amino acid sequence that comprises a loop domain with at least 20% identity, at least 30% identity, at least 40% identity, at least 50% identity, at least 60% identity, at least 70% identity, at least 80% identity, or at least 90% or more identity with the loop domain of any of SEQ ID NOs: 17-19, 23-28, or 31-39.

74. The method of any one of embodiments 43-73, wherein the modified cleavase comprises one or more amino acid modifications in an unmodified cleavase, corresponding to position(s) 183, 184, 185, 186, 187, 188, 189, 190, 191, 192, 193, 194, 195, 196, 197, 198, 199, 200, 201, and/or 202, with reference to numbering of SEQ ID NO: 13.

75. The method of any one of embodiments 43-73, wherein the modified cleavase comprises one or more amino acid modifications in an unmodified cleavase, corresponding to position(s) 188, 189, 190, 191, 192, 302, and/or 310, with reference to numbering of SEQ ID NO: 13.

76. The method of any one of embodiments 43-73, wherein the modified cleavase comprises one or more amino acid modifications in an unmodified cleavase, corresponding to position(s) 191, 192, 196, 306, 310, 627, 628, 630, 648, 650, 651, 655, 656, and/or 669 with reference to numbering of SEQ ID NO: 13.

77. The method of any one of embodiments 43-73, wherein the modified cleavase comprises one or more amino acid modifications in an unmodified cleavase, corresponding to any of position(s) 323 to 544, with reference to numbering of SEQ ID NO: 13.

78. The method of any one of embodiments 43-78, further comprising contacting a precursor polypeptide with a reagent for labeling the terminal amino acid of the precursor polypeptide, to provide a polypeptide prepared for treatment with the modified cleavase.

79. The method of embodiment 78, wherein the reagent for labeling the terminal amino acid is a chemical reagent or an enzymatic reagent.

80. The method of any one of embodiments 43-79, wherein the label comprises a blocked amino acid.

81. The method of any of embodiments 43-80, wherein the label comprises an exogenous labeled amino acid.

82. The method of any one of embodiments 43-81, wherein the label comprises a chemical label.

83. The method of any one of embodiments 78-82, wherein the contacting with the reagent for labeling the terminal amino acid and contacting with the modified cleavase is performed in sequential order.

84. The method of any one of embodiments 78-83, wherein the contacting with the reagent for labeling the terminal amino acid and contacting with the modified cleavase are repeated one or more times.

85. The method of any one of embodiments 79-84, wherein the chemical reagent is selected from the group consisting of a phenyl isothiocyanate (PITC), a nitro-PITC, a sulfo-PITC, a phenyl isocyanate (PIC), a nitro-PIC, a sulfo-PIC, Cbz-Cl (benzyl chloroformate) or Cbz-OSu (benzyloxycarbonyl N-succinimide), a carboxyl-activated amino-blocked amino acid, a 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), an anhydride, 2-Pyridinecarboxaldehyde, 2-Formylphenylboronic acid, 2-Acetylphenylboronic acid, 1-Fluoro-2,4-dinitrobenzene, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N'-Bis(pivaloyl)-1H-pyrazole-1-carboxamidine, N,N'-Bis(benzyloxycarbonyl)-1H-pyrazole-1-carboxamidine, an acetylating reagent, a guanidinylation reagent, a thioacylation reagent, a thioacetylation reagent, a thiobenzylation reagent, and a diheterocyclic methanimine reagent, or a derivative thereof.

86. The method of any one of embodiments 79-85, wherein the chemical reagent is an isatoic anhydride, an isonicotinic anhydride, an azaisatoic anhydride, a succinic anhydride, or a derivative thereof.

87. The method of embodiment 86, wherein the chemical reagent is selected from the group consisting of 4-Nitrophenyl Anthranilate, N-Methyl-isatoic anhydride, N-acetyl-isatoic anhydride, 4-carboxylic acid isatoic anhydride, 5-methoxy-isatoic anhydride, 5-nitro-isatoic anhydride, 4-chloro-isatoic anhydride, 4-fluoro-isatoic anhydride, 6-fluoro-isatoic anhydride, N-benzyl-isatoic anhydride, 4-trifluoromethyl-isatoic anhydride, 5-trifluoromethyl-isatoic anhydride, 4-nitro-isatoic anhydride, 4-methoxy-isatoic anhydride, 5-Amino-2-fluoro-isonicotinic anhydride (6-fluoro-1H-pyrido[3,4-d][1,3]oxazine-2,4-dione), 3,6, difluorophthalic anhydride, and 2,3 pyrazinedicarboxylic anhydride, or a derivative thereof.

88. The method of any one of embodiments 43-87, further comprising contacting the polypeptide with a binding agent capable of binding to the terminal amino acid of the polypeptide, wherein the binding agent comprises a coding tag with identifying information regarding the binding agent.

89. The method of embodiment 88, wherein the binding agent comprises two or more binding agents.

90. The method of embodiment 88 or embodiment 89, wherein the binding agent binds to an N-terminal amino acid (NTAA).

91. The method of embodiment 88 or embodiment 89, wherein the binding agent binds to a C-terminal amino acid (CTAA).

92. The method of any one of embodiments 88-91, wherein the binding agent is capable of binding to a labeled or an unlabeled terminal amino acid.

93. The method of any one of embodiments 88-92, wherein the contacting with the binding agent is:
before contacting the polypeptide with the reagent for labeling the terminal amino acid; and/or
before contacting the polypeptide with the modified cleavase.

94. The method of any one of embodiments 88-93, wherein the contacting with the binding agent is after contacting the polypeptide with the reagent for labeling the terminal amino acid.

95. The method of any one of embodiments 88-92, wherein:
the contacting with the reagent for labeling the terminal amino acid is before the contacting with the binding agent; and
the contacting with the binding agent is before the contacting of the polypeptide with the modified cleavase.

96. The method of any one of embodiments 88-95, wherein the contacting of the polypeptide with the binding agent, the reagent for labeling the terminal amino acid, and the modified cleavase, is repeated one or more times.

97. The method of any one of embodiments 88-96, further comprising transferring the identifying information of the coding tag to a recording tag attached to the polypeptide, thereby generating an extended recording tag on the polypeptide.

98. The method of embodiment 97, wherein transferring of the identifying information is performed:
after the binding of the polypeptide with the binding agent; and
before the contacting of the polypeptide with the modified cleavase.

99. The method of embodiment 97 or embodiment 98, wherein the steps of:
(a) contacting the polypeptide with the binding agent;
(b) transferring identifying information to the recording tag;
(c) contacting the polypeptide with a reagent for labeling the terminal amino acid; and
(d) contacting the polypeptide with a modified cleavase;

are repeated in sequential order to generate one or more additional extended recording tags.

100. The method of embodiment 99, further comprising removing the binding agent after step (b) and before step (c).

101. The method of embodiment 97 or embodiment 98, wherein the steps of:
(a) contacting the polypeptide with a reagent for labeling the terminal amino acid;
(b) contacting the polypeptide with the binding agent capable of binding the labeled terminal amino acid;
(c) transferring identifying information to the recording tag; and
(d) contacting the polypeptide with a modified cleavase;
are repeated in sequential order to generate one or more additional extended recording tags.

102. The method of embodiment 101, further comprising removing the binding agent after step (c) and before step (d).

103. The method of any one of embodiments 97-102, further comprising analyzing the one or more extended recording tag.

104. A method for analyzing a polypeptide, comprising the steps of:
(a) contacting a polypeptide with a binding agent capable of binding to the terminal amino acid of the polypeptide, wherein the binding agent comprises a coding tag with identifying information regarding the binding agent;
(b) transferring the identifying information of the coding tag to a recording tag associated with the polypeptide to generate an extended recording tag;
(c) contacting the polypeptide with a reagent to label the terminal amino acid of the polypeptide; and
(d) contacting the polypeptide with a modified cleavase comprising a mutation, e.g., one or more amino acid modification(s), in an unmodified cleavase, wherein:
the modified cleavase is derived from a dipeptide cleavase and removes or is configured to remove a single terminal amino acid labeled by the reagent in step (c) from the polypeptide; or
the modified cleavase is derived from a tripeptide cleavase and removes or is configured to remove a single terminal amino acid or a single terminal dipeptide labeled by the reagent in step (c) from the polypeptide.

105. The method of embodiment 104, wherein the modified cleavase derived from the dipeptide cleavase or tripeptide cleavase is configured to cleave the peptide bond between a terminal labeled amino acid residue and a penultimate terminal amino acid residue of the polypeptide.

106. The method of embodiment 104, wherein the modified cleavase derived from the tripeptide cleavase is configured to cleave the peptide bond between a penultimate terminal labeled amino acid residue and a antepenultimate terminal amino acid residue of the polypeptide.

107. The method of any one of embodiments 104-106, wherein the unmodified cleavase is selected from the group consisting of a metallopeptidase, a zinc-dependent metallopeptidase, or a zinc-dependent hydrolase.

108. The method of any one of embodiments 104-107, wherein the unmodified cleavase is a protein classified in EC 3.4.14, EC 3.4.15, MEROPS S8, MEROPS S9, MEROPS S33, MEROPS S46, MEROPS M49, or MEROPS S53, or a functional homolog or fragment thereof.

109. The method of any one of embodiments 104-108, wherein the unmodified cleavase is a dipeptidyl peptidase, a dipeptidyl aminopeptidase, a peptidyl-dipeptidase, a dipeptidyl carboxypeptidase, a sedolisin, or a tripeptidyl peptidase.

110. The method of any one of embodiments 104-109, wherein the unmodified cleavase is a dipeptidyl peptidase 3, dipeptidyl peptidase 5, dipeptidyl peptidase 7, dipeptidyl peptidase 11, dipeptidyl aminopeptidase BII, or dipeptidyl peptidase BII.

111. The method of any one of embodiments 104-110, wherein the binding agent comprises two or more binding agents.

112. The method of any one of embodiments 104-111, wherein the polypeptide comprises two or more polypeptides.

113. The method of any one of embodiments 104-112, wherein steps (a)-(d) are repeated for "n" binding cycles, wherein the identifying information of each coding tag of each binding agent that binds to the polypeptide is transferred to the extended recording tag generated from the previous binding cycle to generate an $n^{th}$ order extended recording tag.

114. The method of any one of embodiments 104-113, further comprising:
(b1) removing the binding agent.

115. The method of embodiment 113 or embodiment 114, further comprising:
(e) analyzing the $n^{th}$ order extended recording tag.

116. The method of any one of embodiments 104-115, wherein:
step (a) is performed before step (b);
step (a) is performed before step (c);
step (a) is performed before step (d);
step (b) is performed before step (c);
step (b) is performed before step (d);
step (b1) is performed after step (a);
step (b1) is performed after step (b);
step (b1) is performed before step (c);
step (b1) is performed before step (d);
step (c) is performed before step (a);
step (c) is performed before step (b); and/or
step (c) is performed before step (d).

117. The method of any one of embodiments 104-116, wherein the terminal amino acid is an N-terminal amino acid (NTAA).

118. The method of any one of embodiments 104-116, wherein the terminal amino acid is a C-terminal amino acid (CTAA).

119. The method of any one of embodiments 97-118, wherein the recording tag is a DNA molecule, an RNA molecule, a PNA molecule, a BNA molecule, an XNA, molecule, an LNA molecule, a γPNA molecule, or a combination thereof.

120. The method of any one of embodiments 97-119, wherein the recording tag comprises a unique molecular identifier (UMI).

121. The method of any one of embodiments 97-120, wherein the recording tag comprises a universal priming site.

122. The method of any one of embodiments 88-121, wherein the binding agent and the coding tag are joined by a linker.

123. The method of any one of embodiments 97-122, wherein transferring the identifying information of the recording tag to the coding tag is effected by primer extension.

124. The method of any one of embodiments 97-122, wherein transferring the identifying information of the recording tag to the coding tag is effected by ligation.

125. The method of any one of embodiments 88-124, wherein the coding tag comprises a UMI.

126. The method of any one of embodiments 88-125, wherein the coding tag comprises a universal priming site.

127. The method of any one of embodiments 43-126, wherein the polypeptide is directly or indirectly joined to a solid support.

128. The method of embodiment 127, wherein the solid support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

129. The method of embodiment 128, wherein the solid support comprises a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or any combinations thereof.

130. The method of any one of embodiments 88-129, wherein the binding agent is a polypeptide or protein.

131. The method of embodiment 130, wherein the binding agent is an aminopeptidase or variant, mutant, or modified protein thereof; an aminoacyl tRNA synthetase or variant, mutant, or modified protein thereof; an anticalin or variant, mutant, or modified protein thereof; a ClpS, ClpS2, or variant, mutant, or modified protein thereof; a UBR box protein or variant, mutant, or modified protein thereof; or a modified small molecule that binds amino acid(s), i.e. vancomycin or a variant, mutant, or modified molecule thereof; or an antibody or binding fragment thereof; or any combination thereof.

132. The method of any one of embodiments 88-131, wherein the binding agent binds to a single amino acid residue, a dipeptide, a tripeptide or a post-translational modification of the polypeptide.

133. The method of embodiment 104-133, wherein the binding agent binds to an N-terminal amino acid residue.

134. The method of embodiment 104-133, wherein the binding agent binds to a C-terminal amino acid residue.

135. The method of any one of embodiments 103-134, wherein the one or more extended recording tags are amplified prior to analysis.

136. The method of any one of embodiments 103-135, wherein analyzing the one or more extended recording tags comprises a nucleic acid sequencing method.

137. The method of embodiment 136, wherein the nucleic acid sequencing method is sequencing by synthesis, sequencing by ligation, sequencing by hybridization, polony sequencing, ion semiconductor sequencing, or pyrosequencing.

138. The method of embodiment 136 or embodiment 137, wherein the nucleic acid sequencing method is single molecule real-time sequencing, nanopore-based sequencing, or direct imaging of DNA using advanced microscopy.

139. The method of any one of embodiments 43-138, wherein the contacting the polypeptide with the modified cleavase to remove the single terminal amino acid is performed in less than 5 minutes, less than 10 minutes, less than 20 minutes, less than 30 minutes, less than 40 minutes, less than 50 minutes, less than 60 minutes, less than 2 hours, less than 5 hours, less than 8 hours, or less than 10 hours.

140. The method of any one of embodiments 43-139, which is conducted in the absence of a condition that degrades nucleic acids, e.g., DNA, RNA or a mixture or combination thereof.

141. The method of embodiment 140, wherein the condition that degrades nucleic acids is a chemical condition.

142. The method of any one of embodiments 43-141, which is conducted in the presence of a condition that is compatible with nucleic acids.

143. The method of any one of embodiments 140-142, which is conducted in the absence of a strong acid or strong base.

144. The method of embodiment 143, which is conducted in the absence of a strong anhydrous acid.

145. The method of embodiment 144, wherein the strong anhydrous is anhydrous TFA.

146. A kit for treating a polypeptide, comprising:
a modified cleavase comprising a mutation, e.g., one or more amino acid modification(s), in an unmodified cleavase, wherein:
the modified cleavase is derived from a dipeptide cleavase and removes or is configured to remove a single labeled terminal amino acid from a polypeptide; or
the modified cleavase is derived from a tripeptide cleavase and removes or is configured to remove a single labeled terminal amino acid from a polypeptide or a single labeled terminal dipeptide from a polypeptide; and
a reagent for labeling the terminal amino acid of the polypeptide.

147. The kit of embodiment 146, wherein the modified cleavase derived from the dipeptide cleavase or tripeptide cleavase is configured to cleave the peptide bond between a terminal labeled amino acid residue and a penultimate terminal amino acid residue of the polypeptide.

148. The kit of embodiment 146, wherein the modified cleavase derived from the tripeptide cleavase is configured to cleave the peptide bond between a penultimate terminal labeled amino acid residue and a antepenultimate terminal amino acid residue of the polypeptide 149. The kit of any one of embodiments 146-148, wherein the modified cleavase comprises an active site that interacts with the amide bond between the terminal labeled amino acid residue and a penultimate terminal amino acid residue of the polypeptide.

150. The kit of any one of embodiments 146-149, wherein the unmodified cleavase is selected from the group consisting of a metallopeptidase, a zinc-dependent metallopeptidase, or a zinc-dependent hydrolase.

151. The kit of any one of embodiments 146-150, wherein the unmodified cleavase is a protein classified in EC 3.4.14, EC 3.4.15, MEROPS S8, MEROPS S9, MEROPS S33, MEROPS S46, MEROPS M49, or MEROPS S53, or a homolog thereof.

152. The kit of any one of embodiments 146-151, wherein the unmodified cleavase is a dipeptidyl peptidase, a dipeptidyl aminopeptidase, a peptidyl-dipeptidase, a dipeptidyl carboxypeptidase, a sedolisin, or a tripeptidyl peptidase.

153. The kit of any one of embodiments 146-152, wherein the unmodified cleavase is a dipeptidyl peptidase 3, dipeptidyl peptidase 5, dipeptidyl peptidase 7, dipeptidyl peptidase 11, dipeptidyl aminopeptidase BII, or dipeptidyl peptidase BIT 154. The kit of any one of embodiments 146-153, wherein the labeled terminal amino acid or dipeptide comprises an N-terminal amino acid (NTAA).

155. The kit of any one of embodiments 146-153, wherein the labeled terminal amino acid or dipeptide comprises a C-terminal amino acid (CTAA).

156. The kit of any one of embodiments 146-155, wherein the modified cleavase does not cleave the peptide bond between a penultimate terminal amino acid residue and an antepenultimate terminal amino acid residue of the polypeptide.

157. The kit of any one of embodiments 146-156, wherein the modified cleavase comprises an amino acid sequence that exhibits at least 50% identity, at least 60% identity, at least 70% identity, at least 80% identity, or at least 90% or more identity with the unmodified cleavase.

158. The kit of any one of embodiments 146-157, wherein the mutation comprises an amino acid substitution, deletion, addition, or a combination thereof.

159. The kit of any one of embodiments 146-158, wherein the length of the polypeptide is greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids.

160. The kit of any one of embodiments 146-159, wherein the length of the polypeptide is greater than 10 amino acids.

161. The kit of any one of embodiments 146-160, wherein the modified cleavase comprises a modification within its substrate binding site.

162. The kit of any one of embodiments 146-161, wherein the modified cleavase comprises a modification within its catalytic domain.

163. The kit of any one of embodiments 146-162, wherein the modified cleavase comprises a modification within its chymotrypsin fold.

164. The kit of any one of embodiments 146-163, wherein the modified cleavase comprises a modification at an amine binding site.

165. The kit of any one of embodiments 146-164, wherein the modified cleavase comprises a modification in its loop domain.

166. The kit of any one of embodiments 146-165, wherein the modified cleavase comprises a modification for improving accessibility to the active site of the modified cleavase.

167. The kit of any one of embodiments 146-166, wherein the modified cleavase is derived from a dipeptidyl aminopeptidase BII or dipeptidyl peptidase BII as provided in SEQ ID NO: 13 or 20.

168. The kit of any one of embodiments 146-167, wherein the modified cleavase comprises an amino acid sequence that exhibits at least 20% identity, at least 30% identity, at least 128% identity, at least 50% identity, at least 60% identity, at least 70% identity, at least 80% identity, or at least 90% or more identity to any of SEQ ID NOs: 17-19, 23-28, 31-39, or a specific binding fragment thereof.

169. The kit of any one of embodiments 146-168, wherein the modified cleavase comprises the sequence of amino acids set forth in any of SEQ ID NOs: 17-19, 23-28, or a sequence of amino acids that exhibits at least 95% sequence identity to any of SEQ ID NOs: 17-19, 23-28, 31-39, or a specific binding fragment thereof.

170. The kit of any one of embodiments 146-169, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13.

171. The kit of any one of embodiments 146-170, wherein the modified cleavase comprises one or more amino acid modifications in an unmodified cleavase, corresponding to position(s) 126, 188, 189, 190, 191, 192, 196, 238, 302, 306, 307, 310, 525, 528, 546, 604, 650, 651, 655, 656, 665, and/or 692, with reference to numbering of SEQ ID NO: 13, and comprises an amino acid sequence that exhibits at least 30% identity, at least 128% identity, at least 50% identity, at least 60% identity, at least 70% identity, at least 80% identity, or at least 90% or more identity to any of SEQ ID NOs: 17-19, 23-28, 31-39.

172. The kit of any one of embodiments 146-171, wherein the one or more amino acid substitution is A126T, D188V, I189A, D190S, N191C, N191F, N191L, N191M, N191R, N191S, N191T, N191V, W192F, W192G, W192L, R196H, R196K, R196S, R196T, R196V, G238V, A302W, N306A, N306G, N306R, N306S, T307K, N310D, N310G, N310K, N310L, N525K, A528V, F546L, A604V, D650A, D650G, D650S, G651H, G651T, G651V, G651Y, S655G, S655T, V656E, V656G, V656S, K665I, K692N, and/or a conservative amino acid substitution thereof.

173. The kit of any one of embodiments 146-172, wherein the one or more amino acid modification(s) is N191M/W192G/R196V/N306R/D650A, D188V/I189A/D190S/N191L/W192G/R196S/A302W/N310K/D650A, N191M/W192G/R196T/N306R/T307K/D650A, N191M/W192G/R196T/N306R/N525K/A528V/A604V/D650A/K692N, A126T/N191M/W192G/R196T/G238V/N306R/D650A, N191M/W192G/R196T/N306R/F546L/D650A, N191M/W192G/R196T/N306R/D650A/G651V/K665I, N191M/W192G/R196T/N306R/D650A/G651V, N191C/W192L/R196K/N306R/N310D/G651Y/S655G/V656G, N191C/W192L/N306R/N310D/G651Y/S655G/V656G, N191F/W192F/N306R/N310G/G651H/V656E, N191R/W192L/N306S/N310L/G651T/S655T/V656S, N191S/R196H/N306A/D650G, N191T/R196H/N306A/D650G, N191M/R196H/N306A/D650G, N191V/N306A/D650S, or N191S/N306G/D650S.

174. The kit of any one of embodiments 146-173, wherein the modified cleavase exhibits the substrate specificity of any of the sequences in SEQ ID NOs: 17-19, 23-28, or 31-39.

175. The kit of any one of embodiments 146-174, wherein the modified cleavase comprises an amino acid sequence that comprises a catalytic domain with at least 20% identity, at least 30% identity, at least 128% identity, at least 50% identity, at least 60% identity, at least 70% identity, at least 80% identity, or at least 90% or more identity with the catalytic domain of any of SEQ ID NOs: 17-19, 23-28, or 31-39.

176. The kit of any one of embodiments 146-175, wherein the modified cleavase comprises an amino acid sequence that comprises an amine binding site with at least 20% identity, at least 30% identity, at least 128% identity, at least 50% identity, at least 60% identity, at least 70% identity, at least 80% identity, or at least 90% or more identity with the amine binding site of any of SEQ ID NOs: 17-19, 23-28, or 31-39.

177. The kit of any one of embodiments 146-176, wherein the modified cleavase comprises an amino acid sequence that comprises a loop domain with at least 20% identity, at least 30% identity, at least 128% identity, at least 50% identity, at least 60% identity, at least 70% identity, at least 80% identity, or at least 90% or more identity with the loop domain of any of SEQ ID NOs: 17-19, 23-28, or 31-39.

178. The kit of any one of embodiments 146-177, wherein the modified cleavase comprises one or more amino acid modifications in an unmodified cleavase, corresponding to position(s) 183, 184, 185, 186, 187, 188, 189, 190, 191, 192, 193, 194, 195, 196, 197, 198, 199, 200, 201, and/or 202, with reference to numbering of SEQ ID NO: 13.

179. The kit of any one of embodiments 146-177, wherein the modified cleavase comprises one or more amino acid modifications in an unmodified cleavase, corresponding to position(s) 188, 189, 190, 191, 192, 302, and/or 310, with reference to numbering of SEQ ID NO: 13.

180. The kit of any one of embodiments 146-177, wherein the modified cleavase comprises one or more amino acid modifications in an unmodified cleavase, corresponding to position(s) 191, 192, 196, 306, 310, 627, 628, 630, 648, 650, 651, 655, 656, and/or 669, with reference to numbering of SEQ ID NO: 13.

181. The kit of any one of embodiments 146-177, wherein the modified cleavase comprises one or more amino acid modifications in an unmodified cleavase, corresponding to any of position(s) 323 to 544, with reference to numbering of SEQ ID NO: 13.

182. The kit of any of embodiments 146-181, wherein the terminal amino acid is labeled with a chemical or an enzymatic reagent or moiety.

183. The kit of any of embodiments 146-182, wherein the label comprises a blocked amino acid.

184. The kit of any of embodiments 146-183, wherein the label comprises an exogenous labeled amino acid.

185. The kit of any of embodiments 146-184, wherein the label comprises a chemical label.

186. The kit of embodiment 182, wherein the chemical reagent is selected from the group consisting of a phenyl isothiocyanate (PITC), a nitro-PITC, a sulfo-PITC, a phenyl isocyanate (PIC), a nitro-PIC, a sulfo-PIC, Cbz-Cl (benzyl chloroformate) or Cbz-OSu (benzyloxycarbonyl N-succinimide), a carboxyl-activated amino-blocked amino acid, a 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), an anhydride, 2-Pyridinecarboxaldehyde, 2-Formylphenylboronic acid, 2-Acetylphenylboronic acid, 1-Fluoro-2,4-dinitrobenzene, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N'-Bis(pivaloyl)-1H-pyrazole-1-carboxamidine, N,N'-Bis(benzyloxycarbonyl)-1H-pyrazole-1-carboxamidine, an acetylating reagent, a guanidinylation reagent, a thioacylation reagent, a thioacetylation reagent, a thiobenzylation reagent, a diheterocyclic methanimine reagent, or a derivative thereof.

187. The kit of embodiment 182, wherein the chemical reagent is an isatoic anhydride, an isonicotinic anhydride, an azaisatoic anhydride, a succinic anhydride, or a derivative thereof.

188. The kit of embodiment 187, wherein the chemical reagent is selected from the group consisting of 4-Nitrophenyl Anthranilate, N-Methyl-isatoic anhydride, N-acetyl-isatoic anhydride, 4-carboxylic acid isatoic anhydride, 5-methoxy-isatoic anhydride, 5-nitro-isatoic anhydride, 4-chloro-isatoic anhydride, 4-fluoro-isatoic anhydride, 6-fluoro-isatoic anhydride, N-benzyl-isatoic anhydride, 4-trifluoromethyl-isatoic anhydride, 5-trifluoromethyl-isatoic anhydride, 4-nitro-isatoic anhydride, 4-methoxy-isatoic anhydride, 5-Amino-2-fluoro-isonicotinic anhydride (6-fluoro-1H-pyrido[3,4-d][1,3]oxazine-2,4-dione), 3,6, difluorophthalic anhydride, and 2,3 pyrazinedicarboxylic anhydride, or a derivative thereof.

189. The kit of any one of embodiments 146-188, further comprising a binding agent, wherein the binding agent comprises a coding tag with identifying information regarding the binding agent.

190. The kit of embodiment 189, wherein the kit comprises two or more binding agents.

191. The kit of embodiment 189 or embodiment 190, wherein the binding agent is configured to bind to an unlabeled terminal amino acid.

192. The kit of embodiment 189 or embodiment 190, wherein the binding agent is configured to bind to a labeled terminal amino acid.

193. The kit of any one of embodiments 189-192, wherein the binding agent binds to a single amino acid residue, a dipeptide, a tripeptide or a post-translational modification of the polypeptide.

194. The kit of embodiment 193, wherein the binding agent binds to an N-terminal amino acid residue.

195. The kit of embodiment 193, wherein the binding agent binds to a C-terminal amino acid residue.

196. The kit of any one of embodiments 189-195, wherein the binding agent is a polypeptide or protein.

197. The kit of any one of embodiments 189-196, wherein the binding agent comprises an aminopeptidase or variant, mutant, or modified protein thereof; an aminoacyl tRNA synthetase or variant, mutant, or modified protein thereof; an anticalin or variant, mutant, or modified protein thereof; a ClpS (such as ClpS2) or variant, mutant, or modified protein thereof; a UBR box protein or variant, mutant, or modified protein thereof; or a modified small molecule that binds amino acid(s), i.e. vancomycin or a variant, mutant, or modified molecule thereof; or an antibody or binding fragment thereof; or any combination thereof.

198. The kit of any one of embodiments 146-197, further comprising a reagent for transferring the identifying information of the coding tag to a recording tag attached to the polypeptide, wherein the transferring of the identifying information to the recording tag generates an extended recording tag on the polypeptide.

199. The kit of embodiment 198, wherein the reagent for transferring the identifying information is a chemical ligation reagent or a biological ligation reagent.

200. The kit of embodiment 198, wherein the reagent for transferring the identifying information is a reagent for primer extension of single-stranded nucleic acid or double-stranded nucleic acid.

201. The kit of any one of embodiments 198-200, further comprising an amplification reagent for amplifying the extended recording tags.

202. The kit of any of embodiments 146-201, further comprising a solid support selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, and any combination thereof.

203. The kit of embodiment 202, wherein the solid support comprises a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or any combinations thereof.

204. The kit of any one of embodiments 146-203, further comprising a reagent for nucleic acid sequencing analysis.

205. The kit of embodiment 204, wherein the nucleic acid sequencing analysis comprises sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

206. A method of treating a target polypeptide, which method comprises:
a) contacting a target polypeptide with a N-terminal modifier agent to form a N-terminally modified target polypeptide having a formula:
NTM-P1-P2-polypeptide, said NTM being a N-terminal modification, said P1 being the N-terminal amino acid residue of said target polypeptide, and P2 being a penultimate terminal amino acid residue of said target polypeptide; and
b) contacting a binder with said N-terminally modified target polypeptide to allow said binder to specifically bind to said N-terminally modified target polypeptide through interaction between said binder and said NTM and P1 of said N-terminally modified target polypeptide, wherein the binding specificity between said binder and said N-terminally modified target polypeptide is predominantly or substantially determined by said interaction between said binder and said P1 of said N-terminally modified target polypeptide.

207. The method of embodiment 206, wherein the length of the target polypeptide and/or the N-terminally modified target polypeptide is greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids.

208. The method of any one of embodiments 206-207, wherein the NTM comprises an amino acid moiety and/or has a size, e.g., length axis or volume, shape, and/or configuration similar to or exceeding a natural amino acid.

209. The method of embodiment 208, wherein the NTM comprises an amino acid moiety.

210. The method of embodiment 209, wherein the NTM is a bipartite N-terminal modification that comprises a natural or unnatural amino acid portion (NTMaa) and a N-terminal blocking group ($NTM_{blk}$), the amino acid portion (NTMaa) and the N-terminal blocking group ($NTM_{blk}$) being optionally connected with an amide bond.

211. The method of embodiment 206, wherein the NTM does not comprise an amino acid moiety.

212. The method of embodiment 211, wherein the NTM is a bipartite N-terminal modification that comprises a small (or small molecule) chemical entity having a size, e.g., length axis or volume, shape, and/or configuration similar to or exceeding a natural amino acid, and a N-terminal blocking group ($NTM_{blk}$),
the small (or small molecule) chemical entity and the N-terminal blocking group optionally connected with an amide bond, and/or
optionally, the small (or small molecule) chemical entity having a size, e.g., length axis of ~5-10 Å and volume of 100-1,000 Å$^3$.

213. The method of any one of embodiments 206-212, wherein the NTM comprises a compound having a structural formula selected from the group consisting of: (1) Formula (3'):

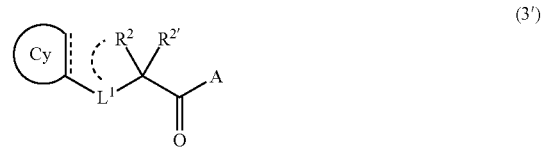

wherein A represents the point of attachment of the group to P1 residue;
Cy is a 5 to 7 membered ring or an 8-10 membered bicyclic ring system, and Cy may be absent or present;
when present, ring Cy may be saturated, unsaturated, or aromatic, and the dashed bond may be a single bond, double bond, or aromatic bond;
when Cy is present, it may be a carbocyclic ring, or it may contain one to three heteroatoms selected from N, O, B, and S as ring members; and Cy is optionally substituted with one to six groups (or with one to four groups when Cy is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, $—SR^4$, $—S(O)_nR^4$, $—NR^4SO_2R^4$, $—SO_2N(R^4)_2$, heteroaryl, $C_1$-$C_2$ alkyl, $C_1$-$C_2$ haloalkyl, $C_1$-$C_2$ haloalkoxy, and $—OR^4$;
when ring Cy is absent, the dashed bond may be a single bond or a double bond, and the dashed bond is optionally substituted by one or two groups selected from halo, CN, $C_1$-$C_2$ alkyl, $C_1$-$C_2$ haloalkyl, $C_1$-$C_2$ haloalkoxy, $CO_2R^4$, and $—OR^4$;
each $L^1$ is independently a bond or $C_1$-$C_2$ alkylene, $C_1$-$C_2$ haloalkylene, NHC(O), $SO_2$, or $NHSO_2$;
$R^2$ and $R^{2'}$ can each be H or a side chain of an amino acid, e.g. one of the side chains of the 20 common amino acid side chains, optionally protected amino acid side chains, post-translationally modified amino acid side chains, unnatural amino acid sidechains;
or $R^2$ or $R^{2'}$ can be an aryl, heteroaryl, bicyclic aryl, or bicyclic heteroaryl, each of which is optionally substituted with up to three groups independently selected from halo, cyano, azido, amino, $C_1$-$C_2$ alkyl, $C_1$-$C_2$ haloalkyl, $C_1$-$C_2$ alkoxy, and $C_1$-$C_2$ haloalkoxy;

represents an optional link between $R^2$ and $L^1$, forming a 5-6 membered ring;
n at each occurrence is independently 1 or 2; and
each R and $R^4$ is independently selected from H, $C_{1-2}$ alkyl, and $C_1$-$C_2$ haloalkyl;
(2) Formula (4'):

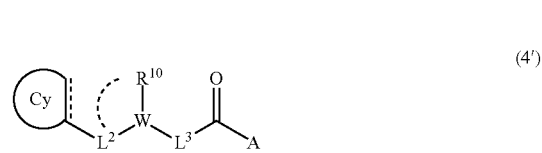

wherein A represents the point of attachment of the group to P1;
W is a bond or a group selected from alkyl, cycloalkyl, heterocyclyl, aryl, heteroaryl, and bicyclic heteroaryl, each of which is optionally substituted with up to four groups independently selected from halo, OH, cyano, azido, $—SR^4$, —S(O)$_n$R$^4$, —NR$^4$SO$_2$R$^4$, —SO$_2$N(R$^4$)$_2$, —B(OR$^4$)$_2$, oxo (unless W is aromatic), amino, C$_1$-C$_2$ alkyl, C$_1$-C$_2$ haloalkyl, C$_1$-C$_2$ alkoxy, and C$_1$-C$_2$ haloalkoxy;

when W is a ring, ring W may be saturated, unsaturated, or aromatic; when W is a heterocyclic or heteroaromatic ring, it may contain one or two heteroatoms selected from N, O and S as ring members;

⁁ represents an optional linkage connecting R$^{10}$ and L$^2$ into a 5-6 membered ring, optionally including an additional N, O or S as a ring member;

R$^{10}$ is selected from H, halo, CN, NH$_2$, NH(CH$_3$), N(CH$_3$)$_2$, NO$_2$, NHFmoc, NHBoc, C(O)NR$_2$, NHC(O)R, NHC(O)OR, B(OR)$_2$, aryl, heteroaryl, C$_1$-C$_2$ alkyl, C$_1$-C$_2$ haloalkyl, C$_1$-C$_2$ haloalkoxy, and —OR$^4$; and R$^{10}$ is absent when W is a bond;

L$^2$ and L$^3$ are independently selected from a bond, CH$_2$, SO$_2$R, NHSO$_2$R, C(=O)R, RNHC(=O), RNCH$_3$C(=O), C$_1$-C$_2$ alkylene, C$_1$-C$_2$ haloalkylene, or triazole;

each R is independently selected from C$_{1-6}$ alkyl, phenyl, and benzyl, each of which is optionally substituted with up to three groups selected from halo, CN, C$_1$-C$_2$ haloalkyl, C$_1$-C$_2$ haloalkoxy, CO$_2$R$^4$, and —OR$^4$;

Cy is a 5 to 7 membered ring or an 8-10 membered bicyclic ring system, and Cy may be absent or present;

when present, ring Cy may be saturated, unsaturated, or aromatic, and the dashed bond may be a single bond, double bond, or aromatic bond;

when Cy is present, it may be a carbocyclic ring, or it may contain one to three heteroatoms selected from N, O, B and S as ring members; and Cy is optionally substituted with one to six groups (or with one to four groups when Cy is aromatic) selected from halo, CN, NH$_2$, NH(CH$_3$), N(CH$_3$)$_2$, protected amine (e.g., N$_3$, NO$_2$, NHFmoc, NHBoc), C(O)NR$_2$, NHC(O)R, B(OR)$_2$, aryl, heteroaryl, C$_1$-C$_2$ alkyl, C$_1$-C$_2$ haloalkyl, C$_1$-C$_2$ haloalkoxy, —SR$^4$, —S(O)$_n$R$^4$, —NR$^4$SO$_2$R$^4$, —SO$_2$N(R$^4$)$_2$, and —OR$^4$;

when ring Cy is absent, the dashed bond may be a single bond or a double bond, and the dashed bond is optionally substituted by one or two groups selected from halo, CN, C$_1$-C$_2$ alkyl, C$_1$-C$_2$ haloalkyl, C$_1$-C$_2$ haloalkoxy, CO$_2$R$^4$, and —OR$^4$;

each L$^1$ is independently a bond or C$_1$-C$_2$ alkylene, C$_1$-C$_2$ haloalkylene, NHC(O), SO$_2$, or NHSO$_2$;

n at each occurrence is independently 1 or 2; and each R$^4$ is independently selected at each occurrence from H, C$_1$-C$_2$ alkyl, and C$_1$-C$_2$ haloalkyl;

(3) Formula (5'):

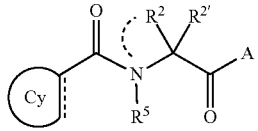

(5')

wherein A represents the point of attachment of the group to P1;

⁁ represents an optional link between R$^2$ and nitrogen, forming a 5-6 membered ring: when the optional link is present, R$^5$ is absent;

Cy is a 5 to 7 membered ring or an 8-10 membered bicyclic ring system, and Cy may be absent or present;

when present, ring Cy may be saturated, unsaturated, or aromatic, and the dashed bond may be a single bond, double bond, or aromatic bond;

when Cy is present, it may be a carbocyclic ring, or it may contain one to three heteroatoms selected from N, O, B, and S as ring members; and Cy is optionally substituted with one to six groups (or with one to four groups when Cy is aromatic) selected from halo, CN, NH$_2$, NH(CH$_3$), N(CH$_3$)$_2$, protected amine (e.g., N$_3$, NO$_2$, NHFmoc, NHBoc), C(O)NR$_2$, NHC(O)R, B(OR)$_2$, aryl, heteroaryl, C$_1$-C$_2$ alkyl, C$_1$-C$_2$ haloalkyl, C$_1$-C$_2$ haloalkoxy, —SR$^4$, —S(O)$_n$R$^4$, —NR$^4$SO$_2$R$^4$, —SO$_2$N(R$^4$)$_2$, and —OR$^4$;

when ring Cy is absent, the dashed bond may be a single bond or a double bond, and the dashed bond is optionally substituted by one or two groups selected from halo, CN, C$_1$-C$_2$ alkyl, C$_1$-C$_2$ haloalkyl, C$_1$-C$_2$ haloalkoxy, CO$_2$R$^4$, and —OR$^4$;

R$^2$ and R$^{2'}$ can each be the side chain of an amino acid, e.g. one of the side chains of the 20 common amino acid side chains, optionally protected amino acid side chains, post-translationally modified amino acid side chains, unnatural amino acid sidechains; or R$^2$ and R$^{2'}$ can each be H or a group selected from aryl, heteroaryl, bicyclic aryl, bicyclic heteroaryl, and heterocyclyl, each of which is optionally substituted with one to six groups (or with one to four groups when R$^2$ or R$^{2'}$ is aromatic) selected from halo, CN, NH$_2$, NH(CH$_3$), N(CH$_3$)$_2$, protected amine (e.g., N$_3$, NO$_2$, NHFmoc, NHBoc), C(O)NR$_2$, NHC(O)R, B(OR)$_2$, aryl, heteroaryl, C$_1$-C$_2$ alkyl, C$_1$-C$_2$ haloalkyl, C$_1$-C$_2$ haloalkoxy, and —OR$^4$;

each R and R$^4$ is independently selected at each occurrence from H, C$_1$-C$_2$ alkyl, and C$_1$-C$_2$ haloalkyl;

n at each occurrence is independently 1 or 2; and

R$^5$ is independently selected at each occurrence from H, C$_1$-C$_2$ alkyl, C$_1$-C$_2$ haloalkyl, C$_1$-C$_2$ alkoxy, and C$_1$-C$_2$ haloalkoxy;

(4) Formula (6'):

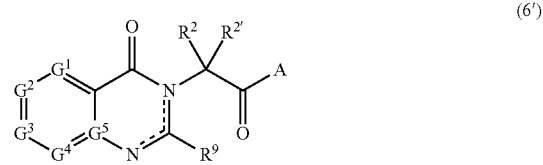

(6')

wherein A represents the point of attachment of the group to P1;

G$^1$-G$^5$ are each independently selected from CH, CJ, BN, BO, and N, provided not more than 3 of G$^1$-G$^5$ are N;

the dashed bonds can be single bonds or double bonds;

J at each occurrence is independently selected from H, C$_1$-C$_2$ alkyl, NO$_2$, C$_1$-C$_2$ haloalkyl, C$_1$-C$_2$ haloalkoxy, halo, —OR$^8$, —N(R$^8$)$_2$, —SR$^8$, —S(O)$_n$R$^8$, —NR$^8$SO$_2$R$^8$, —SO$_2$N(R$^8$)$_2$, SO$_3$R$^8$, —B(OR$^8$)$_2$, C(=O)R$^8$, CN, CON(R$^8$)$_2$, —COOR$^8$, —C(=O)Ar, and tetrazole, where Ar represents a phenyl or 5-6 membered heteroaryl ring that is optionally substituted with one or two groups selected from halo, CN, R$^8$ and OR$^8$;

R$^2$ and R$^{2'}$ can each be the side chain of an amino acid, e.g. one of the side chains of the 20 common amino acid side chains, optionally protected amino acid side chains, post-translationally modified amino acid side chains, unnatural amino acid sidechains; or R² and R²' can each be H or a group selected from aryl, heteroaryl, bicyclic aryl, bicyclic heteroaryl, and heterocyclyl, each of which is optionally substituted with one to six groups (or with one to four groups when R² or R²' is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —OR⁴;

each R, R⁴ and R⁸ is independently selected at each occurrence from H, $C_1$-$C_2$ alkyl, and $C_1$-$C_2$ haloalkyl; and n at each occurrence is independently 1 or 2; and R⁹ is H, $CH_3$, benzyl, substituted benzyl;

(5) Formula (7'):

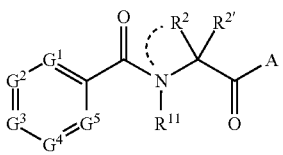

(7')

wherein A represents the point of attachment of the group to P1;

$G^1$-$G^5$ are each independently selected from CH, CJ, BN, BO, and N, provided not more than 3 of $G^1$-$G^5$ are N;

↺ represents an optional link between R² and the nitrogen atom, forming a 5-6 membered ring: when the link is present, R¹¹ is absent;

J at each occurrence is independently selected from H, $C_1$-$C_2$ alkyl, $NO_2$, $C_1$-$C_2$ haloalkyl, $C_1$-$C_2$ haloalkoxy, halo, —OR⁸, —N(R⁸)₂, —SR⁸, —S(O)ₙR⁸, —NR⁸SO₂R⁸, —SO₂N(R⁸)₂, SO₃R⁸, —B(OR⁸)₂, C(=O)R⁸, CN, CON(R⁸)₂, —COOR⁸, —C(=O)Ar, and tetrazole, where Ar represents a phenyl or 5-6 membered heteroaryl ring that is optionally substituted with one or two groups selected from halo, CN, R⁸ and OR⁸;

R² and R²' can each be the side chain of an amino acid, e.g. one of the side chains of the 20 common amino acid side chains, optionally protected amino acid side chains, post-translationally modified amino acid side chains, unnatural amino acid sidechains;

or R² and R²' can each be H or a group selected from aryl, heteroaryl, bicyclic aryl, bicyclic heteroaryl, and heterocyclyl, each of which is optionally substituted with one to six groups (or with one to four groups when R² or R²' is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —OR⁴; each R, R⁴ and R⁸ is independently selected at each occurrence from H, $C_1$-$C_2$ alkyl, and $C_1$-$C_2$ haloalkyl;

n at each occurrence is independently 1 or 2; and

R¹¹ is H, $CH_3$, benzyl, or substituted benzyl;

(6) Formula (8'):

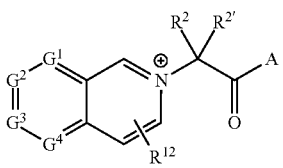

(8')

wherein A represents the point of attachment of the group to P1;

$G^1$-$G^5$ are each independently selected from CH, CJ, BN, BO, and N, provided not more than 3 of $G^1$-$G^5$ are N;

J at each occurrence is independently selected from H, $C_1$-$C_2$ alkyl, $NO_2$, $C_1$-$C_2$ haloalkyl, $C_1$-$C_2$ haloalkoxy, halo, —OR⁸, —N(R⁸)₂, —SR⁸, —S(O)ₙR⁸, —NR⁸SO₂R⁸, —SO₂N(R⁸)₂, SO₃R⁸, —B(OR⁸)₂, C(=O)R⁸, CN, CON(R⁸)₂, —COOR⁸, —C(=O)Ar, and tetrazole, where Ar represents a phenyl or 5-6 membered heteroaryl ring that is optionally substituted with one or two groups selected from halo, CN, R⁸ and OR⁸;

R² and R²' can each be the side chain of an amino acid, e.g. one of the side chains of the 20 common amino acid side chains, optionally protected amino acid side chains, post-translationally modified amino acid side chains, unnatural amino acid sidechains;

or R² and R²' can each be H or a group selected from aryl, heteroaryl, bicyclic aryl, bicyclic heteroaryl, and heterocyclyl, each of which is optionally substituted with one to six groups (or with one to four groups when R² or R²' is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —OR⁴;

each R, R⁴ and R⁸ is independently selected at each occurrence from H, $C_1$-$C_2$ alkyl, and $C_1$-$C_2$ haloalkyl;

n at each occurrence is independently 1 or 2; and

R¹² represents one or two optional substituents on the pyridinium ring, which are independently selected from $C_1$-$C_2$ alkyl, $C_1$-$C_2$ haloalkyl, $C_1$-$C_2$ haloalkoxy, and halo; and (7) Formula (10):

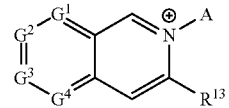

(10)

wherein A represents the point of attachment of the group to P1 of a target polypeptide;

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —OR⁸, —N(R⁸)₂, —SR⁸, —S(O)ₙR⁸, —NR⁸SO₂R⁸, —SO₂N(R⁸)₂, SO₃R⁸, —B(OR⁸)₂, C(=O)R⁸, CN, CON(R⁸)₂, —COOR⁸, —C(=O)Ar, and tetrazole, where Ar represents a phenyl or 5-6 membered heteroaryl ring that is optionally substituted with one or two groups selected from halo, CN, R⁹ and OR⁹;

each R⁸ and each R⁹ is independently selected from H, $C_1$-$C_2$ alkyl, and $C_1$-$C_2$ haloalkyl;

n at each occurrence is independently 1 or 2; and

R¹³ is selected from H, $C_1$-$C_2$ alkyl, $C_1$-$C_2$ alkoxy, $C_1$-$C_2$ haloalkyl, and $C_1$-$C_2$ haloalkoxy.

214. The method of any one of embodiments 206-213, which further comprises a step:

c) cleaving the peptide bond between the P1 and P2 to form a polypeptide wherein the P2 becomes N-terminal amino acid residue of the polypeptide.

215. The method of embodiment 214 wherein the peptide bond between the P1 and P2 is cleaved using a modified cleavase, e.g., a modified cleavase of any one of embodiments 1-42.

216. The method of any one of embodiments 214-215, wherein step c) is conducted while the binder is bound with the N-terminally modified target polypeptide.

217. The method of any one of embodiments 214-216, wherein step c) is conducted after the binder is released and/or removed from the N-terminally modified target polypeptide.

218. The method of any one of embodiments 214-217, wherein steps a)-c) are repeated one or more times to form a polypeptide having newly exposed N-terminal amino acid residue.

219. The method of any one of embodiments 206-218, wherein the N-terminal modifier agent comprises a compound of any one of Formulas (3)-(9), and optionally a peptide coupling reagent, wherein Formula (3) is:

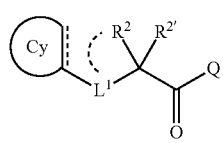

(3)

wherein Q is $OR^Q$, OH, or OM, where M is a cationic counterion;

each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR;

Cy is a 5 to 7 membered ring or an 8-10 membered bicyclic ring system, and Cy may be absent or present;

when present, ring Cy may be saturated, unsaturated, or aromatic, and the dashed bond may be a single bond, double bond, or aromatic bond;

when Cy is present, it may be a carbocyclic ring, or it may contain one to three heteroatoms selected from N, O, B, and S as ring members; and Cy is optionally substituted with one to six groups (or with one to four groups when Cy is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, —$SR^4$, —$S(O)_nR^4$, —$NR^4SO_2R^4$, —$SO_2N(R^4)_2$, heteroaryl, $C_1$-$C_2$ alkyl, $C_1$-$C_2$ haloalkyl, $C_1$-$C_2$ haloalkoxy, and —$OR^4$;

when ring Cy is absent, the dashed bond may be a single bond or a double bond, and the dashed bond is optionally substituted by one or two groups selected from halo, CN, $C_1$-$C_2$ alkyl, $C_1$-$C_2$ haloalkyl, $C_1$-$C_2$ haloalkoxy, $CO_2R^4$, and —$OR^4$;

each $L^1$ is independently a bond or $C_1$-$C_2$ alkylene, $C_1$-$C_2$ haloalkylene, NHC(O), $SO_2$, or $NHSO_2$;

$R^2$ and $R^{2'}$ can each be H or a side chain of an amino acid, e.g. one of the side chains of the 20 common amino acid side chains, optionally protected amino acid side chains, post-translationally modified amino acid side chains, unnatural amino acid sidechains;

or $R^2$ or $R^{2'}$ can be an aryl, heteroaryl, bicyclic aryl, or bicyclic heteroaryl, each of which is optionally substituted with up to three groups independently selected from halo, cyano, azido, amino, $C_1$-$C_2$ alkyl, $C_1$-$C_2$ haloalkyl, $C_1$-$C_2$ alkoxy, and $C_1$-$C_2$ haloalkoxy;

represents an optional link between $R^2$ and $L^1$, forming a 5-6 membered ring;

n at each occurrence is independently 1 or 2; and each R and $R^4$ is independently selected from H, $C_{1-2}$ alkyl, and $C_1$-$C_2$ haloalkyl;

Formula (4) is:

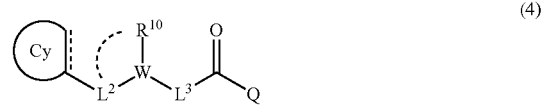

(4)

wherein;

wherein Q is OH, $OR^Q$ or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR;

and M is cationic counterion;

W is a bond or a group selected from alkyl, cycloalkyl, heterocyclyl, aryl, heteroaryl, and bicyclic heteroaryl, each of which is optionally substituted with up to four groups independently selected from halo, OH, cyano, azido, —$SR^4$, —$S(O)_nR^4$, —$NR^4SO_2R^4$, —$SO_2N(R^4)_2$, —$B(OR^4)_2$, oxo (unless W is aromatic), amino, $C_1$-$C_2$ alkyl, $C_1$-$C_2$ haloalkyl, $C_1$-$C_2$ alkoxy, and $C_1$-$C_2$ haloalkoxy;

when W is a ring, ring W may be saturated, unsaturated, or aromatic; when W is a heterocyclic or heteroaromatic ring, it may contain one or two heteroatoms selected from N, O and S as ring members;

represents an optional linkage connecting $R^{10}$ and $L^2$ into a 5-6 membered ring, optionally including an additional N, O or S as a ring member;

$R^{10}$ is selected from H, halo, CN, $NH_2$, $NH(CH_3)$, $N(CH_3)_2$, $NO_2$ NHFmoc, NHBoc, $C(O)NR_2$, NHC(O)R, NHC(O)OR, $B(OR)_2$, aryl, heteroaryl, $C_1$-$C_2$ alkyl, $C_1$-$C_2$ haloalkyl, $C_1$-$C_2$ haloalkoxy, and —$OR^4$; and $R^{10}$ is absent when W is a bond;

$L^2$ and $L^3$ are independently selected from a bond, $CH_2$, $SO_2R$, $NHSO_2R$, C(=O)R, RNHC(=O), $RNCH_3C(=O)$, $C_1$-$C_2$ alkylene, $C_1$-$C_2$ haloalkylene, or triazole;

each R is independently selected from $C_{1-6}$ alkyl, phenyl, and benzyl, each of which is optionally substituted with up to three groups selected from halo, CN, $C_1$-$C_2$ haloalkyl, $C_1$-$C_2$ haloalkoxy, $CO_2R^4$, and —$OR^4$;

Cy is a 5 to 7 membered ring or an 8-10 membered bicyclic ring system, and Cy may be absent or present;

when present, ring Cy may be saturated, unsaturated, or aromatic, and the dashed bond may be a single bond, double bond, or aromatic bond;

when Cy is present, it may be a carbocyclic ring, or it may contain one to three heteroatoms selected from N, O, B and S as ring members; and Cy is optionally substituted with one to six groups (or with one to four groups when Cy is aromatic) selected from halo, CN, $NH_2$, $NH(CH_3)$, $N(CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, —$SR^4$, —$S(O)_nR^4$, —$NR^4SO_2R^4$, —$SO_2N(R^4)_2$, and —$OR^4$;

when ring Cy is absent, the dashed bond may be a single bond or a double bond, and the dashed bond is optionally substituted by one or two groups selected from halo, CN, $C_1$-$C_2$ alkyl, $C_1$-$C_2$ haloalkyl, $C_1$-$C_2$ haloalkoxy, $CO_2R^4$, and —$OR^4$;

each $L^1$ is independently a bond or $C_1$-$C_2$ alkylene, $C_1$-$C_2$ haloalkylene, NHC(O), $SO_2$, or $NHSO_2$;

n at each occurrence is independently 1 or 2; and $R^4$ is independently selected at each occurrence from H, $C_1$-$C_2$ alkyl, and $C_1$-$C_2$ haloalkyl;

Formula (5) is:

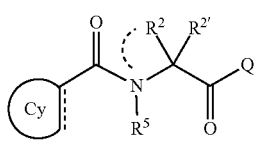

(5)

wherein Q is OH, $OR^Q$ or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR; and M is cationic counterion;

represents an optional link between $R^2$ and nitrogen, forming a 5-6 membered ring: when the optional link is present, $R^5$ is absent;

Cy is a 5 to 7 membered ring or an 8-10 membered bicyclic ring system, and Cy may be absent or present;

when present, ring Cy may be saturated, unsaturated, or aromatic, and the dashed bond may be a single bond, double bond, or aromatic bond;

when Cy is present, it may be a carbocyclic ring, or it may contain one to three heteroatoms selected from N, O, B, and S as ring members; and Cy is optionally substituted with one to six groups (or with one to four groups when Cy is aromatic) selected from halo, CN, $NH_2$, $NH(CH_3)$, N($CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, —$SR^4$, —$S(O)_nR^4$, —$NR^4SO_2R^4$, —$SO_2N(R^4)_2$, and —$OR^4$;

when ring Cy is absent, the dashed bond may be a single bond or a double bond, and the dashed bond is optionally substituted by one or two groups selected from halo, CN, $C_1$-$C_2$ alkyl, $C_1$-$C_2$ haloalkyl, $C_1$-$C_2$ haloalkoxy, $CO_2R^4$, and —$OR^4$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains; or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, N($CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —$OR^4$;

each R and $R^4$ is independently selected at each occurrence from H, $C_1$-$C_2$ alkyl, and $C_1$-$C_2$ haloalkyl;

n at each occurrence is independently 1 or 2; and $R^5$ is independently selected at each occurrence from H, $C_1$-$C_2$ alkyl, $C_1$-$C_2$ haloalkyl, $C_1$-$C_2$ alkoxy, and $C_1$-$C_2$ haloalkoxy, $C_3$-$C_6$ cycloalkyl, benzyl, mono- or disubstituted benzyl;

Formula (6) is:

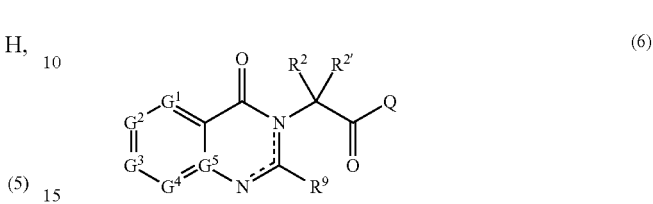

(6)

wherein Q is OH, $OR^Q$ or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR;

M is a cationic counterion;

$G^1$-$G^5$ are each independently selected from CH, CJ, BN, BO, and N, provided not more than 3 of $G^1$-$G^5$ are N;

the dashed bonds can be single bonds or double bonds;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, C(=O)$R^8$, CN, CON($R^8)_2$, —$COOR^8$, —C(=O)Ar, and tetrazole, where Ar represents a phenyl or 5-6 membered heteroaryl ring that is optionally substituted with one or two groups selected from halo, CN, $R^8$ and $OR^8$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains; or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, N($CH_3)_2$, protected amine (e.g., $N_3$, $NO_2$, NHFmoc, NHBoc), $C(O)NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —$OR^4$;

each R, $R^4$ and $R^8$ is independently selected at each occurrence from H, $C_1$-$C_2$ alkyl, and $C_1$-$C_2$ haloalkyl; and n at each occurrence is independently 1 or 2; and $R^9$ is H, $CH_3$, benzyl, substituted benzyl;

Formula (7) is:

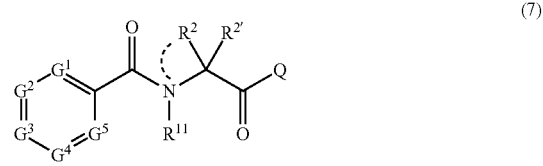

(7)

wherein Q is OH, $OR^Q$ or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR;

in some embodiments, $R^Q$ is 4-nitrophenyl, 2,4-dinitrophenyl, 4-fluorophenyl, 2,4-difluorophenyl, 2,3,4,5,6-pentafluorophenyl, 2,3,5,6-tetrafluorophenyl, 4-sulfo-2,3,5,6, tetrafluorophenyl, halogen, imidazole, pyrazole, benzotriazole, and triazole;

and M is a cationic counterion;

$G^1$-$G^5$ are each independently selected from CH, CJ, BN, BO, and N, provided not more than 3 of $G^1$-$G^5$ are N;

⌢ represents an optional link between $R^2$ and the nitrogen atom, forming a 5-6 membered ring: when the link is present, $R^{11}$ is absent;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, C(=O)$R^8$, CN, CON($R^8$)$_2$, —COO$R^8$, —C(=O)Ar, and tetrazole, where Ar represents a phenyl or 5-6 membered heteroaryl ring that is optionally substituted with one or two groups selected from halo, CN, $R^8$ and $OR^8$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains;

or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, N($CH_3$)$_2$, protected amine (e.g., $N_3$, $NO_2$, NHFmoc, NHBoc), C(O)$NR_2$, NHC(O)R, B(OR)$_2$, aryl, heteroaryl, $C_1$-$C_2$ alkyl, $C_1$-$C_2$ haloalkyl, $C_1$-$C_2$ haloalkoxy, and —$OR^4$;

each R, $R^4$ and $R^8$ is independently selected at each occurrence from H, $C_1$-$C_2$ alkyl, and $C_1$-$C_2$ haloalkyl;

n at each occurrence is independently 1 or 2; and $R^{11}$ is H, $CH_3$, alkyl, cycloalkyl, benzyl, or mono- or disubstituted benzyl; and Formula (8) is:

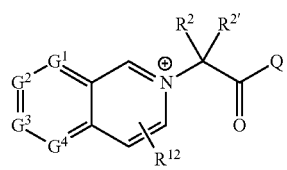

(8)

wherein Q is OH, $OR^Q$, or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(=O)R or —C(=O)—OR;

M is a cationic counterion;

$G^1$-$G^5$ are each independently selected from CH, CJ, BN, BO, and N, provided not more than 3 of $G^1$-$G^5$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, C(=O)$R^8$, CN, CON($R^8$)$_2$, —COO$R^8$, —C(=O)Ar, and tetrazole, where Ar represents a phenyl or 5-6 membered heteroaryl ring that is optionally substituted with one or two groups selected from halo, CN, $R^8$ and $OR^8$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains;

or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, N($CH_3$)$_2$, protected amine (e.g., $N_3$, $NO_2$, NHFmoc, NHBoc), C(O)$NR_2$, NHC(O)R, B(OR)$_2$, aryl, heteroaryl, $C_1$-$C_2$ alkyl, $C_1$-$C_2$ haloalkyl, $C_1$-$C_2$ haloalkoxy, and —$OR^4$;

each R, $R^4$ and $R^8$ is independently selected at each occurrence from H, $C_1$-$C_2$ alkyl, and $C_1$-$C_2$ haloalkyl;

n at each occurrence is independently 1 or 2; and $R^{12}$ represents one or two optional substituents on the pyridinium ring, which are independently selected from $C_1$-$C_2$ alkyl, $C_1$-$C_2$ alkoxy, $C_1$-$C_2$ haloalkyl, $C_1$-$C_2$ haloalkoxy, and halo; and Formula (9) is:

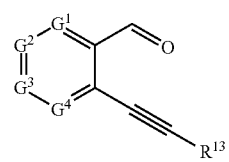

(9)

wherein:

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, C(=O)$R^8$, CN, CON($R^8$)$_2$, —COO$R^8$, —C(=O)Ar, and tetrazole, where Ar represents a phenyl or 5-6 membered heteroaryl ring that is optionally substituted with one or two groups selected from halo, CN, $R^8$ and $OR^8$;

each $R^8$ is independently selected from H, $C_1$-$C_2$ alkyl, and $C_1$-$C_2$ haloalkyl;

n at each occurrence is independently 1 or 2; and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

220. The method of embodiment 219, wherein the peptide coupling reagent is an aminium, uronium, or carbodiimide coupling reagent.

221. The method of embodiment 219, wherein the peptide coupling reagent is a compound of Formula (1) or (2), wherein:

Formula (1) is

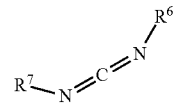

(1)

or a salt or conjugate thereof,
wherein
$R^6$ and $R^7$ are each independently $C_{1-6}$ alkyl, —$CO_2C_{1-4}$ alkyl, —$OR^k$, aryl, heteroaryl, cycloalkyl or heterocyclyl, wherein the $C_{1-6}$ alkyl, —$CO_2C_{1-4}$ alkyl, —$OR^k$, aryl, and cycloalkyl are each unsubstituted or substituted; and $R^k$ is H, $C_{1-6}$ alkyl, or heterocyclyl, wherein the $C_{1-6}$ alkyl and heterocyclyl are each unsubstituted or substituted; wherein heterocyclyl can be 5-8 membered ring comprising one or two heteroatoms selected from N, O and S as ring members, where the heteroaryl can be a 5-6 membered single ring or 8-10 membered bicyclic ring, each of which comprises one to three heteroatoms selected from N, O and S as ring members; and Formula (2) is:

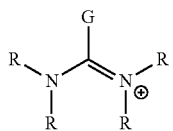

(2)

wherein:
each R is independently $C_{1-4}$ alkyl, optionally substituted with up to three groups selected from halo, $C_{1-2}$alkoxy, $C_{1-2}$haloalkyl, and $C_{1-2}$ haloalkoxy;

and two R groups on the same N can optionally cyclize to form a 5-7 membered ring optionally containing an additional heteroatom selected from N, O and S as a ring member, and optionally substituted with one or two groups selected from oxo, $C_{1-2}$ alkyl, $C_{1-2}$ alkoxy, $C_{1-2}$haloalkyl, and $C_{1-2}$ haloalkoxy; and G is selected from halo, benzotriazolyloxy, halobenzotriazolyloxy, pyridinotriazolyloxy, benzotriazolyl-N-oxide, pyridinotriazolyl-N-oxide, —O—(N-succinimide), 1-cyano-2-ethoxy-2-oxoethylideneaminooxy, and —O—(N-phthalimide).

222. The method of any one of embodiments 219-221, wherein the peptide coupling reagent is selected from dicyclohexyl carbodiimide (DCC), diisopropyl carbodiimide (DIPC), 1-ethyl-3-(3-dimethylaminopropyl)carbodiimide (EDC), 1-cyclohexyl-(2-morpholinoethyl)carbodiimide tosylate (CMCT), COMU, HATU, HBTU, TBTU, HCTU, and TSTU, PyBOP, PyAOP, PyOxim, and BOP, and (3-(diethoxyphosphoryloxy)-1,2,3-benzotriazin-4(3H)-one) (DEPBT).

223. The method of any one of embodiments 206-222, wherein step b) comprises contacting a plurality of binders with the N-terminally modified target polypeptide to allow the binders to specifically bind to the N-terminally modified target polypeptide.

224. The method of any one of embodiments 206-223, wherein the binder comprises a coding tag with identifying information regarding the binder.

225. The method of any one of embodiments 206-224, wherein the coding tag comprises a unique molecular identifier (UMI) and/or a universal priming site.

226. The method of any one of embodiments 206-225, which further comprises a step:
d) transferring the identifying information of the coding tag to a recording tag attached to the N-terminally modified target polypeptide, thereby generating an extended recording tag on the N-terminally modified target polypeptide.

227. A set of dipeptide cleavase enzymes, comprising at least two different modified dipeptide cleavases, wherein: (i) each of the modified dipeptide cleavases from the set of dipeptide cleavase enzymes is configured to remove a single labeled terminal amino acid from a polypeptide, and comprises an unmodified dipeptide cleavase comprising at least one mutation in a substrate binding site; (ii) the unmodified dipeptide cleavase is configured to remove two terminal amino acids from the polypeptide; and (iii) the modified dipeptide cleavases from the set of dipeptide cleavase enzymes have different specificities for the labeled terminal amino acids, which the modified dipeptide cleavases are configured to remove.

228. The set of dipeptide cleavase enzymes of embodiment 227, wherein each of the modified dipeptide cleavases from the set of dipeptide cleavase enzymes does not remove an unlabeled terminal dipeptide from the polypeptide.

229. The set of dipeptide cleavase enzymes of embodiment 227, wherein the unmodified dipeptide cleavase comprises an amino acid sequence having at least 30% sequence identity to the amino acid sequence of SEQ ID NO: 13 and also comprising an asparagine residue at a position corresponding to position 191 of SEQ ID NO: 13, a tryptophan residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, an aspartate residue at a position corresponding to position 650 of SEQ ID NO: 13; and wherein each of the modified dipeptide cleavases from the set of dipeptide cleavase enzymes comprises one or more amino acid modifications in residues corresponding to positions 191, 192, 196, 306, 650 of SEQ ID NO: 13.

230. A kit for treating a polypeptide, comprising:
(a) a chemical reagent for labeling a terminal amino acid of the polypeptide; and
(b) a modified dipeptide cleavase comprising an unmodified dipeptide cleavase comprising at least one mutation in a substrate binding site, wherein:
(i) the unmodified dipeptide cleavase is configured to remove two terminal amino acids from the polypeptide; and
(ii) the modified dipeptide cleavase is configured to remove from the polypeptide a single labeled terminal amino acid; or
(c) a set of dipeptide cleavase enzymes, comprising at least two different modified dipeptide cleavases, wherein:
(i) each of the modified dipeptide cleavases from the set of dipeptide cleavase enzymes is configured to remove a single labeled terminal amino acid from the polypeptide, and comprises an unmodified dipeptide cleavase comprising at least one mutation in a substrate binding site;
(ii) the unmodified dipeptide cleavase is configured to remove two terminal amino acids from the polypeptide; and
(iii) the modified dipeptide cleavases from the set of dipeptide cleavase enzymes have different specificities for labeled terminal amino acids that these dipeptide cleavases are configured to remove.

231. The kit of embodiment 230, further comprising a binding agent configured to bind to the single labeled terminal amino acid or to the labeled terminal dipeptide.

VI. Examples

The following examples are offered to illustrate but not to limit the methods, compositions, and uses provided herein.

Example 1. Selection, Design, and Isolation of Modified Cleavases

This example describes the selection and isolation of modified cleavases, and engineering of dipeptidyl peptidase 3 (DPP3), dipeptidyl peptidase 5 (DPP5) and dipeptidyl aminopeptidase BII (DAP BII) proteins for selected activities by rational design.

A. Genetic Selection for DPP3, DPP5, and DAP BII Variants Active on Modified NTAA Peptides To identify optimal engineered modified cleavases such as DPP3, DPP5, and DAP BII variants, genetic selection is carried out using an amino acid-specific auxotrophic E. coli strain (available from CSSC E. coli Genetic Stock Center at Yale) that only survives on minimal media plates when supplied with the auxotrophic amino acid or a short peptide containing the auxotrophic amino acid. See e.g., Neuenschwander et al., Nat Biotechnol. (2007) 25(10):1145-1147). This cell-based assay system is used to select variants functional on labeled polypeptides as follows: The cleavase genes (such as DPP3, DPP5, and DAP BII) are separately expressed in an auxotrophic strain supplemented with a Cbz-labeled tetrapeptide (Cbz-AAAR, SEQ ID NO: 21) in which the C-terminal diamino acid acts as the auxotrophic supplement upon native dipeptide uptake and cleavage in the cytosol. Short oligopeptide substrates permeate into the periplasm through outer membrane porin channels but require active transport into the cytoplasm via three main oligopeptide/dipeptide uptake systems in E. coli: Opp, Tpp, and Dpp (Abouhamad et al., Mol Microbiol. (1991) 5(5): 1035-1047); after uptake into the cytoplasm, short peptides are digested by endogenous endopeptidases within the cytosol. Oligopeptide or dipeptide transport by these three systems is inhibited by N-terminal modified (e.g., Cbz) oligopeptides/dipeptides (Smith et al., Microbiology (1999) 145 (Pt 10):2891-901; Payne et al., Arch Biochem Biophys. (2000) 384(1):9-23; Fang et al., J Bacteriol. 2000 May; 182(9):2530-2535). The growth of auxotrophic E. coli on the Cbz-labeled feedstocks will be inhibited. Genetic selection is accomplished by relieving this inhibition by expression and secretion of functional protein in the periplasm using an appropriate signal peptide (e.g. pelB) (Speck et al., Protein Eng Des Sel. (2011) 24(6):473-484; Thie et al., N Biotechnol. (2008) 25(1):49-54). Once in the periplasm, functional protein converts the Cbz-oligopeptide to free auxotrophic dipeptides that are taken up into the cell cytoplasm.

E. coli strains auxotrophic for an amino acid; such as arginine, glutamine, or tryptophan; are employed in the genetic selection. Other suitable strains can also be used for selection. The growth media for the genetic selection is M9 minimal media salts supplemented with $MgSCl_4$, $CaCl_2$, glucose, and agar. The appropriate Cbz-labeled peptide is also added to the growth media before the solution is poured into a plate to solidify.

A general approach to testing families of cleavase genes (e.g., DPP3, DPP5, and DAP BII), is to select a family in the NCBI database cluster based on the homology of their encoded proteins. A pool of genes that contains a representative from each cluster is selected. The genes for selected proteins are synthesized using codons optimized for expression in E. coli. The genes, encoding proteins from various organisms, are pooled and libraries of mutated genes are generated by error prone PCR or rational mutagenesis using the crystal structure of proteins with known structure. Furthermore, a combination of error prone PCR and rational mutagenesis is used to generate additional mutated libraries. The pool of mutated genes is subsequently cloned into a vector which has a promoter that is compatible with gene expression in the auxotroph strains, such as a T5 or arabinose promoter. The library of mutated genes, is cloned into a vector, which adds a periplasmic targeting signal (e.g., pelB) to the N-terminus of the encoded protein. The cloned library is then transformed into an E. coli auxotroph strain. After recovery of the transformed cells in rich media (e.g., SOC), the cells are washed with M9 minimal liquid media to remove all traces of proteins that will allow the auxotroph strain to subvert the genetic selection by presenting as false positives. The cells are then spread onto the selection media containing the Cbz-labeled peptide. The plates are incubated at a temperature ranging from 25 to 37 degrees Celsius until colonies are observed. Colonies growing on the selection media are isolated, and plasmid DNA is extracted. The cleavase gene is then sequenced to identify the protein sequence that can remove the Cbz-labeled peptide.

Various lengths and sequences of Cbz-labeled peptides can be used in the genetic selection to generate enzymes with specificities that can remove all 20 modified natural amino acids used in polypeptide synthesis.

B. Rational Design of DPP3, DPP5, and DAP BII for Activity on Modified NTAA Peptides A rational design approach for engineering DPP3 to remove a labeled N-terminal amino acid (NTAA) is guided using crystal structures of DPP3 in complex with substrates. In structures of human DPP3 in complex with substrates, the residues Glu 316, Asn 391, and Asn 394 (based on the sequence of the protein set forth in SEQ ID NO: 5; UniProt Accession No. Q9NY33) make hydrogen bonding interactions with the peptide N-terminal amine group. These residues, individually or in combination, are altered to select for modified dipeptidyl peptidases that accommodate a labeled NTAA.

Due to the lack of crystal structure of DPP5 with substrate, comparative modeling tools such as Rosetta macromolecular modeling suite is used to generate a homology model of DPP5. Based on the model and sequence analysis, the loop between Thr127-Thr180 (based on NCBI reference sequence WP_012457755.1, SEQ ID NO: 16) was identified to be a hypothetical region for binding native N-terminal amino acid and thus a region for engineering to recognize modified amino acid. Multiple acidic residues that can bind N-terminal amine in this region are highly conserved, including Asp142, Asp153 and Asp160. Multiple approaches can be used to explore this loop region, including error prone PCR, site saturated mutagenesis, and replacement with homologous loops from Blast search. These different diversification strategies are built into a library via Kunkel based approach using in vitro generated oligos by PCR or commercially synthesized oligos. In addition to testing small changes in the loop region, in vitro recombination can also be used to combine large sequence changes, and/or error prone PCR of the full length to explore regions outside of the loop. Mutational scanning and random error prone based approach can identify hotspot region for next round of library creation and screening.

A rational design approach for engineering DAP BII to remove a labeled N-terminal amino acid (NTAA) is guided using crystal structures of DAP BII in complex with substrates (Sakamoto et al., Scientific Reports 2014, 4:4977). In the DAP BII structure in complex with a peptide substrate, the residues N191, W192, R196, N306, and D650 (based on the sequence of the protein set forth in SEQ ID NO: 13; UniProt Accession No. V5YM14) make hydrogen bonding interactions with the peptide N-terminal amine group. Additionally, in the native DAP BII crystal structure, a loop of approximately 20 residues (residue 183-202) makes contact with the N-terminal residue and penultimate residue of a bound peptide substrate. These amine binding residues and NTAA and penultimate NTAA binding residues, individually or in combination, are altered to select for modified cleavases that cleaves after the labeled NTAA residue with minimal bias. A combinatorial variant libraries of these residues with Kunkel and related methods (Kunkel, T (1985). PNAS 82(2): 488-492) is created, and genetic selection libraries is used to screen for variants with altered activities toward modified N-terminal amino acid. An error prone based library is built based on the hits from initial screening for next round of library creation and screening.

C. Engineered Variants of DPP3 Active on Longer Peptides

In some cases, DPP3 enzymes may be limited in their maximal peptide substrate length. For example, the human enzyme has a peptide substrate length limit of 8 to 10 amino acids. A genetic selection is carried out to identify modified dipeptidyl peptidase enzymes that are able to cleave peptide sizes or lengths that are increased compared to the unmodified dipeptidyl peptidase. The porin size in the E. coli outer membrane limits the peptide length that can be uptaken to five or six amino acids. To subvert this size limit, biotinylated peptides up to 31 amino acids in length that can be uptaken by E. coli via the biotin transporter are used as in vivo substrates for a DPP3 enzyme.

A rational design approach for increasing the peptide length that can be cleaved by DPP3 is carried out using crystal structures of DPP3 in complex with substrates. In the structure of human DPP3 in complex with the eight amino acid peptide, DRVYIHPF (SEQ ID NO: 9), the region of DPP3 which constrains the peptide length is deduced. For example, amino acid residues 419-426 (numbered according to human DPP3 set forth in SEQ ID NO: 5) is targeted for mutagenesis or removal to allow DPP3 to be active with longer peptides.

D. Purification and Characterization Conditions

Selected cleavase enzymes (e.g., DPP3, DPP5, DAP BII) are produced with a purification tag, such as a six histidine tag, and purified using the tag. Fluorescent or colorimetric substrates are generated by Cbz modifying amino acids that are conjugated to a molecule produces a signal upon cleavage of the Cbz modified amino acid. The amino acid conjugated substrates that are used include amino acid-nitroanilides, amino acid-ß-naphthylamides, and amino acid-amidomethyl coumarins. These substrates are used to rapidly assay and optimize the activity of selected modified enzymes.

Example 2. Labeling of N-Terminal Amino Acid (NTAA) of Peptides with Chemical Compounds Mimicking "Amino-Acid" Like Profiles This example describes the labeling of the N-terminal amino acid by treating the polypeptides with various chemical reagents. Addition of a benzyloxycarbonyl (Cbz), phenylisothiocyanate (PITC) or PITC derivative to the N-terminus of a peptide resembles adding a tyrosine or phenylalanine to the N-terminal amino acid, which is a natural substrate for dipeptidyl peptidase such as DPP3, DPP5, or DAP BII. The main distinguishing feature is the absence of an N-terminal amine group. Several reagents for labeling the N-terminal amino acid were tested for the ability to efficiently label the N-terminus. The chemical reagents for labeling the amino acid were also tested for its effect on modifying native DNA. For example, four different N-terminal modifying reagents are shown:

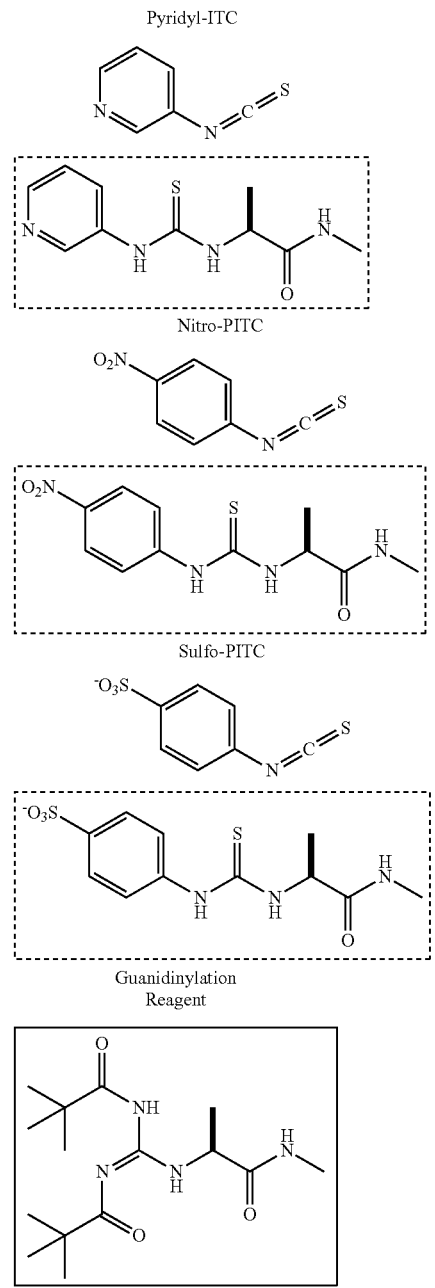

The modifying reagents for labeling the peptides include three isothiocyanates (Pyridyl-ITC, Nitro-PITC and Sulfo-ITC). In some cases, isocyanates could be used in place of isothiocyanates to create a urea (oxygen) rather than thiourea (sulfur) in the final modified NTAA. The fourth reagent shown is a proprietary guanidinylation derivative. Pyridyl-ITC is from a class of known Edman modifying reagents based on isothiocyanates, which generate an N-terminus that self-eliminates under acidic conditions. Nitro-PITC and Sulfo-PITC are more active Edman derivatives of phenylisothiocyanate (PITC). All isothiocyanate reagents were tested for peptide NTAA modification of two exemplary peptides (a peptide with an N-terminal G (NT-G)=GRFSGIY (SEQ ID NO:40); a peptide with an N-terminal W (NT-W)= WTQIFGA (SEQ ID NO: 41)) under aqueous conditions. The PITC-related derivatizations were performed at 60° C.

for 15 min. in IX PBS buffer with 25 mM of the indicated reagent. The guandinylation derivatization was performed at 60° C. for 1 hour in IX PBS buffer (pH 7.4) with 10% DMSO using 15 mM of the guandinylation reagent. A total of 50 equivalents of the reagent was used in the solution assay. LC-MS was used to quantitate conversion efficiency of the peptides by the various modifying reagents.

Figure 3:
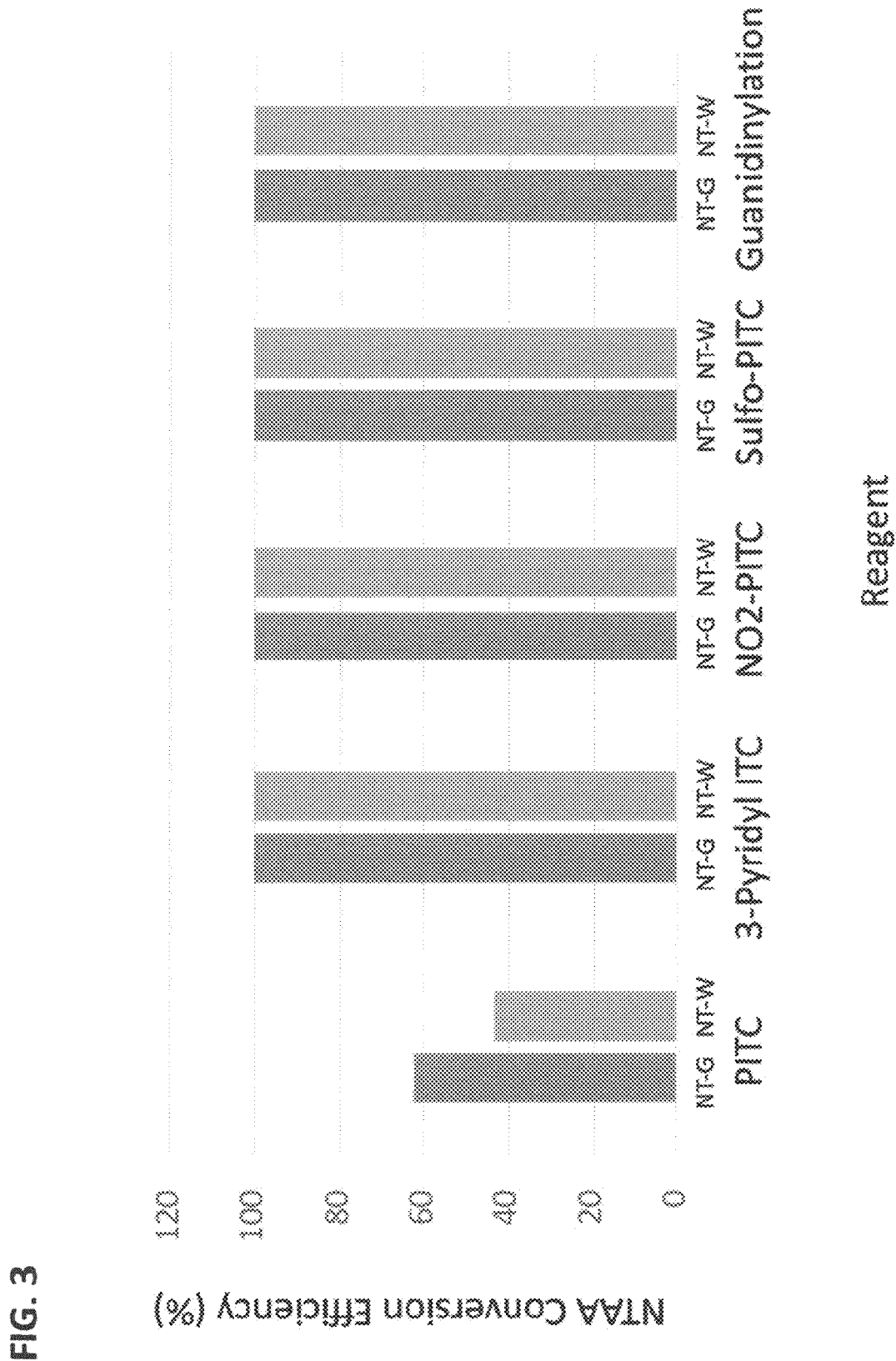
FIG. 3. depicts N-terminal amino acid (NTAA) conversion efficiency with different exemplary reagents for labeling the N-terminal amino acid. Two different peptides were tested in solution: N-Terminal G (NT-G)=GRFSGIY (SEQ ID NO: 40); N-Terminal W (NT-W)=WTQIFGA (SEQ ID NO: 41). LC-MS was used to quantitate conversion efficiency.

In all cases, for the modifying reagents for labeling the peptides shown, quantitative modification was observed without any DNA modification. PITC was also run as a control, but under the conditions tested did not generate complete modification. As shown in FIG. 3, high-yield labeling of the peptides with Pyridyl-ITC, Nitro-PITC and Sulfo-ITC and high-yield guanidinylation was observed with both peptides.

Example 3. Labeling of N-Terminal Amino Acid (NTAA) of Peptides with an N-Terminal "Protected" Amino Acid This example describes using a blocked or protected amino acid for labeling of the N-terminal amino acid.

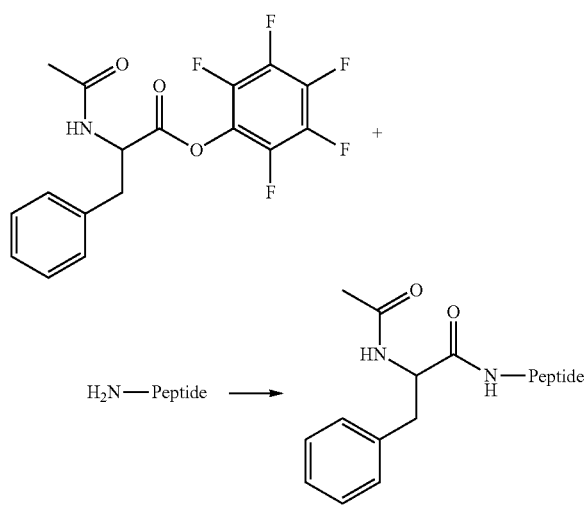

A mixture of N-terminal free peptides (0.1 mmol total) is dissolved in acetonitrile/TEAA (1 mL, 50 mM TEAA, 1:1, v/v, pH=8.5) to which Ac-Phe-Pfp (1 mmol) is added. The mixture is stirred for 1 hour at room temperature. The acetonitrile is evaporated under reduced pressure and the peptide mixture filtered through a C18 column to yield Ac-Phe terminated peptide In another example, a mixture of N-terminal free peptides (0.1 mmol total) is dissolved in acetonitrile/TEAA (1 mL, 50 mM TEAA, 1:1, v/v, pH=8.5) to which Cbz(Z)-Ala-OSu (1 mmol, Bachem) is added. The mixture is stirred for 30 min. at room temperature. The acetonitrile is evaporated under reduced pressure and the peptide mixture filtered through a C18 column to yield Cbz (Z)-Ala terminated peptide.

In some cases, PfP can be replaced by NHS or sulfo-NHS. In other examples, the Ac protected amine of the amino acid could be Fmoc, Boc, or Cbz protected. In other examples, the amine of the amino acid is dialkyl. In other examples, the carboxylic acid of the amino acid is free and the amino acid is coupled using standard peptide coupling reagents such as HATU+DIEA or EDC+DIEA+HOBt. In other examples, the amino acid could be D or L chirality. The amino acid could be any amino acid, naturally occurring or synthetic.

Example 4. Selection, Isolation, and Assessment of DAP BII Derived Modified Cleavases This example describes the generation of libraries of variant DAP BII genes and identification of active modified cleavases from genetic selection.

A DAP BII library was generated substantially as described in Example 1, targeting various combinations of residues selected from positions 191, 192, 196, 306, 310, 650, 651, 655, and 656 (based on the sequence of the protein set forth in SEQ ID NO: 13). The variant DAP BII libraries were transformed into an arginine auxotroph strain of *E. coli*, which has a deletion in the argA gene (strain JW2786-1). The cleavase genes were expressed with a periplasm targeting sequence PelB signal sequence. Genetic selection was performed on the transformed *E. coli* using M9 minimal media agar plates supplemented with arginine N-terminal modified peptides. The plates were incubated at 35° C. until colonies appeared. In the selection, cells harboring a modified (e.g. DAP BII) cleavase that is active against N-terminally modified arginine peptides (AAAR (SEQ ID NO: 21) or ARAA (SEQ ID NO: 29)) will cleave the peptide and release arginine. This release of arginine will enable the cells to survive. Various exemplary chemical reagents were used to label the N-terminal of arginine-containing peptides, including isatoic anhydride, 5-nitro isatoic anhydride, and succinic anhydride. The plates were incubated at 35° C. until colonies appeared. From the surviving cells, plasmid DNA was subsequently isolated and sequenced to identify the mutations that generate an active modified cleavase that recognizes labeled amino acids.

Using the described genetic selection approach, mutations in DAP BII were identified in exemplary active modified cleavases derived from wildtype DAP BII genes. Candidates that were identified in the genetic selection were confirmed by purification of the enzyme variant which was subjected to in-solution assays. The cleavase gene encodes a hexa-histidine tag fused to the C-terminus of the protein, which enables the cleavase to be purified via immobilized metal affinity chromatography. Purified modified cleavase candidates were assayed in reaction mixtures consisting of HEPES (50 mM, pH 7.5), EDTA (1 mM), cleavase enzyme (100 nM to 1 µM), and N-terminal labeled peptide with the sequence AAGVAMPGAEDDVVGSGSK(N$_3$) as set forth in SEQ ID NO: 22 (100 µM). The reactions were incubated between 25° C. and 37° C. for 30 min to 3 h. Reaction mixtures were then analyzed via LC-MS for product identification.

Exemplary cleavases that removed a single labeled terminal amino acid were identified and shown to exhibit similar cleaving activity as shown in Table 10. The confirmed active modified dipeptide cleavases contained mutations as set forth in Table 11, where the exemplary amino acid substitutions are designated by amino acid position number corresponding to the respective reference unmodified DAP BII sequence set forth in SEQ ID NO:13. The amino acid position is indicated in the middle, with the corresponding unmodified (e.g., wild-type) amino acid listed before the number and the identified variant amino acid substitution listed after the number. As shown, the LC-MS data identified a product with an observed mass of 836.4, which matches the expected mass of the C-terminal product, AGVAMPGAEDDVVGSGSK(N$_3$) (SEQ ID NO:56), after cleavage and removal of the labeled terminal amino acid (A). These data demonstrate that the described process modified a wildtype dipeptide cleavase, DAP BII, which naturally removes unlabeled dipeptides, to remove a single labeled terminal amino acid.

TABLE 10

LC-MS data of Cleavase reaction products.

| Product 1 Observed Mass | Expected Mass for [AGVAMPGAEDDVVGSGSK(azide)] (M/2) |
|---|---|
| 836.4 | 836.4 |

TABLE 11

Exemplary Modified Cleavases

| SEQ ID NO | Mutations | Chemical Reagent Used to Label Target Peptide | Product Removed by Modified Cleavase |
|---|---|---|---|
| 31 | N191C/W192L/R196K/N306R/N310D/G651Y/S655G/V656G | Isatoic Anhydride | 2-aminobenzamide-P1 |
| 32 | N191C/W192L/N306R/N310D/G651Y/S655G/V656G | Isatoic Anhydride | 2-aminobenzamide-P1 |
| 33 | N191F/W192F/N306R/N310G/G651H/V656E | Isatoic Anhydride | 2-aminobenzamide-P1 |
| 34 | N191R/W192L/N306S/N310L/G651T/S655T/V656S | Isatoic Anhydride | 2-aminobenzamide-P1 |
| 35 | N191S/R196H/N306A/D650G | 5-nitro isatoic anhydride | 5-nitro-2-aminobenzamide-P1 |
| 36 | N191T/R196H/N306A/D650G | 5-nitro isatoic anhydride | 5-nitro-2-aminobenzamide-P1 |
| 37 | N191M/R196H/N306A/D650G | 5-nitro isatoic anhydride | 5-nitro-2-aminobenzamide-labeled P1 |
| 38 | N191V/N306A/D650S | Succinic anhydride | Succinic acid-labeled P1 |
| 39 | N191S/N306G/D650S | Succinic anhydride | Succinic acid-labeled P1 |

Example 5. Labeling of N-Terminal Amino Acid (NTAA) of Peptides with an Exogenous Activated Blocked Amino Acid This example describes synthesis of reagents for labeling of the N-terminal amino acid (NTAA) of polypeptides and treatment of the labeled polypeptides with a modified cleavase isolated from a genetic selection. The label used to modify the NTAA of the polypeptide included a chemically labeled alanine residue (2-azidobenzamide-Ala-pFP).

A. Synthesis of 2-azidobenzamide-Ala-pFP (N-(2-azidobenzoyl)-L-alanine-pentafluorophenol ester)

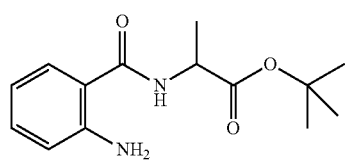

[1a]

A round-bottom flask containing isatoic anhydride was dissolved in dichloromethane (DCM) and stirred. To this, a solution of L-alanine-tert-butyl ester hydrochloride and triethylamine dissolved in DCM was added dropwise to the stirred solution. The mixture was allowed to react for 18h at 25° C. Upon completion (monitored by LCMS), the solution was condensed in vacuo and re-dissolved in 100 mL of ethyl acetate (EtOAc). The organic layer was washed with water, then with brine. The organic layer was separated, dried over sodium sulfate ($Na_2SO_4$), filtered and condensed. The resulting oil was dissolved in a small volume of DCM, dry-loaded onto silica gel ($SiO_2$), and the desired compound N-(2-aminobenzoyl-)L-alanine-tert-butyl ester [1a] was separated using flash chromatography (0-80% EtOAc in n-heptane). The fractions containing the desired product were pooled and condensed giving 87% yield.

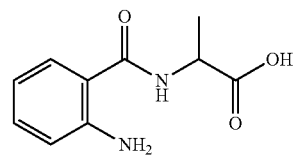

[1b]

A stir bar was added to the round-bottom flask containing 1a and was then dissolved in 10% HCl (aq.) and stir in an ice bath. In a separate vial, 1.1 molar equivalence of sodium nitrite ($NaNO_2$) was dissolved in water and slowly added to the cooled, stirred solution of 1a. After 30 minutes of stirring, an aqueous solution of 1.5 molar equivalence sodium azide ($NaN_3$) was added dropwise to the solution of 1a and $NaNO_2$ and allowed to stir for an additional 30 minutes to 1 hour while slowly rising to room temperature. An off-white precipitate formed as a result and the solution was filtered, washed with additional water and n-heptane to afford a slight yellow solid (90% yield; A-(2-azidobenzoyl-)L-alanine-tert-butyl ester [1b]).

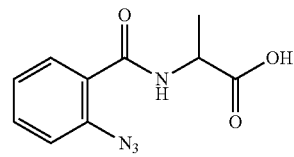

[1c]

The solid 1b was placed in a round-bottom flask with a stir bar and was dissolved in 30 mL 1:9 trifluoroacetic acid (TFA):DCM. The solution was stirred at room temperature for 3.5 hours at which time TLC showed full conversion of the tert-butyl ester to the carboxylic acid. The solution was condensed in vacuo to remove the TFA and the oil was dissolved in DCM and loaded onto $SiO_2$ for column purification (0-100% EtOAc in n-heptane). The fractions containing the desired product N-(2-aminobenzoyl-)L-alanine [1c] were pooled and condensed (99% yield).

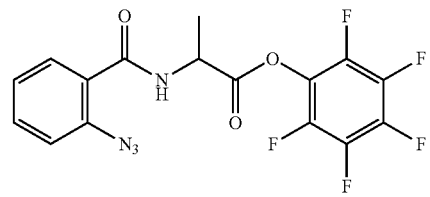

[1d]

The off-white solid [1c] was placed in a round-bottom flask equipped with a stir bar and placed under argon atmosphere. Dry tetrahydrofuran (THF) was delivered to the flask to dissolve the solid. Subsequently, 1.1 eq of pentafluorophenol (pFP) was dissolved in THF and added to the flask containing [1c] and allowed to stir for five minutes at 25 C. Then, 1.1 eq. of dicyclohexane carbodiimide was dissolved in THF and slowly added to the stirring solution. The reaction continued to stir for 18h until a white precipitate formed. Upon the reaction completion, the solids were filtered and washed with THF. The filtrate was condensed and resuspending in a small volume of THF. The solution was again filtered to remove solids. The THF solution was condensed again and was dissolved in a minimal volume of DCM. The solution was dry-loaded onto $SiO_2$ for column chromatography (0-60% EtOAc in n-heptane). The fractions containing the title compound were pooled and condensed to give a white solid (72% yield) [1d].

B. Selection and Isolation of DAP BII Derived Modified Cleavases

Library generation and selection of DAP BII genes was performed as substantially described in Example 4. The DAP BII library targeted various combinations of residues selected from positions 188, 189, 190, 191, 192, 196, 302, 306, 310, and 650 (based on the sequence of the protein set forth in SEQ ID NO: 13). For this experiment, the N-terminally modified arginine peptides (2-aminobenzamide-AAAR (or M15-AAAR), SEQ ID NO: 21) used in the selection were prepared by treating with a chemical reagent, isatoic anhydride. From the surviving cells, plasmid DNA was subsequently isolated and sequenced to identify the mutations that generate an active modified cleavase that recognizes labeled amino acids. Using the described genetic selection approach, mutations in DAP BII were identified in exemplary active modified cleavases derived from wildtype DAP BII genes. Cleavase candidates that were identified in the genetic selection were confirmed by purification of the enzyme variant which was subjected to in-solution assays. The cleavase gene encodes a hexa-histidine tag fused to the C-terminus of the protein, which enables the cleavase to be purified via immobilized metal affinity chromatography. Purified modified cleavase candidates were assayed in reaction mixtures.

Three exemplary dipeptide cleavases containing the sequences as set forth in SEQ ID NOs: 17, 18, and 19 were identified and shown to exhibit activity for 2-aminobenzamide-labeled peptides. The confirmed active modified dipeptide cleavases contained mutations D188V/I189A/D190S/N191L/W192G/R196S/A302W/N310K/D650A, N191M/W192G/R196T/N306R/D650A, or N191M/W192G/R196V/N306R/D650A, where the exemplary amino acid substitutions are designated by amino acid position number corresponding to the respective reference unmodified DAP BII sequence set forth in SEQ ID NO: 13. The amino acid position is indicated in the middle, with the corresponding unmodified (e.g., wild-type) amino acid listed before the number and the identified variant amino acid substitution listed after the number.

C. Evaluating 2-Azidobenzamide-Ala-pFP as Modification for Modified Cleavase Recognition and Activity One of the exemplary modified cleavases identified from genetic selection as described in Section B containing the amino acid sequence as set forth in SEQ ID NO: 18 with mutations N191M/W192G/R196T/N306R/D650A was assessed for recognition and activity towards peptides labeled with an exogenous alanine synthesized as described in Section A above. A synthetic peptide (H-IHAGYAW-OH; SEQ ID NO: 30) was functionalized with [1d] to show viability of the title compound's ability to install a modified alanine for selective cleavage. A solution of [1d] (500 mM dimethylacetamide; DMAc) was prepared fresh. The peptide was also dissolved in DMAc to 100 mM concentration. Then in a 1.5 mL tube, 50 μL of 0.4M MOPS buffer (pH 7.6) and 25 μL of acetonitrile was added. To that, 10 μL of the 100 mM peptide solution was added in and mixed. Lastly, 15 μL of the 500 mM [1d] was added in and the solution in the tube was placed in a thermomixer at 50 C for 30 minutes. During the incubation, a solution in a separate 1.5 mL tube was prepared by making a 80 μL, 1.25 uM solution of a modified cleavase (SEQ ID NO: 18) in 0.1M HEPES buffer (pH 8.0).

After the 30 minute incubation of the IHAGYAW peptide (SEQ ID NO:30), a 20 μL aliquot was removed and added to the solution containing the modified cleavase. The modified cleavase and solution of labeled peptide were then incubated at 37 C for 1-18 h. The progress of the cleavage event was monitored by taking aliquots of the reaction and injecting on the LCMS.

TABLE 12

Assessment of Functionalization, Reduction and Elimination on a Native N-terminal Peptide

| R1 | R2 | Peptide MW |
|---|---|---|
| 2-azidobenzamide-A-pFP | MOPS | IHAGYAW 815.9 |

| Functionalization | | |
|---|---|---|
| Peptide Sequence After Treatment | Expected MW | Observed MS (M + H) |
| 2-azidobenzamide-AIHAGYAW (SEQ ID NO: 58) | 1032.9 | 1034.8 |

| Reduction | | |
|---|---|---|
| Peptide Sequence After Reduction | Expected MW | Observed MS (M + H) |
| 2-aminobenzamide-AIHAGYAW | 1007.4 | 1008.8 |

| Elimination | | |
|---|---|---|
| Peptide Sequence After Elimination | Expected MW | Observed MS (M + H) |
| HAGYAW | 702.3 | 703.6 |

As shown in Table 12, treatment of the peptide with [1d] resulted in a products with the expected MW. Cleavage of the now labeled peptide (2-aminobenzamide-AIHAGYAW, SEQ ID NO:58) was observed to completion after 18 hours. Loss of 2-aminobenzamide-AI was the only cleavage event observed by LC-MS. No remaining 2-aminobenzamide-AIHAGYAW was observed after the 18 hour incubation. These data demonstrate that the tested isolated modified cleavase from genetic selection removed the expected labeled dipeptide from the treated polypeptide, including the exogenous added chemically-labeled alanine as part of the dipeptide (2-aminobenzamide-AI). Using this exemplary approach, the tested modified cleavase derived from a wild-type dipeptide cleavase (DAP BII) was modified to remove a single labeled amino acid (labeled with an exogenous N-terminal blocked amino acid, 2-aminobenzamide-A) from the polypeptide.

D. Generation and Selection of Modified Cleavases from Error Prone Libraries

Starting from the identified dipeptide cleavase as set forth in SEQ ID NO: 18, error prone PCR combined with Kunkel mutagenesis was further used to generate libraries of ~$10^9$ complexity with precise control over a desired mutation frequency range (Holland et al., J Immunol Methods. (2013) 394(1-2):55-61). Expression and selection was performed substantially as described above for genetic selection. Identified and purified modified cleavase candidates were assessed using the in-solution assays substantially as described above to test cleavage of the 2-aminobenzamide-AAGVAMPGAEDDVVGSGSK($N_3$) peptide (SEQ ID NO:22) and LC-MS was performed for product identification. Confirmed modified dipeptide cleavases shown in Table 13 were observed to exhibit cleaving activity with observed cleaved products as expected, removing a labeled dipeptide from the tested 2-aminobenzamide labeled-peptide. In the table, the exemplary amino acid substitutions are designated by amino acid position number corresponding to the respective reference unmodified DAP BII sequence set forth in SEQ ID NO: 13. The amino acid position is indicated in the middle, with the corresponding unmodified (e.g., wild-type) amino acid listed before the number and the identified variant amino acid substitution listed after the number. In some cases, a modified cleavase identified using the described methods may be used to remove labeled dipeptides from a peptide which includes an exogenous amino acid, resulting in a net removal of a single amino acid (P1) from the original peptide.

TABLE 13

Exemplary Modified Dipeptide Cleavases

| SEQ ID NO | Mutations |
|---|---|
| 23 | N191M/W192G/R196T/N306R/T307K/D650A |
| 24 | N191M/W192G/R196T/N306R/N525K/A528V/ A604V/D650A/K692N |
| 25 | A126T/N191M/W192G/R196T/G238V/N306R/D650A |
| 26 | N191M/W192G/R196T/N306R/F546L/D650A |
| 27 | N191M/W192G/R196T/N306R/D650A/G651V/K665I |
| 28 | N191M/W192G/R196T/N306R/D650A/G651V |

Example 6. Development of N-Terminal Modifications (NTMs) for Evolving NTM-P1 Anticalin-Based Binding Agents with Minimal P2 Bias Anticalin scaffold selection and library design. Lipocalins were used as starting scaffolds for directed evolution toward modified NTAAs. Anticalins have an intrinsic cup-like binding pocket, highly stable structure, good recombinant expression in *E. coli*, binding pocket evolvability using phage display, and demonstrated potential for strong and specific binding to small molecules. Based on internal data and computational modeling, NTMs were designed such that when combined with the P1 amino acid (N-terminal residue), the NTM-P1 moiety occupies the anticalin β-barrel core, with the P1 sidechain oriented closer to the surface of the pocket. Many anticalins have an intrinsic ability to bind a modified-dipeptide residue. This design forces the P2 residue (penultimate residue) of the peptide to be located just outside the pocket or affinity determining region and contribute less energy to binding. In particular, an $NTM_{blk}$ comprised of a Abz-L was evaluated, wherein Abz is 2-amino benzyl group and is attached to a Leucine amino acid (2-aminobenzamide-Leu NTM, also called Ml 5-Leu). This $NTM_{blk}$ group was attached to the N-terminal of the peptide by use of an activate ester form (pentafluorylbenzyl). The leucine can be substituted for any other amino acid either natural or non-natural in order to better optimize fit and discrimination between various P1 residues. The M15-Leu NTM was also used for selection of cleavases that will specifically cut M15-Leu-P1 residue of the polypeptide.

Library construction, phage panning, and done characterization. High diversity (~$10^{10}$) phage libraries using NNK variant site encoding were constructed targeting residues positions within the pocket of the anticalin (FIG. 5), the sequence of anticalin is set forth in SEQ ID NO: 46. Using standard protocols, phage library was panned against different mod-NTAA target peptides. Clones from the panning output were isolated and characterized using a panel of peptides in a multiplex Luminex binding assay. Specific binders were isolated against a variety of M15-L-NTAAs (FIG. 6). An exemplary engineered anticalin comprises an amino acid sequence that has at least 80%, 90%, 95% or more identity to an amino acid sequence set forth in SEQ ID NO: 46. In some embodiments, an engineered anticalin comprises a mutation in the scaffold set forth in SEQ ID NO: 46 selected from the group consisting of V33T, L36R, Y52R, T54L, L70M, R79S, W81E, F85Q, L96E, N98L, H100T, R101W, Y102H, Y108W, F125S, K127P, K136R, Y140L corresponding to positions of SEQ ID NO: 46.

Evaluation of M15-L-P1P2 peptide binding. The ProteoCode™ assay was used to generate binding profiles across a set of 288 peptides (17×17 combination of different P1 and P2 residues) for the anticalin binders. To enable ProteoCode™ encoding, the anticalin binders were expressed with a SpyCatcher fusion at the C-terminus of the anticalin enabling easy bio-conjugation of a SpyTag-DNA coding tag chimera. Proximity and binding between binders and different peptides allows the transfer of information from the DNA coding tag to the DNA recording tag attached to the queried peptide. The use of Abz-L (Ml 5-LEU) group enabled generation of a set of P1 discriminatory binders, which also minimized the effect of the P2 group on binding/encoding (FIG. 7). The same NTM group was used successfully to generate modified cleavases that can recognize and cleave the modified terminal residue of a polypeptide (Example 4). The set of binders and cleavases selected specifically again recognize and cleave the modified terminal residues of a polypeptide can be used in combination and allows to encode sequentially every or majority of amino acids of the immobilized polypeptide (ProteoCode™ encoding, shown on FIG. 8).

Example 7. Syntheses of Exemplary Compounds compound [1]

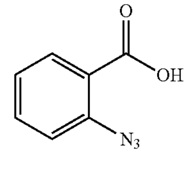

Synthesis of 2-azidobenzoic acid (compound [1]): To a 100 mL round-bottom flask equipped with a magnetic stirbar, 1 g of isatoic anhydride (6.13 mmol) was dissolved in a mixture of tetrahydrofuran (THF) and 5 equiv. (30.65 mmol) of sodium hydroxide (NaOH) in water. The mixture was stirred vigorously at room temperature for 30 minutes. LCMS of the solution showed that complete hydrolysis of the anhydride had taken place (forming the 2-aminobenzoic acid), so the solution was placed in an ice bath and acidified by addition of 20 equiv. (122.6 mmol) of conc. HCl. To this, 1.2 equiv. of sodium nitrite (NaNO$_2$; 7.36 mmol) dissolved in water was added dropwise and allowed to stir at 0° C. for 20 minutes. Then, 1.5 equiv. of sodium azide (NaN$_3$; 9.195 mmol) was dissolved in water and added dropwise to the solution and proceeded to react for 15 minutes. The upon completion monitored by LCMS, the solution was extracted (3×50 mL) with ethyl acetate (EtOAc), washed with brine, and dried over Na$_2$SO$_4$. The pooled organic solution was filtered, condensed, taken up in minimal diethyl ether (Et$_2$O), and precipitated with n-heptane. The solution was filtered and the remaining orange-brown powder collected was used without further purification (>99% pure by LC-MS; 932 mg, 93% yield).

Synthesis of N-(2-azidobenzamid)-L-leucine (compound [3]): To a 200 mL round-bottom flask containing 1.121 g of compound [2], a stirbar was added and the solid was dissolved in 40 mL of DCM. To this solution, 15 mL of trifluoroacetic acid (TFA) was carefully added and the solution was allowed to stir at room temperature for 5 hours. Upon completion (monitored by TLC), the stirbar was removed, washed with DCM and n-heptane, and the solution was condensed in vacuo. The remaining residue was washed with n-heptane and condensed in vacuo until most of the TFA was removed. The oil was dissolved in a minimal volume of DCM, dry-loaded onto silica gel, and purified on ISCO CombiFlash (0-70% EtOAc in n-heptane). The fractions containing the desired product [3] were pooled, condensed, and analyzed by LCMS. This produced 932 mg of [3] (>99% purity; 99% yield) as an amorphous solid.

compound [2]

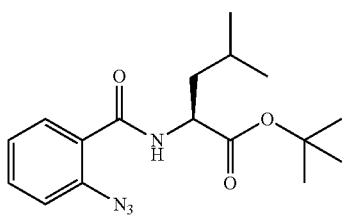

compound [4]

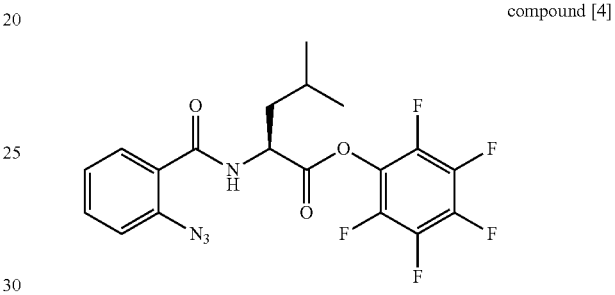

Synthesis of N-(2-azidobenzamid)-L-leucine-O-tert-butyl ester (compound [2]): To a 100 mL round-bottom flask containing a magnetic stirbar, 632 mg of compound [1] (3.874 mmol) was added and dissolved in anhydrous N,N-dimethylformamide (DMF), followed by 1.2 equiv. of diisopropylethylamine (DIPEA; 4.469 mmol). The solution was allowed to stir at room temperature for 10 minutes and then 1.1 equiv. of COMU ((1-Cyano-2-ethoxy-2-oxoethylidenaminooxy)dimethylamino-morpholino-carbenium hexafluorophosphate; 4.261 mmol) was added to the solution and continued to stir for 30 minutes. In a separate vial, 1.2 equiv. of L-leucine-O-tert-butyl ester HCl (4.469 mmol) was dissolved in dichloromethane (DCM) and 2.4 equiv. of DIPEA (8.938 mmol). After 30 minutes, the leucine solution was added dropwise to the [1]-containing solution and allowed to react for 18 hours. Upon completion, the solution was diluted in 150 mL of EtOAc and was washed with 1M HCl, then sat. NaHCO$_3$, and lastly brine. The organic layer was dried over Na$_2$SO$_4$, filtered, and condensed. The remaining oil was dissolved in a minimal volume of DCM and dry-loaded onto silica gel for purification on ISCO CombiFlash (0-50% EtOAc in n-heptane). The fractions containing the desired product [2] were pooled, condensed in vacuo, and analyzed by LCMS. This resulted in 1.121 g of [2] isolated (>98% purity; 87% yield) as a waxy solid.

Synthesis of N-(2-azidobenzamid)-L-leucine-tert-(2,3,4,5,6-pentafluorophenyl) ester (compound [4]): To a 20 mL amber vial equipped with a stirbar, 296 mg of compound [3](0.890 mmol) was added and dissolved in 3 mL of anhydrous THF. To this, 1.1 equiv. 2,3,4,5,6-pentafluorophenol (0.980 mmol) was added and stirred until dissolved. In a separate vial, 1.0 equiv. of N,N'-dicyclohexylcarbodiimide (DCC; 0.890 mmol) was dissolved in THF and added dropwise to the stirred solution of [3], The reaction was stirred at 25° C. for 3.5 hours and upon completion was diluted in EtOAc, filtered to remove DCU (dicyclohexylurea), and condensed in vacuo. The resulting oil was taken up in minimal volume of DCM and purified by ISCO CombiFlash (0-50% EtOAc in n-heptane). The resulting fractions containing the desired product were pooled, condensed, and placed under high vacuum to afford 392 mg of compound [4] as a waxy solid (>95% purity; 99% yield).

Example 8. Evaluating 2-Azidobenzamide-LEU-pFP as a Suitable Modification for Modified Cleavase Recognition and Activity One of the exemplary modified cleavases identified from genetic selection as described in Example 4 containing the amino acid sequence as set forth in SEQ ID NO: 18 with mutations N191M/W192G/R196T/N306R/D650A was assessed for recognition and activity towards peptides labeled with M15-LEU synthesized as described in the Example 7. A synthetic peptide (IHAGYAW; SEQ ID NO: 47) was functionalized with the compound [4] to show viability of the approach to install Ml 5-LEU to provide selective cleavage. A solution of [4](150 mM in dimethylacetamide; DMAc) was prepared fresh. The peptide was also dissolved in DMAc to 10 mM concentration. Then in a 1.5 mL tube, 50 μL of acetonitrile and 25 μL MOPS buffer (pH compound [3]

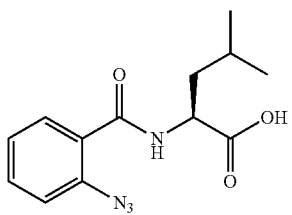

7.6) were added. To that, 10 μL of the 10 mM peptide solution was added in and mixed. Lastly, 15 μL of the 150 mM [4] was added in and the solution in the tube was placed in a thermomixer at 40° C. for 60 minutes. During the incubation, a solution was prepared by making a 1.25 uM solution of the modified cleavase (having sequence set forth in SEQ ID NO: 18) in 0.1M HEPES buffer (pH 8.0).

After the 60 minute incubation of the IHAGYAW peptide, 100 μL of 0.5M TCEP (tris(2-carboxyethyl)phosphine) solution was added and incubated for 20 minutes at 40° C. to reduce the azide to amine. A 20 μL aliquot was removed and added to the 0.05M MES (2-(N-morpholino)ethanesulfonic acid) with 0.1% Tween 20 at pH 6.4 solution containing the modified cleavase. The modified cleavase and solution of labeled peptide were then incubated at 65° C. for 1-18 h. The progress of the cleavage event was monitored by taking aliquots of the reaction and injecting on the LC-MS. The results of mass spectrometry analysis have shown that treatment of the peptide with the compound [4] resulted in products with expected molecular weights. Cleavage of the labeled peptide (2-aminobenzamide-LIHAGYAW; SEQ ID NO: 57) was observed to completion after 18 hours. Loss of 2-aminobenzamide-LI was the only cleavage event observed by LC-MS. No remaining 2-aminobenzamide-LIHAGYAW was observed after the 18 hour incubation. These data demonstrate that the tested isolated modified cleavase from genetic selection removed the expected labeled dipeptide from the treated polypeptide, including the exogenous added chemically-labeled leucine as part of the dipeptide (2-aminobenzamide-LI). Using this exemplary approach, the tested modified cleavase derived from a wildtype dipeptide cleavase (DAP BII) was modified to remove a single labeled amino acid (labeled with an exogenous 2-aminobenzamide-LEU, also designated as M15-L) from the polypeptide.

Example 9. Development of Thermophilic Cleavases for Removal of M15-L-P1 from M15-L-Modified Peptides A genetic selection approach was used to evolve thermophilic dipeptidyl peptidase to cleave a single labelled N-terminal amino acid from a peptide similarly to the described in Example 4 (the M15-L NTM was used). High diversity combinatorial libraries on different dipeptidyl peptidase scaffolds were created, and the libraries were transformed into an *E. coli*. selection strain. Structure based design was used to define variant sites for library creation. Peptides with different N-terminally modified P1 amino acids were used to evolve Cleavases for the respective targets.

A genetic selection-based approach to cleavase engineering enables high-throughput enzyme selection (Evnin, L. B., J. R. Vasquez and C. S. Craik (1990). "Substrate specificity of trypsin investigated by using a genetic selection." *Proc Natl Acad Sci USA* 87(17): 6659-6663). The selection makes use of short N-terminally modified peptides that contain the auxotrophic amino acid. The peptides readily enter the periplasm of a bacterium but are unable to enter the cytoplasm due to the inability of transporters to recognize the modified N-terminus (Smith, M. W., D. R. Tyreman, G. M. Payne, N. J. Marshall and J. W. Payne (1999). "Substrate specificity of the periplasmic dipeptide-binding protein from *Escherichia coli*: experimental basis for the design of peptide prodrugs." *Microbiology* 145 (Pt 10): 2891-2901). To relieve the amino acid auxotrophy during growth on minimal media, a cleavase scaffold is expressed on a plasmid and targeted to the periplasm, via a pelB leader sequence. The active cleavase variant removes the N-terminally modified amino acid, revealing a native peptide amino terminus. This allows the rest of the peptide, which contains the essential amino acid, to be uptaken and support growth of the bacterium. For studies disclosed herein, an arginine auxotroph was used, which demonstrated an absence of background growth on peptides with the N-terminal M1 5-LEU modification.

Figure 7A:
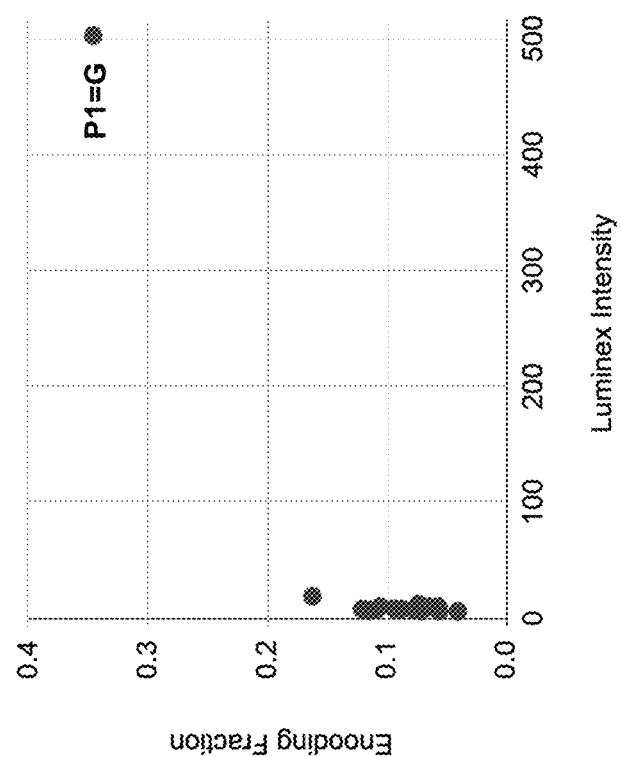
FIG. 7A-B illustrates exemplary analysis of P2 dependence via ProteoCode™ encoding assay.
Figure 7B:
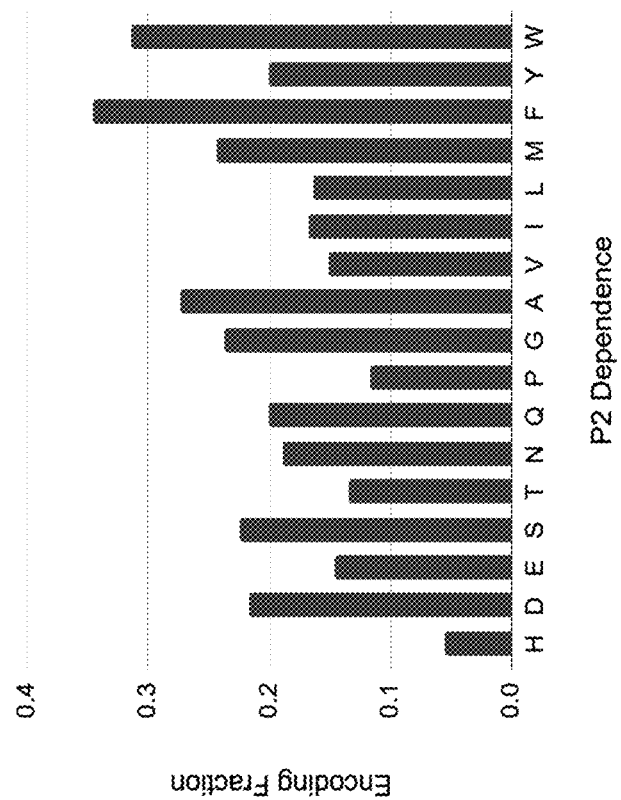
Figure 8:
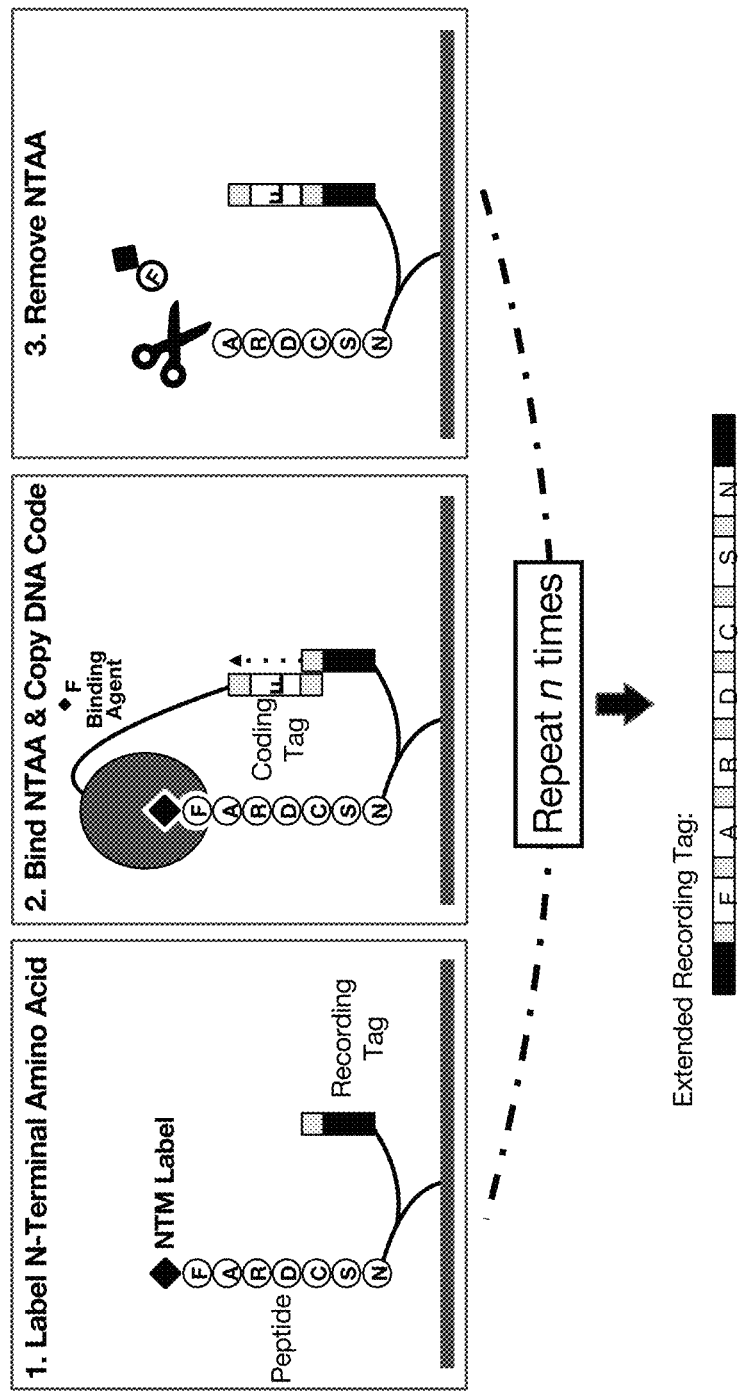
FIG. 8 shows ProteoCode™ encoding assay with modified NTAA binders and modified cleavases used for high-throughput polypeptide sequencing. Polypeptide molecules are each labeled with a DNA recording tag and attached to a solid support (beads) at a low molecular density, a sparsity that permits only intramolecular information transfer to occur. (1) At the beginning of a sequencing cycle, the polypeptide N-terminal amino acid (NTAA) is functionalized with a N-terminal modification (NTM) or label. (2) Next, an engineered NTAA binding agent labelled with a DNA coding tag binds to the labeled NTAA residue. After binding and washing, the coding tag information is transferred enzymatically to the recording tag (by extension or ligation). (3) Removal of the NTM-labeled N-terminal residue is accomplished by using a modified Cleavase enzyme that specifically cleaves the NTM-labeled N-terminal residue. After n cycles, a DNA library element representing the n amino acids of the polypeptide sequence is formed as a part of extended recording tag and can be sequenced by a next-generation sequencing (NGS) method. A representative structure of an NGS library element after 7 cycles is shown.

Using this genetic selection approach, an active cleavase variant was identified from an S46 DPP library {N214X, W215X,R219X,N329X,D673X; X=20 amino acids} and error prone library from *Thermomonas hydrothermalis* with the following amino acid mutations: {N214M,W215G, R219T,N329R,D673A,G674V} with reference to SEQ ID NO: 43 (an unmodified scaffold). Moreover, this variant was further evolved by creating an additional library with variant sites as follows {N214M,W215G,R219T,N329R; N333X, I651X,A671X,D673A,G674X,N682X,M692X; X=any one of 20 natural amino acids; the indicated residue numbers correspond to positions of SEQ ID NO: 43} and by genetic selection generated a set of enzymatic cleavases. Each evolved cleavase was individually assayed on all M15-L-P1 targets. In this assay, individual cleavase clone was expressed and purified, and then incubated with each peptide substrate for 3 hours at 52° C. The UV absorbance of both product and starting material in the final reaction was measured on HPLC and converted to percentage of conversion. Collectively, they can provide broad activity for removal of almost all M15-L-P1 residues (FIG. 7A and FIG. 7B). The individual data in FIG. 7A is constructed using best conversion rate for each M15-L-P1 targets among all tested Cleavase clones.

Figure 9A:
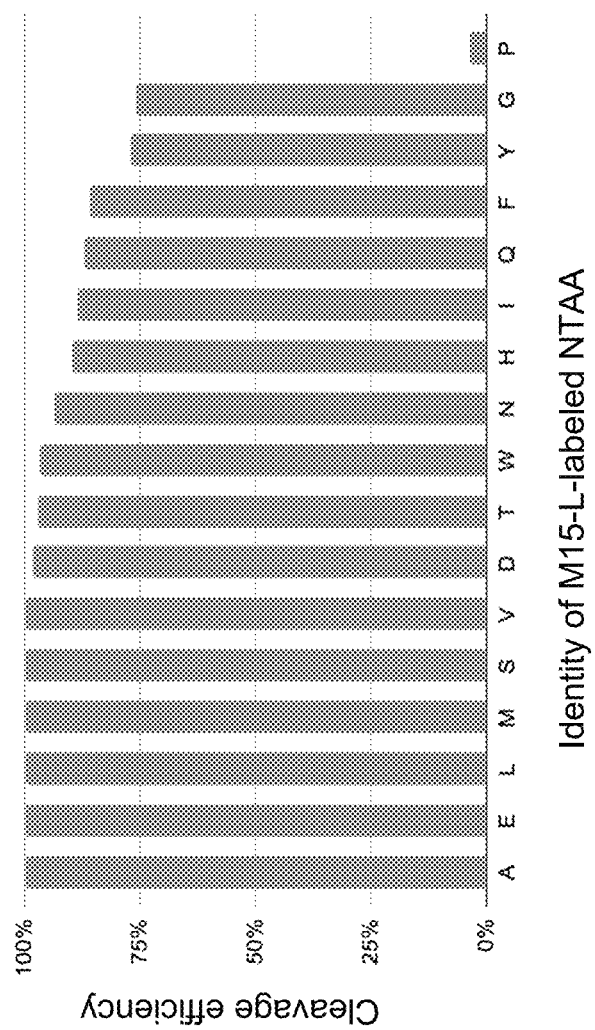
FIG. 9A illustrates exemplary cleavage of M15-L-modified NTAAs of a model polypeptide (M15-L-P1-AR) with Cleavase enzymes. A compilation of seven different modified Cleavase clones was used to generate the spectrum of cleavage profile across the M15-L-modified NTAAs as shown. Data were generated by HPLC analysis (UV absorbance) of cleaved versus intact peptides after cleavase assay.
Figure 9B:
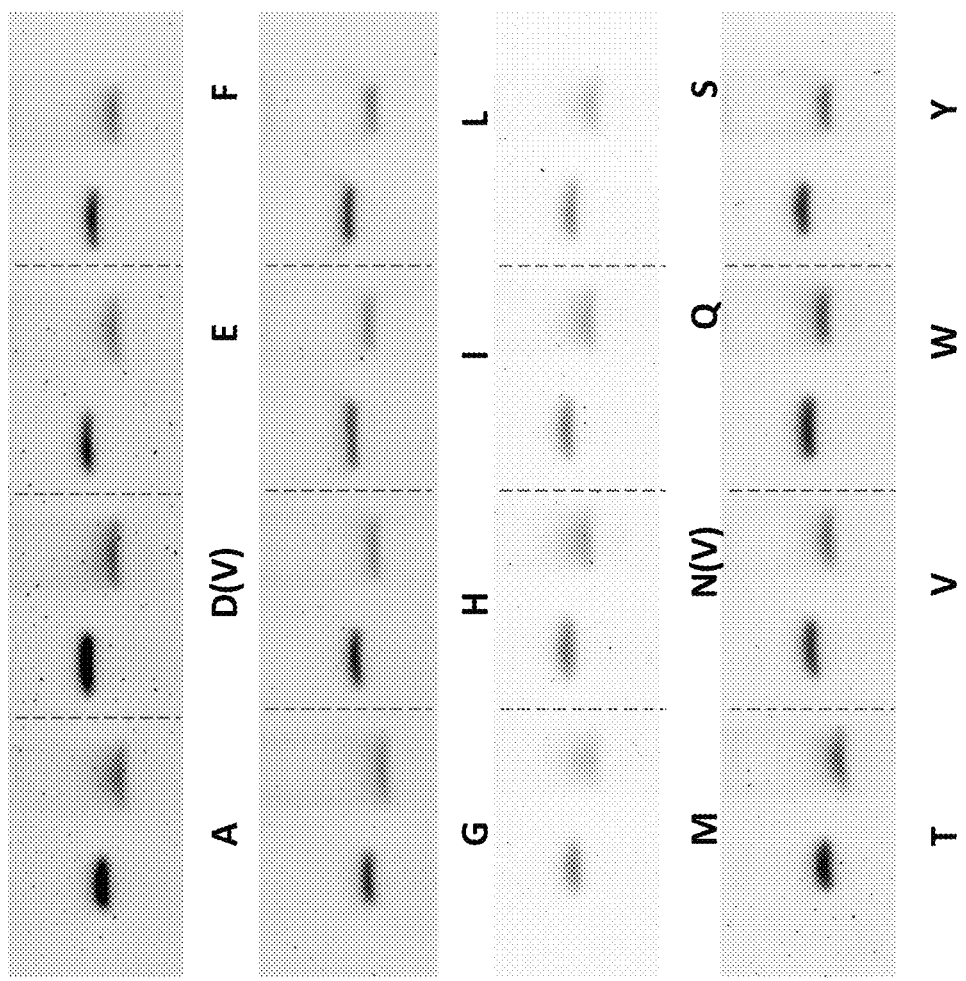
FIG. 9B shows the same cleavage events using SDS-PAGE analysis.

Example 10. Engineered Dipeptide Cleavases can Remove Single Labeled NTAAs of a Model Polypeptide A set of dipeptide cleavase enzymes was evolved from an S46 DPP library as described in Examples 4 and 9 using M15-L-P1 target polypeptides (polypeptide sequences: M15-L-P1-AR, where P1 is one of the 17 natural amino acids, excluding C, K, R) and the dipeptide cleavase scaffold from *Thermomonas hydrothermalis* (SEQ ID NO: 42 or SEQ ID NO: 43). The enzymes can efficiently cleave M15-L-labeled polypeptides between P1 and P2 amino acid residues, thus are configured to remove a single labeled terminal amino acid from the polypeptide (FIG. 9A and FIG. 9B). To accommodate the M15-L label in the substrate binding site, all modified dipeptide cleavases contained the following mutations at the conserved residues that form an amine binding site in unmodified dipeptidyl aminopeptidases: N214M, W215G, R219T, N329R, D673A (the indicated residue numbers correspond to positions of SEQ ID NO: 43). These mutations are specific to the M15 NTM$_{blk}$ group and may be different for other NTMs including bipartite NTMs of M15 with other amino acid-like groups. At the same time the cleavage efficiency of the evolved enzymes depended on the nature of the P1 residue.

Each evolved cleavase was individually assayed on all M15-L-P1 target polypeptides. In this assay, an individual cleavase clone is expressed and purified, and then incubated with each peptide substrate for 3 hours at 52° C. Six μM enzyme in 5 mM phosphate buffer at pH 8 were used. The UV absorbance of both product and starting material in the final reaction was measured on HPLC and converted to percentage of conversion (FIG. 9A). M15-L-P-AR exhibited poor cleavage efficiency with the set of seven Cleavase clones, but further directed evolution can be used to address this issue. Additionally, efficiency of cleavage reactions were assessed on peptide-DNA fusions. In this assay, peptide substrates were modified to have an azide group at the C-terminal lysine that was linked to dibenzocyclooctyne (DBCO)-activated PEG12 linker connected with a DNA oligo. M15-L-P1-GAEIAGDVAGGK peptides were used (SEQ ID NO: 48), and for D and N as P1, the Gly residue at P2 position was replaced with Val. In FIG. 9B, the cleavage events were monitored by UREA-PAGE assay. It was found that the first selected modified cleavase (M15-L_Z001) provided 100% cleavage for polypeptides with the following M15-L-labeled P1 residues: A, I, L, M, Q, V. Other selected modified cleavases provided 80-100% cleavage for polypeptides with the following groups of M15-L-labeled P1 residues: D,E; S,T; G; N; H,Y; F,W. A broad cleavage of a single labeled terminal amino acid from the polypeptide can be achieved by combining two or more dipeptide cleavases in a set. For example, as shown in FIG. 9A and FIG. 9B, a set of 7 selected dipeptide cleavases can provide broad activity for removal of almost all M15-L-labeled P1 residues from the polypeptide. In another example, a set of two modified dipeptide cleavases can also cleave the majority of M15-L-labeled P1 residues from the polypeptide, except for F, G, H, P, W residues (FIG. 9C). In this assay, short peptides with M15-L-P1-AR sequence are used, same as in FIG. 9A. Other cleavase combinations can be created to achieve a desired level of cleavage specificity, such as different sets of two, three, four or more enzymes.

Figure 10:
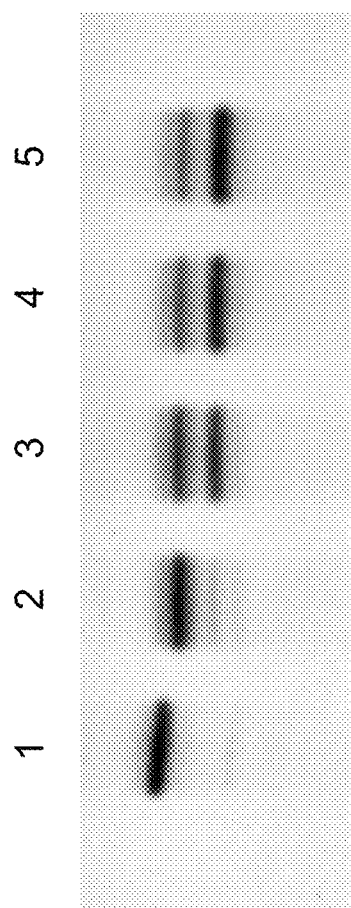
FIG. 10 illustrates cleavage of an exemplary polypeptide by unmodified dipeptide cleavase (dipeptidyl aminopeptidase DAP BII, SEQ ID NO: 13). Lanes 1-5 correspond to cleavage results at the following time points: 0 min, 5 min, 30 min, 45 min, 60 min.

Importantly, it should be noted that the selected modified dipeptide cleavases does not remove an unlabeled terminal dipeptide from the polypeptide, as evident from FIG. 9B, showing solid single bands after the cleavage reaction. It means that the selected modified dipeptide cleavases would not continue cleaving the polypeptide after initial cleavage of the modified NTAA. In contrast, unmodified dipeptide cleavase having natural amine binding site residues (N191, W192, R196, N306, D650 corresponding to positions of SEQ ID NO: 42) would continue gradually cleaving the polypeptide, creating multiple bands during the cleavage reaction (FIG. 10). In this experiment, a test peptide LMSHNARGAEDDVVRGGGGK (SEQ ID NO: 49) was derivatized to have an azide group at the C-terminal lysine that was linked to DBCO-activated PEG12 linker connected with a DNA oligo by a click chemistry reaction, and incubated with wild type DAP BII enzyme (40 µM; 1:20 peptide:enzyme ratio) at 30° C. in the following buffer: 20 mM HEPES pH 7.5, 1 mM EDTA, 100 mM NaCl, 10% glycerol. FIG. 10 indicates cleavage results at several time points: 0 min, 5 min, 30 min, 45 min, 60 min (1-5 at the FIG. 10, respectively).

Figure 11B:
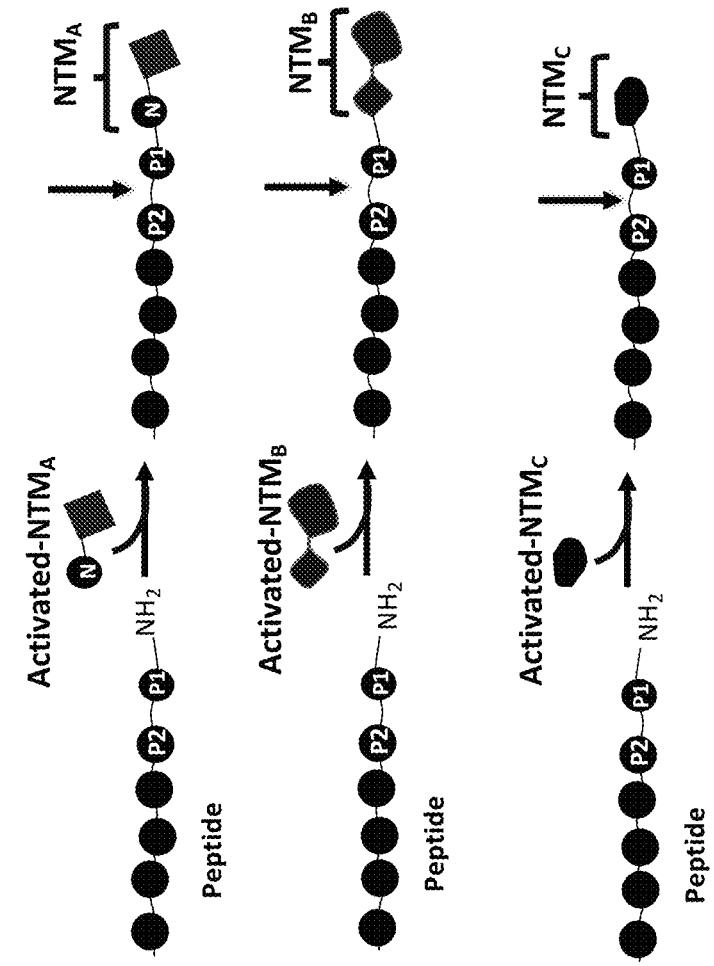
FIG. 11A-B. illustrate exemplary N-terminal modifications (NTMs) to enable NTM-NTAA cleavage at P1 residue by modified dipeptide cleavases.
Figure 11A:
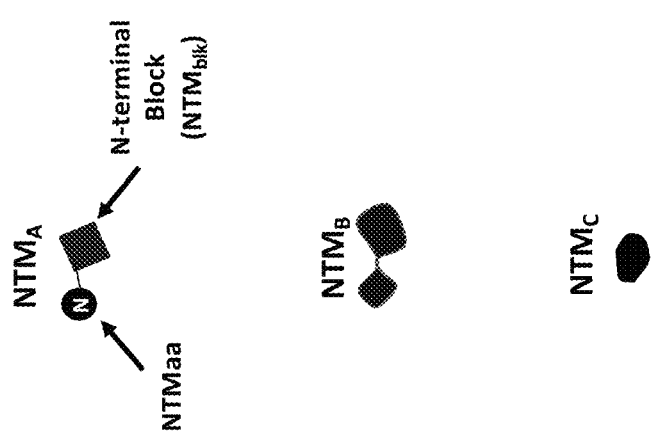
Figure 12:
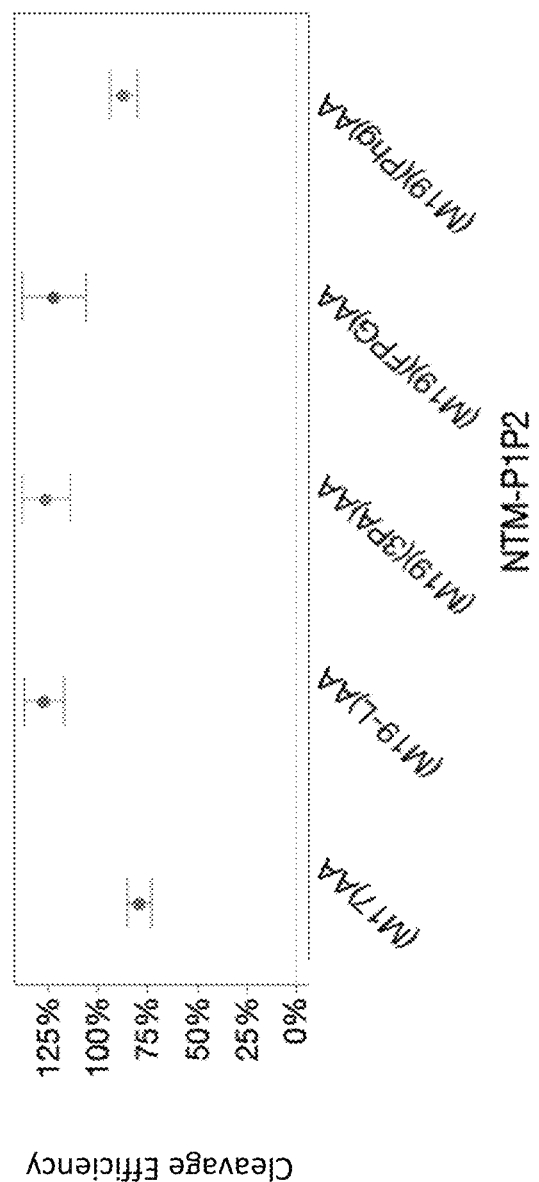
FIG. 12. illustrates exemplary cleavage efficiency of the NTM-labeled NTAA of a target polypeptide depends on a particular NTM.

The engineered cleavases were further tested for their ability to cleave labeled polypeptides having different bipartite NTMs. Bipartite NTMs comprise an amino acid-like portion (natural or unnatural amino acid, or a chemical entity having a size, e.g., length axis or volume, shape, and/or configuration similar to a natural amino acid; designated here as NTMaa) and a N-terminal blocking group (NTM$_{blk}$) that provides specificity during the selection process. Such NTM at the N-terminus of a polypeptide would fit in a substrate pocket of a modified dipeptide aminopeptidase, and cause the dipeptide aminopeptidase to cleave a single labeled amino acid from the polypeptide, effectively changing the cleavage mode of the enzyme (FIG. 11A, B, upper drawings). Initial examinations of bipartite NTMs were performed by a colorimetric assay developed to assess the cleavases' ability to recognize and hydrolyze the NTM-P1 from a small molecule substrate. An initial library was synthesized to probe the individual pocket(s) of the cleavase by independently exploring the NTM$_{blk}$ and NTMaa. The library was composed of either NTM$_{blk}$-AA-pNA or M15-NTMaa-A-pNA substrate compounds and compared against M15-AA-pNA; where pNA is p-nitroaniline. In a 96-well transparent, flat-bottom plate, wells containing 45 µL of cleavase (0.5 µM) in 50 mM MES (pH 6.4) with 0.1% Tween 20 was incubated at 65° C. for 5 minutes. Separately, the pNA substrate compounds were prepared in individual 10 mM DMSO solutions. After the incubation period, 5 µL of the substrates in DMSO were added to the individual wells containing cleavase (n=3). The subsequent reactions were monitored by a plate reader at a wavelength of 405 nm for 150 seconds. Assuming steady-state kinetics, initial velocities monitoring the release of free pNA (at 405 nm) from the substrate in the presence of a cleavase enzyme was used to determine whether a NTM$_{blk}$ or NTMaa was a suitable recognition partner to the cleavase; providing down-selection criteria for further testing. Various bipartite NTMs have been tested, including different combinations of a N-terminal blocking group (NTM$_{blk}$) chosen from the following list: M15 (2-aminobenzamide), M18 (pyrazine-2-carboxamide), M19 (3,4-difluorobenzamide), M20 (3-cyano-4-fluorobenzamide) M21 (3-fluoro-4-cyanobenzamide) M22 (3,4-difluoro-2-aminobenzamide) and an "amino acid-like" part (NTMaa) chosen from the following list: Leu (Leucine), Ala (alanine), Gly (glycine), 3PA (3-pyridylalanine), FPG (4-fluorophenylglycine), Phg (phenylglycine), 3AZ (3-azetidine), C5G (cyclopentylglycine), CPG (cyclopropylglycine), and N-alkylated derivatives of these molecules. In one example, cleavage efficiencies of the M15-L_Z001 cleavase were tested against a model polypeptide (AAAEIRGDVRGGK; SEQ ID NO: 51) labeled with the following bipartite NTMs: M15-Leu (designated as M17), M19-Leu, M19-3PA, M19-FPG, M19-Phg. The model polypeptide was derivatized to have an azide group at the C-terminal lysine, attached to DBCO-modified beads by a click chemistry reaction, and incubated with 5 uM of the M15-L_Z001 cleavase in 50 mM MES (pH 6.5) supplemented with 0.1% Tween 20 at 65° C. for 1 hour. Beads were washed with 50 mM Tris (pH 8.0); and peptides were digested with Trypsin in 50 mM Tris (pH 8.0) at 37° C. for 1 hour. In parallel, beads were prepared with the anticipated cleavage product sequence (AAEIRGDVRGGK; SEQ ID NO: 52) and were also digested as a reference control. Cleavage efficiency was determined by comparing the ratios of the N-terminal tryptic peptide product fragment's (AAEIR; SEQ ID NO: 53) mass signal intensity to the internal standard tryptic peptide's (GDVR; SEQ ID NO: 54) mass signal intensity versus the reference control (n=3). The results shown in FIG. 12 demonstrate that the cleavage efficiency of the NTM-labeled NTAA by a given dipeptidyl cleavase can be adjusted by altering the "amino acid-like" part (NTMaa) of the bipartite NTM.

Further bipartite NTMs were screened against a library of modified dipeptidyl cleavases containing substitutions in their substrate binding sites (as shown in the above examples) in order to optimize efficiency of the cleavage and its specificity for the particular bipartite NTM. The screened bipartite NTMs contain one of the following NTM$_{blk}$ structures: 4-methylbenzoic acid, 4-(dimethylamio)benzoic acid, nicotinic acid, 3-aminonicotinic acid, 2-pyrazinecarbooxylic acid, 5-amino-2-fluoro-isonicotinic acid, 2,3-pyrazinedicarboxylic acid, 4,7-Difluoroisobenzofuran-1,3-dicarboxylic acid, 4-chloro-2-aminobenzoic acid, 4-nitro-2-aminobenzoic acid, 7-methoxy-1h-benzo[d][1,3]oxazine-2,4-dione, 4-carboxy-2-aminobenzoic acid, 6-(Trifluoromethyl)-2,4- dihydro-1h-3,1-benzoxazine-2,4-dione, 7-(Trifluoromethyl)-1h-benzo[d][1,3]oxazine-2,4-dione, 6-fluoro-2-aminobenzoic acid, 4-fluoro-2-aminobenzoic acid, 5-methoxy-2-aminobenzoic acid, 4-fluorobenzoic acid, 4-(trifluoromethyl)benzoic acid, 2-ethynyl-6-fluorobenzaldehyde, 2-aminobenzoic acid, Succinic anhydride, 3,6-Difluoropyridine-2-carboxylic acid, 2-Fluoronicotinic acid, 5-Bromo-2-hydroxynicotinic acid, 4-(Trifluoromethyl)pyrimidine-5-carboxylic acid, 2-Oxo-1,2-dihydropyridine-3-carboxylic acid, 5-Methyl-2-aminobenzoic acid, 6-Fluoropicolinic acid, 3-Methyl-2-aminobenzoic acid, 4-Methyl-2-aminobenzoic acid, 2-Amino-6-methylbenzoic acid, 2-Amino-6-fluorobenzoic acid, 2-Amino-5-fluorobenzoic acid, 2-Amino-3-fluorobenzoic acid, 2-Amino-4-fluorobenzoic acid, 2-Aminonicotinic acid, 4-Aminonicotinic acid, 3-Aminopicolinic acid, 2-Amino-4,5-difluorobenzoic acid, 3,4-difluorobenzoic acid, 3,4,5-difluorobenzoic acid, 3-(Methoxycarbonyl)bicyclo[1.1.1]pentane-1-carboxylic acid, 3,3-Difluorocyclobutane-1-carboxylic acid, 1-Methyl-2-oxo-piperidine-4-carboxylic acid, Tetrahydropyran-4-carboxylic acid, 5-Fluoroorotic acid, 3-Fluoro-4-nitrobenzoic acid, 3-(Difluoromethyl)-1-methyl-1H-pyrazole-4-carboxylic acid, 4-(Difluoromethoxy)benzoic acid, 1-(Difluoromethyl)-1h-pyrazole-3-carboxylic acid, 4-(Methanesulfonylamino)benzoic acid, 5-Fluoro-6-methoxynicotinic acid, Tetrahydro-2H-thiopyran-4-carboxylic acid 1,1-dioxide, 4-(1H-Tetrazol-5-yl)benzoic acid, 1,2,3-Thiadiazole-4-carboxylic acid, 1,3-Benzodioxole-4-carboxylic acid, 2,1,3-Benzoxadiazole-5-carboxylic acid, 1-Benzyl-3-methyl-1h-pyrazole-5-carboxylic acid, 1-Cyclopropyl-6,7-difluoro-1,4-dihydro-4-oxoquinoline-3-carboxylic acid, 3,4-Dichlorobenzoic acid, 5-Fluoro-6-methylpyridine-2-carboxylic acid, 4,5-Dimethyl-2-(1h-pyrrol-1-yl)thiophene-3-carboxylic acid, 1,3-Dimethyl-1h-thieno[2,3-c]pyrazole-5-carboxylic acid, 1-[(4-Fluorobenzene)sulfonyl]piperidine-3-carboxylic acid, 1-(4-Fluorobenzyl)-5-oxopyrrolidine-3-carboxylic acid, 3-Fluoro-4-methoxybenzoic acid, 4-Fluoro-3-nitrobenzoic acid, 6-Fluoro-4-oxochromene-2-carboxylic acid, 3-Fluorophenylacetic acid, 4-Fluoro-3-(trifluoromethyl)benzoic acid, 5-Furan-2-yl-isoxazole-3-carboxylic acid, 1-Isopropyl-2-(trifluoromethyl)-1h-benzimidazole-5-carboxylic acid, Levofloxacin carboxylic acid, 3,5,7-Trifluoroadamantane-1-carboxylic acid, 3,4,5-Trimethoxybenzoic acid, 2-Oxo-2,3-dihydro-1h-benzo[d]imidazole-4-carboxylic acid, 1-Methyl-3-(trifluoromethyl)-1h-pyrazole-5-carboxylic acid, 2-Morpholin-4-yl-isonicotinic acid, 1,3-Oxazole-4-carboxylic acid, 4-Carboxybenzenesulfonamide, 3,4-difluorobenzenesulfonyl chloride. In addition, the screened bipartite NTMs also contain one of the following NTMaa structures: a naturally-occurring amino acid residue (alanine, cysteine, aspartic acid, glutamic acid, phenylalanine, glycine, histidine, isoleucine, lysine, leucine, methionine, asparagine, glutamine, arginine, serine, threonine, valine, tryptophan or tyrosine), 3-(3'-pyridyl)-L-alanine, L-cyclohexylglycine, α-aminoisobutyric acid, 3-(4'-pyridyl)-L-alanine, L-azetidine-2-carboxylic acid, isonipecotic acid, L-phenylglycine, β-(2-thienyl)-L-alanine, 3-(4-thiazolyl)-L-alanine, 1-aminocyclopentane-1-carboxylic acid, (2-trifluoromethyl)-L-Phenylalanine, L-cyclopropylalanine, 3-(2'-pyridyl)-L-alanine, beta-cyano-L-alanine, α-methyl-L-4-Fluorophenylalanine, α-methyl-D-4-fluorophenylalanine, 3-amino-2,2-difluoro-propionic acid, O-sulfo-L-tyrosine sodium salt, L-2-furylalanine, 1-aminocyclopropane-1-carboxylic acid, 3,5-dinitro-L-tyrosine, pentafluoro-L-phenylalanine, 3,5-difluoro-L-phenylalanine, 3-fluoro-L-phenylalanine, N-cyclopentylglycine, 1-(amino)cyclohexanecarboxylic acid, N-methylalanine, 4-amino-tetrahydropyran-4-carboxylic acid, 4-amino-1,1-dioxothiane-4-carboxylic acid, 4-amino-1-methyl-4-piperidinecarboxylic acid, 2-amino-N-(2,4-dimethoxybenzyl)acetamido)acetic acid, or N-alkylated derivatives. In some cases, L- or D-configurations of NTMaa structures were alkylated to prevent racemization.

As a result of this screen, multiple combinations of modified cleavase enzymes that specifically cleave a single N-terminal amino acid of a polypeptide modified by a particular bipartite NTM can be selected. The cleavage of the labeled polypeptide by the selected modified cleavase enzyme can be confirmed by LC-MS as described in Example 4.

Figure 13B:
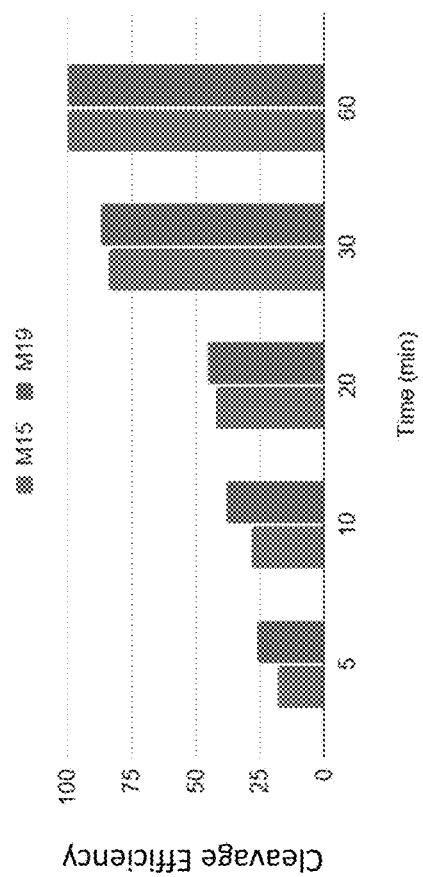
FIG. 13A-B. illustrate exemplary time course of cleavage reactions of two labeled peptides (M15-LAAR and M19-LAAR, cleavage efficiencies are shown in left and right columns, respectively, for each time point) by two modified dipeptidyl cleavases selected using M15 NTM (FIG. 13A) and M19 NTM (FIG. 13B).
Figure 13A:
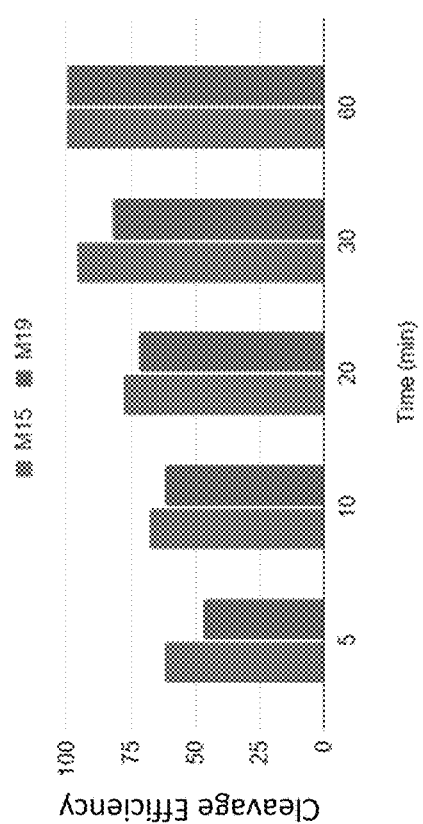
Figure 14:
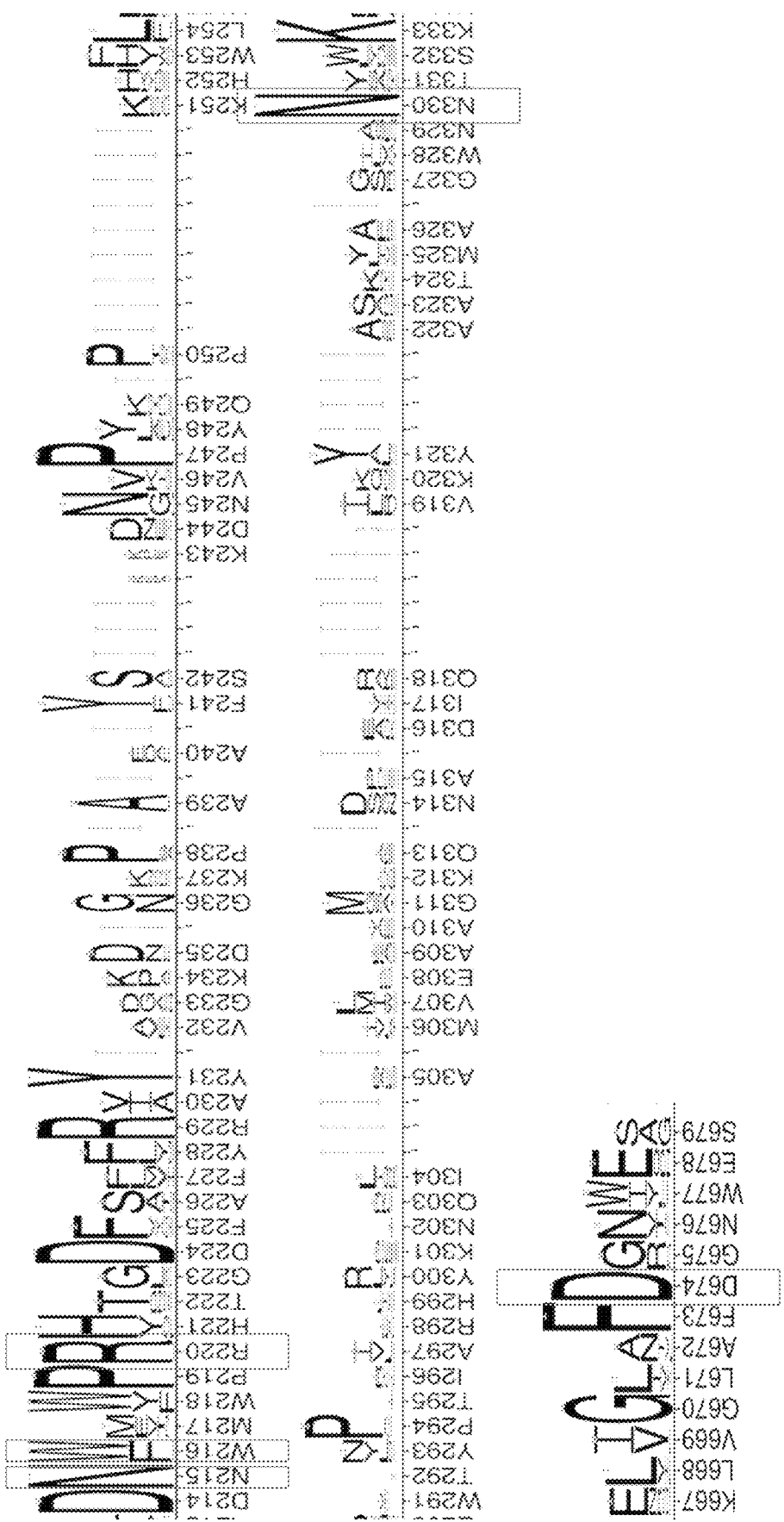
FIG. 14 depicts results from a WebLogo analysis of sequence conservation of DAP BII homologs. The height of each stack indicates the sequence conservation at that position (measured in bits), and the height of symbols within the stack reflects the relative frequency of the corresponding amino acid at the indicated position (in reference to positions of SEQ ID NO: 20). Conservation of N215, W216(F), R220, N330, D674 positions is highlighted.
Figure 15:
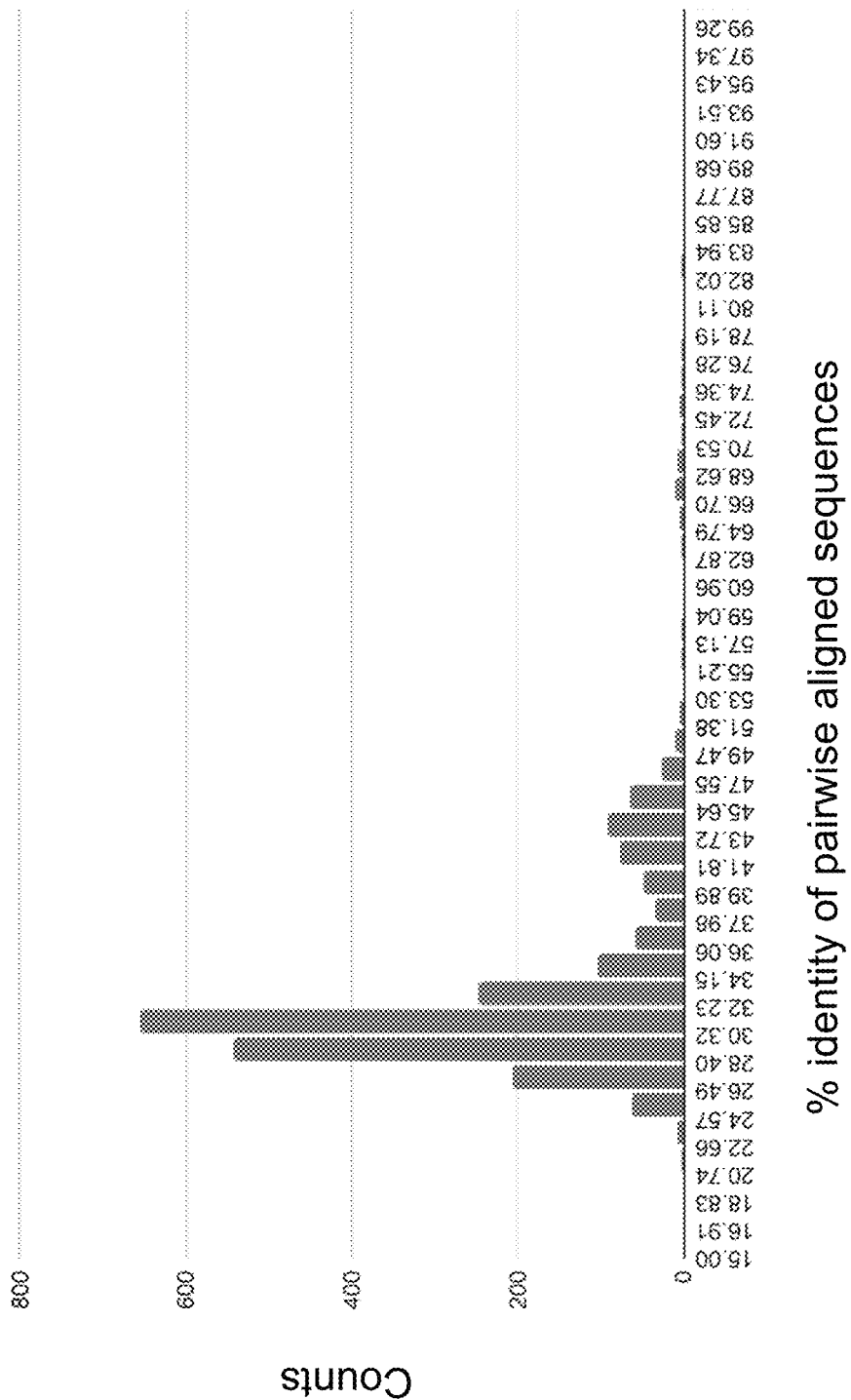
FIG. 15. illustrates similarity distribution relative to DapBII (*Pseudoxanthomonas mexicana*) of 2125 sequences clustered at 80% sequence identity.

Next, it can be shown that specific changes in the conserved residues in the substrate binding site of the cleavase can determine specificity to the particular NTMs. As described above, the selected modified cleavase M15-L_Z001 has the following amino acid substitutions in the amine binding site in comparison to the unmodified dipeptidyl aminopeptidase scaffold: N214M, W215G, R219T, N329R, D673A (the indicated residue numbers correspond to positions of SEQ ID NO: 43). These changes drive specificity of the M15-L_Z001 cleavase towards M15-L-labeled polypeptides. Then, using S46 DPP from *Thermomonas hydrothermalis* as a starting scaffold, combinatorial libraries were created (such as N214X, W215X, R219X, N329X, D673X; the indicated residue numbers correspond to positions of SEQ ID NO: 43), and genetic selection was performed using M19-L-AR peptide as described in the previous examples. Several modified cleavases have been selected that are specific towards a different NTM (M19). The selected clones share a mutation in the amine binding site: N329P, which is different from the N329R substitution present in the M15-L_Z001 cleavase. This substitution was also observed in other cleavase clones selected using different M19-UAA-labeled polypeptides, where UAA designates unnatural amino acids. Thus, N329P mutation drives specificity of modified cleavases towards M19-labeled polypeptides. As an example, the M19_053 cleavase clone selected for the M19-L-labeled peptides shows almost the same substitutions in the amine binding site as in the M15-L_Z001 cleavase, except for N329P: N214M, W215G, R219T, N329P, D673A (the indicated residue numbers correspond to positions of SEQ ID NO: 43). The cleavage efficiencies of the selected clones M19_053 and M15-L_Z001 were compared on a model polypeptide (polypeptide sequence: LAAR, SEQ ID NO: 50) labeled with either M15 or M19 labels (FIG. 13). The cleavage results were monitored in 5, 10, 20, 30 and 60 minutes, and showed that the newly selected cleavase clone M19_053 provided better specificity towards the M19-labeled polypeptide, whereas the M15-L_Z001 cleavase provided better specificity towards the M15-labeled polypeptide.

Next, it can be shown that different dipeptidyl aminopeptidase scaffolds are evolved to have similar amino acid changes in the amine binding site to recognize a particular NTM. In addition to the above-described scaffold from *Thermomonas hydrothermalis*, showing N214M, W215G, R219T, N329R, D673A amino acid changes for the M15-A-labeled polypeptides (SEQ ID NO:61), two additional scaffolds were similarly and independently evolved to cleave the M15-A-labeled polypeptides, namely dipeptidyl aminopeptidase scaffolds Dap BIT from *Pseudoxanthomonas mexicana* (SEQ ID NO: 13) and DPP11 from *Porphyromonas gingivalis* (SEQ ID NO: 12). All three unmodified scaffolds show conservation of the residues N214, W215, R219, N329, D673 in the amine binding site (the given residue numbers correspond to positions of SEQ ID NO: 43), although the sequence identity between Dap BIT and DPP11 scaffolds is about 32%, and the sequence identity between Dap BIT and the Thermomonas hydrothermalis scaffolds is about 74%. After selection on the M15-A-labeled polypeptides, the scaffold from *Thermomonas hydrothermalis* showed N214M, W215G, R219T, N329R, D673A amino acid changes (SEQ ID NO:61), whereas the Dap BII scaffold shows corresponding N214M, W215G, R219T, N329R, D673A changes (SEQ ID NO:60), and the DPP11 scaffold shows corresponding N214M, W215G, R219V, N329I, D673A changes (SEQ ID NO:59) (the indicated residue numbers correspond to positions of SEQ ID NO: 43). Thus, very similar amino acid changes can be selected in the amine binding sites of different dipeptidyl aminopeptidases to recognize a particular specific NTM.

Next, it can be shown that the same dipeptidyl aminopeptidase scaffold can be evolved to recognize and cleave a single terminal amino acid of a polypeptide labeled with different NTMs having various shapes. In addition to bipartite NTMs having an NTMaa part (see above), a relatively small, single part NTM (FIG. 11A, B, lower drawings) can also be used. Similar to described above, using S46 DPP from *Thermomonas hydrothermalis* as a starting scaffold, combinatorial libraries were created (such as N214X, W215X, R219X, N329X, D673X; the residue numbers correspond to positions of SEQ ID NO: 43), and genetic selection was performed using M19-AAAR peptide. Two types of Cleavases can be selected from the same scaffold: P1 cutters that cleave polypeptides after P1 residue, and P2 cutters that cleave polypeptides after P2 residue. P2 cutters are similar to enzymes described above, such as M15-L_Z001 cleavase, having a large substrate-binding pocket that can accommodate two amino acids and a label. P2 cutters selected for the M19 NTM comprise the following exemplary mutations of the conserved residues that form an amine binding site of the cleavase: (a) N214M, W215G, R219T, N329R, D673A (SEQ ID NO:61); (b) N214M, W215G, R219T, N329P, D673S (SEQ ID NO:62); (c) N214M, W215G, R219A, N329P, D673A (SEQ ID NO:63); (d) N214M, W215G, R219V, N329P, D673A (SEQ ID NO:64) (all the indicated residue numbers correspond to positions of SEQ ID NO: 43), sharing significant level of similarity with the M15-L_Z001 cleavase. In contrast, the selected exemplary P1 cutter comprises the following mutations of the conserved residues that form an amine binding site of the cleavase: N214T, W215M, R219K, N329Y (SEQ ID NO:65) (P1 cutter 1, the residue numbers correspond to positions of SEQ ID NO: 43). This mutation pattern differs dramatically from the mutations in the M15-L_Z001 cleavase. This allows for a different geometry of the substrate-binding pocket that can now accommodate a single amino acid and the M19 label. The cleavage reaction of the model peptide M19-AAAR (SEQ ID NO: 21) by the selected P1 cutter 1 was set up as follows: 300 mcM M19-AAAR, 0.1 mcM P1 cutter 1 enzyme in 5 mM sodium phosphate buffer, pH=8, 52° C. 1 hour incubation time. Reaction mixtures were then analyzed via LC-MS for product identification; the observed mass of the cleaved product was 230.2 Da, which matched well with the expected mass for the M19-A (M+H) part (231.2 Da).

Example 11. Diversity of the DPP Family of Dipeptidyl Cleavases

In order to better understand the diversity of potential dipeptidyl cleavase scaffolds, enzymes from the DPP family (based on MEROPS classification) were downloaded, and aligned using a WebLogo analysis of sequence conservation of DAP BII homologs (Crooks G E, et al., WebLogo: A sequence logo generator, Genome Research, 14:1188-1190, (2004)). These sequences (7903 sequences were assessed) were first clustered at 80% identity to reduce complexity, and cluster centers were used for alignment and WebLogo analysis. All the sequences analyzed after clustering were no more than 80% close to each other. 2125 sequences were aligned and show conservation of N215, W(F)216, R220, N330, and D674 residues in reference to the wildtype DAP BII sequence set forth in SEQ ID NO: 20 (FIG. 14). The height of each stack indicates the sequence conservation at that position (measured in bits), and the height of symbols within the stack reflects the relative frequency of the corresponding amino acid at the indicated position (amino acid numbers correspond to positions of SEQ ID NO: 20). Then, a pairwise identity distribution relative to DapBII (*Pseudoxanthomonas mexicana*) was calculated and shown in FIG. 15. FIG. 15 depicts results from a WebLogo analysis of sequence conservation of different DAP BII homologs selected to have no more than 80% sequence identity. The most frequent percent identity for DapBII homologs among the family members was found to be from 27 to 36% identity.

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE TABLE

| SEQ ID NO | sequence (5'-3') |
|---|---|
| 1 | HEXXGH |
| 2 | EEXRAE/D |
| 3 | AATGATACGGCGACCACCGA |
| 4 | CAAGCAGAAGACGGCATACGAGAT |

| SEQ ID NO | sequence (5'-3') |
|---|---|
| 5 | MADTQYILPNDIGVSSLDCREAFRLLSPTERLYAYHLSRAAWYGGLAVLLQTSPEAPYIYALLSRLF RAQDPDQLRQHALAEGLTEEEYQAFLVYAAGVYSNMGNYKSFGDTKFVPNLPKEKLERVILGSEA AQQHPEEVRGLWQTCGELMFSLEPRLRHLGLGKEGITTYFSGNCTMEDAKLAQDFLDSQNLSAYNT RLFKEVDGEGKPYYEVRLASVLGSEPSLDSEVTSKLKSYEFRGSPFQVTRGDYAPILQKVVEQLEKA KAYAANSHQGQMLAQYIESFTQGSIEAHKRGSRFWIQDKGPIVESYIGFIESYRDPFGSRGEFEGFVA VVNKAMSAKFERLVASAEQLLKELPWPPTFEKDKFLTPDFTSLDVLTFAGSGIPAGINIPNYDDLRQT EGFKNVSLGNVLAVAYATQREKLTFLEEDDKDLYILWKGPSFDVQVGLHELLGHGSGKLFVQDEK GAFNFDQETVINPETGEQIQSWYRSGETWDSKFSTIASSYEECRAESVGLYLCLHPQVLEIFGFEGAD AEDVIYVNWLNMVRAGLLALEFYTPEAFNWRQAHMQARFVILRVLLEAGEGLVTITPTTGSDGRPD ARVRLDRSKIRSVGKPALERFLRRLQVLKSTGDVAGGRALYEGYATVTDAPPECFLTLRDTVLLRK ESRKLIVQPNTRLEGSDVQLLEYEASAAGLIRSFSERFPEDGPELEEILTQLATADARFWKGPSEAPSG QA |
| 6 | MSHFFADHDAPLSMLSVKTEYFPQLTDKEQKYAHFMSKASHAGSRVVMRQVSHESEPIFDLILAIHS KLNGKYPEDDITQKQQTGLYLEYVSQFLSNLGNFKSFGDTKFIPRCEVKFFKQLLELAKINPCSSPLT LSPVDVNHEFTSHHLFSTINELIDIGIYHVEEKAALLGFPSQGYTSAYYLGLPVTPEDMALLKEQLFA ELAILPENTRINKVGENSFQIWVASENVKNQITETYPSGQITLSNAVTKVEFIFGDHSREMRLVASYL KEAQKFAANDTQKAMLQEYINHFVTGSSQAHKEAQKLWVKDISPVIETNIGFIETYREPSGIIGEFES LVAIQNKERTAKFSSVNNAEEFISLLPWSKDYEKPIFNPPDFTSLEVLTFTGSGIPAGINIPNYDDVRLK IGFKNVSLGNILSAAAKSSSKHPPSFISQEDRPIFEKYQSDSFEVQVGIHELLGHGSGKLLTEFTDGFNF DKENPPLGLDGKPVSTYYKVGETWGSKFGQLAGPFEECRAEVIAMFLLTNKKILDIFGFHDVESQDK VIYAGYLQMARAGLLALEYWNPKTGKWGQPHMQARFSIMKTFMKHSTDKNFLKLEMNSTNDDFA IKLDKSLIKTAGHECVKDYLKHLHVYKCSGDVEQGSKYFIDRSTVTPDLASLRDIVLSKRLPRRQFIQ SNSYIDDNNKVTLKEYDETPQGMLQSFLDREL |
| 7 | MAVTATILASCGGAKTTTAEADKFDYTVEQFADLQILRYKVPEFETLTLKQKELVYYLTQAALEGR DILFDQNGKYNLRIRRMLEAVYTNYKGDKSAPDFKNMEVYLKRVWFSNGIHHHYGMEKFVPGFSQ DFLKQAVLGTDAQLLPLSEGQTAEQLCDELFPVMFDPAILAKRVNQADGEDLVLTSACNYYDGVT QQEAESFYGAMKDPKDETPVSYGLNSRLVKEDGKQEKVWKVGGLYTQAIEKIVYWLKKAETVAE NDAQKAVISKLIQFYETGSLKDFDEYAILWVKDLDSRIDFVNGFTESYGDPLGVKASWESLVNFKDL DATHRTEIISSNAQWFEDHSPVDKSFKKEKVKGVSAKVITAAILAGDLYPATAIGINLPNANWIRAH HGSKSVTIGNITDAYNKAAHGNGFNEEFVCNDEERQRIDQYGDLTGELHTDLHECLGHGSGKLLPG VDPDALKAYGSTIEEARADLFGLYYVADPKLVELKLVPDAEAYKAEYYTFLMNGLMTQLVRIEPG NNIEEAHMRNRQLIARWVFEKGAPDKVVEMVKKDGKTYVVVNDYEKVRQLFGELLAEIQRIKSTG DFEGARTLVENYAVKVDPALHAEVLARYKKLNLAPYKGFINPVYELVTDKDGNITDVTVSYNEDY VEQMLRYSKDYSPLPSVNN |
| 8 | MKRILLVLLTLVFLGAIACQKKEENKTEMVKLKRMIAQFAPTEIKYDHSLLDERKQKVVENLYRAA KIMDEIFLDQVYSKNFEIREQLRASSDPLDQLRLEYFTIMFGPFDRLNHDKPFIGNTPKPKGANFYPPD MTREEFENWLKAHPEDEAAFTSEFTVIRRQDGKLVAIPYSEYYKEYLTRAADYLKKAAEFADNPSL KKYLQLRAEAFLNNDYYESDLAWMDLNDHTIEVVIGPYEVYEDKLFNYKAAFEAFITLRDPVESAK LKKFVGYLDEMEKNLPIPDAYKNFNRGSESPMVVVQEVFSAGDTKAGVQTLAFNLPNDERVREAK GSKKVMLKNIHEAKFDKLLKPIAEKVLFAEQLPLVTFEGFFNHTLMHEISHGLGPGKIVLNGRQTEV KKELKETYSSIEECKADVLGMYNNLFMIEKGVYPPEFEKQIYVTFLAGIFRTIRFGINEAHGAGNAVI FNYLLEKGAYQFDPAAHRVKVNFEKIKDGVRDLANKVLTIQAQGDYMAAKNLLETYAVESEPIMI MRARLQELPVDIKPIFQIEKELGNSN |
| 9 | DRVYIHPF |
| 10 | LTPEQLITAPRRSEAIPDPSGKVAVFSTSQYSFETHKRTSWWSLLDLKTGQTKVLTNDSSVSEIVWLS DDSILYVNSTNADIPGGVELWVTQASSFAKGYKAASLPASFSGLKTAKTKSGDIRFVAYGQSYPNGT AYNEELATAPLSSARIYDSIYVRHWDYWLSTTFNAVFSGTLKKGHGKNGYSLDGELKNLVSPVKNA ESPYPPFGGASDYDLSPDGKWVAFKSKAPELPKANFTTSYIYLVPHDASETARPINGPDSPGTPKGIK GDSSSPVFSPNGDKLAYFQMRDETYESDRRVLYVYSLGSKKTIPSVAGDWDRSPDSVKWTPDGKTL IVGSEDLGRTRLFSLPANAKDDYKPKNFTDGGSASAYYFLPDSSLLVTGSALWTNWNVYTAKPEKG VIKKIASANEIDPELKGLGPSDISEFYFQGNFTDIHAWVIYPENFDKSKKYPLIFFIHGGPQGNWADG WSTRWNPKAWADQGYVVVAPNPTGSTGFGQALTDAIQNNWGGAPYDDLVKCWEYVHENLDYV DTDHGVAAGASYGGFMINWIQGSPLGRKFKALVSHDGTFVADAKVSTEELWFMQREFNGTFWDA RDNYRRWDPSAPERILQFATPMLVIHSDKDYRLPVAEGLSLFNVLQERGVPSRFLNFPDENHWVVN PENSLVWHQQALGWINKYSGVEKSNPNAVSLEDTVVPVVNYN |
| 11 | ADKGMWLLNELNQENLDRMRELGFTLPLDSLYSFDKPSIANAVVIFGGGCTGITVSDQGLIFTNHHC GYGAIQSQSTVDHDYLRDGFVSRTMGEELPIPGLSVKYLRKIVKVTDKVEGQLKGITDEMERLRKA QEVCQELAKKENADENQLCIVEPFYSNNEYFLIVYDVFKDVRMVFAPPSSVGKFGGDTDNWMWPR HTGDPSVFRVYAGADNRPAEYSKDNKPYKPVYFAAVSMQGYKADDYAMTIGFPGSTDRYLTSWG VEDRIENENNPRIEVRGIKQGIWKEAMSADQATRIKYASKYAQSANYWKNSIGMNRGLARLDVIGR KRAEERAFADWIRKNGKSAVYGDVLSSLEKAYKEGAKANREMTYLSETLFGGTEVVRFAQFANAL ATNPDAHAGILKSLDDKYKDYLPSLDRKVLPAMLDIVRRRIPADKLPDIFKNVIDKKFKGDTKKYA DFVFDKSVVPYSDKFHAMLKSMDKEKFAKAIEKDPAVELSKSVIAAARAIQADAMANAYAIEKGK RLFFAGLREMYPGRALPSDANFTMRMSYGSIKGYEPQDGAWYNYHTTGKGVLEKQDPKSDEFAVQ ENILDLFRTKNYGRYAENGQLHIAFLSNNDITGGNSGSPVFDKNGRLIGLAFDGNWEAMSGDIEFEP DLQRTISVDIRYVLFMIDKWGQCPRLIQELKLI |

SEQUENCE TABLE

| SEQ ID NO | sequence (5'-3') |
|---|---|
| 12 | DEGMWLMQQLGRKYAQMKERGLKMKEYDLYNPNGTSLKDAVVLFDGGCTGEVVSDRGLVLTNH HCGYDMIQAHSTLEHNYLENGFWAMREADELPNKDISVVFIDKIEDVTDYVKKELKAIKDPNSMDY LSPKYLQKLADKKAGKNFSAKNPGLSVEIKAFYGGNLYLMFTKKTYTDVRLVGAPPSSIGKFGADT DNWIWPRHTGDFSIFRIYADKNGNPAPYSEDNVPLKPKRFFNISLGGVQENDYAMIMGFPGTTHRYF TASEVDEWKSIDNDIRIRMRDIRQGVMLREMLADPQIKIMYSAKYAASQNAYKRAIGANWAIKTRG LRQNKQAMQDRLIAWGAKQGTPRYEEAVHEIDATVAKRADLRRRYWMIEEGIIRGIEFARSPIPTED ETKALQGNDASARKEAIDKIRTRYSKFANKDYSAEVDKKVAVAMLTEYLKEIPYENLPLHLRLVKD RFAGDVQAYVDDIFARSVFGSEAQFDAFAAVPSVEKLAEDPMVLFASSVFDEYRKLYNELRPYDDP ILRAQRTYIAGLLEMDGDQDQFPDANLTLRFTYGQVKGYSPRDNVYYGHQTTLDGVMEKEDPDN WEFVVDPKLKAVYERKDFGRYADRSGRMPVAFCATTHTTGGNSGSPVMNANGELIGLNFDRNWE GVGGDIQYLADYQRSIIVDIRYVLLVIDKVGGCQRLLDEMNIVP |
| 13 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDNWMWPRH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNNTSKNYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF DGNWESVSSNWVFDPKMTRMIAVDGRYLRWIMQEVYPAPQLLKEMNVGK |
| 14 | DGGMWLMQQINGQVARMKSLGMQLEAADIYNPNGSSLKDAVVMFDGGCTGVLVSNQGLLLTNH HCGYDQIQKHSSVQHNYLKDGFWSYSLAEELVNPGLEVEIVDEITDVTAAVKKELERIKKPSGLEFL SPRYLSSLAPEIVGKKAASRPGYRYEIKAFYGGNRYYMFTKKVFRDVRLVAAPPSSIGKFGSDTDNW AWPRHTGDFSIFRLYADKNGNPAEYSKDNVPYRPKRWVKVNAQGVKEGDFALIMGYPGTTYKFFT ADEVTEWSEIDNNIRIEMRGILQDVMLREMLADPKINIMYAAKYASSQNGYKRAQGANWAIRRRSL REIKLAQQQEVLAWAKQKGIATTEEAVRAISKAIEGRQDLRMRQRYLLEGILMGIEMSNAPAADSDI ADHWDDPARREAGLQSIRKQFEAFFNKDYSPEVEKDQLAIALLTRYAERIPAEKQPISIREGIAEYGS AKAYVEMIFDKSIYASRERFEEFMKNPDRDRLLRDPMSRFAASVAYEHQKLAKEVAAFDAPLAAA QRSYVASVLDMKGQPNLAPDANLTLRFTYGEIKGYQPRDVVTYGAKSTLEGVMEKEDPNNWEYV VDPKLKALYEAKNYGRYAN SDGSMPVNFCATTHTTGGNSGSPVMNARGELIGLNFDRNWEGVGG DIEYLPNYQRSIILDIRYLLFIIDKFAGCQRLIDEIQPQF |
| 15 | MADTQYILPNDIGVSSLDCREAFRLLSPTERLYAHHLSRAAWYGGLAVLLQTSPEAPYIYALLSRLF RAQDPDQLRQHALAEGLTEEEYQAFLVYAAGVYSNMGNYKSFGDTKFVPNLPKEKLERVILGSKA AQQHPEEVRSLWQTCGELMFSLEPRLRHLGLGKEGVTTYFSGDCAMEDAKLAQDFLDSQNLSAYN TRLFKVVGQEGKYHYEVRLASVLNTEPALDSELTSKLKSYEFQGNHFQVTRGDYAPILQKVVEHLE KAKAYAANSHQEQMLAQYVESFTQGSIEAHKRGSRFWIQDKGPIVESYIGFIESYRDPFGSRGEFEGF VAMVNKDMSAKFERLVASAEQLLKELPWPPAFEKDKFLTPDFTSLDVLTFAGSGIPAGINIPNYDDL RQTEGFKNVSLGNVLAVAYATKREKLTFMEEEDKDLYIRWKGPSFDVQVGLHELLGHGSGKLFVQ DEKGAFNFDQETVINPETGEQIQSWYRSGETWDSKFSTIASSYEECRAESVGLYLCLNPQVLQIFGFE GTDAEDVIYVNWLNMVRAGLLALEFYTPETANWRQAHMQARFVILRVLLEAGEGLVTVTPTTGSD GRPDARVHLDRSKIRSVGKPALERFLRRLQVLKSTGDVVAGRALYEGYAAVTDAPPECFLTLRDTV LLRKESRKLIVQPNTRLEGSEVQLVEYEASAAGLIRSFCERFPEDGPELEEVLTQLATADAQFWRDQ VQEAPSGQA |
| 16 | TNTGEHLTPELFMTLSRVSEMALSPDGKTAVYAVSFPDVKTNKATRELFTVNLDGSGRKQITDTESN EYAPAWMADGKRIAFMSNEGGSMQLWVMNADGTERRQLSNIEGGITGFLFSPDEKQVLFTKDIKF GKRTKDIYPDLDKATGRIITDLMYKHWDEWVETIPHPFIANATDGMITTGKDIMEGEPYEAPMKPW SGIEDFSWSPDGQNIAYASRKKTGMAYSLSTNSDIYIYNLTSGRTHNISEGMMGYDTYPKFSPDGKSI AWISMERDGYESDLKRLFVADLATGKRTHVNPTFDYNVDMIQWAPDSKGIYFLACKEAETNLWEI TLKTGKIRQITQGQHDYADFSVRNDVMLAKRHSFELPDDLYRVNPKNGAAQAVTAENKAILDRLTP IACEKRWMKTTDGGNMLTWVVLPPDFDKNKKYPAILYCQGGPQNTVSQFWSFRWNLRLMAEQGY IVIAPNRHGVPGFGQKWNEQISGDYGGQNMRDYLTAVDEMKKEPYVDGDRIGAVGASYGGFSVY WLAGHHDKRFAAFIAHAGIFNLEMQYATTEEMWFANWDIGGPFWEKDNVVAQRTYATSPHKYVQ NWDTPILMIHGELDFRILASQAMAAFDAAQLRGVPSEMLIYPDENHWVLQPQNALLFHRTFFGWLD RWLKK |
| 17 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGVASLGMWPSH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMWGWNNTSKKYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF AGNWESVSSNWVFDPKMTRMIAVDGRYLRWIMQEVYPAPQLLKEMNVGK |

SEQUENCE TABLE

| SEQ ID NO | sequence (5'-3') |
|---|---|
| 18 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDMGMWPTH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNRTSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>AGNWESVSSNWVFDPKMTRMIAVDGRYLRWIMQEVYPAPQLLKEMNVGK |
| 19 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDMGMWPVH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNRTSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>AGNWESVSSNWVFDPKMTRMIAVDGRYLRWIMQEVYPAPQLLKEMNVGK |
| 20 | MRPNLLAAAIAVPLSLLAAQIQAGAGEGMWVPQQLPEIAGPLKKAGLKLSPQQISDLTGDPMGAVVA<br>LGGCTASFVSPNGLVVTNHHCAYGAIQLNSTAENNLIKNGFNAPTTADEVSAGPNARVFVLDEITDV<br>TKDAKAAIAAAGDDALARTKALEAFEKKLIADCEAEAGFRCRLYSFSGGNTYRLFKNLEIKDVRLA<br>YAPPGSVGKFGGDIDNWMWPRHTGDFAFYRAYVGKDGKPAAFSKDNVPYQPKHWLKFADQPLG<br>AGDFVMVAGYPGSTNRYALAAEFDNTAQWTYPTIARHYKNQIAMVEAAGKQNADIQVKYAATM<br>AGWNNTSKNYDGQLEGFKRIDAAGQKLREEAAVLGWLKGQGAKGQPALDAHAKLLDLLEQSKAT<br>RDRDLTLALFNNTAMLGSATQLYRLSIEREKPNAERESGYQERDLPAIEGGLKQLERRYVAAMDRQ<br>LQEYWLNEYIKLPADQRVAAVDAWLGGNDAAAVKRALDRLAGTKLGSTEERLKWFAADRKAFE<br>ASNDPAIQYAVAVMPTLLKLEQERKTRAGENLAARPVYLQALADYKKSQGEFVYPDANLSLRITFG<br>NVMGYAPKDGMEYTPFTTLEGVVAKETGQDPFDSPKALLDAVAAKRYGGLEDKRIGSVPVNYLSD<br>LDITGGNSGSPVLDAHGKLVGLAFDGNWESVSSNWVFDPKMTRMIAVDGRYLRWIMQEVYPAPQL<br>LKEMNVGK |
| 21 | AAAR |
| 22 | AAGVAMPGAEDDVVGSGSK(N$_3$) |
| 23 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDMGMWPTH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNRKSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>AGNWESVSSNWVFDPKMTRMIAVDGRYLRWIMQEVYPAPQLLKEMNVGK |
| 24 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDMGMWPTH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNRTSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGEKLAVRPVYLQALADYKKSQGEFVYPDANLSLRITFGNVMGYAPKDGMEYTPFTTLEGVV<br>AKETGQDPFDSPKALLDAVAVKRYGGLEDKRIGSVPVNYLSDLDITGGNSGSPVLDAHGKLVGLAF<br>AGNWESVSSNWVFDPKMTRMIAVDGRYLRWIMQEVYPAPQLLNEMNVGK |
| 25 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALTRTKAL<br>EAFEKKLIADCEAEAGFRCRLYSFSGGNTYRLFKNLEIKDVRLAYAPPGSVGKFGGDIDMGMWPTH<br>TGDFAFYRAYVGKDGKPAAFSKDNVPYQPKHWLKFADQPLVAGDFVMVAGYPGSTNRYALAAEF<br>DNTAQWTYPTIARHYKNQIAMVEAAGKQNADIQVKYAATMAGWNRTSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER |

SEQUENCE TABLE

| SEQ ID NO | sequence (5'-3') |
|---|---|
| | KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF AGNWESVSSNWVFDPKMTRMIAVDGRYLRWIMQEVYPAPQLLKEMNVGK |
| 26 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDMGMWPTH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNRTSKNYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGELVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF AGNWESVSSNWVFDPKMTRMIAVDGRYLRWIMQEVYPAPQLLKEMNVGK |
| 27 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDMGMWPTH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNRTSKNYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF AVNWESVSSNWVFDPIMTRMIAVDGRYLRWIMQEVYPAPQLLKEMNVGK |
| 28 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDMGMWPTH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNRTSKNYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF AVNWESVSSNWVFDPKMTRMIAVDGRYLRWIMQEVYPAPQLLKEMNVGK |
| 29 | ARAA |
| 30 | IHAGYAW |
| 31 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDCLMWPKH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNRTSKDYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF DYNWEGGS SNWVFDPKMTRMIAVDGRYLRWIMQEVYPAPQLLKEMNVGK |
| 32 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDCLMWPRH TGDFAFYRAYVGKDGKPAAFSKDNVPYQPKHWLKFADQPLGAGDFVMVAGYPGSTNRYALAAEF DNTAQWTYPTIARHYKNQIAMVEAAGKQNADIQVKYAATMAGWNRTSKDYDGQLEGFKRIDAA GQKLREEAAVLGWLKGQGAKGQPALDAHAKLLDLLEQSKATRDRDLTLALFNNTAMLGSATQLY RLSIEREKPNAERESGYQERDLPAIEGGLKQLERRYVAAMDRQLQEYWLNEYIKLPADQRVAAVDA WLGGNDAAAVKRALDRLAGTKLGSTEERLKWFAADRKAFEASNDPAIQYAVAVMPTLLKLEQER KTRAGENLAARPVYLQALADYKKSQGEFVYPDANLSLRITFGNVMGYAPKDGMEYTPFTTLEGVV AKETGQDPFDSPKALLDAVAAKRYGGLEDKRIGSVPVNYLSDLDITGGNSGSPVLDAHGKLVGLAF DYNWEGGSSNWVFDPKMTRMIAVDGRYLRWIMQEVYPAPQLLKEMNVGK |
| 33 | GEGMWVPQQLPEIAGPLKKAGLKLSPQQISDLTGDPMGAVVALGGCTASFVSPNGLVVTNHHCAY GAIQLNSTAENNLIKNGFNAPTTADEVSAGPNARVFVLDEITDVTKDAKAAIAAAGDDALARTKAL EAFEKKLIADCEAEAGFRCRLYSFSGGNTYRLFKNLEIKDVRLAYAPPGSVGKFGGDIDFFMWPRHT GDFAFYRAYVGKDGKPAAFSKDNVPYQPKHWLKFADQPLGAGDFVMVAGYPGSTNRYALAAEFD NTAQWTYPTIARHYKNQIAMVEAAGKQNADIQVKYAATMAGWNRTSKGYDGQLEGFKRIDAAG QKLREEAAVLGWLKGQGAKGQPALDAHAKLLDLLEQSKATRDRDLTLALFNNTAMLGSATQLYR |

| SEQ ID NO | sequence (5'-3') |
|---|---|
| | LSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>DHNWESESSNWVFDPKMTRMIAVDGRYLRWIMQEVYPAPQLLKEMNVGK |
| 34 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDRLMWPRH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNSTSKLYDGQLEGFKRIDAAG<br>QKLREEAAVLGWLKGQGAKGQPALDAHAKLLDLLEQSKATRDRDLTLALFNNTAMLGSATQLYR<br>LSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>DTNWETSSSNWVFDPKMTRMIAVDGRYLRWIMQEVYPAPQLLKEMNVGK |
| 35 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDSWMPHH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNATSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>GGNWESVSSNWVFDPKMTRMIAVDGRYLRWIMQEVYPAPQLLKEMNVGK |
| 36 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDTWMWPHH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNATSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>GGNWESVSSNWVFDPKMTRMIAVDGRYLRWIMQEVYPAPQLLKEMNVGK |
| 37 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDMWMWPH<br>HTGDFAFYRAYVGKDGKPAAFSKDNVPYQPKHWLKFADQPLGAGDFVMVAGYPGSTNRYALAAE<br>FDNTAQWTYPTIARHYKNQIAMVEAAGKQNADIQVKYAATMAGWNATSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>GGNWESVSSNWVFDPKMTRMIAVDGRYLRWIMQEVYPAPQLLKEMNVGK |
| 38 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDVWMWPRH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNATSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER<br>KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>SGNWESVSSNWVFDPKMTRMIAVDGRYLRWIMQEVYPAPQLLKEMNVGK |
| 39 | GEGMWVPQQLPEIAGPLKKAGLKLSPQQISDLTGDPMGAVVALGGCTASFVSPNGLVVTNHHCAY<br>GAIQLNSTAENNLIKNGFNAPTTADEVSAGPNARVFVLDEITDVTKDAKAAIAAAGDDALARTKAL<br>EAFEKKLIADCEAEAGFRCRLYSFSGGNTYRLFKNLEIKDVRLAYAPPGSVGKFGGDIDSWMPRH<br>TGDFAFYRAYVGKDGKPAAFSKDNVPYQPKHWLKFADQPLGAGDFVMVAGYPGSTNRYALAAEF<br>DNTAQWTYPTIARHYKNQIAMVEAAGKQNADIQVKYAATMAGWNTSKNYDGQLEGFKRIDAA<br>GQKLREEAAVLGWLKGQGAKGQPALDAHAKLLDLLEQSKATRDRDLTLALFNNTAMLGSATQLY<br>RLSIEREKPNAERESGYQERDLPAIEGGLKQLERRYVAAMDRQLQEYWLNEYIKLPADQRVAAVDA<br>WLGGNDAAAVKRALDRLAGTKLGSTEERLKWFAADRKAFEASNDPAIQYAVAVMPTLLKLEQER |

SEQUENCE TABLE

| SEQ ID NO | sequence (5'-3') |
|---|---|
| | KTRAGENLAARPVYLQALADYKKSQGEFVYPDANLSLRITFGNVMGYAPKDGMEYTPFTTLEGVV<br>AKETGQDPFDSPKALLDAVAAKRYGGLEDKRIGSVPVNYLSDLDITGGNSGSPVLDAHGKLVGLAF<br>SGNWESVSSNWVFDPKMTRMIAVDGRYLRWIMQEVYPAPQLLKEMNVGK |
| 40 | GRFSGIY |
| 41 | WTQIFGA |
| 42 | DEGMWVPQQLPEIAGALKKAGLKLDPKQLSDLTGDPMGAVVSLGGCTGSFVSPQGLVATNHHCA<br>YGAIQLNSTPEKNLIKDGFNAPTQADELSAGPNARIYVLEGITDVTAQAKAAMAAAGNDPVARANA<br>LEAFEKKITSDCEAEPGYRCRVYSFMGGITYRLFKNLEIKDVRLVYAPPSSVGKFGGDIDNWMWPR<br>HTGDFSFYRAYVGKDGKPAPYSKDNVPYRPKHWLKIADTPLGEGDFVMVAGYPGRTDRYALVAEF<br>ENTQNWLYPAISKAYKDQIALVEAAAKDNPEIAVKYAAALAGWNNTSKNFDGQLEGFKRNDVLAI<br>KRREEAAVLEWLRARGKAGTPALEAHAALVKLVADTARTQERDLVLGSFNRTGIIGVAVNLYRLAI<br>ERQKPDAEREPGYQQRDLPVIEGSLKQMERRYVPAMDRQLRAYWLDRYVALPAAQHVAAVDAW<br>LGGSDKAAAEAALARLDQSRLGSLEERLKWFNADRAAFEASTDPAIQYAVAVMPTLLAMEQQAKT<br>RYGVALEARPRYLQAVVDYKKSKGQAVYPDANSTLRITYGHVKGYTGLNGKVYTPFTTLEEVAAK<br>ETGVEPFDNPKALLEAVAAKRYAGLADARLGTVPVNFLADLDITGGNSGSPVLDANGRLVGLAFD<br>GTLESVASNWVFDPVLTRMISVDQRYMRWIMQEVMPAPQLLEELGVPPRQ |
| 43 | MHKTRLVAALAAALATLAPAAWADEGMWVPQQLPEIAGALKKAGLKLDPKQLSDLTGDPMGAV<br>VSLGGCTGSFVSPQGLVATNHHCAYGAIQLNSTPEKNLIKDGFNAPTQADELSAGPNARIYVLEGIT<br>DVTAQAKAAMAAAGNDPVARANALEAFEKKITSDCEAEPGYRCRVYSFMGGITYRLFKNLEIKDV<br>RLVYAPPSSVGKFGGDIDNWMWPRHTGDFSFYRAYVGKDGKPAPYSKDNVPYRPKHWLKIADTPL<br>GEGDFVMVAGYPGRTDRYALVAEFENTQNWLYPAISKAYKDQIALVEAAAKDNPEIAVKYAAALA<br>GWNNTSKNFDGQLEGFKRNDVLAIKRREEAAVLEWLRARGKAGTPALEAHAALVKLVADTARTQ<br>ERDLVLGSFNRTGIIGVAVNLYRLAIERQKPDAEREPGYQQRDLPVIEGSLKQMERRYVPAMDRQL<br>RAYWLDRYVALPAAQHVAAVDAWLGGSDKAAAEAALARLDQSRLGSLEERLKWFNADRAAFEA<br>STDPAIQYAVAVMPTLLAMEQQAKTRYGVALEARPRYLQAVVDYKKSKGQAVYPDANSTLRITYG<br>HVKGYTGLNGKVYTPFTTLEEVAAKETGVEPFDNPKALLEAVAAKRYAGLADARLGTVPVNFLAD<br>LDITGGNSGSPVLDANGRLVGLAFDGTLESVASNWVFDPVLTRMISVDQRYMRWIMQEVMPAPQL<br>LEELGVPPRQ |
| 44 | EEGMYPITEIHKLNLKKLGIELSADQIFSENEVSLSDAIVQIGGCTGSFISPEGLILTNHHCAFRAIQNIS<br>STENDYLTNGFVAHTLQEERPAKGYTVRITERVEDVSQRVLNAVKHIEDPIEREKAIEKITKQIVKEQ<br>EQKHPGKRAAVSEMFPGKTYYLFIYTYLKDVRLVYAPPRSIGEFGGEFDNWEWPRHTGDFTLMRA<br>YVAPDGSPSDYSEENVPYRPKSYLKVAAKGVEEGDRVFILGYPGRTYRHRTSAFLAFEYEFRMPFV<br>VDWYQWQIDLLTTLGKDDADRSLKFSSWIKGLANTEKNYRGKLQGIRRIGLLEQKKNEEEKIQVFI<br>AENNLKKYQHVLTEIKQIYHTYRQSAVREMLLSYFGRSPVLPAVARTLVLAAEERQKEDLERERAF<br>MDRNFKRTQTYTLLRLKNFDSQADQLILQELLKKAAALPEDQRISALRSIFKLDDAAETRQVISEAY<br>RKTRLSDPEFVKTCFAKTPDELKALNDPLINWMLALKEDYETLKNIRKERNGKLRRLRALWLEAKQ<br>AYLKTDFIPDANGTYRNITFGFIEGYAPADAVYKAPITTGRGILEKHTGKSPFDTPEKLLALLKAKQF<br>GPFVSKTVGTLPVGILYSCDTTGGNSGSPVLNARGQLVGLNFDRAFEATINDYAWNHQYSRSIGVDI<br>RYILFLLKYFSGAEHLLEEMGVQ |
| 45 | MKIRLFGVLLLFTFSLFAEEGMYPITEIHKLNLKKLGIELSADQIFSENEVSLSDAIVQIGGCTGSFISPE<br>GLILTNHHCAFRAIQNISSTENDYLTNGFVAHTLQEERPAKGYTVRITERVEDVSQRVLNAVKHIEDP<br>IEREKAIEKITKQIVKEQEQKHPGKRAAVSEMFPGKTYYLFIYTYLKDVRLVYAPPRSIGEFGGEFDN<br>WEWPRHTGDFTLMRAYVAPDGSPSDYSEENVPYRPKSYLKVAAKGVEEGDRVFILGYPGRTYRHR<br>TS APLAFEYEFRMPVVDWYQWQIDLLTTLGKDDADRSLKFSSWIKGLANTEKNYRGKLQGIRRIG<br>LLEQKKNEEEKIQVFIAENNLKKYQHVLTEIKQIYHTYRQSAVREMLLSYFGRSPVLPAVARTLVLA<br>AEEERQKEDLERERAFMDRNFKRTQTYTLLRLKNFDSQADQLILQELLKKAAALPEDQRISALRSIFK<br>LDDAAETRQVISEAYRKTRLSDPEFVKTCFAKTPDELKALNDPLINWMLALKEDYETLKNIRKERN<br>GKLRRLRALWLEAKQAYLKTDFIPDANGTYRNITFGFIEGYAPADAVYKAPITTGRGILEKHTGKSPF<br>DTPEKLLALLKAKQFGPFVSKTVGTLPVGILYSCDTTGGNSGSPVLNARGQLVGLNFDRAFEATIND<br>YAWNHQYSRSIGVDIRYILFLLKYFSGAEHLLEEMGVQ |
| 46 | QDSTQNLIPAPSLLTVPLQPDFRSDQFRGRWYVVGLAGNAVQKKTEGSFTMYSTIYELQENNSYNV<br>TSILVRDQDQGCRYWIRTFVPSSRAGQFTLGNMHRYPQVQSYNVQVATTDYNQFANIVFFRKTSEN<br>KQYFKITLYGRTKELSPELKERFTRFAKSLGLKDDNIIFSVPTDQCIDNSAWSHPQFEK |
| 47 | IHAGYAW |
| 48 | XGAEIAGDVAGGK |
| 49 | LMSHNARGAEDDVVRGGGGK |
| 50 | LAAR |
| 51 | AAAEIRGDVRGGK |
| 52 | AAEIRGDVRGGK |
| 53 | AAEIR |

SEQUENCE TABLE

| SEQ ID NO | sequence (5'-3') |
|---|---|
| 54 | GDVR |
| 55 | GVAMPGAEDDVVGSGSK(N$_3$) |
| 56 | AGVAMPGAEDDVVGSGSK(N$_3$) |
| 57 | LIHAGYAW |

What is claimed is:

1. A modified cleavase, which is configured to cleave a peptide bond between a terminally labeled amino acid residue and a penultimate terminal amino acid residue of a polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 13 and also comprising an asparagine residue at a position corresponding to position 191 of SEQ ID NO: 13, a tryptophan residue or phenylalanine residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, and an aspartate residue at a position corresponding to position 650 of SEQ ID NO: 13; and wherein the modified cleavase comprises two or more amino acid substitutions in the residues corresponding to positions N191, W/F192, R196, N306, and D650 of SEQ ID NO: 13.

2. A modified cleavase, which is configured to cleave a peptide bond between a terminally labeled amino acid residue and a penultimate terminal amino acid residue of a polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 42 and also comprising an asparagine residue at a position corresponding to position 191 of SEQ ID NO: 42, a tryptophan residue or phenylalanine residue at a position corresponding to position 192 of SEQ ID NO: 42, an arginine residue at a position corresponding to position 196 of SEQ ID NO: 42, an asparagine residue at a position corresponding to position 306 of SEQ ID NO: 42, an aspartate residue at a position corresponding to position 650 of SEQ ID NO: 42; and wherein the modified cleavase comprises two or more amino acid substitutions in the residues corresponding to positions N191, W/F192, R196, N306, and D650 of SEQ ID NO: 42.

3. The modified cleavase of claim 2, wherein the modified cleavase does not remove an unlabeled terminal dipeptide from the polypeptide.

4. The modified cleavase of claim 1, wherein the dipeptidyl aminopeptidase is a protein classified in MEROPS S46, or a functional homolog or fragment thereof.

5. The modified cleavase of claim 1, wherein the label comprises an amino acid and a chemical group.

6. The modified cleavase of claim 1, wherein the terminal amino acid is labeled with a chemical reagent selected from the group consisting of a phenyl isothiocyanate (PITC), a nitro-PITC, a sulfo-PITC, a phenyl isocyanate (PIC), a nitro-PIC, a sulfo-PIC, Cbz-Cl (benzyl chloroformate) or Cbz-OSu (benzyloxycarbonyl N-succinimide), a carboxyl-activated amino-blocked amino acid, an anhydride, a 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), 2-Pyridinecarboxaldehyde, 2-Formylphenylboronic acid, 2-Acetylphenylboronic acid, 1-Fluoro-2,4-dinitrobenzene, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N'-Bis(pivaloyl)-1H-pyrazole-1-carboxamidine, N,N'-Bis(benzyloxycarbonyl)-1H-pyrazole-1-carboxamidine, an acetylating reagent, a guanidinylation reagent, a thioacylation reagent, a thioacetylation reagent, a thiobenzylation reagent, an isatoic anhydride, an isonicotinic anhydride, an azaisatoic anhydride, a succinic anhydride, and a diheterocyclic methanimine reagent.

7. The modified cleavase of claim 1, wherein the modified cleavase comprises at least three amino acid substitutions in the residues corresponding to positions N191, W/F192, R196, N306, and D650 of SEQ ID NO: 13.

8. The modified cleavase of claim 1, wherein the modified cleavase comprises at least four amino acid substitutions in the residues corresponding to positions N191, W/F192, R196, N306, and D650 of SEQ ID NO: 13.

9. The modified cleavase of claim 1, wherein the length of the polypeptide is greater than 10 amino acids.

10. The modified cleavase of claim 1, wherein the modified cleavase comprises an amino acid sequence that is at least 30% identical to the amino acid sequence set forth in SEQ ID NO: 13, but does not comprise SEQ ID NO: 13.

11. The modified cleavase of claim 1, wherein the dipeptidyl aminopeptidase comprises an amino acid sequence that is at least 30% identical to the sequence set forth in SEQ ID NO: 13.

12. The modified cleavase of claim 11, wherein the two or more amino acid substitutions are selected from the group consisting of: N191C, N191F, N191L, N191M, N191R, N191S, N191T, N191V, W192F, W192G, W192L, R196H, R196K, R196S, R196T, R196V, N306A, N306G, N306R, N306S, D650A, D650G, and D650S.

13. A method of treating a polypeptide, comprising the steps of:
(a) contacting the polypeptide with a reagent for labeling a terminal amino acid of the polypeptide to produce a labeled polypeptide; and
(b) contacting the labeled polypeptide with a modified cleavase, which is configured to cleave a peptide bond between the terminally labeled amino acid residue and a penultimate terminal amino acid residue of the polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 13 and also comprising an asparagine residue at a position corresponding to position 191 of SEQ ID NO: 13, a tryptophan residue or phenylalanine residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, and an aspartate residue at a position corresponding to position 650 of SEQ ID NO: 13; and wherein the modified cleavase comprises two or more amino acid substitutions in the residues corresponding to positions N191, W/F192, R196, N306, and D650 of SEQ ID NO: 13.

14. The method of claim 13, wherein the modified cleavase comprises at least three amino acid substitutions in the residues corresponding to positions N191, W/F192, R196, N306, and D650 of SEQ ID NO: 13.

15. The method of claim 13, wherein the modified cleavase does not remove an unlabeled terminal dipeptide from the polypeptide.

16. The method of claim 13, wherein the modified cleavase comprises an amino acid sequence that exhibits at least 50% identity to the amino acid sequence of SEQ ID NO: 13.

17. The method of claim 13, wherein the modified cleavase comprises an amino acid sequence that is at least 30% identical to the amino acid sequence set forth in SEQ ID NO: 13, but does not comprise SEQ ID NO: 13.

18. The method of claim 13, wherein the dipeptidyl aminopeptidase comprises an amino acid sequence that is at least 30% identical to the sequence set forth in SEQ ID NO: 13.

19. The method of claim 18, wherein the two or more amino acid substitutions is or are selected from the group consisting of: N191C, N191F, N191L, N191M, N191R, N191S, N191T, N191V, W192F, W192G, W192L, R196H, R196K, R196S, R196T, R196V, N306A, N306G, N306R, N306S,D650A, D650G, and D650S.

20. The method of claim 18, further comprising contacting the polypeptide with a binding agent configured to bind to the labeled terminal amino acid of the polypeptide.

21. The method of claim 20, wherein the binding agent comprises a coding tag with identifying information regarding the binding agent.

22. The method of claim 20, wherein:
the contacting with the reagent for labeling the terminal amino acid is before the contacting with the binding agent; and
the contacting with the binding agent is before the contacting of the polypeptide with the modified cleavase.

23. The method of claim 22, wherein the steps of the contacting of the polypeptide with the binding agent, with the reagent for labeling the terminal amino acid, and with the modified cleavase, are repeated one or more times.

24. The method of claim 23, further comprising transferring the identifying information of the coding tag to a recording tag attached to the polypeptide, thereby generating an extended recording tag on the polypeptide, wherein transferring of the identifying information is performed:
after the binding of the polypeptide with the binding agent; and
before the contacting of the polypeptide with the modified cleavase.

25. The method of claim 13, wherein the polypeptide is directly or indirectly joined to a solid support.

26. A kit for treating a polypeptide, comprising:
a reagent for labeling a terminal amino acid residue of the polypeptide configured to produce a terminally labeled amino acid residue of the polypeptide; and
a modified cleavase, which is configured to cleave a peptide bond between the terminally labeled amino acid residue and a penultimate terminal amino acid residue of the polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 13 and also comprising an asparagine residue at a position corresponding to position 191 of SEQ ID NO: 13, a tryptophan residue or phenylalanine residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, and an aspartate residue at a position corresponding to position 650 of SEQ ID NO: 13; and wherein the modified cleavase comprises two or more amino acid substitutions in the residues corresponding to positions N191, W/F192, R196, N306, and D650 of SEQ ID NO: 13.

27. A set of modified cleavases, comprising at least two different modified cleavases, wherein:
(i) each of the modified cleavases from the set of modified cleavases is configured to cleave a peptide bond between a terminally labeled amino acid residue and a penultimate terminal amino acid residue of a polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 13 and also comprising an asparagine residue at a position corresponding to position 191 of SEQ ID NO: 13, a tryptophan residue or phenylalanine residue at a position corresponding to position 192 of SEQ ID NO: 13, an arginine residue at a position corresponding to position 196 of SEQ ID NO: 13, an asparagine residue at a position corresponding to position 306 of SEQ ID NO: 13, and an aspartate residue at a position corresponding to position 650 of SEQ ID NO: 13; and wherein the modified cleavase comprises two or more amino acid substitutions in the residues corresponding to positions N191, W/F192, R196, N306, and D650 of SEQ ID NO: 13; and
(ii) the modified cleavases from the set of modified cleavases have different specificities for terminally labeled amino acids, which the modified cleavases are configured to remove.

* * * * *

SEQUENCE LISTING

```
<160> NUMBER OF SEQ ID NOS: 65

<210> SEQ ID NO 1
<211> LENGTH: 6
<212> TYPE: PRT
<213> ORGANISM: Artificial Sequence
<220> FEATURE:
<223> OTHER INFORMATION: DPP3 motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

His Glu Xaa Xaa Gly His
1               5

<210> SEQ ID NO 2
<211> LENGTH: 6
<212> TYPE: PRT
<213> ORGANISM: Artificial Sequence
<220> FEATURE:
<223> OTHER INFORMATION: DPP3 motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be naturally occurring glutamic acid
      (Glu) or aspartic acid (Asp)

<400> SEQUENCE: 2

Glu Glu Xaa Arg Ala Xaa
1               5

<210> SEQ ID NO 3
<211> LENGTH: 20
<212> TYPE: DNA
<213> ORGANISM: Artificial Sequence
<220> FEATURE:
<223> OTHER INFORMATION: P5 primer

<400> SEQUENCE: 3
aatgatacgg cgaccaccga                                          20

<210> SEQ ID NO 4
<211> LENGTH: 24
<212> TYPE: DNA
<213> ORGANISM: Artificial Sequence
<220> FEATURE:
<223> OTHER INFORMATION: P7 primer
```

-continued

```
<400> SEQUENCE: 4
caagcagaag acggcatacg agat                                          24

<210> SEQ ID NO 5
<211> LENGTH: 737
<212> TYPE: PRT
<213> ORGANISM: Homo sapiens
<220> FEATURE:
<221> NAME/KEY: Dipeptidyl peptidase 3 (DPP3)
<222> LOCATION: (1)..(737)
<223> OTHER INFORMATION: UniProt Accession No. Q9NY33

<400> SEQUENCE: 5

Met Ala Asp Thr Gln Tyr Ile Leu Pro Asn Asp Ile Gly Val Ser Ser
1               5                   10                  15

Leu Asp Cys Arg Glu Ala Phe Arg Leu Leu Ser Pro Thr Glu Arg Leu
            20                  25                  30

Tyr Ala Tyr His Leu Ser Arg Ala Ala Trp Tyr Gly Gly Leu Ala Val
        35                  40                  45

Leu Leu Gln Thr Ser Pro Glu Ala Pro Tyr Ile Tyr Ala Leu Leu Ser
    50                  55                  60

Arg Leu Phe Arg Ala Gln Asp Pro Asp Gln Leu Arg Gln His Ala Leu
65                  70                  75                  80

Ala Glu Gly Leu Thr Glu Glu Tyr Gln Ala Phe Leu Val Tyr Ala
                85                  90                  95

Ala Gly Val Tyr Ser Asn Met Gly Asn Tyr Lys Ser Phe Gly Asp Thr
            100                 105                 110

Lys Phe Val Pro Asn Leu Pro Lys Glu Lys Leu Glu Arg Val Ile Leu
        115                 120                 125

Gly Ser Glu Ala Ala Gln His Pro Glu Glu Val Arg Gly Leu Trp
    130                 135                 140

Gln Thr Cys Gly Glu Leu Met Phe Ser Leu Glu Pro Arg Leu Arg His
145                 150                 155                 160

Leu Gly Leu Gly Lys Glu Gly Ile Thr Thr Tyr Phe Ser Gly Asn Cys
                165                 170                 175

Thr Met Glu Asp Ala Lys Leu Ala Gln Asp Phe Leu Asp Ser Gln Asn
            180                 185                 190

Leu Ser Ala Tyr Asn Thr Arg Leu Phe Lys Glu Val Asp Gly Glu Gly
        195                 200                 205

Lys Pro Tyr Tyr Glu Val Arg Leu Ala Ser Val Leu Gly Ser Glu Pro
    210                 215                 220

Ser Leu Asp Ser Glu Val Thr Ser Lys Leu Lys Ser Tyr Glu Phe Arg
225                 230                 235                 240

Gly Ser Pro Phe Gln Val Thr Arg Gly Asp Tyr Ala Pro Ile Leu Gln
                245                 250                 255

Lys Val Val Glu Gln Leu Glu Lys Ala Lys Tyr Ala Ala Asn Ser
            260                 265                 270

His Gln Gly Gln Met Leu Ala Gln Tyr Ile Glu Ser Phe Thr Gln Gly
        275                 280                 285

Ser Ile Glu Ala His Lys Arg Gly Ser Arg Phe Trp Ile Gln Asp Lys
    290                 295                 300

Gly Pro Ile Val Glu Ser Tyr Ile Gly Phe Ile Glu Ser Tyr Arg Asp
305                 310                 315                 320

Pro Phe Gly Ser Arg Gly Glu Phe Glu Gly Phe Val Ala Val Val Asn
                325                 330                 335
```

```
Lys Ala Met Ser Ala Lys Phe Glu Arg Leu Val Ala Ser Ala Glu Gln
            340                 345                 350

Leu Leu Lys Glu Leu Pro Trp Pro Thr Phe Glu Lys Asp Lys Phe
        355                 360                 365

Leu Thr Pro Asp Phe Thr Ser Leu Asp Val Leu Thr Phe Ala Gly Ser
    370                 375                 380

Gly Ile Pro Ala Gly Ile Asn Ile Pro Asn Tyr Asp Asp Leu Arg Gln
385                 390                 395                 400

Thr Glu Gly Phe Lys Asn Val Ser Leu Gly Asn Val Leu Ala Val Ala
                405                 410                 415

Tyr Ala Thr Gln Arg Glu Lys Leu Thr Phe Leu Glu Glu Asp Asp Lys
            420                 425                 430

Asp Leu Tyr Ile Leu Trp Lys Gly Pro Ser Phe Asp Val Gln Val Gly
        435                 440                 445

Leu His Glu Leu Leu Gly His Gly Ser Gly Lys Leu Phe Val Gln Asp
    450                 455                 460

Glu Lys Gly Ala Phe Asn Phe Asp Gln Glu Thr Val Ile Asn Pro Glu
465                 470                 475                 480

Thr Gly Glu Gln Ile Gln Ser Trp Tyr Arg Ser Gly Thr Trp Asp
                485                 490                 495

Ser Lys Phe Ser Thr Ile Ala Ser Ser Tyr Glu Glu Cys Arg Ala Glu
            500                 505                 510

Ser Val Gly Leu Tyr Leu Cys Leu His Pro Gln Val Leu Glu Ile Phe
        515                 520                 525

Gly Phe Glu Gly Ala Asp Ala Glu Asp Val Ile Tyr Val Asn Trp Leu
    530                 535                 540

Asn Met Val Arg Ala Gly Leu Leu Ala Leu Glu Phe Tyr Thr Pro Glu
545                 550                 555                 560

Ala Phe Asn Trp Arg Gln Ala His Met Gln Ala Arg Phe Val Ile Leu
                565                 570                 575

Arg Val Leu Leu Glu Ala Gly Glu Gly Leu Val Thr Ile Thr Pro Thr
            580                 585                 590

Thr Gly Ser Asp Gly Arg Pro Asp Ala Arg Val Arg Leu Asp Arg Ser
        595                 600                 605

Lys Ile Arg Ser Val Gly Lys Pro Ala Leu Glu Arg Phe Leu Arg Arg
    610                 615                 620

Leu Gln Val Leu Lys Ser Thr Gly Asp Val Ala Gly Arg Ala Leu
625                 630                 635                 640

Tyr Glu Gly Tyr Ala Thr Val Thr Asp Ala Pro Pro Glu Cys Phe Leu
                645                 650                 655

Thr Leu Arg Asp Thr Val Leu Leu Arg Lys Glu Ser Arg Lys Leu Ile
            660                 665                 670

Val Gln Pro Asn Thr Arg Leu Glu Gly Ser Asp Val Gln Leu Leu Glu
        675                 680                 685

Tyr Glu Ala Ser Ala Ala Gly Leu Ile Arg Ser Phe Ser Glu Arg Phe
    690                 695                 700

Pro Glu Asp Gly Pro Glu Leu Glu Glu Ile Leu Thr Gln Leu Ala Thr
705                 710                 715                 720

Ala Asp Ala Arg Phe Trp Lys Gly Pro Ser Glu Ala Pro Ser Gly Gln
                725                 730                 735

Ala
```

```
<210> SEQ ID NO 6
<211> LENGTH: 710
<212> TYPE: PRT
<213> ORGANISM: Saccharomyces cerevisiae
<220> FEATURE:
<221> NAME/KEY: Dipeptidyl peptidase 3 (DPP3)
<222> LOCATION: (1)..(710)
<223> OTHER INFORMATION: UniProt Accession No. Q08225

<400> SEQUENCE: 6

Met Ser His Phe Phe Ala Asp His Asp Ala Pro Leu Ser Met Leu Ser
1               5                   10                  15

Val Lys Thr Glu Tyr Phe Pro Gln Leu Thr Asp Lys Glu Gln Lys Tyr
            20                  25                  30

Ala His Phe Met Ser Lys Ala Ser His Ala Gly Ser Arg Val Val Met
        35                  40                  45

Arg Gln Val Ser His Glu Ser Glu Pro Ile Phe Asp Leu Ile Leu Ala
    50                  55                  60

Ile His Ser Lys Leu Asn Gly Lys Tyr Pro Glu Asp Ile Thr Gln
65                  70                  75                  80

Lys Gln Gln Thr Gly Leu Tyr Leu Glu Tyr Val Ser Gln Phe Leu Ser
                85                  90                  95

Asn Leu Gly Asn Phe Lys Ser Phe Gly Asp Thr Lys Phe Ile Pro Arg
            100                 105                 110

Cys Glu Val Lys Phe Phe Lys Gln Leu Leu Glu Leu Ala Lys Ile Asn
        115                 120                 125

Pro Cys Ser Ser Pro Leu Thr Leu Ser Pro Val Asp Val Asn His Glu
    130                 135                 140

Phe Thr Ser His His Leu Phe Ser Thr Ile Asn Glu Leu Ile Asp Ile
145                 150                 155                 160

Gly Ile Tyr His Val Glu Glu Lys Ala Ala Leu Leu Gly Phe Pro Ser
                165                 170                 175

Gln Gly Tyr Thr Ser Ala Tyr Tyr Leu Gly Leu Pro Val Thr Pro Glu
            180                 185                 190

Asp Met Ala Leu Leu Lys Glu Gln Leu Phe Ala Glu Leu Ala Ile Leu
        195                 200                 205

Pro Glu Asn Thr Arg Ile Asn Lys Val Gly Glu Asn Ser Phe Gln Ile
    210                 215                 220

Trp Val Ala Ser Glu Asn Val Lys Asn Gln Ile Thr Glu Thr Tyr Pro
225                 230                 235                 240

Ser Gly Gln Ile Thr Leu Ser Asn Ala Val Thr Lys Val Glu Phe Ile
                245                 250                 255

Phe Gly Asp His Ser Arg Glu Met Arg Leu Val Ala Ser Tyr Leu Lys
            260                 265                 270

Glu Ala Gln Lys Phe Ala Ala Asn Asp Thr Gln Lys Ala Met Leu Gln
        275                 280                 285

Glu Tyr Ile Asn His Phe Val Thr Gly Ser Ser Gln Ala His Lys Glu
    290                 295                 300

Ala Gln Lys Leu Trp Val Lys Asp Ile Ser Pro Val Ile Glu Thr Asn
305                 310                 315                 320

Ile Gly Phe Ile Glu Thr Tyr Arg Glu Pro Ser Gly Ile Ile Gly Glu
                325                 330                 335

Phe Glu Ser Leu Val Ala Ile Gln Asn Lys Glu Arg Thr Ala Lys Phe
            340                 345                 350

Ser Ser Val Asn Asn Ala Glu Glu Phe Ile Ser Leu Leu Pro Trp Ser
        355                 360                 365
```

Lys Asp Tyr Glu Lys Pro Ile Phe Asn Pro Pro Asp Phe Thr Ser Leu
370                 375                 380

Glu Val Leu Thr Phe Thr Gly Ser Gly Ile Pro Ala Gly Ile Asn Ile
385                 390                 395                 400

Pro Asn Tyr Asp Asp Val Arg Leu Lys Ile Gly Phe Lys Asn Val Ser
            405                 410                 415

Leu Gly Asn Ile Leu Ser Ala Ala Lys Ser Ser Ser Lys His Pro
        420                 425                 430

Pro Ser Phe Ile Ser Gln Glu Asp Arg Pro Ile Phe Glu Lys Tyr Gln
            435                 440                 445

Ser Asp Ser Phe Glu Val Gln Val Gly Ile His Glu Leu Leu Gly His
        450                 455                 460

Gly Ser Gly Lys Leu Leu Thr Glu Phe Thr Asp Gly Phe Asn Phe Asp
465                 470                 475                 480

Lys Glu Asn Pro Pro Leu Gly Leu Asp Gly Lys Pro Val Ser Thr Tyr
            485                 490                 495

Tyr Lys Val Gly Glu Thr Trp Gly Ser Lys Phe Gly Gln Leu Ala Gly
            500                 505                 510

Pro Phe Glu Glu Cys Arg Ala Glu Val Ile Ala Met Phe Leu Leu Thr
        515                 520                 525

Asn Lys Lys Ile Leu Asp Ile Phe Gly Phe His Asp Val Glu Ser Gln
530                 535                 540

Asp Lys Val Ile Tyr Ala Gly Tyr Leu Gln Met Ala Arg Ala Gly Leu
545                 550                 555                 560

Leu Ala Leu Glu Tyr Trp Asn Pro Lys Thr Gly Lys Trp Gly Gln Pro
            565                 570                 575

His Met Gln Ala Arg Phe Ser Ile Met Lys Thr Phe Met Lys His Ser
        580                 585                 590

Thr Asp Lys Asn Phe Leu Lys Leu Glu Met Asn Ser Thr Asn Asp Asp
            595                 600                 605

Phe Ala Ile Lys Leu Asp Lys Ser Leu Ile Lys Thr Ala Gly His Glu
        610                 615                 620

Cys Val Lys Asp Tyr Leu Lys His Leu His Val Tyr Lys Cys Ser Gly
625                 630                 635                 640

Asp Val Glu Gln Gly Ser Lys Tyr Phe Ile Asp Arg Ser Thr Val Thr
            645                 650                 655

Pro Asp Leu Ala Ser Leu Arg Asp Ile Val Leu Ser Lys Arg Leu Pro
        660                 665                 670

Arg Arg Gln Phe Ile Gln Ser Asn Ser Tyr Ile Asp Asn Asn Lys
            675                 680                 685

Val Thr Leu Lys Glu Tyr Asp Glu Thr Pro Gln Gly Met Leu Gln Ser
        690                 695                 700

Phe Leu Asp Arg Glu Leu
705             710

<210> SEQ ID NO 7
<211> LENGTH: 674
<212> TYPE: PRT
<213> ORGANISM: Bacteroides thetaiotaomicron
<220> FEATURE:
<221> NAME/KEY: Dipeptidyl peptidase 3 (DPP3)
<222> LOCATION: (1)..(674)
<223> OTHER INFORMATION: UniProt Accession No. Q8A6N1

<400> SEQUENCE: 7

```
Met Ala Val Thr Ala Thr Ile Leu Ala Ser Cys Gly Gly Ala Lys Thr
1               5                   10                  15

Thr Thr Ala Glu Ala Asp Lys Phe Asp Tyr Thr Val Glu Gln Phe Ala
            20                  25                  30

Asp Leu Gln Ile Leu Arg Tyr Lys Val Pro Glu Phe Glu Thr Leu Thr
            35                  40                  45

Leu Lys Gln Lys Glu Leu Val Tyr Tyr Leu Thr Gln Ala Ala Leu Glu
50                  55                  60

Gly Arg Asp Ile Leu Phe Asp Gln Asn Gly Lys Tyr Asn Leu Arg Ile
65                  70                  75                  80

Arg Arg Met Leu Glu Ala Val Tyr Thr Asn Tyr Lys Gly Asp Lys Ser
            85                  90                  95

Ala Pro Asp Phe Lys Asn Met Glu Val Tyr Leu Lys Arg Val Trp Phe
            100                 105                 110

Ser Asn Gly Ile His His His Tyr Gly Met Glu Lys Phe Val Pro Gly
            115                 120                 125

Phe Ser Gln Asp Phe Leu Lys Gln Ala Val Leu Gly Thr Asp Ala Gln
    130                 135                 140

Leu Leu Pro Leu Ser Glu Gly Gln Thr Ala Glu Gln Leu Cys Asp Glu
145                 150                 155                 160

Leu Phe Pro Val Met Phe Asp Pro Ala Ile Leu Ala Lys Arg Val Asn
                165                 170                 175

Gln Ala Asp Gly Glu Asp Leu Val Leu Thr Ser Ala Cys Asn Tyr Tyr
            180                 185                 190

Asp Gly Val Thr Gln Gln Glu Ala Glu Ser Phe Tyr Gly Ala Met Lys
            195                 200                 205

Asp Pro Lys Asp Glu Thr Pro Val Ser Tyr Gly Leu Asn Ser Arg Leu
210                 215                 220

Val Lys Glu Asp Gly Lys Gln Glu Lys Val Trp Lys Val Gly Gly Leu
225                 230                 235                 240

Tyr Thr Gln Ala Ile Glu Lys Ile Val Tyr Trp Leu Lys Lys Ala Glu
                245                 250                 255

Thr Val Ala Glu Asn Asp Ala Gln Lys Ala Val Ile Ser Lys Leu Ile
                260                 265                 270

Gln Phe Tyr Glu Thr Gly Ser Leu Lys Asp Phe Asp Glu Tyr Ala Ile
            275                 280                 285

Leu Trp Val Lys Asp Leu Asp Ser Arg Ile Asp Phe Val Asn Gly Phe
            290                 295                 300

Thr Glu Ser Tyr Gly Asp Pro Leu Gly Val Lys Ala Ser Trp Glu Ser
305                 310                 315                 320

Leu Val Asn Phe Lys Asp Leu Asp Ala Thr His Arg Thr Glu Ile Ile
                325                 330                 335

Ser Ser Asn Ala Gln Trp Phe Glu Asp His Ser Pro Val Asp Lys Ser
            340                 345                 350

Phe Lys Lys Glu Lys Val Lys Gly Val Ser Ala Lys Val Ile Thr Ala
            355                 360                 365

Ala Ile Leu Ala Gly Asp Leu Tyr Pro Ala Thr Ala Ile Gly Ile Asn
370                 375                 380

Leu Pro Asn Ala Asn Trp Ile Arg Ala His Gly Ser Lys Ser Val
385                 390                 395                 400

Thr Ile Gly Asn Ile Thr Asp Ala Tyr Asn Lys Ala Ala His Gly Asn
                405                 410                 415

Gly Phe Asn Glu Glu Phe Val Cys Asn Asp Glu Glu Arg Gln Arg Ile
```

```
                420             425             430
Asp Gln Tyr Gly Asp Leu Thr Gly Glu Leu His Thr Asp Leu His Glu
            435             440             445

Cys Leu Gly His Gly Ser Gly Lys Leu Leu Pro Gly Val Asp Pro Asp
        450             455             460

Ala Leu Lys Ala Tyr Gly Ser Thr Ile Glu Glu Ala Arg Ala Asp Leu
465             470             475             480

Phe Gly Leu Tyr Tyr Val Ala Asp Pro Lys Leu Val Glu Leu Lys Leu
                485             490             495

Val Pro Asp Ala Glu Ala Tyr Lys Ala Glu Tyr Tyr Thr Phe Leu Met
            500             505             510

Asn Gly Leu Met Thr Gln Leu Val Arg Ile Glu Pro Gly Asn Asn Ile
        515             520             525

Glu Glu Ala His Met Arg Asn Arg Gln Leu Ile Ala Arg Trp Val Phe
            530             535             540

Glu Lys Gly Ala Pro Asp Lys Val Val Glu Met Val Lys Lys Asp Gly
545             550             555             560

Lys Thr Tyr Val Val Asn Asp Tyr Glu Lys Val Arg Gln Leu Phe
                565             570             575

Gly Glu Leu Leu Ala Glu Ile Gln Arg Ile Lys Ser Thr Gly Asp Phe
            580             585             590

Glu Gly Ala Arg Thr Leu Val Glu Asn Tyr Ala Val Lys Val Asp Pro
        595             600             605

Ala Leu His Ala Glu Val Leu Ala Arg Tyr Lys Lys Leu Asn Leu Ala
    610             615             620

Pro Tyr Lys Gly Phe Ile Asn Pro Val Tyr Glu Leu Val Thr Asp Lys
625             630             635             640

Asp Gly Asn Ile Thr Asp Val Thr Val Ser Tyr Asn Glu Asp Tyr Val
                645             650             655

Glu Gln Met Leu Arg Tyr Ser Lys Asp Tyr Ser Pro Leu Pro Ser Val
            660             665             670

Asn Asn

<210> SEQ ID NO 8
<211> LENGTH: 558
<212> TYPE: PRT
<213> ORGANISM: Caldithrix abyssi
<220> FEATURE:
<221> NAME/KEY: Dipeptidyl peptidase 3 (DPP3)
<222> LOCATION: (1)..(558)
<223> OTHER INFORMATION: UniProt Accession No. H1XW48

<400> SEQUENCE: 8

Met Lys Arg Ile Leu Leu Val Leu Leu Thr Leu Val Phe Leu Gly Ala
1               5                   10                  15

Ile Ala Cys Gln Lys Lys Glu Glu Asn Lys Thr Glu Met Val Lys Leu
            20                  25                  30

Lys Arg Met Ile Ala Gln Phe Ala Pro Thr Glu Ile Lys Tyr Asp His
        35                  40                  45

Ser Leu Leu Asp Glu Arg Lys Gln Lys Val Val Glu Asn Leu Tyr Arg
    50                  55                  60

Ala Ala Lys Ile Met Asp Glu Ile Phe Leu Asp Gln Val Tyr Ser Lys
65                  70                  75                  80

Asn Phe Glu Ile Arg Glu Gln Leu Arg Ala Ser Ser Asp Pro Leu Asp
                85                  90                  95
```

```
Gln Leu Arg Leu Glu Tyr Phe Thr Ile Met Phe Gly Pro Phe Asp Arg
                100                 105                 110

Leu Asn His Asp Lys Pro Phe Ile Gly Asn Thr Pro Lys Pro Lys Gly
            115                 120                 125

Ala Asn Phe Tyr Pro Pro Asp Met Thr Arg Glu Glu Phe Glu Asn Trp
        130                 135                 140

Leu Lys Ala His Pro Glu Asp Glu Ala Ala Phe Thr Ser Glu Phe Thr
145                 150                 155                 160

Val Ile Arg Arg Gln Asp Gly Lys Leu Val Ala Ile Pro Tyr Ser Glu
                165                 170                 175

Tyr Tyr Lys Glu Tyr Leu Thr Arg Ala Ala Asp Tyr Leu Lys Lys Ala
            180                 185                 190

Ala Glu Phe Ala Asp Asn Pro Ser Leu Lys Lys Tyr Leu Gln Leu Arg
        195                 200                 205

Ala Glu Ala Phe Leu Asn Asn Asp Tyr Tyr Glu Ser Asp Leu Ala Trp
210                 215                 220

Met Asp Leu Asn Asp His Thr Ile Glu Val Val Ile Gly Pro Tyr Glu
225                 230                 235                 240

Val Tyr Glu Asp Lys Leu Phe Asn Tyr Lys Ala Ala Phe Glu Ala Phe
                245                 250                 255

Ile Thr Leu Arg Asp Pro Val Glu Ser Ala Lys Leu Lys Lys Phe Val
            260                 265                 270

Gly Tyr Leu Asp Glu Met Glu Lys Asn Leu Pro Ile Pro Asp Ala Tyr
        275                 280                 285

Lys Asn Phe Asn Arg Gly Ser Glu Ser Pro Met Val Val Gln Glu
290                 295                 300

Val Phe Ser Ala Gly Asp Thr Lys Ala Gly Val Gln Thr Leu Ala Phe
305                 310                 315                 320

Asn Leu Pro Asn Asp Glu Arg Val Arg Glu Ala Lys Gly Ser Lys Lys
                325                 330                 335

Val Met Leu Lys Asn Ile His Glu Ala Lys Phe Asp Lys Leu Leu Lys
            340                 345                 350

Pro Ile Ala Glu Lys Val Leu Phe Ala Glu Gln Leu Pro Leu Val Thr
        355                 360                 365

Phe Glu Gly Phe Phe Asn His Thr Leu Met His Glu Ile Ser His Gly
370                 375                 380

Leu Gly Pro Gly Lys Ile Val Leu Asn Gly Arg Gln Thr Glu Val Lys
385                 390                 395                 400

Lys Glu Leu Lys Glu Thr Tyr Ser Ser Ile Glu Glu Cys Lys Ala Asp
                405                 410                 415

Val Leu Gly Met Tyr Asn Asn Leu Phe Met Ile Glu Lys Gly Val Tyr
            420                 425                 430

Pro Pro Glu Phe Glu Lys Gln Ile Tyr Val Thr Phe Leu Ala Gly Ile
        435                 440                 445

Phe Arg Thr Ile Arg Phe Gly Ile Asn Glu Ala His Gly Ala Gly Asn
450                 455                 460

Ala Val Ile Phe Asn Tyr Leu Leu Glu Lys Gly Ala Tyr Gln Phe Asp
465                 470                 475                 480

Pro Ala Ala His Arg Val Lys Val Asn Phe Glu Lys Ile Lys Asp Gly
                485                 490                 495

Val Arg Asp Leu Ala Asn Lys Val Leu Thr Ile Gln Ala Gln Gly Asp
            500                 505                 510

Tyr Met Ala Ala Lys Asn Leu Leu Glu Thr Tyr Ala Val Glu Ser Glu
```

```
                515                 520                 525
Pro Ile Met Ile Met Arg Ala Arg Leu Gln Glu Leu Pro Val Asp Ile
            530                 535                 540

Lys Pro Ile Phe Gln Ile Glu Lys Glu Leu Gly Asn Ser Asn
545                 550                 555
```

<210> SEQ ID NO 9
<211> LENGTH: 8
<212> TYPE: PRT
<213> ORGANISM: Artificial Sequence
<220> FEATURE:
<223> OTHER INFORMATION: Substrate Sequence

<400> SEQUENCE: 9

```
Asp Arg Val Tyr Ile His Pro Phe
1               5
```

<210> SEQ ID NO 10
<211> LENGTH: 703
<212> TYPE: PRT
<213> ORGANISM: Aspergillus fumigatus
<220> FEATURE:
<221> NAME/KEY: Dipeptidyl peptidase 5 (DPP5)
<222> LOCATION: (1)..(703)
<223> OTHER INFORMATION: Uniprot accession P0C959

<400> SEQUENCE: 10

```
Leu Thr Pro Glu Gln Leu Ile Thr Ala Pro Arg Arg Ser Glu Ala Ile
1               5                   10                  15

Pro Asp Pro Ser Gly Lys Val Ala Val Phe Ser Thr Ser Gln Tyr Ser
            20                  25                  30

Phe Glu Thr His Lys Arg Thr Ser Trp Trp Ser Leu Leu Asp Leu Lys
        35                  40                  45

Thr Gly Gln Thr Lys Val Leu Thr Asn Asp Ser Ser Val Ser Glu Ile
    50                  55                  60

Val Trp Leu Ser Asp Asp Ser Ile Leu Tyr Val Asn Ser Thr Asn Ala
65                  70                  75                  80

Asp Ile Pro Gly Gly Val Glu Leu Trp Val Thr Gln Ala Ser Ser Phe
                85                  90                  95

Ala Lys Gly Tyr Lys Ala Ala Ser Leu Pro Ala Ser Phe Ser Gly Leu
            100                 105                 110

Lys Thr Ala Lys Thr Lys Ser Gly Asp Ile Arg Phe Val Ala Tyr Gly
        115                 120                 125

Gln Ser Tyr Pro Asn Gly Thr Ala Tyr Asn Glu Glu Leu Ala Thr Ala
    130                 135                 140

Pro Leu Ser Ser Ala Arg Ile Tyr Asp Ser Ile Tyr Val Arg His Trp
145                 150                 155                 160

Asp Tyr Trp Leu Ser Thr Thr Phe Asn Ala Val Phe Ser Gly Thr Leu
                165                 170                 175

Lys Lys Gly His Gly Lys Asn Gly Tyr Ser Leu Asp Gly Glu Leu Lys
            180                 185                 190

Asn Leu Val Ser Pro Val Lys Asn Ala Glu Ser Pro Tyr Pro Pro Phe
        195                 200                 205

Gly Gly Ala Ser Asp Tyr Asp Leu Ser Pro Asp Gly Lys Trp Val Ala
    210                 215                 220

Phe Lys Ser Lys Ala Pro Glu Leu Pro Lys Ala Asn Phe Thr Thr Ser
225                 230                 235                 240

Tyr Ile Tyr Leu Val Pro His Asp Ala Ser Glu Thr Ala Arg Pro Ile
```

```
                245                 250                 255
Asn Gly Pro Asp Ser Pro Gly Thr Pro Lys Gly Ile Lys Gly Asp Ser
            260                 265                 270

Ser Ser Pro Val Phe Ser Pro Asn Gly Asp Lys Leu Ala Tyr Phe Gln
            275                 280                 285

Met Arg Asp Glu Thr Tyr Glu Ser Asp Arg Arg Val Leu Tyr Val Tyr
            290                 295                 300

Ser Leu Gly Ser Lys Lys Thr Ile Pro Ser Val Ala Gly Asp Trp Asp
305                 310                 315                 320

Arg Ser Pro Asp Ser Val Lys Trp Thr Pro Asp Gly Lys Thr Leu Ile
            325                 330                 335

Val Gly Ser Glu Asp Leu Gly Arg Thr Arg Leu Phe Ser Leu Pro Ala
            340                 345                 350

Asn Ala Lys Asp Asp Tyr Lys Pro Lys Asn Phe Thr Asp Gly Gly Ser
            355                 360                 365

Ala Ser Ala Tyr Tyr Phe Leu Pro Asp Ser Ser Leu Leu Val Thr Gly
            370                 375                 380

Ser Ala Leu Trp Thr Asn Trp Asn Val Tyr Thr Ala Lys Pro Glu Lys
385                 390                 395                 400

Gly Val Ile Lys Lys Ile Ala Ser Ala Asn Glu Ile Asp Pro Glu Leu
                405                 410                 415

Lys Gly Leu Gly Pro Ser Asp Ile Ser Glu Phe Tyr Phe Gln Gly Asn
                420                 425                 430

Phe Thr Asp Ile His Ala Trp Val Ile Tyr Pro Glu Asn Phe Asp Lys
                435                 440                 445

Ser Lys Lys Tyr Pro Leu Ile Phe Phe Ile His Gly Gly Pro Gln Gly
            450                 455                 460

Asn Trp Ala Asp Gly Trp Ser Thr Arg Trp Asn Pro Lys Ala Trp Ala
465                 470                 475                 480

Asp Gln Gly Tyr Val Val Val Ala Pro Asn Pro Thr Gly Ser Thr Gly
                485                 490                 495

Phe Gly Gln Ala Leu Thr Asp Ala Ile Gln Asn Asn Trp Gly Gly Ala
            500                 505                 510

Pro Tyr Asp Asp Leu Val Lys Cys Trp Glu Tyr Val His Glu Asn Leu
            515                 520                 525

Asp Tyr Val Asp Thr Asp His Gly Val Ala Ala Gly Ala Ser Tyr Gly
            530                 535                 540

Gly Phe Met Ile Asn Trp Ile Gln Gly Ser Pro Leu Gly Arg Lys Phe
545                 550                 555                 560

Lys Ala Leu Val Ser His Asp Gly Thr Phe Val Ala Asp Ala Lys Val
                565                 570                 575

Ser Thr Glu Glu Leu Trp Phe Met Gln Arg Gly Phe Asn Gly Thr Phe
            580                 585                 590

Trp Asp Ala Arg Asp Asn Tyr Arg Arg Trp Asp Pro Ser Ala Pro Glu
            595                 600                 605

Arg Ile Leu Gln Phe Ala Thr Pro Met Leu Val Ile His Ser Asp Lys
            610                 615                 620

Asp Tyr Arg Leu Pro Val Ala Glu Gly Leu Ser Leu Phe Asn Val Leu
625                 630                 635                 640

Gln Glu Arg Gly Val Pro Ser Arg Phe Leu Asn Phe Pro Asp Glu Asn
                645                 650                 655

His Trp Val Val Asn Pro Glu Asn Ser Leu Val Trp His Gln Gln Ala
                660                 665                 670
```

-continued

Leu Gly Trp Ile Asn Lys Tyr Ser Gly Val Glu Lys Ser Asn Pro Asn
            675                 680                 685

Ala Val Ser Leu Glu Asp Thr Val Pro Val Val Asn Tyr Asn
690                 695                 700

<210> SEQ ID NO 11
<211> LENGTH: 689
<212> TYPE: PRT
<213> ORGANISM: Porphyromonas gingivalis
<220> FEATURE:
<221> NAME/KEY: Dipeptidyl peptidase 7 (DPP7)
<222> LOCATION: (1)..(689)
<223> OTHER INFORMATION: UniProt Accession No. B2RKV3

<400> SEQUENCE: 11

Ala Asp Lys Gly Met Trp Leu Leu Asn Glu Leu Asn Gln Glu Asn Leu
1               5                   10                  15

Asp Arg Met Arg Glu Leu Gly Phe Thr Leu Pro Leu Asp Ser Leu Tyr
                20                  25                  30

Ser Phe Asp Lys Pro Ser Ile Ala Asn Ala Val Val Ile Phe Gly Gly
            35                  40                  45

Gly Cys Thr Gly Ile Thr Val Ser Asp Gln Gly Leu Ile Phe Thr Asn
50                  55                  60

His His Cys Gly Tyr Gly Ala Ile Gln Ser Gln Ser Thr Val Asp His
65                  70                  75                  80

Asp Tyr Leu Arg Asp Gly Phe Val Ser Arg Thr Met Gly Glu Glu Leu
                85                  90                  95

Pro Ile Pro Gly Leu Ser Val Lys Tyr Leu Arg Lys Ile Val Lys Val
            100                 105                 110

Thr Asp Lys Val Glu Gly Gln Leu Lys Gly Ile Thr Asp Glu Met Glu
        115                 120                 125

Arg Leu Arg Lys Ala Gln Glu Val Cys Gln Glu Leu Ala Lys Lys Glu
130                 135                 140

Asn Ala Asp Glu Asn Gln Leu Cys Ile Val Glu Pro Phe Tyr Ser Asn
145                 150                 155                 160

Asn Glu Tyr Phe Leu Ile Val Tyr Asp Val Phe Lys Asp Val Arg Met
                165                 170                 175

Val Phe Ala Pro Pro Ser Ser Val Gly Lys Phe Gly Gly Asp Thr Asp
            180                 185                 190

Asn Trp Met Trp Pro Arg His Thr Gly Asp Phe Ser Val Phe Arg Val
        195                 200                 205

Tyr Ala Gly Ala Asp Asn Arg Pro Ala Glu Tyr Ser Lys Asp Asn Lys
210                 215                 220

Pro Tyr Lys Pro Val Tyr Phe Ala Ala Val Ser Met Gln Gly Tyr Lys
225                 230                 235                 240

Ala Asp Asp Tyr Ala Met Thr Ile Gly Phe Pro Gly Ser Thr Asp Arg
                245                 250                 255

Tyr Leu Thr Ser Trp Gly Val Glu Asp Arg Ile Glu Asn Glu Asn Asn
            260                 265                 270

Pro Arg Ile Glu Val Arg Gly Ile Lys Gln Gly Ile Trp Lys Glu Ala
        275                 280                 285

Met Ser Ala Asp Gln Ala Thr Arg Ile Lys Tyr Ala Ser Lys Tyr Ala
290                 295                 300

Gln Ser Ala Asn Tyr Trp Lys Asn Ser Ile Gly Met Asn Arg Gly Leu
305                 310                 315                 320

```
Ala Arg Leu Asp Val Ile Gly Arg Lys Arg Ala Glu Glu Arg Ala Phe
            325                 330                 335

Ala Asp Trp Ile Arg Lys Asn Gly Lys Ser Ala Val Tyr Gly Asp Val
            340                 345                 350

Leu Ser Ser Leu Glu Lys Ala Tyr Lys Glu Gly Ala Lys Ala Asn Arg
            355                 360                 365

Glu Met Thr Tyr Leu Ser Glu Thr Leu Phe Gly Gly Thr Glu Val Val
            370                 375                 380

Arg Phe Ala Gln Phe Ala Asn Ala Leu Ala Thr Asn Pro Asp Ala His
385                 390                 395                 400

Ala Gly Ile Leu Lys Ser Leu Asp Asp Lys Tyr Lys Asp Tyr Leu Pro
            405                 410                 415

Ser Leu Asp Arg Lys Val Leu Pro Ala Met Leu Asp Ile Val Arg Arg
            420                 425                 430

Arg Ile Pro Ala Asp Lys Leu Pro Asp Ile Phe Lys Asn Val Ile Asp
            435                 440                 445

Lys Lys Phe Lys Gly Asp Thr Lys Lys Tyr Ala Asp Phe Val Phe Asp
            450                 455                 460

Lys Ser Val Val Pro Tyr Ser Asp Lys Phe His Ala Met Leu Lys Ser
465                 470                 475                 480

Met Asp Lys Glu Lys Phe Ala Lys Ala Ile Glu Lys Asp Pro Ala Val
            485                 490                 495

Glu Leu Ser Lys Ser Val Ile Ala Ala Arg Ala Ile Gln Ala Asp
            500                 505                 510

Ala Met Ala Asn Ala Tyr Ala Ile Glu Lys Gly Lys Arg Leu Phe Phe
            515                 520                 525

Ala Gly Leu Arg Glu Met Tyr Pro Gly Arg Ala Leu Pro Ser Asp Ala
            530                 535                 540

Asn Phe Thr Met Arg Met Ser Tyr Gly Ser Ile Lys Gly Tyr Glu Pro
545                 550                 555                 560

Gln Asp Gly Ala Trp Tyr Asn Tyr His Thr Thr Gly Lys Gly Val Leu
            565                 570                 575

Glu Lys Gln Asp Pro Lys Ser Asp Glu Phe Ala Val Gln Glu Asn Ile
            580                 585                 590

Leu Asp Leu Phe Arg Thr Lys Asn Tyr Gly Arg Tyr Ala Glu Asn Gly
            595                 600                 605

Gln Leu His Ile Ala Phe Leu Ser Asn Asn Asp Ile Thr Gly Gly Asn
            610                 615                 620

Ser Gly Ser Pro Val Phe Asp Lys Asn Gly Arg Leu Ile Gly Leu Ala
625                 630                 635                 640

Phe Asp Gly Asn Trp Glu Ala Met Ser Gly Asp Ile Glu Phe Glu Pro
            645                 650                 655

Asp Leu Gln Arg Thr Ile Ser Val Asp Ile Arg Tyr Val Leu Phe Met
            660                 665                 670

Ile Asp Lys Trp Gly Gln Cys Pro Arg Leu Ile Gln Glu Leu Lys Leu
            675                 680                 685

Ile

<210> SEQ ID NO 12
<211> LENGTH: 699
<212> TYPE: PRT
<213> ORGANISM: Porphyromonas gingivalis
<220> FEATURE:
<221> NAME/KEY: Dipeptidyl peptidase 11 (DPP11)
<222> LOCATION: (1)..(699)
```

<223> OTHER INFORMATION: UniProt Accession No. B2RID1

<400> SEQUENCE: 12

```
Asp Glu Gly Met Trp Leu Met Gln Gln Leu Gly Arg Lys Tyr Ala Gln
1               5                   10                  15
Met Lys Glu Arg Gly Leu Lys Met Lys Glu Tyr Asp Leu Tyr Asn Pro
            20                  25                  30
Asn Gly Thr Ser Leu Lys Asp Ala Val Val Leu Phe Asp Gly Gly Cys
        35                  40                  45
Thr Gly Glu Val Val Ser Asp Arg Gly Leu Val Leu Thr Asn His His
    50                  55                  60
Cys Gly Tyr Asp Met Ile Gln Ala His Ser Thr Leu Glu His Asn Tyr
65                  70                  75                  80
Leu Glu Asn Gly Phe Trp Ala Met Arg Glu Ala Asp Glu Leu Pro Asn
                85                  90                  95
Lys Asp Ile Ser Val Val Phe Ile Asp Lys Ile Glu Asp Val Thr Asp
            100                 105                 110
Tyr Val Lys Lys Glu Leu Lys Ala Ile Lys Asp Pro Asn Ser Met Asp
        115                 120                 125
Tyr Leu Ser Pro Lys Tyr Leu Gln Lys Leu Ala Asp Lys Lys Ala Gly
    130                 135                 140
Lys Asn Phe Ser Ala Lys Asn Pro Gly Leu Ser Val Glu Ile Lys Ala
145                 150                 155                 160
Phe Tyr Gly Gly Asn Leu Tyr Leu Met Phe Thr Lys Lys Thr Tyr Thr
                165                 170                 175
Asp Val Arg Leu Val Gly Ala Pro Pro Ser Ser Ile Gly Lys Phe Gly
            180                 185                 190
Ala Asp Thr Asp Asn Trp Ile Trp Pro Arg His Thr Gly Asp Phe Ser
        195                 200                 205
Ile Phe Arg Ile Tyr Ala Asp Lys Asn Gly Asn Pro Ala Pro Tyr Ser
    210                 215                 220
Glu Asp Asn Val Pro Leu Lys Pro Lys Arg Phe Phe Asn Ile Ser Leu
225                 230                 235                 240
Gly Gly Val Gln Glu Asn Asp Tyr Ala Met Ile Met Gly Phe Pro Gly
                245                 250                 255
Thr Thr His Arg Tyr Phe Thr Ala Ser Glu Val Asp Glu Trp Lys Ser
            260                 265                 270
Ile Asp Asn Asp Ile Arg Ile Arg Met Arg Asp Ile Arg Gln Gly Val
        275                 280                 285
Met Leu Arg Glu Met Leu Ala Asp Pro Gln Ile Lys Ile Met Tyr Ser
    290                 295                 300
Ala Lys Tyr Ala Ala Ser Gln Asn Ala Tyr Lys Arg Ala Ile Gly Ala
305                 310                 315                 320
Asn Trp Ala Ile Lys Thr Arg Gly Leu Arg Gln Asn Lys Gln Ala Met
                325                 330                 335
Gln Asp Arg Leu Ile Ala Trp Gly Ala Lys Gln Gly Thr Pro Arg Tyr
            340                 345                 350
Glu Glu Ala Val His Glu Ile Asp Ala Thr Val Ala Lys Arg Ala Asp
        355                 360                 365
Leu Arg Arg Arg Tyr Trp Met Ile Glu Glu Gly Ile Ile Arg Gly Ile
    370                 375                 380
Glu Phe Ala Arg Ser Pro Ile Pro Thr Glu Asp Glu Thr Lys Ala Leu
385                 390                 395                 400
```

```
Gln Gly Asn Asp Ala Ser Ala Arg Lys Glu Ala Ile Asp Lys Ile Arg
                405                 410                 415

Thr Arg Tyr Ser Lys Phe Ala Asn Lys Asp Tyr Ser Ala Glu Val Asp
            420                 425                 430

Lys Lys Val Ala Val Ala Met Leu Thr Glu Tyr Leu Lys Glu Ile Pro
        435                 440                 445

Tyr Glu Asn Leu Pro Leu His Leu Arg Leu Val Lys Asp Arg Phe Ala
    450                 455                 460

Gly Asp Val Gln Ala Tyr Val Asp Asp Ile Phe Ala Arg Ser Val Phe
465                 470                 475                 480

Gly Ser Glu Ala Gln Phe Asp Ala Phe Ala Ala Val Pro Ser Val Glu
                485                 490                 495

Lys Leu Ala Glu Asp Pro Met Val Leu Phe Ala Ser Ser Val Phe Asp
            500                 505                 510

Glu Tyr Arg Lys Leu Tyr Asn Glu Leu Arg Pro Tyr Asp Asp Pro Ile
        515                 520                 525

Leu Arg Ala Gln Arg Thr Tyr Ile Ala Gly Leu Leu Glu Met Asp Gly
    530                 535                 540

Asp Gln Asp Gln Phe Pro Asp Ala Asn Leu Thr Leu Arg Phe Thr Tyr
545                 550                 555                 560

Gly Gln Val Lys Gly Tyr Ser Pro Arg Asp Asn Val Tyr Tyr Gly His
                565                 570                 575

Gln Thr Thr Leu Asp Gly Val Met Glu Lys Glu Asp Pro Asp Asn Trp
            580                 585                 590

Glu Phe Val Val Asp Pro Lys Leu Lys Ala Val Tyr Glu Arg Lys Asp
        595                 600                 605

Phe Gly Arg Tyr Ala Asp Arg Ser Gly Arg Met Pro Val Ala Phe Cys
    610                 615                 620

Ala Thr Thr His Thr Thr Gly Gly Asn Ser Gly Ser Pro Val Met Asn
625                 630                 635                 640

Ala Asn Gly Glu Leu Ile Gly Leu Asn Phe Asp Arg Asn Trp Glu Gly
                645                 650                 655

Val Gly Gly Asp Ile Gln Tyr Leu Ala Asp Tyr Gln Arg Ser Ile Ile
            660                 665                 670

Val Asp Ile Arg Tyr Val Leu Leu Val Ile Asp Lys Val Gly Gly Cys
        675                 680                 685

Gln Arg Leu Leu Asp Glu Met Asn Ile Val Pro
    690                 695

<210> SEQ ID NO 13
<211> LENGTH: 698
<212> TYPE: PRT
<213> ORGANISM: Pseudoxanthomonas mexicana
<220> FEATURE:
<221> NAME/KEY: Dipeptidyl Aminopeptidase BII (DAP BII)
<222> LOCATION: (1)..(698)
<223> OTHER INFORMATION: UniProt Accession No. V5YM14

<400> SEQUENCE: 13

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
```

```
            50                  55                  60
Tyr Gly Ala Ile Gln Leu Asn Ser Thr Ala Glu Asn Leu Ile Lys
 65                  70                  75                  80

Asn Gly Phe Asn Ala Pro Thr Thr Ala Asp Glu Val Ser Ala Gly Pro
                 85                  90                  95

Asn Ala Arg Val Phe Val Leu Asp Glu Ile Thr Asp Val Thr Lys Asp
                100                 105                 110

Ala Lys Ala Ala Ile Ala Ala Ala Gly Asp Asp Ala Leu Ala Arg Thr
                115                 120                 125

Lys Ala Leu Glu Ala Phe Glu Lys Lys Leu Ile Ala Asp Cys Glu Ala
                130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Asn Trp
                180                 185                 190

Met Trp Pro Arg His Thr Gly Asp Phe Ala Phe Tyr Arg Ala Tyr Val
                195                 200                 205

Gly Lys Asp Gly Lys Pro Ala Ala Phe Ser Lys Asp Asn Val Pro Tyr
                210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
                260                 265                 270

Ala Arg His Tyr Lys Asn Gln Ile Ala Met Val Glu Ala Ala Gly Lys
                275                 280                 285

Gln Asn Ala Asp Ile Gln Val Lys Tyr Ala Ala Thr Met Ala Gly Trp
                290                 295                 300

Asn Asn Thr Ser Lys Asn Tyr Asp Gly Gln Leu Glu Gly Phe Lys Arg
305                 310                 315                 320

Ile Asp Ala Ala Gly Gln Lys Leu Arg Glu Glu Ala Ala Val Leu Gly
                325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
                355                 360                 365

Asp Leu Thr Leu Ala Leu Phe Asn Asn Thr Ala Met Leu Gly Ser Ala
                370                 375                 380

Thr Gln Leu Tyr Arg Leu Ser Ile Glu Arg Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
                420                 425                 430

Gln Glu Tyr Trp Leu Asn Glu Tyr Ile Lys Leu Pro Ala Asp Gln Arg
                435                 440                 445

Val Ala Ala Val Asp Ala Trp Leu Gly Gly Asn Asp Ala Ala Ala Val
                450                 455                 460

Lys Arg Ala Leu Asp Arg Leu Ala Gly Thr Lys Leu Gly Ser Thr Glu
465                 470                 475                 480
```

Glu Arg Leu Lys Trp Phe Ala Ala Asp Arg Lys Ala Phe Glu Ala Ser
            485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
            530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
            595                 600                 605

Gly Leu Glu Asp Lys Arg Ile Gly Ser Val Pro Val Asn Tyr Leu Ser
            610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Asp Gly Asn Trp Glu Ser Val
                645                 650                 655

Ser Ser Asn Trp Val Phe Asp Pro Lys Met Thr Arg Met Ile Ala Val
                660                 665                 670

Asp Gly Arg Tyr Leu Arg Trp Ile Met Gln Val Tyr Pro Ala Pro
                675                 680                 685

Gln Leu Leu Lys Glu Met Asn Val Gly Lys
            690                 695

<210> SEQ ID NO 14
<211> LENGTH: 696
<212> TYPE: PRT
<213> ORGANISM: Porphyromonas endodontalis
<220> FEATURE:
<221> NAME/KEY: Dipeptidyl peptidase 11 (DPP11)
<222> LOCATION: (1)..(696)
<223> OTHER INFORMATION: UniProt Accession No. F8WQK8

<400> SEQUENCE: 14

Asp Gly Gly Met Trp Leu Met Gln Gln Ile Asn Gly Gln Val Ala Arg
1               5                   10                  15

Met Lys Ser Leu Gly Met Gln Leu Glu Ala Ala Asp Ile Tyr Asn Pro
            20                  25                  30

Asn Gly Ser Ser Leu Lys Asp Ala Val Val Met Phe Asp Gly Gly Cys
        35                  40                  45

Thr Gly Val Leu Val Ser Asn Gln Gly Leu Leu Leu Thr Asn His His
    50                  55                  60

Cys Gly Tyr Asp Gln Ile Gln Lys His Ser Ser Val Gln His Asn Tyr
65                  70                  75                  80

Leu Lys Asp Gly Phe Trp Ser Tyr Ser Leu Ala Glu Glu Leu Val Asn
                85                  90                  95

Pro Gly Leu Glu Val Glu Ile Val Asp Glu Ile Thr Asp Val Thr Ala
            100                 105                 110

Ala Val Lys Lys Glu Leu Glu Arg Ile Lys Lys Pro Ser Gly Leu Glu
            115                 120                 125

-continued

```
Phe Leu Ser Pro Arg Tyr Leu Ser Ser Leu Ala Pro Glu Ile Val Gly
    130                 135                 140

Lys Lys Ala Ala Ser Arg Pro Gly Tyr Arg Tyr Glu Ile Lys Ala Phe
145                 150                 155                 160

Tyr Gly Gly Asn Arg Tyr Tyr Met Phe Thr Lys Lys Val Phe Arg Asp
                165                 170                 175

Val Arg Leu Val Ala Ala Pro Pro Ser Ser Ile Gly Lys Phe Gly Ser
            180                 185                 190

Asp Thr Asp Asn Trp Ala Trp Pro Arg His Thr Gly Asp Phe Ser Ile
        195                 200                 205

Phe Arg Leu Tyr Ala Asp Lys Asn Gly Asn Pro Ala Glu Tyr Ser Lys
    210                 215                 220

Asp Asn Val Pro Tyr Arg Pro Lys Arg Trp Val Lys Val Asn Ala Gln
225                 230                 235                 240

Gly Val Lys Glu Gly Asp Phe Ala Leu Ile Met Gly Tyr Pro Gly Thr
                245                 250                 255

Thr Tyr Lys Phe Phe Thr Ala Asp Glu Val Thr Glu Trp Ser Glu Ile
            260                 265                 270

Asp Asn Asn Ile Arg Ile Glu Met Arg Gly Ile Leu Gln Asp Val Met
        275                 280                 285

Leu Arg Glu Met Leu Ala Asp Pro Lys Ile Asn Ile Met Tyr Ala Ala
    290                 295                 300

Lys Tyr Ala Ser Ser Gln Asn Gly Tyr Lys Arg Ala Gln Gly Ala Asn
305                 310                 315                 320

Trp Ala Ile Arg Arg Ser Leu Arg Glu Ile Lys Leu Ala Gln Gln
                325                 330                 335

Gln Glu Val Leu Ala Trp Ala Lys Gln Lys Gly Ile Ala Thr Thr Glu
            340                 345                 350

Glu Ala Val Arg Ala Ile Ser Lys Ala Ile Glu Gly Arg Gln Asp Leu
        355                 360                 365

Arg Met Arg Gln Arg Tyr Leu Leu Glu Gly Ile Leu Met Gly Ile Glu
    370                 375                 380

Met Ser Asn Ala Pro Ala Ala Asp Ser Asp Ile Ala Asp His Trp Asp
385                 390                 395                 400

Asp Pro Ala Arg Arg Glu Ala Gly Leu Gln Ser Ile Arg Lys Gln Phe
                405                 410                 415

Glu Ala Phe Phe Asn Lys Asp Tyr Ser Pro Glu Val Glu Lys Asp Gln
            420                 425                 430

Leu Ala Ile Ala Leu Leu Thr Arg Tyr Ala Glu Arg Ile Pro Ala Glu
        435                 440                 445

Lys Gln Pro Ile Ser Ile Arg Glu Gly Ile Ala Glu Tyr Gly Ser Ala
    450                 455                 460

Lys Ala Tyr Val Glu Met Ile Phe Asp Lys Ser Ile Tyr Ala Ser Arg
465                 470                 475                 480

Glu Arg Phe Glu Glu Phe Met Lys Asn Pro Asp Arg Asp Arg Leu Leu
                485                 490                 495

Arg Asp Pro Met Ser Arg Phe Ala Ala Ser Val Ala Tyr Glu His Gln
            500                 505                 510

Lys Leu Ala Lys Glu Val Ala Ala Phe Asp Ala Pro Leu Ala Ala Ala
        515                 520                 525

Gln Arg Ser Tyr Val Ala Ser Val Leu Asp Met Lys Gly Gln Pro Asn
    530                 535                 540

Leu Ala Pro Asp Ala Asn Leu Thr Leu Arg Phe Thr Tyr Gly Glu Ile
```

```
545                 550                 555                 560
Lys Gly Tyr Gln Pro Arg Asp Val Val Thr Tyr Gly Ala Lys Ser Thr
                565                 570                 575

Leu Glu Gly Val Met Glu Lys Glu Asp Pro Asn Asn Trp Glu Tyr Val
            580                 585                 590

Val Asp Pro Lys Leu Lys Ala Leu Tyr Glu Ala Lys Asn Tyr Gly Arg
        595                 600                 605

Tyr Ala Asn Ser Asp Gly Ser Met Pro Val Asn Phe Cys Ala Thr Thr
    610                 615                 620

His Thr Thr Gly Gly Asn Ser Gly Ser Pro Val Met Asn Ala Arg Gly
625                 630                 635                 640

Glu Leu Ile Gly Leu Asn Phe Asp Arg Asn Trp Glu Val Gly Gly
                645                 650                 655

Asp Ile Glu Tyr Leu Pro Asn Tyr Gln Arg Ser Ile Ile Leu Asp Ile
                660                 665                 670

Arg Tyr Leu Leu Phe Ile Ile Asp Lys Phe Ala Gly Cys Gln Arg Leu
                675                 680                 685

Ile Asp Glu Ile Gln Pro Gln Phe
    690                 695

<210> SEQ ID NO 15
<211> LENGTH: 738
<212> TYPE: PRT
<213> ORGANISM: Rattus norvegicus
<220> FEATURE:
<221> NAME/KEY: Dipeptidyl peptidase 3 (DPP3)
<222> LOCATION: (1)..(738)
<223> OTHER INFORMATION: UniProt Accession No. O55096

<400> SEQUENCE: 15

Met Ala Asp Thr Gln Tyr Ile Leu Pro Asn Asp Ile Gly Val Ser Ser
1               5                   10                  15

Leu Asp Cys Arg Glu Ala Phe Arg Leu Leu Ser Pro Thr Glu Arg Leu
            20                  25                  30

Tyr Ala His His Leu Ser Arg Ala Ala Trp Tyr Gly Gly Leu Ala Val
        35                  40                  45

Leu Leu Gln Thr Ser Pro Glu Ala Pro Tyr Ile Tyr Ala Leu Leu Ser
    50                  55                  60

Arg Leu Phe Arg Ala Gln Asp Pro Asp Gln Leu Arg Gln His Ala Leu
65                  70                  75                  80

Ala Glu Gly Leu Thr Glu Glu Tyr Gln Ala Phe Leu Val Tyr Ala
                85                  90                  95

Ala Gly Val Tyr Ser Asn Met Gly Asn Tyr Lys Ser Phe Gly Asp Thr
            100                 105                 110

Lys Phe Val Pro Asn Leu Pro Lys Glu Lys Leu Glu Arg Val Ile Leu
        115                 120                 125

Gly Ser Lys Ala Ala Gln Gln His Pro Glu Glu Val Arg Ser Leu Trp
    130                 135                 140

Gln Thr Cys Gly Glu Leu Met Phe Ser Leu Glu Pro Arg Leu Arg His
145                 150                 155                 160

Leu Gly Leu Gly Lys Glu Gly Val Thr Thr Tyr Phe Ser Gly Asp Cys
                165                 170                 175

Ala Met Glu Asp Ala Lys Leu Ala Gln Asp Phe Leu Asp Ser Gln Asn
            180                 185                 190

Leu Ser Ala Tyr Asn Thr Arg Leu Phe Lys Val Val Gly Gln Glu Gly
        195                 200                 205
```

```
Lys Tyr His Tyr Glu Val Arg Leu Ala Ser Val Leu Asn Thr Glu Pro
    210                 215                 220

Ala Leu Asp Ser Glu Leu Thr Ser Lys Leu Lys Ser Tyr Glu Phe Gln
225                 230                 235                 240

Gly Asn His Phe Gln Val Thr Arg Gly Asp Tyr Ala Pro Ile Leu Gln
                245                 250                 255

Lys Val Glu His Leu Glu Lys Ala Lys Ala Tyr Ala Ala Asn Ser
            260                 265                 270

His Gln Glu Gln Met Leu Ala Gln Tyr Val Glu Ser Phe Thr Gln Gly
        275                 280                 285

Ser Ile Glu Ala His Lys Arg Gly Ser Arg Phe Trp Ile Gln Asp Lys
        290                 295                 300

Gly Pro Ile Val Glu Ser Tyr Ile Gly Phe Ile Glu Ser Tyr Arg Asp
305                 310                 315                 320

Pro Phe Gly Ser Arg Gly Glu Phe Glu Gly Phe Val Ala Met Val Asn
                325                 330                 335

Lys Asp Met Ser Ala Lys Phe Glu Arg Leu Val Ala Ser Ala Glu Gln
            340                 345                 350

Leu Leu Lys Glu Leu Pro Trp Pro Pro Ala Phe Glu Lys Asp Lys Phe
        355                 360                 365

Leu Thr Pro Asp Phe Thr Ser Leu Asp Val Leu Thr Phe Ala Gly Ser
    370                 375                 380

Gly Ile Pro Ala Gly Ile Asn Ile Pro Asn Tyr Asp Asp Leu Arg Gln
385                 390                 395                 400

Thr Glu Gly Phe Lys Asn Val Ser Leu Gly Asn Val Leu Ala Val Ala
                405                 410                 415

Tyr Ala Thr Lys Arg Glu Lys Leu Thr Phe Met Glu Glu Asp Lys
            420                 425                 430

Asp Leu Tyr Ile Arg Trp Lys Gly Pro Ser Phe Asp Val Gln Val Gly
        435                 440                 445

Leu His Glu Leu Leu Gly His Gly Ser Gly Lys Leu Phe Val Gln Asp
    450                 455                 460

Glu Lys Gly Ala Phe Asn Phe Asp Gln Glu Thr Val Ile Asn Pro Glu
465                 470                 475                 480

Thr Gly Glu Gln Ile Gln Ser Trp Tyr Arg Ser Gly Glu Thr Trp Asp
                485                 490                 495

Ser Lys Phe Ser Thr Ile Ala Ser Ser Tyr Glu Glu Cys Arg Ala Glu
            500                 505                 510

Ser Val Gly Leu Tyr Leu Cys Leu Asn Pro Gln Val Leu Gln Ile Phe
        515                 520                 525

Gly Phe Glu Gly Thr Asp Ala Glu Asp Val Ile Tyr Val Asn Trp Leu
    530                 535                 540

Asn Met Val Arg Ala Gly Leu Leu Ala Leu Glu Phe Tyr Thr Pro Glu
545                 550                 555                 560

Thr Ala Asn Trp Arg Gln Ala His Met Gln Ala Arg Phe Val Ile Leu
                565                 570                 575

Arg Val Leu Leu Glu Ala Gly Glu Gly Leu Val Thr Val Thr Pro Thr
            580                 585                 590

Thr Gly Ser Asp Gly Arg Pro Asp Ala Arg Val His Leu Asp Arg Ser
        595                 600                 605

Lys Ile Arg Ser Val Gly Lys Pro Ala Leu Glu Arg Phe Leu Arg Arg
    610                 615                 620
```

-continued

```
Leu Gln Val Leu Lys Ser Thr Gly Asp Val Val Ala Gly Arg Ala Leu
625                 630                 635                 640

Tyr Glu Gly Tyr Ala Ala Val Thr Asp Ala Pro Pro Glu Cys Phe Leu
            645                 650                 655

Thr Leu Arg Asp Thr Val Leu Leu Arg Lys Glu Ser Arg Lys Leu Ile
            660                 665                 670

Val Gln Pro Asn Thr Arg Leu Glu Gly Ser Glu Val Gln Leu Val Glu
            675                 680                 685

Tyr Glu Ala Ser Ala Ala Gly Leu Ile Arg Ser Phe Cys Glu Arg Phe
690                 695                 700

Pro Glu Asp Gly Pro Glu Leu Glu Glu Val Leu Thr Gln Leu Ala Thr
705                 710                 715                 720

Ala Asp Ala Gln Phe Trp Arg Asp Gln Val Gln Glu Ala Pro Ser Gly
            725                 730                 735

Gln Ala

<210> SEQ ID NO 16
<211> LENGTH: 660
<212> TYPE: PRT
<213> ORGANISM: Porphyromonas gingivalis
<220> FEATURE:
<221> NAME/KEY: Dipeptidyl peptidase 5 (DPP5)
<222> LOCATION: (1)..(660)
<223> OTHER INFORMATION: Uniprot accession B2RIT0

<400> SEQUENCE: 16

Thr Asn Thr Gly Glu His Leu Thr Pro Glu Leu Phe Met Thr Leu Ser
1               5                   10                  15

Arg Val Ser Glu Met Ala Leu Ser Pro Asp Gly Lys Thr Ala Val Tyr
            20                  25                  30

Ala Val Ser Phe Pro Asp Val Lys Thr Asn Lys Ala Thr Arg Glu Leu
        35                  40                  45

Phe Thr Val Asn Leu Asp Gly Ser Gly Arg Lys Gln Ile Thr Asp Thr
    50                  55                  60

Glu Ser Asn Glu Tyr Ala Pro Ala Trp Met Ala Asp Gly Lys Arg Ile
65                  70                  75                  80

Ala Phe Met Ser Asn Glu Gly Gly Ser Met Gln Leu Trp Val Met Asn
                85                  90                  95

Ala Asp Gly Thr Glu Arg Arg Gln Leu Ser Asn Ile Glu Gly Gly Ile
            100                 105                 110

Thr Gly Phe Leu Phe Ser Pro Asp Glu Lys Gln Val Leu Phe Thr Lys
        115                 120                 125

Asp Ile Lys Phe Gly Lys Arg Thr Lys Asp Ile Tyr Pro Asp Leu Asp
    130                 135                 140

Lys Ala Thr Gly Arg Ile Ile Thr Asp Leu Met Tyr Lys His Trp Asp
145                 150                 155                 160

Glu Trp Val Glu Thr Ile Pro His Pro Phe Ile Ala Asn Ala Thr Asp
                165                 170                 175

Gly Met Ile Thr Thr Gly Lys Asp Ile Met Glu Gly Glu Pro Tyr Glu
            180                 185                 190

Ala Pro Met Lys Pro Trp Ser Gly Ile Glu Asp Phe Ser Trp Ser Pro
        195                 200                 205

Asp Gly Gln Asn Ile Ala Tyr Ala Ser Arg Lys Lys Thr Gly Met Ala
    210                 215                 220

Tyr Ser Leu Ser Thr Asn Ser Asp Ile Tyr Ile Tyr Asn Leu Thr Ser
225                 230                 235                 240
```

-continued

```
Gly Arg Thr His Asn Ile Ser Glu Gly Met Met Gly Tyr Asp Thr Tyr
            245                 250                 255

Pro Lys Phe Ser Pro Asp Gly Lys Ser Ile Ala Trp Ile Ser Met Glu
            260                 265                 270

Arg Asp Gly Tyr Glu Ser Asp Leu Lys Arg Leu Phe Val Ala Asp Leu
            275                 280                 285

Ala Thr Gly Lys Arg Thr His Val Asn Pro Thr Phe Asp Tyr Asn Val
            290                 295                 300

Asp Met Ile Gln Trp Ala Pro Asp Ser Lys Gly Ile Tyr Phe Leu Ala
305                 310                 315                 320

Cys Lys Glu Ala Glu Thr Asn Leu Trp Glu Ile Thr Leu Lys Thr Gly
            325                 330                 335

Lys Ile Arg Gln Ile Thr Gln Gly Gln His Asp Tyr Ala Asp Phe Ser
            340                 345                 350

Val Arg Asn Asp Val Met Leu Ala Lys Arg His Ser Phe Glu Leu Pro
            355                 360                 365

Asp Asp Leu Tyr Arg Val Asn Pro Lys Asn Gly Ala Ala Gln Ala Val
            370                 375                 380

Thr Ala Glu Asn Lys Ala Ile Leu Asp Arg Leu Thr Pro Ile Ala Cys
385                 390                 395                 400

Glu Lys Arg Trp Met Lys Thr Thr Asp Gly Gly Asn Met Leu Thr Trp
            405                 410                 415

Val Val Leu Pro Pro Asp Phe Asp Lys Asn Lys Lys Tyr Pro Ala Ile
            420                 425                 430

Leu Tyr Cys Gln Gly Gly Pro Gln Asn Thr Val Ser Gln Phe Trp Ser
            435                 440                 445

Phe Arg Trp Asn Leu Arg Leu Met Ala Glu Gly Tyr Ile Val Ile
            450                 455                 460

Ala Pro Asn Arg His Gly Val Pro Gly Phe Gly Gln Lys Trp Asn Glu
465                 470                 475                 480

Gln Ile Ser Gly Asp Tyr Gly Gly Gln Asn Met Arg Asp Tyr Leu Thr
            485                 490                 495

Ala Val Asp Glu Met Lys Lys Glu Pro Tyr Val Asp Gly Asp Arg Ile
            500                 505                 510

Gly Ala Val Gly Ala Ser Tyr Gly Gly Phe Ser Val Tyr Trp Leu Ala
            515                 520                 525

Gly His His Asp Lys Arg Phe Ala Ala Phe Ile Ala His Ala Gly Ile
            530                 535                 540

Phe Asn Leu Glu Met Gln Tyr Ala Thr Thr Glu Glu Met Trp Phe Ala
545                 550                 555                 560

Asn Trp Asp Ile Gly Gly Pro Phe Trp Glu Lys Asp Asn Val Val Ala
            565                 570                 575

Gln Arg Thr Tyr Ala Thr Ser Pro His Lys Tyr Val Gln Asn Trp Asp
            580                 585                 590

Thr Pro Ile Leu Met Ile His Gly Glu Leu Asp Phe Arg Ile Leu Ala
            595                 600                 605

Ser Gln Ala Met Ala Ala Phe Asp Ala Ala Gln Leu Arg Gly Val Pro
            610                 615                 620

Ser Glu Met Leu Ile Tyr Pro Asp Glu Asn His Trp Val Leu Gln Pro
625                 630                 635                 640

Gln Asn Ala Leu Leu Phe His Arg Thr Phe Phe Gly Trp Leu Asp Arg
            645                 650                 655
```

-continued

Trp Leu Lys Lys
              660

<210> SEQ ID NO 17
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 17

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Val Ala Ser Leu Gly
            180                 185                 190

Met Trp Pro Ser His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
    210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Trp Gly Trp
    290                 295                 300

Asn Asn Thr Ser Lys Lys Tyr Asp Gly Gln Leu Glu Gly Phe Lys Arg
305                 310                 315                 320

Ile Asp Ala Ala Gly Gln Lys Leu Arg Glu Glu Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
        355                 360                 365

Asp Leu Thr Leu Ala Leu Phe Asn Asn Thr Ala Met Leu Gly Ser Ala
    370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
                420                 425                 430

Gln Glu Tyr Trp Leu Asn Glu Tyr Ile Lys Leu Pro Ala Asp Gln Arg
            435                 440                 445

Val Ala Val Asp Ala Trp Leu Gly Gly Asn Asp Ala Ala Ala Val
    450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
        530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 18
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 18

Gly Glu Gly Met Trp Val Pro Gln Gln Leu Pro Glu Ile Ala Gly Pro

-continued

```
1               5                   10                  15
Leu Lys Lys Ala Gly Leu Lys Leu Ser Pro Gln Gln Ile Ser Asp Leu
                20                  25                  30

Thr Gly Asp Pro Met Gly Ala Val Val Ala Leu Gly Gly Cys Thr Ala
                35                  40                  45

Ser Phe Val Ser Pro Asn Gly Leu Val Val Thr Asn His His Cys Ala
                50                  55                  60

Tyr Gly Ala Ile Gln Leu Asn Ser Thr Ala Glu Asn Asn Leu Ile Lys
 65                 70                  75                  80

Asn Gly Phe Asn Ala Pro Thr Thr Ala Asp Glu Val Ser Ala Gly Pro
                    85                  90                  95

Asn Ala Arg Val Phe Val Leu Asp Glu Ile Thr Asp Val Thr Lys Asp
                100                 105                 110

Ala Lys Ala Ala Ile Ala Ala Ala Gly Asp Asp Ala Leu Ala Arg Thr
                115                 120                 125

Lys Ala Leu Glu Ala Phe Glu Lys Lys Leu Ile Ala Asp Cys Glu Ala
            130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
                180                 185                 190

Met Trp Pro Thr His Thr Gly Asp Phe Ala Phe Tyr Arg Ala Tyr Val
                195                 200                 205

Gly Lys Asp Gly Lys Pro Ala Ala Phe Ser Lys Asp Asn Val Pro Tyr
            210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
                260                 265                 270

Ala Arg His Tyr Lys Asn Gln Ile Ala Met Val Glu Ala Ala Gly Lys
                275                 280                 285

Gln Asn Ala Asp Ile Gln Val Lys Tyr Ala Ala Thr Met Ala Gly Trp
            290                 295                 300

Asn Arg Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
            355                 360                 365

Asp Leu Thr Leu Ala Leu Phe Asn Asn Thr Ala Met Leu Gly Ser Ala
370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
            420                 425                 430
```

```
Gln Glu Tyr Trp Leu Asn Glu Tyr Ile Lys Leu Pro Ala Asp Gln Arg
            435                 440                 445

Val Ala Val Asp Ala Trp Leu Gly Gly Asn Asp Ala Ala Val
    450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
                500                 505                 510

Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
        530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
        610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
        690                 695

<210> SEQ ID NO 19
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 19

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
```

```
                    85                  90                  95
Asn Ala Arg Val Phe Val Leu Asp Glu Ile Thr Asp Val Thr Lys Asp
                100                 105                 110

Ala Lys Ala Ala Ile Ala Ala Ala Gly Asp Asp Ala Leu Ala Arg Thr
                115                 120                 125

Lys Ala Leu Glu Ala Phe Glu Lys Lys Leu Ile Ala Asp Cys Glu Ala
            130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
                180                 185                 190

Met Trp Pro Val His Thr Gly Asp Phe Ala Phe Tyr Arg Ala Tyr Val
            195                 200                 205

Gly Lys Asp Gly Lys Pro Ala Ala Phe Ser Lys Asp Asn Val Pro Tyr
            210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
                260                 265                 270

Ala Arg His Tyr Lys Asn Gln Ile Ala Met Val Glu Ala Ala Gly Lys
            275                 280                 285

Gln Asn Ala Asp Ile Gln Val Lys Tyr Ala Ala Thr Met Ala Gly Trp
            290                 295                 300

Asn Arg Thr Ser Lys Asn Tyr Asp Gly Gln Leu Glu Gly Phe Lys Arg
305                 310                 315                 320

Ile Asp Ala Ala Gly Gln Lys Leu Arg Glu Glu Ala Ala Val Leu Gly
                325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
            355                 360                 365

Asp Leu Thr Leu Ala Leu Phe Asn Asn Thr Ala Met Leu Gly Ser Ala
            370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
            420                 425                 430

Gln Glu Tyr Trp Leu Asn Glu Tyr Ile Lys Leu Pro Ala Asp Gln Arg
            435                 440                 445

Val Ala Val Asp Ala Trp Leu Gly Gly Asn Asp Ala Ala Ala Val
                450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
                500                 505                 510
```

```
Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
        530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
        610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
        690                 695

<210> SEQ ID NO 20
<211> LENGTH: 722
<212> TYPE: PRT
<213> ORGANISM: Pseudoxanthomonas mexicana
<220> FEATURE:
<221> NAME/KEY: Dipeptidyl Aminopeptidase BII (DAP BII) with Signal
      Sequence
<222> LOCATION: (1)..(722)
<223> OTHER INFORMATION: UniProt Accession No. V5YM14

<400> SEQUENCE: 20

Met Arg Pro Asn Leu Leu Ala Ala Ile Ala Val Pro Leu Ser Leu
1               5                   10                  15

Leu Ala Ala Gln Ile Ala Gln Ala Gly Glu Gly Met Trp Val Pro Gln
            20                  25                  30

Gln Leu Pro Glu Ile Ala Gly Pro Leu Lys Lys Ala Gly Leu Lys Leu
        35                  40                  45

Ser Pro Gln Gln Ile Ser Asp Leu Thr Gly Asp Pro Met Gly Ala Val
    50                  55                  60

Val Ala Leu Gly Gly Cys Thr Ala Ser Phe Val Ser Pro Asn Gly Leu
65                  70                  75                  80

Val Val Thr Asn His His Cys Ala Tyr Gly Ala Ile Gln Leu Asn Ser
                85                  90                  95

Thr Ala Glu Asn Asn Leu Ile Lys Asn Gly Phe Asn Ala Pro Thr Thr
            100                 105                 110

Ala Asp Glu Val Ser Ala Gly Pro Asn Ala Arg Val Phe Val Leu Asp
        115                 120                 125

Glu Ile Thr Asp Val Thr Lys Asp Ala Lys Ala Ile Ala Ala Ala
    130                 135                 140

Gly Asp Asp Ala Leu Ala Arg Thr Lys Ala Leu Glu Ala Phe Glu Lys
145                 150                 155                 160
```

```
Lys Leu Ile Ala Asp Cys Glu Ala Glu Ala Gly Phe Arg Cys Arg Leu
            165                 170                 175

Tyr Ser Phe Ser Gly Gly Asn Thr Tyr Arg Leu Phe Lys Asn Leu Glu
            180                 185                 190

Ile Lys Asp Val Arg Leu Ala Tyr Ala Pro Pro Gly Ser Val Gly Lys
            195                 200                 205

Phe Gly Gly Asp Ile Asp Asn Trp Met Trp Pro Arg His Thr Gly Asp
            210                 215                 220

Phe Ala Phe Tyr Arg Ala Tyr Val Gly Lys Asp Gly Lys Pro Ala Ala
225                 230                 235                 240

Phe Ser Lys Asp Asn Val Pro Tyr Gln Pro Lys His Trp Leu Lys Phe
            245                 250                 255

Ala Asp Gln Pro Leu Gly Ala Gly Asp Phe Val Met Val Ala Gly Tyr
            260                 265                 270

Pro Gly Ser Thr Asn Arg Tyr Ala Leu Ala Ala Glu Phe Asp Asn Thr
            275                 280                 285

Ala Gln Trp Thr Tyr Pro Thr Ile Ala Arg His Tyr Lys Asn Gln Ile
            290                 295                 300

Ala Met Val Glu Ala Ala Gly Lys Gln Asn Ala Asp Ile Gln Val Lys
305                 310                 315                 320

Tyr Ala Ala Thr Met Ala Gly Trp Asn Asn Thr Ser Lys Asn Tyr Asp
            325                 330                 335

Gly Gln Leu Glu Gly Phe Lys Arg Ile Asp Ala Ala Gly Gln Lys Leu
            340                 345                 350

Arg Glu Glu Ala Ala Val Leu Gly Trp Leu Lys Gly Gln Gly Ala Lys
            355                 360                 365

Gly Gln Pro Ala Leu Asp Ala His Ala Lys Leu Leu Asp Leu Leu Glu
            370                 375                 380

Gln Ser Lys Ala Thr Arg Asp Arg Asp Leu Thr Leu Ala Leu Phe Asn
385                 390                 395                 400

Asn Thr Ala Met Leu Gly Ser Ala Thr Gln Leu Tyr Arg Leu Ser Ile
            405                 410                 415

Glu Arg Glu Lys Pro Asn Ala Glu Arg Glu Ser Gly Tyr Gln Glu Arg
            420                 425                 430

Asp Leu Pro Ala Ile Glu Gly Gly Leu Lys Gln Leu Glu Arg Arg Tyr
            435                 440                 445

Val Ala Ala Met Asp Arg Gln Leu Gln Glu Tyr Trp Leu Asn Glu Tyr
450                 455                 460

Ile Lys Leu Pro Ala Asp Gln Arg Val Ala Val Asp Ala Trp Leu
465                 470                 475                 480

Gly Gly Asn Asp Ala Ala Val Lys Arg Ala Leu Asp Arg Leu Ala
            485                 490                 495

Gly Thr Lys Leu Gly Ser Thr Glu Arg Leu Lys Trp Phe Ala Ala
            500                 505                 510

Asp Arg Lys Ala Phe Glu Ala Ser Asn Asp Pro Ala Ile Gln Tyr Ala
            515                 520                 525

Val Ala Val Met Pro Thr Leu Leu Lys Leu Glu Gln Glu Arg Lys Thr
530                 535                 540

Arg Ala Gly Glu Asn Leu Ala Ala Arg Pro Val Tyr Leu Gln Ala Leu
545                 550                 555                 560

Ala Asp Tyr Lys Lys Ser Gln Gly Glu Phe Val Tyr Pro Asp Ala Asn
            565                 570                 575
```

-continued

```
Leu Ser Leu Arg Ile Thr Phe Gly Asn Val Met Tyr Ala Pro Lys
            580                 585                 590

Asp Gly Met Glu Tyr Thr Pro Phe Thr Thr Leu Glu Gly Val Val Ala
        595                 600                 605

Lys Glu Thr Gly Gln Asp Pro Phe Asp Ser Pro Lys Ala Leu Leu Asp
    610                 615                 620

Ala Val Ala Ala Lys Arg Tyr Gly Gly Leu Glu Asp Lys Arg Ile Gly
625                 630                 635                 640

Ser Val Pro Val Asn Tyr Leu Ser Asp Leu Asp Ile Thr Gly Gly Asn
            645                 650                 655

Ser Gly Ser Pro Val Leu Asp Ala His Gly Lys Leu Val Gly Leu Ala
        660                 665                 670

Phe Asp Gly Asn Trp Glu Ser Val Ser Ser Asn Trp Val Phe Asp Pro
    675                 680                 685

Lys Met Thr Arg Met Ile Ala Val Asp Gly Arg Tyr Leu Arg Trp Ile
690                 695                 700

Met Gln Glu Val Tyr Pro Ala Pro Gln Leu Leu Lys Glu Met Asn Val
705                 710                 715                 720

Gly Lys

<210> SEQ ID NO 21
<211> LENGTH: 4
<212> TYPE: PRT
<213> ORGANISM: Artificial Sequence
<220> FEATURE:
<223> OTHER INFORMATION: Test peptide

<400> SEQUENCE: 21

Ala Ala Ala Arg
1

<210> SEQ ID NO 22
<211> LENGTH: 19
<212> TYPE: PRT
<213> ORGANISM: Artificial Sequence
<220> FEATURE:
<223> OTHER INFORMATION: Test peptide
<220> FEATURE:
<221> NAME/KEY: MISC_FEATURE
<222> LOCATION: (19)..(19)
<223> OTHER INFORMATION: 3' - azide

<400> SEQUENCE: 22

Ala Ala Gly Val Ala Met Pro Gly Ala Glu Asp Val Val Gly Ser
1               5                   10                  15

Gly Ser Lys

<210> SEQ ID NO 23
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 23

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
```

```
            35                  40                  45
Ser Phe Val Ser Pro Asn Gly Leu Val Val Thr Asn His His Cys Ala
 50                  55                  60
Tyr Gly Ala Ile Gln Leu Asn Ser Thr Ala Glu Asn Asn Leu Ile Lys
 65                  70                  75                  80
Asn Gly Phe Asn Ala Pro Thr Thr Ala Asp Glu Val Ser Ala Gly Pro
                 85                  90                  95
Asn Ala Arg Val Phe Val Leu Asp Glu Ile Thr Asp Val Thr Lys Asp
                100                 105                 110
Ala Lys Ala Ala Ile Ala Ala Ala Gly Asp Asp Ala Leu Ala Arg Thr
                115                 120                 125
Lys Ala Leu Glu Ala Phe Glu Lys Lys Leu Ile Ala Asp Cys Glu Ala
130                 135                 140
Glu Ala Gly Phe Arg Cys Arg Leu Tyr Ser Phe Ser Gly Gly Asn Thr
145                 150                 155                 160
Tyr Arg Leu Phe Lys Asn Leu Glu Ile Lys Asp Val Arg Leu Ala Tyr
                165                 170                 175
Ala Pro Pro Gly Ser Val Gly Lys Phe Gly Gly Asp Ile Asp Met Gly
                180                 185                 190
Met Trp Pro Thr His Thr Gly Asp Phe Ala Phe Tyr Arg Ala Tyr Val
                195                 200                 205
Gly Lys Asp Gly Lys Pro Ala Ala Phe Ser Lys Asp Asn Val Pro Tyr
210                 215                 220
Gln Pro Lys His Trp Leu Lys Phe Ala Asp Gln Pro Leu Gly Ala Gly
225                 230                 235                 240
Asp Phe Val Met Val Ala Gly Tyr Pro Gly Ser Thr Asn Arg Tyr Ala
                245                 250                 255
Leu Ala Ala Glu Phe Asp Asn Thr Ala Gln Trp Thr Tyr Pro Thr Ile
                260                 265                 270
Ala Arg His Tyr Lys Asn Gln Ile Ala Met Val Glu Ala Ala Gly Lys
                275                 280                 285
Gln Asn Ala Asp Ile Gln Val Lys Tyr Ala Ala Thr Met Ala Gly Trp
290                 295                 300
Asn Arg Lys Ser Lys Asn Tyr Asp Gly Gln Leu Glu Gly Phe Lys Arg
305                 310                 315                 320
Ile Asp Ala Ala Gly Gln Lys Leu Arg Glu Glu Ala Ala Val Leu Gly
                325                 330                 335
Trp Leu Lys Gly Gln Gly Ala Lys Gly Gln Pro Ala Leu Asp Ala His
                340                 345                 350
Ala Lys Leu Leu Asp Leu Leu Glu Gln Ser Lys Ala Thr Arg Asp Arg
                355                 360                 365
Asp Leu Thr Leu Ala Leu Phe Asn Asn Thr Ala Met Leu Gly Ser Ala
                370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
                420                 425                 430
Gln Glu Tyr Trp Leu Asn Glu Tyr Ile Lys Leu Pro Ala Asp Gln Arg
                435                 440                 445
Val Ala Ala Val Asp Ala Trp Leu Gly Gly Asn Asp Ala Ala Ala Val
450                 455                 460
```

```
Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 24
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 24

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
```

-continued

```
            115                 120                 125
Lys Ala Leu Glu Ala Phe Glu Lys Lys Leu Ile Ala Asp Cys Glu Ala
130                 135                 140
Glu Ala Gly Phe Arg Cys Arg Leu Tyr Ser Phe Ser Gly Gly Asn Thr
145                 150                 155                 160
Tyr Arg Leu Phe Lys Asn Leu Glu Ile Lys Asp Val Arg Leu Ala Tyr
                165                 170                 175
Ala Pro Pro Gly Ser Val Gly Lys Phe Gly Gly Asp Ile Asp Met Gly
                180                 185                 190
Met Trp Pro Thr His Thr Gly Asp Phe Ala Phe Tyr Arg Ala Tyr Val
                195                 200                 205
Gly Lys Asp Gly Lys Pro Ala Ala Phe Ser Lys Asp Asn Val Pro Tyr
210                 215                 220
Gln Pro Lys His Trp Leu Lys Phe Ala Asp Gln Pro Leu Gly Ala Gly
225                 230                 235                 240
Asp Phe Val Met Val Ala Gly Tyr Pro Gly Ser Thr Asn Arg Tyr Ala
                245                 250                 255
Leu Ala Ala Glu Phe Asp Asn Thr Ala Gln Trp Thr Tyr Pro Thr Ile
                260                 265                 270
Ala Arg His Tyr Lys Asn Gln Ile Ala Met Val Glu Ala Ala Gly Lys
                275                 280                 285
Gln Asn Ala Asp Ile Gln Val Lys Tyr Ala Ala Thr Met Ala Gly Trp
290                 295                 300
Asn Arg Thr Ser Lys Asn Tyr Asp Gly Gln Leu Glu Gly Phe Lys Arg
305                 310                 315                 320
Ile Asp Ala Ala Gly Gln Lys Leu Arg Glu Ala Ala Val Leu Gly
                325                 330                 335
Trp Leu Lys Gly Gln Gly Ala Lys Gly Gln Pro Ala Leu Asp Ala His
                340                 345                 350
Ala Lys Leu Leu Asp Leu Leu Glu Gln Ser Lys Ala Thr Arg Asp Arg
                355                 360                 365
Asp Leu Thr Leu Ala Leu Phe Asn Asn Thr Ala Met Leu Gly Ser Ala
                370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
                420                 425                 430
Gln Glu Tyr Trp Leu Asn Glu Tyr Ile Lys Leu Pro Ala Asp Gln Arg
                435                 440                 445
Val Ala Val Asp Ala Trp Leu Gly Gly Asn Asp Ala Ala Ala Val
                450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
                500                 505                 510
Lys Leu Glu Gln Glu Arg Lys Thr Arg Ala Gly Glu Lys Leu Ala Val
                515                 520                 525
Arg Pro Val Tyr Leu Gln Ala Leu Ala Asp Tyr Lys Lys Ser Gln Gly
530                 535                 540
```

```
Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Val Lys Arg Tyr Gly
        595                 600                 605

Gly Leu Glu Asp Lys Arg Ile Gly Ser Val Pro Val Asn Tyr Leu Ser
610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Asn Glu Met Asn Val Gly Lys
    690                 695

<210> SEQ ID NO 25
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 25

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Thr Arg Thr
        115                 120                 125

Lys Ala Leu Glu Ala Phe Glu Lys Lys Leu Ile Ala Asp Cys Glu Ala
    130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
            180                 185                 190

Met Trp Pro Thr His Thr Gly Asp Phe Ala Phe Tyr Arg Ala Tyr Val
```

-continued

```
                195                 200                 205
Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Val Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
                260                 265                 270

Ala Arg His Tyr Lys Asn Gln Ile Ala Met Val Glu Ala Ala Gly Lys
            275                 280                 285

Gln Asn Ala Asp Ile Gln Val Lys Tyr Ala Ala Thr Met Ala Gly Trp
290                 295                 300

Asn Arg Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
            355                 360                 365

Asp Leu Thr Leu Ala Leu Phe Asn Asn Thr Ala Met Leu Gly Ser Ala
            370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
                420                 425                 430

Gln Glu Tyr Trp Leu Asn Glu Tyr Ile Lys Leu Pro Ala Asp Gln Arg
            435                 440                 445

Val Ala Val Asp Ala Trp Leu Gly Gly Asn Asp Ala Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
                500                 505                 510

Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
                580                 585                 590

Asp Ser Pro Lys Ala Leu Leu Asp Ala Val Ala Ala Lys Arg Tyr Gly
            595                 600                 605

Gly Leu Glu Asp Lys Arg Ile Gly Ser Val Pro Val Asn Tyr Leu Ser
610                 615                 620
```

```
Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
            645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
            675                 680                 685

Gln Leu Leu Lys Glu Met Asn Val Gly Lys
690                 695

<210> SEQ ID NO 26
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 26

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
                20                  25                  30

Thr Gly Asp Pro Met Gly Ala Val Ala Leu Gly Gly Cys Thr Ala
            35                  40                  45

Ser Phe Val Ser Pro Asn Gly Leu Val Val Thr Asn His His Cys Ala
50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
            180                 185                 190

Met Trp Pro Thr His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
```

```
            275                 280                 285
Gln Asn Ala Asp Ile Gln Val Lys Tyr Ala Ala Thr Met Ala Gly Trp
290                 295                 300

Asn Arg Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
                355                 360                 365

Asp Leu Thr Leu Ala Leu Phe Asn Asn Thr Ala Met Leu Gly Ser Ala
370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
                420                 425                 430

Gln Glu Tyr Trp Leu Asn Glu Tyr Ile Lys Leu Pro Ala Asp Gln Arg
                435                 440                 445

Val Ala Ala Val Asp Ala Trp Leu Gly Gly Asn Asp Ala Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
                500                 505                 510

Lys Leu Glu Gln Glu Arg Lys Thr Arg Ala Gly Glu Asn Leu Ala Ala
                515                 520                 525

Arg Pro Val Tyr Leu Gln Ala Leu Ala Asp Tyr Lys Lys Ser Gln Gly
530                 535                 540

Glu Leu Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
                580                 585                 590

Asp Ser Pro Lys Ala Leu Leu Asp Ala Val Ala Ala Lys Arg Tyr Gly
                595                 600                 605

Gly Leu Glu Asp Lys Arg Ile Gly Ser Val Pro Val Asn Tyr Leu Ser
                610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
                660                 665                 670

Asp Gly Arg Tyr Leu Arg Trp Ile Met Gln Glu Val Tyr Pro Ala Pro
                675                 680                 685

Gln Leu Leu Lys Glu Met Asn Val Gly Lys
690                 695
```

<210> SEQ ID NO 27
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 27

```
Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
            180                 185                 190

Met Trp Pro Thr His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
    210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
    290                 295                 300

Asn Arg Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
```

```
                355                 360                 365
Asp Leu Thr Leu Ala Leu Phe Asn Asn Thr Ala Met Leu Gly Ser Ala
        370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
            420                 425                 430
Gln Glu Tyr Trp Leu Asn Glu Tyr Ile Lys Leu Pro Ala Asp Gln Arg
        435                 440                 445
Val Ala Val Asp Ala Trp Leu Gly Gly Asn Asp Ala Ala Ala Val
    450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
            500                 505                 510
Lys Leu Glu Gln Glu Arg Lys Thr Arg Ala Gly Glu Asn Leu Ala Ala
        515                 520                 525
Arg Pro Val Tyr Leu Gln Ala Leu Ala Asp Tyr Lys Lys Ser Gln Gly
    530                 535                 540
Glu Phe Val Tyr Pro Asp Ala Asn Leu Ser Leu Arg Ile Thr Phe Gly
545                 550                 555                 560
Asn Val Met Gly Tyr Ala Pro Lys Asp Gly Met Glu Tyr Thr Pro Phe
                565                 570                 575
Thr Thr Leu Glu Gly Val Val Ala Lys Glu Thr Gly Gln Asp Pro Phe
            580                 585                 590
Asp Ser Pro Lys Ala Leu Leu Asp Ala Val Ala Ala Lys Arg Tyr Gly
        595                 600                 605
Gly Leu Glu Asp Lys Arg Ile Gly Ser Val Pro Val Asn Tyr Leu Ser
    610                 615                 620
Asp Leu Asp Ile Thr Gly Gly Asn Ser Gly Ser Pro Val Leu Asp Ala
625                 630                 635                 640
His Gly Lys Leu Val Gly Leu Ala Phe Ala Val Asn Trp Glu Ser Val
                645                 650                 655
Ser Ser Asn Trp Val Phe Asp Pro Ile Met Thr Arg Met Ile Ala Val
            660                 665                 670
Asp Gly Arg Tyr Leu Arg Trp Ile Met Gln Glu Val Tyr Pro Ala Pro
        675                 680                 685
Gln Leu Leu Lys Glu Met Asn Val Gly Lys
    690                 695

<210> SEQ ID NO 28
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 28

Gly Glu Gly Met Trp Val Pro Gln Gln Leu Pro Glu Ile Ala Gly Pro
1               5                   10                  15
```

```
Leu Lys Lys Ala Gly Leu Lys Leu Ser Pro Gln Gln Ile Ser Asp Leu
                20                  25                  30

Thr Gly Asp Pro Met Gly Ala Val Val Ala Leu Gly Gly Cys Thr Ala
            35                  40                  45

Ser Phe Val Ser Pro Asn Gly Leu Val Val Thr Asn His His Cys Ala
        50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
    130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
            180                 185                 190

Met Trp Pro Thr His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
    290                 295                 300

Asn Arg Thr Ser Lys Asn Tyr Asp Gly Gln Leu Gly Phe Lys Arg
305                 310                 315                 320

Ile Asp Ala Ala Gly Gln Lys Leu Arg Glu Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
        355                 360                 365

Asp Leu Thr Leu Ala Leu Phe Asn Asn Thr Ala Met Leu Gly Ser Ala
    370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
            420                 425                 430

Gln Glu Tyr Trp Leu Asn Glu Tyr Ile Lys Leu Pro Ala Asp Gln Arg
```

```
                435                 440                 445
Val Ala Val Asp Ala Trp Leu Gly Gly Asn Asp Ala Ala Val
        450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                    485                 490                 495

Asn Asp Pro Ala Ile Gln Tyr Ala Val Ala Val Met Pro Thr Leu Leu
                500                 505                 510

Lys Leu Glu Gln Glu Arg Lys Thr Arg Ala Gly Glu Asn Leu Ala Ala
                515                 520                 525

Arg Pro Val Tyr Leu Gln Ala Leu Ala Asp Tyr Lys Lys Ser Gln Gly
                530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
                580                 585                 590

Asp Ser Pro Lys Ala Leu Leu Asp Ala Val Ala Ala Lys Arg Tyr Gly
                595                 600                 605

Gly Leu Glu Asp Lys Arg Ile Gly Ser Val Pro Val Asn Tyr Leu Ser
                610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Val Asn Trp Glu Ser Val
                    645                 650                 655

Ser Ser Asn Trp Val Phe Asp Pro Lys Met Thr Arg Met Ile Ala Val
                660                 665                 670

Asp Gly Arg Tyr Leu Arg Trp Ile Met Gln Glu Val Tyr Pro Ala Pro
                675                 680                 685

Gln Leu Leu Lys Glu Met Asn Val Gly Lys
    690                 695

<210> SEQ ID NO 29
<211> LENGTH: 4
<212> TYPE: PRT
<213> ORGANISM: Artificial Sequence
<220> FEATURE:
<223> OTHER INFORMATION: Test Peptide

<400> SEQUENCE: 29

Ala Arg Ala Ala
1

<210> SEQ ID NO 30
<211> LENGTH: 7
<212> TYPE: PRT
<213> ORGANISM: Artificial Sequence
<220> FEATURE:
<223> OTHER INFORMATION: Test Peptide

<400> SEQUENCE: 30

Ile His Ala Gly Tyr Ala Trp
1               5

<210> SEQ ID NO 31
<211> LENGTH: 698
```

<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 31

```
Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
            85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Cys Leu
            180                 185                 190

Met Trp Pro Lys His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
    210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
290                 295                 300

Asn Arg Thr Ser Lys Asp Tyr Asp Gly Gln Leu Glu Gly Phe Lys Arg
305                 310                 315                 320

Ile Asp Ala Ala Gly Gln Lys Leu Arg Glu Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
        355                 360                 365

Asp Leu Thr Leu Ala Leu Phe Asn Asn Thr Ala Met Leu Gly Ser Ala
    370                 375                 380
```

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
            405                 410                 415

Leu Lys Gln Leu Glu Arg Arg Tyr Val Ala Ala Met Asp Arg Gln Leu
        420                 425                 430

Gln Glu Tyr Trp Leu Asn Glu Tyr Ile Lys Leu Pro Ala Asp Gln Arg
    435                 440                 445

Val Ala Val Asp Ala Trp Leu Gly Gly Asn Asp Ala Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Asp Tyr Asn Trp Glu Gly Gly
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 32
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 32

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala

```
                35                  40                  45
    Ser Phe Val Ser Pro Asn Gly Leu Val Val Thr Asn His His Cys Ala
     50                  55                  60
    Tyr Gly Ala Ile Gln Leu Asn Ser Thr Ala Glu Asn Asn Leu Ile Lys
     65                  70                  75                  80
    Asn Gly Phe Asn Ala Pro Thr Thr Ala Asp Glu Val Ser Ala Gly Pro
                     85                  90                  95
    Asn Ala Arg Val Phe Val Leu Asp Glu Ile Thr Asp Val Thr Lys Asp
                    100                 105                 110
    Ala Lys Ala Ala Ile Ala Ala Gly Asp Asp Ala Leu Ala Arg Thr
                    115                 120                 125
    Lys Ala Leu Glu Ala Phe Glu Lys Lys Leu Ile Ala Asp Cys Glu Ala
    130                 135                 140
    Glu Ala Gly Phe Arg Cys Arg Leu Tyr Ser Phe Ser Gly Gly Asn Thr
    145                 150                 155                 160
    Tyr Arg Leu Phe Lys Asn Leu Glu Ile Lys Asp Val Arg Leu Ala Tyr
                    165                 170                 175
    Ala Pro Pro Gly Ser Val Gly Lys Phe Gly Gly Asp Ile Asp Cys Leu
                    180                 185                 190
    Met Trp Pro Arg His Thr Gly Asp Phe Ala Phe Tyr Arg Ala Tyr Val
                    195                 200                 205
    Gly Lys Asp Gly Lys Pro Ala Ala Phe Ser Lys Asp Asn Val Pro Tyr
    210                 215                 220
    Gln Pro Lys His Trp Leu Lys Phe Ala Asp Gln Pro Leu Gly Ala Gly
    225                 230                 235                 240
    Asp Phe Val Met Val Ala Gly Tyr Pro Gly Ser Thr Asn Arg Tyr Ala
                    245                 250                 255
    Leu Ala Ala Glu Phe Asp Asn Thr Ala Gln Trp Thr Tyr Pro Thr Ile
                    260                 265                 270
    Ala Arg His Tyr Lys Asn Gln Ile Ala Met Val Glu Ala Ala Gly Lys
                    275                 280                 285
    Gln Asn Ala Asp Ile Gln Val Lys Tyr Ala Ala Thr Met Ala Gly Trp
    290                 295                 300
    Asn Arg Thr Ser Lys Asp Tyr Asp Gly Gln Leu Glu Gly Phe Lys Arg
    305                 310                 315                 320
    Ile Asp Ala Ala Gly Gln Lys Leu Arg Glu Glu Ala Ala Val Leu Gly
                    325                 330                 335
    Trp Leu Lys Gly Gln Gly Ala Lys Gly Gln Pro Ala Leu Asp Ala His
                    340                 345                 350
    Ala Lys Leu Leu Asp Leu Leu Glu Gln Ser Lys Ala Thr Arg Asp Arg
                    355                 360                 365
    Asp Leu Thr Leu Ala Leu Phe Asn Asn Thr Ala Met Leu Gly Ser Ala
                    370                 375                 380
    Thr Gln Leu Tyr Arg Leu Ser Ile Glu Arg Glu Lys Pro Asn Ala Glu
    385                 390                 395                 400
    Arg Glu Ser Gly Tyr Gln Glu Arg Asp Leu Pro Ala Ile Glu Gly Gly
                    405                 410                 415
    Leu Lys Gln Leu Glu Arg Arg Tyr Val Ala Ala Met Asp Arg Gln Leu
                    420                 425                 430
    Gln Glu Tyr Trp Leu Asn Glu Tyr Ile Lys Leu Pro Ala Asp Gln Arg
                    435                 440                 445
    Val Ala Ala Val Asp Ala Trp Leu Gly Gly Asn Asp Ala Ala Ala Val
    450                 455                 460
```

```
Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Asp Tyr Asn Trp Glu Gly Gly
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 33
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 33

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
```

```
            115                 120                 125
Lys Ala Leu Glu Ala Phe Glu Lys Lys Leu Ile Ala Asp Cys Glu Ala
    130                 135                 140
Glu Ala Gly Phe Arg Cys Arg Leu Tyr Ser Phe Ser Gly Gly Asn Thr
145                 150                 155                 160
Tyr Arg Leu Phe Lys Asn Leu Glu Ile Lys Asp Val Arg Leu Ala Tyr
                165                 170                 175
Ala Pro Pro Gly Ser Val Gly Lys Phe Gly Gly Asp Ile Asp Phe Phe
                180                 185                 190
Met Trp Pro Arg His Thr Gly Asp Phe Ala Phe Tyr Arg Ala Tyr Val
                195                 200                 205
Gly Lys Asp Gly Lys Pro Ala Ala Phe Ser Lys Asp Asn Val Pro Tyr
            210                 215                 220
Gln Pro Lys His Trp Leu Lys Phe Ala Asp Gln Pro Leu Gly Ala Gly
225                 230                 235                 240
Asp Phe Val Met Val Ala Gly Tyr Pro Gly Ser Thr Asn Arg Tyr Ala
                245                 250                 255
Leu Ala Ala Glu Phe Asp Asn Thr Ala Gln Trp Thr Tyr Pro Thr Ile
                260                 265                 270
Ala Arg His Tyr Lys Asn Gln Ile Ala Met Val Glu Ala Ala Gly Lys
                275                 280                 285
Gln Asn Ala Asp Ile Gln Val Lys Tyr Ala Ala Thr Met Ala Gly Trp
            290                 295                 300
Asn Arg Thr Ser Lys Gly Tyr Asp Gly Gln Leu Glu Gly Phe Lys Arg
305                 310                 315                 320
Ile Asp Ala Ala Gly Gln Lys Leu Arg Glu Ala Ala Val Leu Gly
                325                 330                 335
Trp Leu Lys Gly Gln Gly Ala Lys Gly Gln Pro Ala Leu Asp Ala His
                340                 345                 350
Ala Lys Leu Leu Asp Leu Leu Glu Gln Ser Lys Ala Thr Arg Asp Arg
            355                 360                 365
Asp Leu Thr Leu Ala Leu Phe Asn Asn Thr Ala Met Leu Gly Ser Ala
            370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
                420                 425                 430
Gln Glu Tyr Trp Leu Asn Glu Tyr Ile Lys Leu Pro Ala Asp Gln Arg
            435                 440                 445
Val Ala Val Asp Ala Trp Leu Gly Gly Asn Asp Ala Ala Ala Val
            450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
                500                 505                 510
Lys Leu Glu Gln Glu Arg Lys Thr Arg Ala Gly Glu Asn Leu Ala Ala
            515                 520                 525
Arg Pro Val Tyr Leu Gln Ala Leu Ala Asp Tyr Lys Lys Ser Gln Gly
            530                 535                 540
```

-continued

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Asp His Asn Trp Glu Ser Glu
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 34
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 34

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
    130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Arg Leu
            180                 185                 190

Met Trp Pro Arg His Thr Gly Asp Phe Ala Phe Tyr Arg Ala Tyr Val

```
            195                 200                 205
Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                    245                 250                 255

Leu Ala Ala Glu Phe Asp Asn Thr Ala Gln Trp Thr Tyr Pro Thr Ile
                260                 265                 270

Ala Arg His Tyr Lys Asn Gln Ile Ala Met Val Glu Ala Ala Gly Lys
            275                 280                 285

Gln Asn Ala Asp Ile Gln Val Lys Tyr Ala Ala Thr Met Ala Gly Trp
290                 295                 300

Asn Ser Thr Ser Lys Leu Tyr Asp Gly Gln Leu Glu Gly Phe Lys Arg
305                 310                 315                 320

Ile Asp Ala Ala Gly Gln Lys Leu Arg Glu Glu Ala Ala Val Leu Gly
                    325                 330                 335

Trp Leu Lys Gly Gln Gly Ala Lys Gly Gln Pro Ala Leu Asp Ala His
                340                 345                 350

Ala Lys Leu Leu Asp Leu Leu Glu Gln Ser Lys Ala Thr Arg Asp Arg
            355                 360                 365

Asp Leu Thr Leu Ala Leu Phe Asn Asn Thr Ala Met Leu Gly Ser Ala
370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                    405                 410                 415

Leu Lys Gln Leu Glu Arg Arg Tyr Val Ala Ala Met Asp Arg Gln Leu
                420                 425                 430

Gln Glu Tyr Trp Leu Asn Glu Tyr Ile Lys Leu Pro Ala Asp Gln Arg
            435                 440                 445

Val Ala Val Asp Ala Trp Leu Gly Gly Asn Asp Ala Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                    485                 490                 495

Asn Asp Pro Ala Ile Gln Tyr Ala Val Ala Val Met Pro Thr Leu Leu
                500                 505                 510

Lys Leu Glu Gln Glu Arg Lys Thr Arg Ala Gly Glu Asn Leu Ala Ala
            515                 520                 525

Arg Pro Val Tyr Leu Gln Ala Leu Ala Asp Tyr Lys Lys Ser Gln Gly
530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                    565                 570                 575

Thr Thr Leu Glu Gly Val Val Ala Lys Glu Thr Gly Gln Asp Pro Phe
                580                 585                 590

Asp Ser Pro Lys Ala Leu Leu Asp Ala Val Ala Ala Lys Arg Tyr Gly
            595                 600                 605

Gly Leu Glu Asp Lys Arg Ile Gly Ser Val Pro Val Asn Tyr Leu Ser
610                 615                 620
```

-continued

Asp Leu Asp Ile Thr Gly Gly Asn Ser Gly Ser Pro Val Leu Asp Ala
625                 630                 635                 640

His Gly Lys Leu Val Gly Leu Ala Phe Asp Thr Asn Trp Glu Thr Ser
            645                 650                 655

Ser Ser Asn Trp Val Phe Asp Pro Lys Met Thr Arg Met Ile Ala Val
        660                 665                 670

Asp Gly Arg Tyr Leu Arg Trp Ile Met Gln Glu Val Tyr Pro Ala Pro
            675                 680                 685

Gln Leu Leu Lys Glu Met Asn Val Gly Lys
690                 695

<210> SEQ ID NO 35
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 35

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
    130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Ser Trp
            180                 185                 190

Met Trp Pro His His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
    210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys

```
            275                 280                 285
Gln Asn Ala Asp Ile Gln Val Lys Tyr Ala Ala Thr Met Ala Gly Trp
290                 295                 300
Asn Ala Thr Ser Lys Asn Tyr Asp Gly Gln Leu Glu Gly Phe Lys Arg
305                 310                 315                 320
Ile Asp Ala Ala Gly Gln Lys Leu Arg Glu Ala Ala Val Leu Gly
            325                 330                 335
Trp Leu Lys Gly Gln Gly Ala Lys Gly Gln Pro Ala Leu Asp Ala His
            340                 345                 350
Ala Lys Leu Leu Asp Leu Leu Glu Gln Ser Lys Ala Thr Arg Asp Arg
            355                 360                 365
Asp Leu Thr Leu Ala Leu Phe Asn Asn Thr Ala Met Leu Gly Ser Ala
            370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
            420                 425                 430
Gln Glu Tyr Trp Leu Asn Glu Tyr Ile Lys Leu Pro Ala Asp Gln Arg
            435                 440                 445
Val Ala Val Asp Ala Trp Leu Gly Gly Asn Asp Ala Ala Ala Val
450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
                500                 505                 510
Lys Leu Glu Gln Glu Arg Lys Thr Arg Ala Gly Glu Asn Leu Ala Ala
            515                 520                 525
Arg Pro Val Tyr Leu Gln Ala Leu Ala Asp Tyr Lys Lys Ser Gln Gly
            530                 535                 540
Glu Phe Val Tyr Pro Asp Ala Asn Leu Ser Leu Arg Ile Thr Phe Gly
545                 550                 555                 560
Asn Val Met Gly Tyr Ala Pro Lys Asp Gly Met Glu Tyr Thr Pro Phe
                565                 570                 575
Thr Thr Leu Glu Gly Val Val Ala Lys Glu Thr Gly Gln Asp Pro Phe
            580                 585                 590
Asp Ser Pro Lys Ala Leu Leu Asp Ala Val Ala Ala Lys Arg Tyr Gly
            595                 600                 605
Gly Leu Glu Asp Lys Arg Ile Gly Ser Val Pro Val Asn Tyr Leu Ser
            610                 615                 620
Asp Leu Asp Ile Thr Gly Gly Asn Ser Gly Ser Pro Val Leu Asp Ala
625                 630                 635                 640
His Gly Lys Leu Val Gly Leu Ala Phe Gly Gly Asn Trp Glu Ser Val
                645                 650                 655
Ser Ser Asn Trp Val Phe Asp Pro Lys Met Thr Arg Met Ile Ala Val
                660                 665                 670
Asp Gly Arg Tyr Leu Arg Trp Ile Met Gln Glu Val Tyr Pro Ala Pro
            675                 680                 685
Gln Leu Leu Lys Glu Met Asn Val Gly Lys
            690                 695
```

<210> SEQ ID NO 36
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 36

```
Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Thr Trp
            180                 185                 190

Met Trp Pro His His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
    210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
    290                 295                 300

Asn Ala Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
```

```
                355                 360                 365
Asp Leu Thr Leu Ala Leu Phe Asn Asn Thr Ala Met Leu Gly Ser Ala
            370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
            420                 425                 430
Gln Glu Tyr Trp Leu Asn Glu Tyr Ile Lys Leu Pro Ala Asp Gln Arg
                435                 440                 445
Val Ala Val Asp Ala Trp Leu Gly Gly Asn Asp Ala Ala Ala Val
            450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
            500                 505                 510
Lys Leu Glu Gln Glu Arg Lys Thr Arg Ala Gly Glu Asn Leu Ala Ala
            515                 520                 525
Arg Pro Val Tyr Leu Gln Ala Leu Ala Asp Tyr Lys Lys Ser Gln Gly
            530                 535                 540
Glu Phe Val Tyr Pro Asp Ala Asn Leu Ser Leu Arg Ile Thr Phe Gly
545                 550                 555                 560
Asn Val Met Gly Tyr Ala Pro Lys Asp Gly Met Glu Tyr Thr Pro Phe
                565                 570                 575
Thr Thr Leu Glu Gly Val Val Ala Lys Glu Thr Gly Gln Asp Pro Phe
            580                 585                 590
Asp Ser Pro Lys Ala Leu Leu Asp Ala Val Ala Ala Lys Arg Tyr Gly
            595                 600                 605
Gly Leu Glu Asp Lys Arg Ile Gly Ser Val Pro Val Asn Tyr Leu Ser
            610                 615                 620
Asp Leu Asp Ile Thr Gly Gly Asn Ser Gly Ser Pro Val Leu Asp Ala
625                 630                 635                 640
His Gly Lys Leu Val Gly Leu Ala Phe Gly Gly Asn Trp Glu Ser Val
                645                 650                 655
Ser Ser Asn Trp Val Phe Asp Pro Lys Met Thr Arg Met Ile Ala Val
                660                 665                 670
Asp Gly Arg Tyr Leu Arg Trp Ile Met Gln Glu Val Tyr Pro Ala Pro
            675                 680                 685
Gln Leu Leu Lys Glu Met Asn Val Gly Lys
            690                 695

<210> SEQ ID NO 37
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 37

Gly Glu Gly Met Trp Val Pro Gln Gln Leu Pro Glu Ile Ala Gly Pro
1               5                   10                  15
```

```
Leu Lys Lys Ala Gly Leu Lys Leu Ser Pro Gln Gln Ile Ser Asp Leu
             20                  25                  30

Thr Gly Asp Pro Met Gly Ala Val Val Ala Leu Gly Gly Cys Thr Ala
         35                  40                  45

Ser Phe Val Ser Pro Asn Gly Leu Val Val Thr Asn His His Cys Ala
     50                  55                  60

Tyr Gly Ala Ile Gln Leu Asn Ser Thr Ala Glu Asn Asn Leu Ile Lys
 65                  70                  75                  80

Asn Gly Phe Asn Ala Pro Thr Thr Ala Asp Glu Val Ser Ala Gly Pro
                 85                  90                  95

Asn Ala Arg Val Phe Val Leu Asp Glu Ile Thr Asp Val Thr Lys Asp
             100                 105                 110

Ala Lys Ala Ala Ile Ala Ala Ala Gly Asp Asp Ala Leu Ala Arg Thr
         115                 120                 125

Lys Ala Leu Glu Ala Phe Glu Lys Lys Leu Ile Ala Asp Cys Glu Ala
     130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                 165                 170                 175

Ala Pro Pro Gly Ser Val Gly Lys Phe Gly Gly Asp Ile Asp Met Trp
             180                 185                 190

Met Trp Pro His His Thr Gly Asp Phe Ala Phe Tyr Arg Ala Tyr Val
         195                 200                 205

Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                 245                 250                 255

Leu Ala Ala Glu Phe Asp Asn Thr Ala Gln Trp Thr Tyr Pro Thr Ile
             260                 265                 270

Ala Arg His Tyr Lys Asn Gln Ile Ala Met Val Glu Ala Ala Gly Lys
         275                 280                 285

Gln Asn Ala Asp Ile Gln Val Lys Tyr Ala Ala Thr Met Ala Gly Trp
     290                 295                 300

Asn Ala Thr Ser Lys Asn Tyr Asp Gly Gln Leu Gly Phe Lys Arg
305                 310                 315                 320

Ile Asp Ala Ala Gly Gln Lys Leu Arg Glu Glu Ala Ala Val Leu Gly
                 325                 330                 335

Trp Leu Lys Gly Gln Gly Ala Lys Gly Gln Pro Ala Leu Asp Ala His
             340                 345                 350

Ala Lys Leu Leu Asp Leu Leu Glu Gln Ser Lys Ala Thr Arg Asp Arg
         355                 360                 365

Asp Leu Thr Leu Ala Leu Phe Asn Asn Thr Ala Met Leu Gly Ser Ala
     370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                 405                 410                 415

Leu Lys Gln Leu Glu Arg Arg Tyr Val Ala Ala Met Asp Arg Gln Leu
             420                 425                 430

Gln Glu Tyr Trp Leu Asn Glu Tyr Ile Lys Leu Pro Ala Asp Gln Arg
```

Val Ala Val Asp Ala Trp Leu Gly Gly Asn Asp Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Gly Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 38
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP BII)

<400> SEQUENCE: 38

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
                20                  25                  30

Thr Gly Asp Pro Met Gly Ala Val Ala Leu Gly Gly Cys Thr Ala
            35                  40                  45

Ser Phe Val Ser Pro Asn Gly Leu Val Val Thr Asn His His Cys Ala
        50                  55                  60

Tyr Gly Ala Ile Gln Leu Asn Ser Thr Ala Glu Asn Leu Ile Lys
65                  70                  75                  80

Asn Gly Phe Asn Ala Pro Thr Thr Ala Asp Glu Val Ser Ala Gly Pro
                85                  90                  95

```
Asn Ala Arg Val Phe Val Leu Asp Glu Ile Thr Asp Val Thr Lys Asp
                100                 105                 110
Ala Lys Ala Ala Ile Ala Ala Ala Gly Asp Asp Ala Leu Ala Arg Thr
            115                 120                 125
Lys Ala Leu Glu Ala Phe Glu Lys Lys Leu Ile Ala Asp Cys Glu Ala
        130                 135                 140
Glu Ala Gly Phe Arg Cys Arg Leu Tyr Ser Phe Ser Gly Gly Asn Thr
145                 150                 155                 160
Tyr Arg Leu Phe Lys Asn Leu Glu Ile Lys Asp Val Arg Leu Ala Tyr
                165                 170                 175
Ala Pro Pro Gly Ser Val Gly Lys Phe Gly Gly Asp Ile Asp Val Trp
            180                 185                 190
Met Trp Pro Arg His Thr Gly Asp Phe Ala Phe Tyr Arg Ala Tyr Val
        195                 200                 205
Gly Lys Asp Gly Lys Pro Ala Ala Phe Ser Lys Asp Asn Val Pro Tyr
210                 215                 220
Gln Pro Lys His Trp Leu Lys Phe Ala Asp Gln Pro Leu Gly Ala Gly
225                 230                 235                 240
Asp Phe Val Met Val Ala Gly Tyr Pro Gly Ser Thr Asn Arg Tyr Ala
                245                 250                 255
Leu Ala Ala Glu Phe Asp Asn Thr Ala Gln Trp Thr Tyr Pro Thr Ile
            260                 265                 270
Ala Arg His Tyr Lys Asn Gln Ile Ala Met Val Glu Ala Ala Gly Lys
        275                 280                 285
Gln Asn Ala Asp Ile Gln Val Lys Tyr Ala Ala Thr Met Ala Gly Trp
290                 295                 300
Asn Ala Thr Ser Lys Asn Tyr Asp Gly Gln Leu Glu Gly Phe Lys Arg
305                 310                 315                 320
Ile Asp Ala Ala Gly Gln Lys Leu Arg Glu Ala Ala Val Leu Gly
                325                 330                 335
Trp Leu Lys Gly Gln Gly Ala Lys Gly Gln Pro Ala Leu Asp Ala His
            340                 345                 350
Ala Lys Leu Leu Asp Leu Leu Glu Gln Ser Lys Ala Thr Arg Asp Arg
        355                 360                 365
Asp Leu Thr Leu Ala Leu Phe Asn Asn Thr Ala Met Leu Gly Ser Ala
370                 375                 380
Thr Gln Leu Tyr Arg Leu Ser Ile Glu Arg Glu Lys Pro Asn Ala Glu
385                 390                 395                 400
Arg Glu Ser Gly Tyr Gln Glu Arg Asp Leu Pro Ala Ile Glu Gly Gly
                405                 410                 415
Leu Lys Gln Leu Glu Arg Arg Tyr Val Ala Ala Met Asp Arg Gln Leu
            420                 425                 430
Gln Glu Tyr Trp Leu Asn Glu Tyr Ile Lys Leu Pro Ala Asp Gln Arg
        435                 440                 445
Val Ala Val Asp Ala Trp Leu Gly Gly Asn Asp Ala Ala Ala Val
450                 455                 460
Lys Arg Ala Leu Asp Arg Leu Ala Gly Thr Lys Leu Gly Ser Thr Glu
465                 470                 475                 480
Glu Arg Leu Lys Trp Phe Ala Ala Asp Arg Lys Ala Phe Glu Ala Ser
                485                 490                 495
Asn Asp Pro Ala Ile Gln Tyr Ala Val Ala Val Met Pro Thr Leu Leu
            500                 505                 510
Lys Leu Glu Gln Glu Arg Lys Thr Arg Ala Gly Glu Asn Leu Ala Ala
```

```
                515                 520                 525
Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Lys Arg Tyr Gly
                595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ser Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
                675                 680                 685

Gln Leu Leu Lys Glu Met Asn Val Gly Lys
    690                 695

<210> SEQ ID NO 39
<211> LENGTH: 698
<212> TYPE: PRT
<213> ORGANISM: Artificial Sequence
<220> FEATURE:
<223> OTHER INFORMATION: Modified Dipeptidyl Aminopeptidase BII (DAP
      BII)

<400> SEQUENCE: 39

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60

Tyr Gly Ala Ile Gln Leu Asn Ser Thr Ala Glu Asn Leu Ile Lys
65                  70                  75                  80

Asn Gly Phe Asn Ala Pro Thr Thr Ala Asp Glu Val Ser Ala Gly Pro
                85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
    130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175
```

-continued

```
Ala Pro Pro Gly Ser Val Gly Lys Phe Gly Asp Ile Asp Ser Trp
            180                 185                 190

Met Trp Pro Arg His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
        210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
        290                 295                 300

Asn Gly Thr Ser Lys Asn Tyr Asp Gly Gln Leu Glu Gly Phe Lys Arg
305                 310                 315                 320

Ile Asp Ala Ala Gly Gln Lys Leu Arg Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
        355                 360                 365

Asp Leu Thr Leu Ala Leu Phe Asn Asn Thr Ala Met Leu Gly Ser Ala
        370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
            420                 425                 430

Gln Glu Tyr Trp Leu Asn Glu Tyr Ile Lys Leu Pro Ala Asp Gln Arg
        435                 440                 445

Val Ala Val Asp Ala Trp Leu Gly Gly Asn Asp Ala Ala Val
450                 455                 460

Lys Arg Ala Leu Asp Arg Leu Ala Gly Thr Lys Leu Gly Ser Thr Glu
465                 470                 475                 480

Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
        530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
```

-continued

```
            595                 600                 605
Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ser Gly Asn Trp Glu Ser Val
                645                 650                 655

Ser Ser Asn Trp Val Phe Asp Pro Lys Met Thr Arg Met Ile Ala Val
                660                 665                 670

Asp Gly Arg Tyr Leu Arg Trp Ile Met Gln Glu Val Tyr Pro Ala Pro
                675                 680                 685

Gln Leu Leu Lys Glu Met Asn Val Gly Lys
    690                 695

<210> SEQ ID NO 40
<211> LENGTH: 7
<212> TYPE: PRT
<213> ORGANISM: Artificial Sequence
<220> FEATURE:
<223> OTHER INFORMATION: Test Peptide

<400> SEQUENCE: 40

Gly Arg Phe Ser Gly Ile Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: Test Peptide

<400> SEQUENCE: 41

Trp Thr Gln Ile Phe Gly Ala
1               5

<210> SEQ ID NO 42
<211> LENGTH: 700
<212> TYPE: PRT
<213> ORGANISM: Thermomonas hydrothermalis
<220> FEATURE:
<221> NAME/KEY: MISC_FEATURE
<222> LOCATION: (1)..(700)
<223> OTHER INFORMATION: Dipeptidyl peptidase (Peptidase S46) without
      the signal peptide

<400> SEQUENCE: 42

Asp Glu Gly Met Trp Val Pro Gln Gln Leu Pro Glu Ile Ala Gly Ala
1               5                   10                  15

Leu Lys Lys Ala Gly Leu Lys Leu Asp Pro Lys Gln Leu Ser Asp Leu
                20                  25                  30

Thr Gly Asp Pro Met Gly Ala Val Val Ser Leu Gly Gly Cys Thr Gly
            35                  40                  45

Ser Phe Val Ser Pro Gln Gly Leu Val Ala Thr Asn His His Cys Ala
    50                  55                  60

Tyr Gly Ala Ile Gln Leu Asn Ser Thr Pro Glu Lys Asn Leu Ile Lys
65                  70                  75                  80

Asp Gly Phe Asn Ala Pro Thr Gln Ala Asp Glu Leu Ser Ala Gly Pro
                85                  90                  95

Asn Ala Arg Ile Tyr Val Leu Glu Gly Ile Thr Asp Val Thr Ala Gln
            100                 105                 110
```

```
Ala Lys Ala Ala Met Ala Ala Ala Gly Asn Asp Pro Val Ala Arg Ala
        115                 120                 125

Asn Ala Leu Glu Ala Phe Glu Lys Lys Ile Thr Ser Asp Cys Glu Ala
        130                 135                 140

Glu Pro Gly Tyr Arg Cys Arg Val Tyr Ser Phe Met Gly Gly Ile Thr
145                 150                 155                 160

Tyr Arg Leu Phe Lys Asn Leu Glu Ile Lys Asp Val Arg Leu Val Tyr
                165                 170                 175

Ala Pro Pro Ser Ser Val Gly Lys Phe Gly Gly Asp Ile Asp Asn Trp
                180                 185                 190

Met Trp Pro Arg His Thr Gly Asp Phe Ser Phe Tyr Arg Ala Tyr Val
                195                 200                 205

Gly Lys Asp Gly Lys Pro Ala Pro Tyr Ser Lys Asp Asn Val Pro Tyr
        210                 215                 220

Arg Pro Lys His Trp Leu Lys Ile Ala Asp Thr Pro Leu Gly Glu Gly
225                 230                 235                 240

Asp Phe Val Met Val Ala Gly Tyr Pro Gly Arg Thr Asp Arg Tyr Ala
                245                 250                 255

Leu Val Ala Glu Phe Glu Asn Thr Gln Asn Trp Leu Tyr Pro Ala Ile
                260                 265                 270

Ser Lys Ala Tyr Lys Asp Gln Ile Ala Leu Val Glu Ala Ala Lys
        275                 280                 285

Asp Asn Pro Glu Ile Ala Val Lys Tyr Ala Ala Leu Ala Gly Trp
        290                 295                 300

Asn Asn Thr Ser Lys Asn Phe Asp Gly Gln Leu Glu Gly Phe Lys Arg
305                 310                 315                 320

Asn Asp Val Leu Ala Ile Lys Arg Arg Glu Ala Ala Val Leu Glu
                325                 330                 335

Trp Leu Arg Ala Arg Gly Lys Ala Gly Thr Pro Ala Leu Glu Ala His
                340                 345                 350

Ala Ala Leu Val Lys Leu Val Ala Asp Thr Ala Arg Thr Gln Glu Arg
        355                 360                 365

Asp Leu Val Leu Gly Ser Phe Asn Arg Thr Gly Ile Ile Gly Val Ala
        370                 375                 380

Val Asn Leu Tyr Arg Leu Ala Ile Glu Arg Gln Lys Pro Asp Ala Glu
385                 390                 395                 400

Arg Glu Pro Gly Tyr Gln Gln Arg Asp Leu Pro Val Ile Glu Gly Ser
                405                 410                 415

Leu Lys Gln Met Glu Arg Arg Tyr Val Pro Ala Met Asp Arg Gln Leu
                420                 425                 430

Arg Ala Tyr Trp Leu Asp Arg Tyr Val Ala Leu Pro Ala Ala Gln His
                435                 440                 445

Val Ala Ala Val Asp Ala Trp Leu Gly Gly Ser Asp Lys Ala Ala Ala
        450                 455                 460

Glu Ala Ala Leu Ala Arg Leu Asp Gln Ser Arg Leu Gly Ser Leu Glu
465                 470                 475                 480

Glu Arg Leu Lys Trp Phe Asn Ala Asp Arg Ala Ala Phe Glu Ala Ser
                485                 490                 495

Thr Asp Pro Ala Ile Gln Tyr Ala Val Ala Val Met Pro Thr Leu Leu
                500                 505                 510

Ala Met Glu Gln Gln Ala Lys Thr Arg Tyr Gly Val Ala Leu Glu Ala
        515                 520                 525
```

```
Arg Pro Arg Tyr Leu Gln Ala Val Val Asp Tyr Lys Lys Ser Lys Gly
        530                 535                 540

Gln Ala Val Tyr Pro Asp Ala Asn Ser Thr Leu Arg Ile Thr Tyr Gly
545                 550                 555                 560

His Val Lys Gly Tyr Thr Gly Leu Asn Gly Lys Val Tyr Thr Pro Phe
                565                 570                 575

Thr Thr Leu Glu Glu Val Ala Ala Lys Glu Thr Gly Val Glu Pro Phe
            580                 585                 590

Asp Asn Pro Lys Ala Leu Leu Glu Ala Val Ala Lys Arg Tyr Ala
                595                 600                 605

Gly Leu Ala Asp Ala Arg Leu Gly Thr Val Pro Val Asn Phe Leu Ala
610                 615                 620

Asp Leu Asp Ile Thr Gly Gly Asn Ser Gly Ser Pro Val Leu Asp Ala
625                 630                 635                 640

Asn Gly Arg Leu Val Gly Leu Ala Phe Asp Gly Thr Leu Glu Ser Val
                645                 650                 655

Ala Ser Asn Trp Val Phe Asp Pro Val Leu Thr Arg Met Ile Ser Val
                660                 665                 670

Asp Gln Arg Tyr Met Arg Trp Ile Met Gln Glu Val Met Pro Ala Pro
                675                 680                 685

Gln Leu Leu Glu Glu Leu Gly Val Pro Pro Arg Gln
            690                 695                 700

<210> SEQ ID NO 43
<211> LENGTH: 723
<212> TYPE: PRT
<213> ORGANISM: Thermomonas hydrothermalis
<220> FEATURE:
<221> NAME/KEY: MISC_FEATURE
<222> LOCATION: (1)..(723)
<223> OTHER INFORMATION: Dipeptidyl peptidase (Peptidase S46) with the
      signal peptide

<400> SEQUENCE: 43

Met His Lys Thr Arg Leu Val Ala Ala Leu Ala Ala Leu Ala Thr
1               5                   10                  15

Leu Ala Pro Ala Ala Trp Ala Asp Glu Gly Met Trp Val Pro Gln Gln
                20                  25                  30

Leu Pro Glu Ile Ala Gly Ala Leu Lys Lys Ala Gly Leu Lys Leu Asp
            35                  40                  45

Pro Lys Gln Leu Ser Asp Leu Thr Gly Asp Pro Met Gly Ala Val Val
50                  55                  60

Ser Leu Gly Gly Cys Thr Gly Ser Phe Val Ser Pro Gln Gly Leu Val
65                  70                  75                  80

Ala Thr Asn His His Cys Ala Tyr Gly Ala Ile Gln Leu Asn Ser Thr
                85                  90                  95

Pro Glu Lys Asn Leu Ile Lys Asp Gly Phe Asn Ala Pro Thr Gln Ala
            100                 105                 110

Asp Glu Leu Ser Ala Gly Pro Asn Ala Arg Ile Tyr Val Leu Glu Gly
        115                 120                 125

Ile Thr Asp Val Thr Ala Gln Ala Lys Ala Ala Met Ala Ala Ala Gly
130                 135                 140

Asn Asp Pro Val Ala Arg Ala Asn Ala Leu Glu Ala Phe Glu Lys Lys
145                 150                 155                 160

Ile Thr Ser Asp Cys Glu Ala Glu Pro Gly Tyr Arg Cys Arg Val Tyr
                165                 170                 175
```

```
Ser Phe Met Gly Gly Ile Thr Tyr Arg Leu Phe Lys Asn Leu Glu Ile
            180                 185                 190

Lys Asp Val Arg Leu Val Tyr Ala Pro Pro Ser Ser Val Gly Lys Phe
            195                 200                 205

Gly Gly Asp Ile Asp Asn Trp Met Trp Pro Arg His Thr Gly Asp Phe
            210                 215                 220

Ser Phe Tyr Arg Ala Tyr Val Gly Lys Asp Gly Lys Pro Ala Pro Tyr
225                 230                 235                 240

Ser Lys Asp Asn Val Pro Tyr Arg Pro Lys His Trp Leu Lys Ile Ala
            245                 250                 255

Asp Thr Pro Leu Gly Glu Gly Asp Phe Val Met Val Ala Gly Tyr Pro
            260                 265                 270

Gly Arg Thr Asp Arg Tyr Ala Leu Val Ala Glu Phe Glu Asn Thr Gln
            275                 280                 285

Asn Trp Leu Tyr Pro Ala Ile Ser Lys Ala Tyr Lys Asp Gln Ile Ala
            290                 295                 300

Leu Val Glu Ala Ala Lys Asp Asn Pro Glu Ile Ala Val Lys Tyr
305                 310                 315                 320

Ala Ala Ala Leu Ala Gly Trp Asn Asn Thr Ser Lys Asn Phe Asp Gly
                325                 330                 335

Gln Leu Glu Gly Phe Lys Arg Asn Asp Val Leu Ala Ile Lys Arg Arg
            340                 345                 350

Glu Glu Ala Ala Val Leu Glu Trp Leu Arg Ala Arg Gly Lys Ala Gly
            355                 360                 365

Thr Pro Ala Leu Glu Ala His Ala Ala Leu Val Lys Leu Val Ala Asp
            370                 375                 380

Thr Ala Arg Thr Gln Glu Arg Asp Leu Val Leu Gly Ser Phe Asn Arg
385                 390                 395                 400

Thr Gly Ile Ile Gly Val Ala Val Asn Leu Tyr Arg Leu Ala Ile Glu
                405                 410                 415

Arg Gln Lys Pro Asp Ala Glu Arg Glu Pro Gly Tyr Gln Gln Arg Asp
            420                 425                 430

Leu Pro Val Ile Glu Gly Ser Leu Lys Gln Met Glu Arg Arg Tyr Val
            435                 440                 445

Pro Ala Met Asp Arg Gln Leu Arg Ala Tyr Trp Leu Asp Arg Tyr Val
450                 455                 460

Ala Leu Pro Ala Ala Gln His Val Ala Val Asp Ala Trp Leu Gly
465                 470                 475                 480

Gly Ser Asp Lys Ala Ala Ala Glu Ala Leu Ala Arg Leu Asp Gln
            485                 490                 495

Ser Arg Leu Gly Ser Leu Glu Glu Arg Leu Lys Trp Phe Asn Ala Asp
            500                 505                 510

Arg Ala Ala Phe Glu Ala Ser Thr Asp Pro Ala Ile Gln Tyr Ala Val
            515                 520                 525

Ala Val Met Pro Thr Leu Leu Ala Met Glu Gln Ala Lys Thr Arg
            530                 535                 540

Tyr Gly Val Ala Leu Glu Ala Arg Pro Arg Tyr Leu Gln Ala Val Val
545                 550                 555                 560

Asp Tyr Lys Lys Ser Lys Gly Gln Ala Val Tyr Pro Asp Ala Asn Ser
            565                 570                 575

Thr Leu Arg Ile Thr Tyr Gly His Val Lys Gly Tyr Thr Gly Leu Asn
            580                 585                 590

Gly Lys Val Tyr Thr Pro Phe Thr Thr Leu Glu Glu Val Ala Ala Lys
```

```
                    595                 600                 605
Glu Thr Gly Val Glu Pro Phe Asp Asn Pro Lys Ala Leu Leu Glu Ala
610                 615                 620

Val Ala Ala Lys Arg Tyr Ala Gly Leu Ala Asp Ala Arg Leu Gly Thr
625                 630                 635                 640

Val Pro Val Asn Phe Leu Ala Asp Leu Asp Ile Thr Gly Gly Asn Ser
                645                 650                 655

Gly Ser Pro Val Leu Asp Ala Asn Gly Arg Leu Val Gly Leu Ala Phe
                660                 665                 670

Asp Gly Thr Leu Glu Ser Val Ala Ser Asn Trp Val Phe Asp Pro Val
                675                 680                 685

Leu Thr Arg Met Ile Ser Val Asp Gln Arg Tyr Met Arg Trp Ile Met
690                 695                 700

Gln Glu Val Met Pro Ala Pro Gln Leu Leu Glu Glu Leu Gly Val Pro
705                 710                 715                 720

Pro Arg Gln

<210> SEQ ID NO 44
<211> LENGTH: 692
<212> TYPE: PRT
<213> ORGANISM: Caldithrix abyssi
<220> FEATURE:
<221> NAME/KEY: MISC_FEATURE
<222> LOCATION: (1)..(692)
<223> OTHER INFORMATION: Dipeptidyl peptidase (S46 family peptidase)
      without the signal peptide

<400> SEQUENCE: 44

Glu Glu Gly Met Tyr Pro Ile Thr Glu Ile His Lys Leu Asn Leu Lys
1               5                   10                  15

Lys Leu Gly Ile Glu Leu Ser Ala Asp Gln Ile Phe Ser Glu Asn Glu
                20                  25                  30

Val Ser Leu Ser Asp Ala Ile Val Gln Ile Gly Gly Cys Thr Gly Ser
            35                  40                  45

Phe Ile Ser Pro Glu Gly Leu Ile Leu Thr Asn His His Cys Ala Phe
        50                  55                  60

Arg Ala Ile Gln Asn Ile Ser Ser Thr Glu Asn Asp Tyr Leu Thr Asn
65                  70                  75                  80

Gly Phe Val Ala His Thr Leu Gln Glu Arg Pro Ala Lys Gly Tyr
                85                  90                  95

Thr Val Arg Ile Thr Glu Arg Val Glu Asp Val Ser Gln Arg Val Leu
                100                 105                 110

Asn Ala Val Lys His Ile Glu Asp Pro Ile Glu Arg Glu Lys Ala Ile
            115                 120                 125

Glu Lys Ile Thr Lys Gln Ile Val Lys Glu Gln Gln Lys His Pro
        130                 135                 140

Gly Lys Arg Ala Ala Val Ser Glu Met Phe Pro Gly Lys Thr Tyr Tyr
145                 150                 155                 160

Leu Phe Ile Tyr Thr Tyr Leu Lys Asp Val Arg Leu Val Tyr Ala Pro
                165                 170                 175

Pro Arg Ser Ile Gly Glu Phe Gly Gly Glu Phe Asp Asn Trp Glu Trp
            180                 185                 190

Pro Arg His Thr Gly Asp Phe Thr Leu Met Arg Ala Tyr Val Ala Pro
        195                 200                 205

Asp Gly Ser Pro Ser Asp Tyr Ser Glu Glu Asn Val Pro Tyr Arg Pro
    210                 215                 220
```

```
Lys Ser Tyr Leu Lys Val Ala Ala Lys Gly Val Glu Glu Gly Asp Arg
225                 230                 235                 240

Val Phe Ile Leu Gly Tyr Pro Gly Arg Thr Tyr Arg His Arg Thr Ser
            245                 250                 255

Ala Phe Leu Ala Phe Glu Tyr Glu Phe Arg Met Pro Phe Val Val Asp
        260                 265                 270

Trp Tyr Gln Trp Gln Ile Asp Leu Leu Thr Thr Leu Gly Lys Asp Asp
        275                 280                 285

Ala Asp Arg Ser Leu Lys Phe Ser Ser Trp Ile Lys Gly Leu Ala Asn
290                 295                 300

Thr Glu Lys Asn Tyr Arg Gly Lys Leu Gln Gly Ile Arg Arg Ile Gly
305                 310                 315                 320

Leu Leu Glu Gln Lys Lys Asn Glu Glu Glu Lys Ile Gln Val Phe Ile
                325                 330                 335

Ala Glu Asn Asn Leu Lys Lys Tyr Gln His Val Leu Thr Glu Ile Lys
            340                 345                 350

Gln Ile Tyr His Thr Tyr Arg Gln Ser Ala Val Arg Glu Met Leu Leu
        355                 360                 365

Ser Tyr Phe Gly Arg Ser Pro Val Leu Pro Ala Val Ala Arg Thr Leu
370                 375                 380

Val Leu Ala Ala Glu Arg Gln Lys Glu Asp Leu Glu Arg Glu Arg
385                 390                 395                 400

Ala Phe Met Asp Arg Asn Phe Lys Arg Thr Gln Thr Tyr Thr Leu Leu
                405                 410                 415

Arg Leu Lys Asn Phe Asp Ser Gln Ala Asp Gln Leu Ile Leu Gln Glu
            420                 425                 430

Leu Leu Lys Lys Ala Ala Leu Pro Glu Asp Gln Arg Ile Ser Ala
                435                 440                 445

Leu Arg Ser Ile Phe Lys Leu Asp Asp Ala Ala Glu Thr Arg Gln Val
450                 455                 460

Ile Ser Glu Ala Tyr Arg Lys Thr Arg Leu Ser Asp Pro Glu Phe Val
465                 470                 475                 480

Lys Thr Cys Phe Ala Lys Thr Pro Asp Glu Leu Lys Ala Leu Asn Asp
                485                 490                 495

Pro Leu Ile Asn Trp Met Leu Ala Leu Lys Glu Asp Tyr Glu Thr Leu
            500                 505                 510

Lys Asn Ile Arg Lys Glu Arg Asn Gly Lys Leu Arg Arg Leu Arg Ala
        515                 520                 525

Leu Trp Leu Glu Ala Lys Gln Ala Tyr Leu Lys Thr Asp Phe Ile Pro
        530                 535                 540

Asp Ala Asn Gly Thr Tyr Arg Met Thr Phe Gly Phe Ile Glu Gly Tyr
545                 550                 555                 560

Ala Pro Ala Asp Ala Val Tyr Lys Ala Pro Ile Thr Thr Gly Arg Gly
            565                 570                 575

Ile Leu Glu Lys His Thr Gly Lys Ser Pro Phe Asp Thr Pro Glu Lys
        580                 585                 590

Leu Leu Ala Leu Leu Lys Ala Lys Gln Phe Gly Pro Phe Val Ser Lys
        595                 600                 605

Thr Val Gly Thr Leu Pro Val Gly Ile Leu Tyr Ser Cys Asp Thr Thr
610                 615                 620

Gly Gly Asn Ser Gly Ser Pro Val Leu Asn Ala Arg Gly Gln Leu Val
625                 630                 635                 640
```

```
Gly Leu Asn Phe Asp Arg Ala Phe Glu Ala Thr Ile Asn Asp Tyr Ala
            645                 650                 655

Trp Asn His Gln Tyr Ser Arg Ser Ile Gly Val Asp Ile Arg Tyr Ile
        660                 665                 670

Leu Phe Leu Leu Lys Tyr Phe Ser Gly Ala Glu His Leu Leu Glu Glu
            675                 680             685

Met Gly Val Gln
    690

<210> SEQ ID NO 45
<211> LENGTH: 710
<212> TYPE: PRT
<213> ORGANISM: Caldithrix abyssi
<220> FEATURE:
<221> NAME/KEY: MISC_FEATURE
<222> LOCATION: (1)..(710)
<223> OTHER INFORMATION: Dipeptidyl peptidase  (S46 family peptidase)
      with the signal peptide

<400> SEQUENCE: 45

Met Lys Ile Arg Leu Phe Gly Val Leu Leu Leu Phe Thr Phe Ser Leu
1               5                   10                  15

Phe Ala Glu Glu Gly Met Tyr Pro Ile Thr Glu Ile His Lys Leu Asn
            20                  25                  30

Leu Lys Lys Leu Gly Ile Glu Leu Ser Ala Asp Gln Ile Phe Ser Glu
        35                  40                  45

Asn Glu Val Ser Leu Ser Asp Ala Ile Val Gln Ile Gly Gly Cys Thr
    50                  55                  60

Gly Ser Phe Ile Ser Pro Glu Gly Leu Ile Leu Thr Asn His His Cys
65                  70                  75                  80

Ala Phe Arg Ala Ile Gln Asn Ile Ser Ser Thr Glu Asn Asp Tyr Leu
                85                  90                  95

Thr Asn Gly Phe Val Ala His Thr Leu Gln Glu Glu Arg Pro Ala Lys
            100                 105                 110

Gly Tyr Thr Val Arg Ile Thr Glu Arg Val Glu Asp Val Ser Gln Arg
        115                 120                 125

Val Leu Asn Ala Val Lys His Ile Glu Asp Pro Ile Glu Arg Glu Lys
    130                 135                 140

Ala Ile Glu Lys Ile Thr Lys Gln Ile Val Lys Glu Gln Glu Gln Lys
145                 150                 155                 160

His Pro Gly Lys Arg Ala Ala Val Ser Glu Met Phe Pro Gly Lys Thr
                165                 170                 175

Tyr Tyr Leu Phe Ile Tyr Thr Tyr Leu Lys Asp Val Arg Leu Val Tyr
            180                 185                 190

Ala Pro Pro Arg Ser Ile Gly Glu Phe Gly Gly Glu Phe Asp Asn Trp
        195                 200                 205

Glu Trp Pro Arg His Thr Gly Asp Phe Thr Leu Met Arg Ala Tyr Val
    210                 215                 220

Ala Pro Asp Gly Ser Pro Ser Asp Tyr Ser Glu Glu Asn Val Pro Tyr
225                 230                 235                 240

Arg Pro Lys Ser Tyr Leu Lys Val Ala Ala Lys Gly Val Glu Glu Gly
                245                 250                 255

Asp Arg Val Phe Ile Leu Gly Tyr Pro Gly Arg Thr Tyr Arg His Arg
            260                 265                 270

Thr Ser Ala Phe Leu Ala Phe Glu Tyr Glu Phe Arg Met Pro Phe Val
        275                 280                 285
```

```
Val Asp Trp Tyr Gln Trp Gln Ile Asp Leu Leu Thr Thr Leu Gly Lys
290                 295                 300

Asp Asp Ala Asp Arg Ser Leu Lys Phe Ser Ser Trp Ile Lys Gly Leu
305                 310                 315                 320

Ala Asn Thr Glu Lys Asn Tyr Arg Gly Lys Leu Gln Gly Ile Arg Arg
                325                 330                 335

Ile Gly Leu Leu Glu Gln Lys Lys Asn Glu Glu Lys Ile Gln Val
            340                 345                 350

Phe Ile Ala Glu Asn Asn Leu Lys Lys Tyr Gln His Val Leu Thr Glu
                355                 360                 365

Ile Lys Gln Ile Tyr His Thr Tyr Arg Gln Ser Ala Val Arg Glu Met
370                 375                 380

Leu Leu Ser Tyr Phe Gly Arg Ser Pro Val Leu Pro Ala Val Ala Arg
385                 390                 395                 400

Thr Leu Val Leu Ala Ala Glu Glu Arg Gln Lys Glu Asp Leu Glu Arg
                405                 410                 415

Glu Arg Ala Phe Met Asp Arg Asn Phe Lys Arg Thr Gln Thr Tyr Thr
                420                 425                 430

Leu Leu Arg Leu Lys Asn Phe Asp Ser Gln Ala Asp Gln Leu Ile Leu
                435                 440                 445

Gln Glu Leu Leu Lys Lys Ala Ala Leu Pro Glu Asp Gln Arg Ile
450                 455                 460

Ser Ala Leu Arg Ser Ile Phe Lys Leu Asp Ala Ala Glu Thr Arg
465                 470                 475                 480

Gln Val Ile Ser Glu Ala Tyr Arg Lys Thr Arg Leu Ser Asp Pro Glu
                485                 490                 495

Phe Val Lys Thr Cys Phe Ala Lys Thr Pro Asp Glu Leu Lys Ala Leu
                500                 505                 510

Asn Asp Pro Leu Ile Asn Trp Met Leu Ala Leu Lys Glu Asp Tyr Glu
                515                 520                 525

Thr Leu Lys Asn Ile Arg Lys Glu Arg Asn Gly Lys Leu Arg Arg Leu
530                 535                 540

Arg Ala Leu Trp Leu Glu Ala Lys Gln Ala Tyr Leu Lys Thr Asp Phe
545                 550                 555                 560

Ile Pro Asp Ala Asn Gly Thr Tyr Arg Met Thr Phe Gly Phe Ile Glu
                565                 570                 575

Gly Tyr Ala Pro Ala Asp Ala Val Tyr Lys Ala Pro Ile Thr Thr Gly
                580                 585                 590

Arg Gly Ile Leu Glu Lys His Thr Gly Lys Ser Pro Phe Asp Thr Pro
                595                 600                 605

Glu Lys Leu Leu Ala Leu Leu Lys Ala Lys Gln Phe Gly Pro Phe Val
610                 615                 620

Ser Lys Thr Val Gly Thr Leu Pro Val Gly Ile Leu Tyr Ser Cys Asp
625                 630                 635                 640

Thr Thr Gly Gly Asn Ser Gly Ser Pro Val Leu Asn Ala Arg Gly Gln
                645                 650                 655

Leu Val Gly Leu Asn Phe Asp Arg Ala Phe Glu Ala Thr Ile Asn Asp
                660                 665                 670

Tyr Ala Trp Asn His Gln Tyr Ser Arg Ser Ile Gly Val Asp Ile Arg
                675                 680                 685

Tyr Ile Leu Phe Leu Leu Lys Tyr Phe Ser Gly Ala Glu His Leu Leu
690                 695                 700

Glu Glu Met Gly Val Gln
```

<210> SEQ ID NO 46
<211> LENGTH: 190
<212> TYPE: PRT
<213> ORGANISM: Mus musculus
<220> FEATURE:
<221> NAME/KEY: MISC_FEATURE
<222> LOCATION: (1)..(190)
<223> OTHER INFORMATION: Lipocalin S066 (Neutrophil Gelatinase-associated Lipocalin)

<400> SEQUENCE: 46

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
            20                  25                  30

Val Val Gly Leu Ala Gly Asn Ala Val Gln Lys Lys Thr Glu Gly Ser
        35                  40                  45

Phe Thr Met Tyr Ser Thr Ile Tyr Glu Leu Gln Glu Asn Asn Ser Tyr
    50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95

Gly Asn Met His Arg Tyr Pro Gln Val Gln Ser Tyr Asn Val Gln Val
            100                 105                 110

Ala Thr Thr Asp Tyr Asn Gln Phe Ala Met Val Phe Phe Arg Lys Thr
        115                 120                 125

Ser Glu Asn Lys Gln Tyr Phe Lys Ile Thr Leu Tyr Gly Arg Thr Lys
    130                 135                 140

Glu Leu Ser Pro Glu Leu Lys Glu Arg Phe Thr Arg Phe Ala Lys Ser
145                 150                 155                 160

Leu Gly Leu Lys Asp Asp Asn Ile Ile Phe Ser Val Pro Thr Asp Gln
                165                 170                 175

Cys Ile Asp Asn Ser Ala Trp Ser His Pro Gln Phe Glu Lys
            180                 185                 190

<210> SEQ ID NO 47
<211> LENGTH: 7
<212> TYPE: PRT
<213> ORGANISM: Artificial Sequence
<220> FEATURE:
<223> OTHER INFORMATION: test peptide

<400> SEQUENCE: 47

Ile His Ala Gly Tyr Ala Trp
1               5

<210> SEQ ID NO 48
<211> LENGTH: 13
<212> TYPE: PRT
<213> ORGANISM: Artificial Sequence
<220> FEATURE:
<223> OTHER INFORMATION: test peptide
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 48

Xaa Gly Ala Glu Ile Ala Gly Asp Val Ala Gly Gly Lys

```
<210> SEQ ID NO 49
<211> LENGTH: 20
<212> TYPE: PRT
<213> ORGANISM: Artificial Sequence
<220> FEATURE:
<223> OTHER INFORMATION: test peptide

<400> SEQUENCE: 49

Leu Met Ser His Asn Ala Arg Gly Ala Glu Asp Asp Val Val Arg Gly
1               5                   10                  15

Gly Gly Gly Lys
            20

<210> SEQ ID NO 50
<211> LENGTH: 4
<212> TYPE: PRT
<213> ORGANISM: Artificial Sequence
<220> FEATURE:
<223> OTHER INFORMATION: test peptide

<400> SEQUENCE: 50

Leu Ala Ala Arg
1

<210> SEQ ID NO 51
<211> LENGTH: 13
<212> TYPE: PRT
<213> ORGANISM: Artificial Sequence
<220> FEATURE:
<223> OTHER INFORMATION: test peptide

<400> SEQUENCE: 51

Ala Ala Ala Glu Ile Arg Gly Asp Val Arg Gly Gly Lys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: test peptide

<400> SEQUENCE: 52

Ala Ala Glu Ile Arg Gly Asp Val Arg Gly Gly Lys
1               5                   10

<210> SEQ ID NO 53
<211> LENGTH: 5
<212> TYPE: PRT
<213> ORGANISM: Artificial Sequence
<220> FEATURE:
<223> OTHER INFORMATION: test peptide

<400> SEQUENCE: 53

Ala Ala Glu Ile Arg
1               5

<210> SEQ ID NO 54
<211> LENGTH: 4
<212> TYPE: PRT
<213> ORGANISM: Artificial Sequence
<220> FEATURE:
<223> OTHER INFORMATION: test peptide

<400> SEQUENCE: 54
```

Gly Asp Val Arg
1

<210> SEQ ID NO 55
<211> LENGTH: 17
<212> TYPE: PRT
<213> ORGANISM: Artificial Sequence
<220> FEATURE:
<223> OTHER INFORMATION: test peptide
<220> FEATURE:
<221> NAME/KEY: MISC_FEATURE
<222> LOCATION: (17)..(17)
<223> OTHER INFORMATION: C-terminal azide modification

<400> SEQUENCE: 55

Gly Val Ala Met Pro Gly Ala Glu Asp Asp Val Val Gly Ser Gly Ser
1               5                   10                  15

Lys

<210> SEQ ID NO 56
<211> LENGTH: 18
<212> TYPE: PRT
<213> ORGANISM: Artificial Sequence
<220> FEATURE:
<223> OTHER INFORMATION: test peptide
<220> FEATURE:
<221> NAME/KEY: MISC_FEATURE
<222> LOCATION: (18)..(18)
<223> OTHER INFORMATION: C-terminal azide modification

<400> SEQUENCE: 56

Ala Gly Val Ala Met Pro Gly Ala Glu Asp Asp Val Val Gly Ser Gly
1               5                   10                  15

Ser Lys

<210> SEQ ID NO 57
<211> LENGTH: 8
<212> TYPE: PRT
<213> ORGANISM: Artificial Sequence
<220> FEATURE:
<223> OTHER INFORMATION: test peptide

<400> SEQUENCE: 57

Leu Ile His Ala Gly Tyr Ala Trp
1               5

<210> SEQ ID NO 58
<211> LENGTH: 8
<212> TYPE: PRT
<213> ORGANISM: Artificial Sequence
<220> FEATURE:
<223> OTHER INFORMATION: test peptide
<220> FEATURE:
<221> NAME/KEY: MISC_FEATURE
<222> LOCATION: (1)..(1)
<223> OTHER INFORMATION: N-terminal 2-azidobenzamide modification

<400> SEQUENCE: 58

Ala Ile His Ala Gly Tyr Ala Trp
1               5

<210> SEQ ID NO 59
<211> LENGTH: 699
<212> TYPE: PRT
<213> ORGANISM: Artificial Sequence
<220> FEATURE:
<223> OTHER INFORMATION: mutated DPP11 from Porphyromonas gingivalis having N214M, W215G, R219V, N329I, D673A amino acids substitutions

<400> SEQUENCE: 59

Asp Glu Gly Met Trp Leu Met Gln Gln Leu Gly Arg Lys Tyr Ala Gln
1               5                   10                  15

Met Lys Glu Arg Gly Leu Lys Met Lys Glu Tyr Asp Leu Tyr Asn Pro
            20                  25                  30

Asn Gly Thr Ser Leu Lys Asp Ala Val Val Leu Phe Asp Gly Gly Cys
        35                  40                  45

Thr Gly Glu Val Val Ser Asp Arg Gly Leu Val Leu Thr Asn His His
    50                  55                  60

Cys Gly Tyr Asp Met Ile Gln Ala His Ser Thr Leu Glu His Asn Tyr
65                  70                  75                  80

Leu Glu Asn Gly Phe Trp Ala Met Arg Glu Ala Asp Glu Leu Pro Asn
                85                  90                  95

Lys Asp Ile Ser Val Val Phe Ile Asp Lys Ile Glu Asp Val Thr Asp
            100                 105                 110

Tyr Val Lys Lys Glu Leu Lys Ala Ile Lys Asp Pro Asn Ser Met Asp
        115                 120                 125

Tyr Leu Ser Pro Lys Tyr Leu Gln Lys Leu Ala Asp Lys Lys Ala Gly
    130                 135                 140

Lys Asn Phe Ser Ala Lys Asn Pro Gly Leu Ser Val Glu Ile Lys Ala
145                 150                 155                 160

Phe Tyr Gly Gly Asn Leu Tyr Leu Met Phe Thr Lys Lys Thr Tyr Thr
                165                 170                 175

Asp Val Arg Leu Val Gly Ala Pro Pro Ser Ser Ile Gly Lys Phe Gly
            180                 185                 190

Ala Asp Thr Asp Met Gly Ile Trp Pro Val His Thr Gly Asp Phe Ser
        195                 200                 205

Ile Phe Arg Ile Tyr Ala Asp Lys Asn Gly Asn Pro Ala Pro Tyr Ser
    210                 215                 220

Glu Asp Asn Val Pro Leu Lys Pro Lys Arg Phe Phe Asn Ile Ser Leu
225                 230                 235                 240

Gly Gly Val Gln Glu Asn Asp Tyr Ala Met Ile Met Gly Phe Pro Gly
                245                 250                 255

Thr Thr His Arg Tyr Phe Thr Ala Ser Glu Val Asp Glu Trp Lys Ser
            260                 265                 270

Ile Asp Asn Asp Ile Arg Ile Arg Met Arg Asp Ile Arg Gln Gly Val
        275                 280                 285

Met Leu Arg Glu Met Leu Ala Asp Pro Gln Ile Lys Ile Met Tyr Ser
    290                 295                 300

Ala Lys Tyr Ala Ala Ser Gln Ile Ala Tyr Lys Arg Ala Ile Gly Ala
305                 310                 315                 320

Asn Trp Ala Ile Lys Thr Arg Gly Leu Arg Gln Asn Lys Gln Ala Met
                325                 330                 335

Gln Asp Arg Leu Ile Ala Trp Gly Ala Lys Gln Gly Thr Pro Arg Tyr
            340                 345                 350

Glu Glu Ala Val His Glu Ile Asp Ala Thr Val Ala Lys Arg Ala Asp
        355                 360                 365

Leu Arg Arg Arg Tyr Trp Met Ile Glu Glu Gly Ile Ile Arg Gly Ile
    370                 375                 380

Glu Phe Ala Arg Ser Pro Ile Pro Thr Glu Asp Glu Thr Lys Ala Leu
385                 390                 395                 400

```
Gln Gly Asn Asp Ala Ser Ala Arg Lys Glu Ala Ile Asp Lys Ile Arg
                405                 410                 415

Thr Arg Tyr Ser Lys Phe Ala Asn Lys Asp Tyr Ser Ala Glu Val Asp
            420                 425                 430

Lys Lys Val Ala Val Ala Met Leu Thr Glu Tyr Leu Lys Glu Ile Pro
        435                 440                 445

Tyr Glu Asn Leu Pro Leu His Leu Arg Leu Val Lys Asp Arg Phe Ala
    450                 455                 460

Gly Asp Val Gln Ala Tyr Val Asp Ile Phe Ala Arg Ser Val Phe
465                 470                 475                 480

Gly Ser Glu Ala Gln Phe Asp Ala Phe Ala Val Pro Ser Val Glu
            485                 490                 495

Lys Leu Ala Glu Asp Pro Met Val Leu Phe Ala Ser Ser Val Phe Asp
        500                 505                 510

Glu Tyr Arg Lys Leu Tyr Asn Glu Leu Arg Pro Tyr Asp Asp Pro Ile
    515                 520                 525

Leu Arg Ala Gln Arg Thr Tyr Ile Ala Gly Leu Leu Glu Met Asp Gly
    530                 535                 540

Asp Gln Asp Gln Phe Pro Asp Ala Asn Leu Thr Leu Arg Phe Thr Tyr
545                 550                 555                 560

Gly Gln Val Lys Gly Tyr Ser Pro Arg Asp Asn Val Tyr Tyr Gly His
            565                 570                 575

Gln Thr Thr Leu Asp Gly Val Met Glu Lys Glu Asp Pro Asp Asn Trp
        580                 585                 590

Glu Phe Val Val Asp Pro Lys Leu Lys Ala Val Tyr Glu Arg Lys Asp
    595                 600                 605

Phe Gly Arg Tyr Ala Asp Arg Ser Gly Arg Met Pro Val Ala Phe Cys
610                 615                 620

Ala Thr Thr His Thr Thr Gly Gly Asn Ser Gly Ser Pro Val Met Asn
625                 630                 635                 640

Ala Asn Gly Glu Leu Ile Gly Leu Asn Phe Ala Arg Asn Trp Glu Gly
            645                 650                 655

Val Gly Gly Asp Ile Gln Tyr Leu Ala Asp Tyr Gln Arg Ser Ile Ile
        660                 665                 670

Val Asp Ile Arg Tyr Val Leu Leu Val Ile Asp Lys Val Gly Gly Cys
    675                 680                 685

Gln Arg Leu Leu Asp Glu Met Asn Ile Val Pro
    690                 695

<210> SEQ ID NO 60
<211> LENGTH: 698
<212> TYPE: PRT
<213> ORGANISM: Artificial Sequence
<220> FEATURE:
<223> OTHER INFORMATION: mutated Dap BII from Pseudoxanthomonas mexicana
      having N214M, W215G, R219T, N329R, D673A amino acids substitutions

<400> SEQUENCE: 60

Gly Glu Gly Met Trp Val Pro Gln Gln Leu Pro Glu Ile Ala Gly Pro
1               5                   10                  15

Leu Lys Lys Ala Gly Leu Lys Leu Ser Pro Gln Gln Ile Ser Asp Leu
            20                  25                  30

Thr Gly Asp Pro Met Gly Ala Val Val Ala Leu Gly Gly Cys Thr Ala
        35                  40                  45

Ser Phe Val Ser Pro Asn Gly Leu Val Val Thr Asn His His Cys Ala
    50                  55                  60
```

-continued

```
Tyr Gly Ala Ile Gln Leu Asn Ser Thr Ala Glu Asn Leu Ile Lys
 65                  70                  75                  80

Asn Gly Phe Asn Ala Pro Thr Thr Ala Asp Glu Val Ser Ala Gly Pro
                 85                  90                  95

Asn Ala Arg Val Phe Val Leu Asp Glu Ile Thr Asp Val Thr Lys Asp
            100                 105                 110

Ala Lys Ala Ala Ile Ala Ala Ala Gly Asp Asp Ala Leu Ala Arg Thr
        115                 120                 125

Lys Ala Leu Glu Ala Phe Glu Lys Lys Leu Ile Ala Asp Cys Glu Ala
130                 135                 140

Glu Ala Gly Phe Arg Cys Arg Leu Tyr Ser Phe Ser Gly Gly Asn Thr
145                 150                 155                 160

Tyr Arg Leu Phe Lys Asn Leu Glu Ile Lys Asp Val Arg Leu Ala Tyr
                165                 170                 175

Ala Pro Pro Gly Ser Val Gly Lys Phe Gly Gly Asp Ile Asp Met Gly
            180                 185                 190

Met Trp Pro Thr His Thr Gly Asp Phe Ala Phe Tyr Arg Ala Tyr Val
        195                 200                 205

Gly Lys Asp Gly Lys Pro Ala Ala Phe Ser Lys Asp Asn Val Pro Tyr
210                 215                 220

Gln Pro Lys His Trp Leu Lys Phe Ala Asp Gln Pro Leu Gly Ala Gly
225                 230                 235                 240

Asp Phe Val Met Val Ala Gly Tyr Pro Gly Ser Thr Asn Arg Tyr Ala
                245                 250                 255

Leu Ala Ala Glu Phe Asp Asn Thr Ala Gln Trp Thr Tyr Pro Thr Ile
            260                 265                 270

Ala Arg His Tyr Lys Asn Gln Ile Ala Met Val Glu Ala Ala Gly Lys
        275                 280                 285

Gln Asn Ala Asp Ile Gln Val Lys Tyr Ala Ala Thr Met Ala Gly Trp
290                 295                 300

Asn Arg Thr Ser Lys Asn Tyr Asp Gly Gln Leu Glu Gly Phe Lys Arg
305                 310                 315                 320

Ile Asp Ala Ala Gly Lys Leu Arg Glu Glu Ala Ala Val Leu Gly
                325                 330                 335

Trp Leu Lys Gly Gln Gly Ala Lys Gly Gln Pro Ala Leu Asp Ala His
            340                 345                 350

Ala Lys Leu Leu Asp Leu Leu Glu Gln Ser Lys Ala Thr Arg Asp Arg
        355                 360                 365

Asp Leu Thr Leu Ala Leu Phe Asn Asn Thr Ala Met Leu Gly Ser Ala
370                 375                 380

Thr Gln Leu Tyr Arg Leu Ser Ile Glu Arg Glu Lys Pro Asn Ala Glu
385                 390                 395                 400

Arg Glu Ser Gly Tyr Gln Glu Arg Asp Leu Pro Ala Ile Glu Gly Gly
                405                 410                 415

Leu Lys Gln Leu Glu Arg Arg Tyr Val Ala Ala Met Asp Arg Gln Leu
            420                 425                 430

Gln Glu Tyr Trp Leu Asn Glu Tyr Ile Lys Leu Pro Ala Asp Gln Arg
        435                 440                 445

Val Ala Ala Val Asp Ala Trp Leu Gly Gly Asn Asp Ala Ala Ala Val
450                 455                 460

Lys Arg Ala Leu Asp Arg Leu Ala Gly Thr Lys Leu Gly Ser Thr Glu
465                 470                 475                 480
```

```
Glu Arg Leu Lys Trp Phe Ala Ala Asp Arg Lys Ala Phe Glu Ala Ser
                485                 490                 495

Asn Asp Pro Ala Ile Gln Tyr Ala Val Ala Val Met Pro Thr Leu Leu
            500                 505                 510

Lys Leu Glu Gln Glu Arg Lys Thr Arg Ala Gly Glu Asn Leu Ala Ala
        515                 520                 525

Arg Pro Val Tyr Leu Gln Ala Leu Ala Asp Tyr Lys Lys Ser Gln Gly
    530                 535                 540

Glu Phe Val Tyr Pro Asp Ala Asn Leu Ser Leu Arg Ile Thr Phe Gly
545                 550                 555                 560

Asn Val Met Gly Tyr Ala Pro Lys Asp Gly Met Glu Tyr Thr Pro Phe
                565                 570                 575

Thr Thr Leu Glu Gly Val Val Ala Lys Glu Thr Gly Gln Asp Pro Phe
            580                 585                 590

Asp Ser Pro Lys Ala Leu Leu Asp Ala Val Ala Ala Lys Arg Tyr Gly
        595                 600                 605

Gly Leu Glu Asp Lys Arg Ile Gly Ser Val Pro Val Asn Tyr Leu Ser
    610                 615                 620

Asp Leu Asp Ile Thr Gly Gly Asn Ser Gly Ser Pro Val Leu Asp Ala
625                 630                 635                 640

His Gly Lys Leu Val Gly Leu Ala Phe Ala Gly Asn Trp Glu Ser Val
                645                 650                 655

Ser Ser Asn Trp Val Phe Asp Pro Lys Met Thr Arg Met Ile Ala Val
            660                 665                 670

Asp Gly Arg Tyr Leu Arg Trp Ile Met Gln Glu Val Tyr Pro Ala Pro
        675                 680                 685

Gln Leu Leu Lys Glu Met Asn Val Gly Lys
    690                 695

<210> SEQ ID NO 61
<211> LENGTH: 723
<212> TYPE: PRT
<213> ORGANISM: Artificial Sequence
<220> FEATURE:
<223> OTHER INFORMATION: mutated DPP from Thermomonas hydrothermalis
      having N214M, W215G, R219T, N329R, D673A amino acids substitutions

<400> SEQUENCE: 61

Met His Lys Thr Arg Leu Val Ala Ala Leu Ala Ala Leu Ala Thr
1               5                   10                  15

Leu Ala Pro Ala Ala Trp Ala Asp Glu Gly Met Trp Val Pro Gln Gln
            20                  25                  30

Leu Pro Glu Ile Ala Gly Ala Leu Lys Lys Ala Gly Leu Lys Leu Asp
        35                  40                  45

Pro Lys Gln Leu Ser Asp Leu Thr Gly Asp Pro Met Gly Ala Val Val
    50                  55                  60

Ser Leu Gly Gly Cys Thr Gly Ser Phe Val Ser Pro Gln Gly Leu Val
65                  70                  75                  80

Ala Thr Asn His His Cys Ala Tyr Gly Ala Ile Gln Leu Asn Ser Thr
                85                  90                  95

Pro Glu Lys Asn Leu Ile Lys Asp Gly Phe Asn Ala Pro Thr Gln Ala
            100                 105                 110

Asp Glu Leu Ser Ala Gly Pro Asn Ala Arg Ile Tyr Val Leu Glu Gly
        115                 120                 125

Ile Thr Asp Val Thr Ala Gln Ala Lys Ala Ala Met Ala Ala Ala Gly
    130                 135                 140
```

-continued

```
Asn Asp Pro Val Ala Arg Ala Asn Ala Leu Glu Ala Phe Glu Lys Lys
145                 150                 155                 160

Ile Thr Ser Asp Cys Glu Ala Glu Pro Gly Tyr Arg Cys Arg Val Tyr
            165                 170                 175

Ser Phe Met Gly Gly Ile Thr Tyr Arg Leu Phe Lys Asn Leu Glu Ile
            180                 185                 190

Lys Asp Val Arg Leu Val Tyr Ala Pro Ser Ser Val Gly Lys Phe
            195                 200                 205

Gly Gly Asp Ile Asp Met Gly Met Trp Pro Thr His Thr Gly Asp Phe
            210                 215                 220

Ser Phe Tyr Arg Ala Tyr Val Gly Lys Asp Gly Lys Pro Ala Pro Tyr
225                 230                 235                 240

Ser Lys Asp Asn Val Pro Tyr Arg Pro Lys His Trp Leu Lys Ile Ala
                245                 250                 255

Asp Thr Pro Leu Gly Glu Gly Asp Phe Val Met Val Ala Gly Tyr Pro
            260                 265                 270

Gly Arg Thr Asp Arg Tyr Ala Leu Val Ala Glu Phe Glu Asn Thr Gln
            275                 280                 285

Asn Trp Leu Tyr Pro Ala Ile Ser Lys Ala Tyr Lys Asp Gln Ile Ala
290                 295                 300

Leu Val Glu Ala Ala Ala Lys Asp Asn Pro Glu Ile Ala Val Lys Tyr
305                 310                 315                 320

Ala Ala Ala Leu Ala Gly Trp Asn Arg Thr Ser Lys Asn Phe Asp Gly
            325                 330                 335

Gln Leu Glu Gly Phe Lys Arg Asn Asp Val Leu Ala Ile Lys Arg Arg
            340                 345                 350

Glu Glu Ala Ala Val Leu Glu Trp Leu Arg Ala Arg Gly Lys Ala Gly
            355                 360                 365

Thr Pro Ala Leu Glu Ala His Ala Ala Leu Val Lys Leu Val Ala Asp
            370                 375                 380

Thr Ala Arg Thr Gln Glu Arg Asp Leu Val Leu Gly Ser Phe Asn Arg
385                 390                 395                 400

Thr Gly Ile Ile Gly Val Ala Val Asn Leu Tyr Arg Leu Ala Ile Glu
            405                 410                 415

Arg Gln Lys Pro Asp Ala Glu Arg Glu Pro Gly Tyr Gln Gln Arg Asp
            420                 425                 430

Leu Pro Val Ile Glu Gly Ser Leu Lys Gln Met Glu Arg Arg Tyr Val
            435                 440                 445

Pro Ala Met Asp Arg Gln Leu Arg Ala Tyr Trp Leu Asp Arg Tyr Val
            450                 455                 460

Ala Leu Pro Ala Ala Gln His Val Ala Ala Val Asp Ala Trp Leu Gly
465                 470                 475                 480

Gly Ser Asp Lys Ala Ala Ala Glu Ala Ala Leu Ala Arg Leu Asp Gln
            485                 490                 495

Ser Arg Leu Gly Ser Leu Glu Glu Arg Leu Lys Trp Phe Asn Ala Asp
            500                 505                 510

Arg Ala Ala Phe Glu Ala Ser Thr Asp Pro Ala Ile Gln Tyr Ala Val
            515                 520                 525

Ala Val Met Pro Thr Leu Leu Ala Met Glu Gln Gln Ala Lys Thr Arg
            530                 535                 540

Tyr Gly Val Ala Leu Glu Ala Arg Pro Arg Tyr Leu Gln Ala Val Val
545                 550                 555                 560
```

```
Asp Tyr Lys Lys Ser Lys Gly Gln Ala Val Tyr Pro Asp Ala Asn Ser
            565                 570                 575

Thr Leu Arg Ile Thr Tyr Gly His Val Lys Gly Tyr Thr Gly Leu Asn
        580                 585                 590

Gly Lys Val Tyr Thr Pro Phe Thr Leu Glu Glu Val Ala Ala Lys
        595                 600                 605

Glu Thr Gly Val Glu Pro Phe Asp Asn Pro Lys Ala Leu Leu Glu Ala
        610                 615                 620

Val Ala Ala Lys Arg Tyr Ala Gly Leu Ala Asp Ala Arg Leu Gly Thr
625                 630                 635                 640

Val Pro Val Asn Phe Leu Ala Asp Leu Asp Ile Thr Gly Gly Asn Ser
                645                 650                 655

Gly Ser Pro Val Leu Asp Ala Asn Gly Arg Leu Val Gly Leu Ala Phe
            660                 665                 670

Ala Gly Thr Leu Glu Ser Val Ala Ser Asn Trp Val Phe Asp Pro Val
        675                 680                 685

Leu Thr Arg Met Ile Ser Val Asp Gln Arg Tyr Met Arg Trp Ile Met
        690                 695                 700

Gln Glu Val Met Pro Ala Pro Gln Leu Leu Glu Glu Leu Gly Val Pro
705                 710                 715                 720

Pro Arg Gln
```

<210> SEQ ID NO 62
<211> LENGTH: 723
<212> TYPE: PRT
<213> ORGANISM: Artificial Sequence
<220> FEATURE:
<223> OTHER INFORMATION: mutated DPP from Thermomonas hydrothermalis
      having N214M, W215G, R219T, N329P, D673S amino acids substitutions

<400> SEQUENCE: 62

```
Met His Lys Thr Arg Leu Val Ala Ala Leu Ala Ala Ala Leu Ala Thr
1               5                   10                  15

Leu Ala Pro Ala Ala Trp Ala Asp Glu Gly Met Trp Val Pro Gln Gln
            20                  25                  30

Leu Pro Glu Ile Ala Gly Ala Leu Lys Lys Ala Gly Leu Lys Leu Asp
        35                  40                  45

Pro Lys Gln Leu Ser Asp Leu Thr Gly Asp Pro Met Gly Ala Val Val
    50                  55                  60

Ser Leu Gly Gly Cys Thr Gly Ser Phe Val Ser Pro Gln Gly Leu Val
65                  70                  75                  80

Ala Thr Asn His His Cys Ala Tyr Gly Ala Ile Gln Leu Asn Ser Thr
                85                  90                  95

Pro Glu Lys Asn Leu Ile Lys Asp Gly Phe Asn Ala Pro Thr Gln Ala
            100                 105                 110

Asp Glu Leu Ser Ala Gly Pro Asn Ala Arg Ile Tyr Val Leu Glu Gly
        115                 120                 125

Ile Thr Asp Val Thr Ala Gln Ala Lys Ala Ala Met Ala Ala Ala Gly
    130                 135                 140

Asn Asp Pro Val Ala Arg Ala Asn Ala Leu Glu Ala Phe Glu Lys Lys
145                 150                 155                 160

Ile Thr Ser Asp Cys Glu Ala Glu Pro Gly Tyr Arg Cys Arg Val Tyr
                165                 170                 175

Ser Phe Met Gly Gly Ile Thr Tyr Arg Leu Phe Lys Asn Leu Glu Ile
            180                 185                 190
```

```
Lys Asp Val Arg Leu Val Tyr Ala Pro Pro Ser Ser Val Gly Lys Phe
            195                 200                 205

Gly Gly Asp Ile Asp Met Gly Met Trp Pro Thr His Thr Gly Asp Phe
        210                 215                 220

Ser Phe Tyr Arg Ala Tyr Val Gly Lys Asp Gly Lys Pro Ala Pro Tyr
225                 230                 235                 240

Ser Lys Asp Asn Val Pro Tyr Arg Pro Lys His Trp Leu Lys Ile Ala
                245                 250                 255

Asp Thr Pro Leu Gly Glu Gly Asp Phe Val Met Val Ala Gly Tyr Pro
            260                 265                 270

Gly Arg Thr Asp Arg Tyr Ala Leu Val Ala Glu Phe Glu Asn Thr Gln
        275                 280                 285

Asn Trp Leu Tyr Pro Ala Ile Ser Lys Ala Tyr Lys Asp Gln Ile Ala
    290                 295                 300

Leu Val Glu Ala Ala Lys Asp Asn Pro Glu Ile Ala Val Lys Tyr
305                 310                 315                 320

Ala Ala Ala Leu Ala Gly Trp Asn Pro Thr Ser Lys Asn Phe Asp Gly
                325                 330                 335

Gln Leu Glu Gly Phe Lys Arg Asn Asp Val Leu Ala Ile Lys Arg Arg
            340                 345                 350

Glu Glu Ala Ala Val Leu Glu Trp Leu Arg Ala Arg Gly Lys Ala Gly
        355                 360                 365

Thr Pro Ala Leu Glu Ala His Ala Ala Leu Val Lys Leu Val Ala Asp
    370                 375                 380

Thr Ala Arg Thr Gln Glu Arg Asp Leu Val Leu Gly Ser Phe Asn Arg
385                 390                 395                 400

Thr Gly Ile Ile Gly Val Ala Val Asn Leu Tyr Arg Leu Ala Ile Glu
                405                 410                 415

Arg Gln Lys Pro Asp Ala Glu Arg Glu Pro Gly Tyr Gln Gln Arg Asp
            420                 425                 430

Leu Pro Val Ile Glu Gly Ser Leu Lys Gln Met Glu Arg Arg Tyr Val
        435                 440                 445

Pro Ala Met Asp Arg Gln Leu Arg Ala Tyr Trp Leu Asp Arg Tyr Val
    450                 455                 460

Ala Leu Pro Ala Ala Gln His Val Ala Ala Val Asp Ala Trp Leu Gly
465                 470                 475                 480

Gly Ser Asp Lys Ala Ala Ala Glu Ala Ala Leu Ala Arg Leu Asp Gln
                485                 490                 495

Ser Arg Leu Gly Ser Leu Glu Glu Arg Leu Lys Trp Phe Asn Ala Asp
            500                 505                 510

Arg Ala Ala Phe Glu Ala Ser Thr Asp Pro Ala Ile Gln Tyr Ala Val
        515                 520                 525

Ala Val Met Pro Thr Leu Leu Ala Met Glu Gln Gln Ala Lys Thr Arg
    530                 535                 540

Tyr Gly Val Ala Leu Glu Ala Arg Pro Arg Tyr Leu Gln Ala Val Val
545                 550                 555                 560

Asp Tyr Lys Lys Ser Lys Gly Gln Ala Val Tyr Pro Asp Ala Asn Ser
                565                 570                 575

Thr Leu Arg Ile Thr Tyr Gly His Val Lys Gly Tyr Thr Gly Leu Asn
            580                 585                 590

Gly Lys Val Tyr Thr Pro Phe Thr Thr Leu Glu Glu Val Ala Ala Lys
        595                 600                 605

Glu Thr Gly Val Glu Pro Phe Asp Asn Pro Lys Ala Leu Leu Glu Ala
```

```
                610                615                620
Val Ala Ala Lys Arg Tyr Ala Gly Leu Ala Asp Ala Arg Leu Gly Thr
625                630                635                640

Val Pro Val Asn Phe Leu Ala Asp Leu Asp Ile Thr Gly Gly Asn Ser
                645                650                655

Gly Ser Pro Val Leu Asp Ala Asn Gly Arg Leu Val Gly Leu Ala Phe
                660                665                670

Ser Gly Thr Leu Glu Ser Val Ala Ser Asn Trp Val Phe Asp Pro Val
        675                680                685

Leu Thr Arg Met Ile Ser Val Asp Gln Arg Tyr Met Arg Trp Ile Met
        690                695                700

Gln Glu Val Met Pro Ala Pro Gln Leu Leu Glu Glu Leu Gly Val Pro
705                710                715                720

Pro Arg Gln

<210> SEQ ID NO 63
<211> LENGTH: 723
<212> TYPE: PRT
<213> ORGANISM: Artificial Sequence
<220> FEATURE:
<223> OTHER INFORMATION: mutated DPP from Thermomonas hydrothermalis
      having N214M, W215G, R219A, N329P, D673A amino acids substitutions

<400> SEQUENCE: 63

Met His Lys Thr Arg Leu Val Ala Ala Leu Ala Ala Leu Ala Thr
1               5                  10                 15

Leu Ala Pro Ala Ala Trp Ala Asp Glu Gly Met Trp Val Pro Gln Gln
                20                 25                 30

Leu Pro Glu Ile Ala Gly Ala Leu Lys Lys Ala Gly Leu Lys Leu Asp
            35                 40                 45

Pro Lys Gln Leu Ser Asp Leu Thr Gly Asp Pro Met Gly Ala Val Val
        50                 55                 60

Ser Leu Gly Gly Cys Thr Gly Ser Phe Val Ser Pro Gln Gly Leu Val
65                 70                 75                 80

Ala Thr Asn His His Cys Ala Tyr Gly Ala Ile Gln Leu Asn Ser Thr
                85                 90                 95

Pro Glu Lys Asn Leu Ile Lys Asp Gly Phe Asn Ala Pro Thr Gln Ala
                100                105                110

Asp Glu Leu Ser Ala Gly Pro Asn Ala Arg Ile Tyr Val Leu Glu Gly
            115                120                125

Ile Thr Asp Val Thr Ala Gln Ala Lys Ala Ala Met Ala Ala Ala Gly
        130                135                140

Asn Asp Pro Val Ala Arg Ala Asn Ala Leu Glu Ala Phe Glu Lys Lys
145                150                155                160

Ile Thr Ser Asp Cys Glu Ala Glu Pro Gly Tyr Arg Cys Arg Val Tyr
                165                170                175

Ser Phe Met Gly Gly Ile Thr Tyr Arg Leu Phe Lys Asn Leu Glu Ile
                180                185                190

Lys Asp Val Arg Leu Val Tyr Ala Pro Pro Ser Ser Val Gly Lys Phe
            195                200                205

Gly Gly Asp Ile Asp Met Gly Met Trp Pro Ala His Thr Gly Asp Phe
        210                215                220

Ser Phe Tyr Arg Ala Tyr Val Gly Lys Asp Gly Lys Pro Ala Pro Tyr
225                230                235                240

Ser Lys Asp Asn Val Pro Tyr Arg Pro Lys His Trp Leu Lys Ile Ala
```

-continued

```
                245                 250                 255
Asp Thr Pro Leu Gly Glu Gly Asp Phe Val Met Val Ala Gly Tyr Pro
                260                 265                 270
Gly Arg Thr Asp Arg Tyr Ala Leu Val Ala Glu Phe Glu Asn Thr Gln
                275                 280                 285
Asn Trp Leu Tyr Pro Ala Ile Ser Lys Ala Tyr Lys Asp Gln Ile Ala
290                 295                 300
Leu Val Glu Ala Ala Lys Asp Asn Pro Glu Ile Ala Val Lys Tyr
305                 310                 315                 320
Ala Ala Ala Leu Ala Gly Trp Asn Pro Thr Ser Lys Asn Phe Asp Gly
                325                 330                 335
Gln Leu Glu Gly Phe Lys Arg Asn Asp Val Leu Ala Ile Lys Arg Arg
                340                 345                 350
Glu Glu Ala Ala Val Leu Glu Trp Leu Arg Ala Arg Gly Lys Ala Gly
                355                 360                 365
Thr Pro Ala Leu Glu Ala His Ala Ala Leu Val Lys Leu Val Ala Asp
                370                 375                 380
Thr Ala Arg Thr Gln Glu Arg Asp Leu Val Leu Gly Ser Phe Asn Arg
385                 390                 395                 400
Thr Gly Ile Ile Gly Val Ala Val Asn Leu Tyr Arg Leu Ala Ile Glu
                    405                 410                 415
Arg Gln Lys Pro Asp Ala Glu Arg Glu Pro Gly Tyr Gln Gln Arg Asp
                420                 425                 430
Leu Pro Val Ile Glu Gly Ser Leu Lys Gln Met Glu Arg Arg Tyr Val
                435                 440                 445
Pro Ala Met Asp Arg Gln Leu Arg Ala Tyr Trp Leu Asp Arg Tyr Val
                450                 455                 460
Ala Leu Pro Ala Ala Gln His Val Ala Ala Val Asp Ala Trp Leu Gly
465                 470                 475                 480
Gly Ser Asp Lys Ala Ala Ala Glu Ala Leu Ala Arg Leu Asp Gln
                    485                 490                 495
Ser Arg Leu Gly Ser Leu Glu Glu Arg Leu Lys Trp Phe Asn Ala Asp
                500                 505                 510
Arg Ala Ala Phe Glu Ala Ser Thr Asp Pro Ala Ile Gln Tyr Ala Val
                515                 520                 525
Ala Val Met Pro Thr Leu Leu Ala Met Glu Gln Gln Ala Lys Thr Arg
                530                 535                 540
Tyr Gly Val Ala Leu Glu Ala Arg Pro Arg Tyr Leu Gln Ala Val Val
545                 550                 555                 560
Asp Tyr Lys Lys Ser Lys Gly Gln Ala Val Tyr Pro Asp Ala Asn Ser
                    565                 570                 575
Thr Leu Arg Ile Thr Tyr Gly His Val Lys Gly Tyr Thr Gly Leu Asn
                580                 585                 590
Gly Lys Val Tyr Thr Pro Phe Thr Thr Leu Glu Glu Val Ala Ala Lys
                595                 600                 605
Glu Thr Gly Val Glu Pro Phe Asp Asn Pro Lys Ala Leu Leu Glu Ala
                610                 615                 620
Val Ala Ala Lys Arg Tyr Ala Gly Leu Ala Asp Ala Arg Leu Gly Thr
625                 630                 635                 640
Val Pro Val Asn Phe Leu Ala Asp Leu Asp Ile Thr Gly Gly Asn Ser
                    645                 650                 655
Gly Ser Pro Val Leu Asp Ala Asn Gly Arg Leu Val Gly Leu Ala Phe
                660                 665                 670
```

```
Ala Gly Thr Leu Glu Ser Val Ala Ser Asn Trp Val Phe Asp Pro Val
        675                 680                 685

Leu Thr Arg Met Ile Ser Val Asp Gln Arg Tyr Met Arg Trp Ile Met
        690                 695                 700

Gln Glu Val Met Pro Ala Pro Gln Leu Glu Glu Leu Gly Val Pro
705                 710                 715                 720

Pro Arg Gln

<210> SEQ ID NO 64
<211> LENGTH: 723
<212> TYPE: PRT
<213> ORGANISM: Artificial Sequence
<220> FEATURE:
<223> OTHER INFORMATION: mutated DPP from Thermomonas hydrothermalis
      having N214M, W215G, R219V, N329P, D673A amino acids substitutions

<400> SEQUENCE: 64

Met His Lys Thr Arg Leu Val Ala Ala Leu Ala Ala Leu Ala Thr
1               5                   10                  15

Leu Ala Pro Ala Ala Trp Ala Asp Glu Gly Met Trp Val Pro Gln Gln
                20                  25                  30

Leu Pro Glu Ile Ala Gly Ala Leu Lys Lys Ala Gly Leu Lys Leu Asp
            35                  40                  45

Pro Lys Gln Leu Ser Asp Leu Thr Gly Asp Pro Met Gly Ala Val Val
50                  55                  60

Ser Leu Gly Gly Cys Thr Gly Ser Phe Val Ser Pro Gln Gly Leu Val
65                  70                  75                  80

Ala Thr Asn His His Cys Ala Tyr Gly Ala Ile Gln Leu Asn Ser Thr
                85                  90                  95

Pro Glu Lys Asn Leu Ile Lys Asp Gly Phe Asn Ala Pro Thr Gln Ala
            100                 105                 110

Asp Glu Leu Ser Ala Gly Pro Asn Ala Arg Ile Tyr Val Leu Glu Gly
        115                 120                 125

Ile Thr Asp Val Thr Ala Gln Ala Lys Ala Ala Met Ala Ala Ala Gly
    130                 135                 140

Asn Asp Pro Val Ala Arg Ala Asn Ala Leu Glu Ala Phe Glu Lys Lys
145                 150                 155                 160

Ile Thr Ser Asp Cys Glu Ala Glu Pro Gly Tyr Arg Cys Arg Val Tyr
                165                 170                 175

Ser Phe Met Gly Gly Ile Thr Tyr Arg Leu Phe Lys Asn Leu Glu Ile
            180                 185                 190

Lys Asp Val Arg Leu Val Tyr Ala Pro Pro Ser Ser Val Gly Lys Phe
        195                 200                 205

Gly Gly Asp Ile Asp Met Gly Met Trp Pro Val His Thr Gly Asp Phe
    210                 215                 220

Ser Phe Tyr Arg Ala Tyr Val Gly Lys Asp Gly Lys Pro Ala Pro Tyr
225                 230                 235                 240

Ser Lys Asp Asn Val Pro Tyr Arg Pro Lys His Trp Leu Lys Ile Ala
                245                 250                 255

Asp Thr Pro Leu Gly Glu Gly Asp Phe Val Met Val Ala Gly Tyr Pro
            260                 265                 270

Gly Arg Thr Asp Arg Tyr Ala Leu Val Ala Glu Phe Glu Asn Thr Gln
        275                 280                 285

Asn Trp Leu Tyr Pro Ala Ile Ser Lys Ala Tyr Lys Asp Gln Ile Ala
    290                 295                 300
```

```
Leu Val Glu Ala Ala Ala Lys Asp Asn Pro Glu Ile Ala Val Lys Tyr
305                 310                 315                 320

Ala Ala Ala Leu Ala Gly Trp Asn Pro Thr Ser Lys Asn Phe Asp Gly
            325                 330                 335

Gln Leu Glu Gly Phe Lys Arg Asn Asp Val Leu Ala Ile Lys Arg Arg
        340                 345                 350

Glu Glu Ala Ala Val Leu Glu Trp Leu Arg Ala Arg Gly Lys Ala Gly
    355                 360                 365

Thr Pro Ala Leu Glu Ala His Ala Ala Leu Val Lys Leu Val Ala Asp
370                 375                 380

Thr Ala Arg Thr Gln Glu Arg Asp Leu Val Leu Gly Ser Phe Asn Arg
385                 390                 395                 400

Thr Gly Ile Ile Gly Val Ala Val Asn Leu Tyr Arg Leu Ala Ile Glu
            405                 410                 415

Arg Gln Lys Pro Asp Ala Glu Arg Glu Pro Gly Tyr Gln Gln Arg Asp
        420                 425                 430

Leu Pro Val Ile Glu Gly Ser Leu Lys Gln Met Glu Arg Arg Tyr Val
    435                 440                 445

Pro Ala Met Asp Arg Gln Leu Arg Ala Tyr Trp Leu Asp Arg Tyr Val
450                 455                 460

Ala Leu Pro Ala Ala Gln His Val Ala Ala Val Asp Ala Trp Leu Gly
465                 470                 475                 480

Gly Ser Asp Lys Ala Ala Ala Glu Ala Ala Leu Ala Arg Leu Asp Gln
            485                 490                 495

Ser Arg Leu Gly Ser Leu Glu Glu Arg Leu Lys Trp Phe Asn Ala Asp
        500                 505                 510

Arg Ala Ala Phe Glu Ala Ser Thr Asp Pro Ala Ile Gln Tyr Ala Val
    515                 520                 525

Ala Val Met Pro Thr Leu Leu Ala Met Glu Gln Gln Ala Lys Thr Arg
530                 535                 540

Tyr Gly Val Ala Leu Glu Ala Arg Pro Arg Tyr Leu Gln Ala Val Val
545                 550                 555                 560

Asp Tyr Lys Lys Ser Lys Gly Gln Ala Val Tyr Pro Asp Ala Asn Ser
            565                 570                 575

Thr Leu Arg Ile Thr Tyr Gly His Val Lys Gly Tyr Thr Gly Leu Asn
        580                 585                 590

Gly Lys Val Tyr Thr Pro Phe Thr Leu Glu Glu Val Ala Ala Lys
    595                 600                 605

Glu Thr Gly Val Glu Pro Phe Asp Asn Pro Lys Ala Leu Leu Glu Ala
610                 615                 620

Val Ala Ala Lys Arg Tyr Ala Gly Leu Ala Asp Ala Arg Leu Gly Thr
625                 630                 635                 640

Val Pro Val Asn Phe Leu Ala Asp Leu Asp Ile Thr Gly Gly Asn Ser
            645                 650                 655

Gly Ser Pro Val Leu Asp Ala Asn Gly Arg Leu Val Gly Leu Ala Phe
        660                 665                 670

Ala Gly Thr Leu Glu Ser Val Ala Ser Asn Trp Val Phe Asp Pro Val
    675                 680                 685

Leu Thr Arg Met Ile Ser Val Asp Gln Arg Tyr Met Arg Trp Ile Met
690                 695                 700

Gln Glu Val Met Pro Ala Pro Gln Leu Leu Glu Glu Leu Gly Val Pro
705                 710                 715                 720
```

Pro Arg Gln

<210> SEQ ID NO 65
<211> LENGTH: 723
<212> TYPE: PRT
<213> ORGANISM: Artificial Sequence
<220> FEATURE:
<223> OTHER INFORMATION: mutated DPP from Thermomonas hydrothermalis having N214T, W215M, R219K, N329Y amino acids substitutions

<400> SEQUENCE: 65

```
Met His Lys Thr Arg Leu Val Ala Ala Leu Ala Ala Ala Leu Ala Thr
1               5                   10                  15
Leu Ala Pro Ala Ala Trp Ala Asp Glu Gly Met Trp Val Pro Gln Gln
            20                  25                  30
Leu Pro Glu Ile Ala Gly Ala Leu Lys Lys Ala Gly Leu Lys Leu Asp
        35                  40                  45
Pro Lys Gln Leu Ser Asp Leu Thr Gly Asp Pro Met Gly Ala Val Val
    50                  55                  60
Ser Leu Gly Gly Cys Thr Gly Ser Phe Val Ser Pro Gln Gly Leu Val
65                  70                  75                  80
Ala Thr Asn His His Cys Ala Tyr Gly Ala Ile Gln Leu Asn Ser Thr
                85                  90                  95
Pro Glu Lys Asn Leu Ile Lys Asp Gly Phe Asn Ala Pro Thr Gln Ala
            100                 105                 110
Asp Glu Leu Ser Ala Gly Pro Asn Ala Arg Ile Tyr Val Leu Glu Gly
        115                 120                 125
Ile Thr Asp Val Thr Ala Gln Ala Lys Ala Ala Met Ala Ala Ala Gly
    130                 135                 140
Asn Asp Pro Val Ala Arg Ala Asn Ala Leu Glu Ala Phe Glu Lys Lys
145                 150                 155                 160
Ile Thr Ser Asp Cys Glu Ala Glu Pro Gly Tyr Arg Cys Arg Val Tyr
                165                 170                 175
Ser Phe Met Gly Gly Ile Thr Tyr Arg Leu Phe Lys Asn Leu Glu Ile
            180                 185                 190
Lys Asp Val Arg Leu Val Tyr Ala Pro Pro Ser Ser Val Gly Lys Phe
        195                 200                 205
Gly Gly Asp Ile Asp Thr Met Met Trp Pro Lys His Thr Gly Asp Phe
    210                 215                 220
Ser Phe Tyr Arg Ala Tyr Val Gly Lys Asp Gly Lys Pro Ala Pro Tyr
225                 230                 235                 240
Ser Lys Asp Asn Val Pro Tyr Arg Pro Lys His Trp Leu Lys Ile Ala
                245                 250                 255
Asp Thr Pro Leu Gly Glu Gly Asp Phe Val Met Val Ala Gly Tyr Pro
            260                 265                 270
Gly Arg Thr Asp Arg Tyr Ala Leu Val Ala Glu Phe Glu Asn Thr Gln
        275                 280                 285
Asn Trp Leu Tyr Pro Ala Ile Ser Lys Ala Tyr Lys Asp Gln Ile Ala
    290                 295                 300
Leu Val Glu Ala Ala Lys Asp Asn Pro Glu Ile Ala Val Lys Tyr
305                 310                 315                 320
Ala Ala Ala Leu Ala Gly Trp Asn Tyr Thr Ser Lys Asn Phe Asp Gly
                325                 330                 335
Gln Leu Glu Gly Phe Lys Arg Asn Asp Val Leu Ala Ile Lys Arg Arg
            340                 345                 350
```

-continued

```
Glu Glu Ala Val Leu Glu Trp Leu Arg Ala Arg Gly Lys Ala Gly
        355                 360                 365

Thr Pro Ala Leu Glu Ala His Ala Ala Leu Val Lys Leu Val Ala Asp
370                 375                 380

Thr Ala Arg Thr Gln Glu Arg Asp Leu Val Leu Gly Ser Phe Asn Arg
385                 390                 395                 400

Thr Gly Ile Ile Gly Val Ala Val Asn Leu Tyr Arg Leu Ala Ile Glu
                    405                 410                 415

Arg Gln Lys Pro Asp Ala Glu Arg Glu Pro Gly Tyr Gln Gln Arg Asp
                420                 425                 430

Leu Pro Val Ile Glu Gly Ser Leu Lys Gln Met Glu Arg Arg Tyr Val
            435                 440                 445

Pro Ala Met Asp Arg Gln Leu Arg Ala Tyr Trp Leu Asp Arg Tyr Val
        450                 455                 460

Ala Leu Pro Ala Ala Gln His Val Ala Ala Val Asp Ala Trp Leu Gly
465                 470                 475                 480

Gly Ser Asp Lys Ala Ala Glu Ala Ala Leu Ala Arg Leu Asp Gln
                    485                 490                 495

Ser Arg Leu Gly Ser Leu Glu Glu Arg Leu Lys Trp Phe Asn Ala Asp
                500                 505                 510

Arg Ala Ala Phe Glu Ala Ser Thr Asp Pro Ala Ile Gln Tyr Ala Val
            515                 520                 525

Ala Val Met Pro Thr Leu Leu Ala Met Glu Gln Gln Ala Lys Thr Arg
        530                 535                 540

Tyr Gly Val Ala Leu Glu Ala Arg Pro Arg Tyr Leu Gln Ala Val Val
545                 550                 555                 560

Asp Tyr Lys Lys Ser Lys Gly Gln Ala Val Tyr Pro Asp Ala Asn Ser
                    565                 570                 575

Thr Leu Arg Ile Thr Tyr Gly His Val Lys Gly Tyr Thr Gly Leu Asn
                580                 585                 590

Gly Lys Val Tyr Thr Pro Phe Thr Leu Glu Glu Val Ala Ala Lys
            595                 600                 605

Glu Thr Gly Val Glu Pro Phe Asp Asn Pro Lys Ala Leu Leu Glu Ala
        610                 615                 620

Val Ala Ala Lys Arg Tyr Ala Gly Leu Ala Asp Ala Arg Leu Gly Thr
625                 630                 635                 640

Val Pro Val Asn Phe Leu Ala Asp Leu Asp Ile Thr Gly Gly Asn Ser
                    645                 650                 655

Gly Ser Pro Val Leu Asp Ala Asn Gly Arg Leu Val Gly Leu Ala Phe
                660                 665                 670

Asp Gly Thr Leu Glu Ser Val Ala Ser Asn Trp Val Phe Asp Pro Val
            675                 680                 685

Leu Thr Arg Met Ile Ser Val Asp Gln Arg Tyr Met Arg Trp Ile Met
        690                 695                 700

Gln Glu Val Met Pro Ala Pro Gln Leu Leu Glu Leu Gly Val Pro
705                 710                 715                 720

Pro Arg Gln
```